(12) United States Patent
Woll et al.

(10) Patent No.: US 12,384,789 B2
(45) Date of Patent: *Aug. 12, 2025

(54) COMPOUNDS FOR TREATING HUNTINGTON'S DISEASE

(71) Applicant: PTC Therapeutics, Inc., South Plainfield, NJ (US)

(72) Inventors: Matthew G. Woll, Dunellen, NJ (US); Lukiana Amedzo, Somerset, NJ (US); Suresh Babu, Pennington, NJ (US); Scott J. Barraza, Piscataway, NJ (US); Anuradha Bhattacharyya, Edison, NJ (US); Gary Mitchell Karp, Princeton Junction, NJ (US); Anthony R. Mazzotti, Rahway, NJ (US); Jana Narasimhan, Scotch Plains, NJ (US); Jigar Patel, Edison, NJ (US); Anthony Turpoff, Hillsborough, NJ (US); Zhenrong Xu, Chalfont, PA (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 40 days.

This patent is subject to a terminal disclaimer.

(21) Appl. No.: 17/723,163

(22) Filed: Apr. 18, 2022

(65) Prior Publication Data
US 2022/0251098 A1  Aug. 11, 2022

Related U.S. Application Data

(63) Continuation of application No. 16/617,450, filed as application No. PCT/US2018/035954 on Jun. 5, 2018, now Pat. No. 11,407,753.

(60) Provisional application No. 62/514,999, filed on Jun. 5, 2017.

(51) Int. Cl.
| | |
|---|---|
| *C07D 487/04* | (2006.01) |
| *C07D 401/14* | (2006.01) |
| *C07D 413/14* | (2006.01) |
| *C07D 417/14* | (2006.01) |
| *C07D 471/04* | (2006.01) |
| *C07D 491/048* | (2006.01) |
| *C07D 498/04* | (2006.01) |
| *C07D 513/04* | (2006.01) |
| *C07D 519/00* | (2006.01) |

(52) U.S. Cl.
CPC ......... *C07D 487/04* (2013.01); *C07D 401/14* (2013.01); *C07D 413/14* (2013.01); *C07D 417/14* (2013.01); *C07D 471/04* (2013.01); *C07D 491/048* (2013.01); *C07D 498/04* (2013.01); *C07D 513/04* (2013.01); *C07D 519/00* (2013.01)

(58) Field of Classification Search
CPC .. C07D 487/04; C07D 401/14; C07D 413/14; C07D 417/14; C07D 471/04; C07D 491/048; C07D 498/04; C07D 513/04; C07D 519/00

See application file for complete search history.

(56) References Cited

U.S. PATENT DOCUMENTS

| | | | |
|---|---|---|---|
| 3,558,618 | A | 1/1971 | Trepanier |
| 4,122,274 | A | 10/1978 | Juby |
| 4,342,870 | A | 8/1982 | Kennis et al. |
| 4,613,603 | A | 9/1986 | Sanofi |
| 4,902,695 | A | 2/1990 | Ornstein |
| 5,089,633 | A | 2/1992 | Powers et al. |
| 5,599,816 | A | 2/1997 | Chu et al. |
| 5,627,274 | A | 5/1997 | Kole et al. |
| 5,665,593 | A | 9/1997 | Kole et al. |
| 5,916,808 | A | 6/1999 | Kole et al. |
| 5,916,916 | A | 6/1999 | Hauser et al. |
| 5,976,879 | A | 11/1999 | Kole et al. |
| 6,172,216 | B1 | 1/2001 | Bennett et al. |
| 6,210,892 | B1 | 4/2001 | Bennett et al. |
| 6,214,986 | B1 | 4/2001 | Bennett et al. |
| 6,468,607 | B1 | 10/2002 | Takehara et al. |
| 6,630,488 | B1 | 10/2003 | Lamothe et al. |
| 6,977,255 | B2 | 12/2005 | Robertson et al. |
| 7,326,711 | B2 | 2/2008 | Wang et al. |
| 7,399,767 | B2 | 7/2008 | Zhang et al. |

(Continued)

FOREIGN PATENT DOCUMENTS

| | | |
|---|---|---|
| CN | 101360738 A | 2/2009 |
| CN | 102971311 A | 3/2013 |

(Continued)

OTHER PUBLICATIONS

Berge et al. "Pharmaceutical Salts". Journal of Pharmaceutical Sciences. 66(1):1-19. (Year: 1977).*

(Continued)

*Primary Examiner* — Jeffrey S Lundgren
*Assistant Examiner* — Ibrahim D Bori
(74) *Attorney, Agent, or Firm* — McCarter & English, LLP; Michael J. DeGrazia

(57) ABSTRACT

The present description relates to compounds, forms, and pharmaceutical compositions thereof and methods of using such compounds, forms, or compositions thereof for treating or ameliorating Huntington's disease. In particular, the present description relates to substituted bicyclic heteroaryl compounds of Formula (I), forms and pharmaceutical compositions thereof and methods of using such compounds, forms, or compositions thereof for treating or ameliorating Huntington's disease.

2 Claims, No Drawings

(56) References Cited

U.S. PATENT DOCUMENTS

| | | |
|---|---|---|
| 7,473,784 B2 | 1/2009 | Liu et al. |
| 7,569,337 B2 | 8/2009 | Auberson |
| 7,576,110 B2 | 8/2009 | Cowart et al. |
| 7,655,657 B2 | 2/2010 | Stoner et al. |
| 7,897,792 B2 | 3/2011 | Iikuea et al. |
| 7,910,578 B2 | 3/2011 | Peters et al. |
| 8,143,274 B2 | 3/2012 | Hattori et al. |
| 8,314,119 B2 | 11/2012 | Schrimpf et al. |
| 8,337,941 B2 | 12/2012 | Gubernator et al. |
| 8,563,550 B2 | 10/2013 | Pevarello et al. |
| 8,633,019 B2 | 1/2014 | Paushkin et al. |
| 8,765,747 B2 | 7/2014 | Choi et al. |
| 8,846,661 B2 | 9/2014 | Schrimpf et al. |
| 8,921,361 B2 | 12/2014 | Cmiljanovic et al. |
| 8,940,716 B2 | 1/2015 | Ye et al. |
| 9,340,537 B2 | 5/2016 | Furet et al. |
| 9,371,336 B2 | 6/2016 | Lee et al. |
| 9,399,649 B2 | 7/2016 | Chen et al. |
| 9,617,268 B2 | 4/2017 | Woll et al. |
| 9,969,754 B2 | 5/2018 | Ratni et al. |
| 2002/0099208 A1 | 7/2002 | Yu et al. |
| 2003/0004164 A1 | 1/2003 | Bebbington et al. |
| 2003/0199526 A1 | 10/2003 | Choquette et al. |
| 2004/0224952 A1 | 11/2004 | Cowart et al. |
| 2005/0054836 A1 | 3/2005 | Krainer et al. |
| 2005/0074801 A1 | 4/2005 | Monia et al. |
| 2005/0159597 A1 | 7/2005 | Ji et al. |
| 2006/0172962 A1 | 8/2006 | Vickers et al. |
| 2006/0205741 A1 | 9/2006 | Zhang et al. |
| 2007/0078144 A1 | 4/2007 | Stockwell et al. |
| 2007/0105807 A1 | 5/2007 | Sazani et al. |
| 2007/0191374 A1 | 8/2007 | Hodgetts |
| 2008/0171792 A1 | 7/2008 | Jobdevairakkam et al. |
| 2008/0255162 A1 | 10/2008 | Bruendl et al. |
| 2009/0163464 A1 | 6/2009 | Black et al. |
| 2009/0163515 A1 | 6/2009 | Birault et al. |
| 2009/0170793 A1 | 7/2009 | Gaur |
| 2009/0264433 A1 | 10/2009 | Russell et al. |
| 2010/0004233 A1 | 1/2010 | Iikura et al. |
| 2010/0035279 A1 | 2/2010 | Gubernator et al. |
| 2010/0267721 A1 | 10/2010 | Hohlweg et al. |
| 2011/0086833 A1 | 4/2011 | Paushkin et al. |
| 2011/0118289 A1 | 5/2011 | Giordani et al. |
| 2012/0083495 A1 | 4/2012 | Heemskerk et al. |
| 2013/0046093 A1 | 2/2013 | Lee et al. |
| 2014/0051672 A1 | 2/2014 | Cheung et al. |
| 2014/0121197 A1 | 5/2014 | Burli et al. |
| 2014/0206661 A1 | 7/2014 | Axford et al. |
| 2014/0329825 A1 | 11/2014 | Heback et al. |
| 2015/0005289 A1 | 1/2015 | Qi et al. |
| 2015/0018301 A1 | 1/2015 | Lee et al. |
| 2015/0057218 A1 | 2/2015 | Zhong et al. |
| 2015/0080383 A1 | 3/2015 | Yang et al. |
| 2015/0119380 A1 | 4/2015 | Woll et al. |
| 2016/0244762 A1 | 8/2016 | Vorechovsky et al. |
| 2017/0000794 A1 | 1/2017 | Naryshkin |
| 2017/0001995 A1 | 1/2017 | Metzger et al. |
| 2017/0002016 A1 | 1/2017 | Shishido et al. |
| 2017/0096411 A1 | 4/2017 | Vechorkin et al. |
| 2017/0151225 A1 | 6/2017 | Dahl |
| 2017/0355989 A1 | 12/2017 | Konstantinova et al. |
| 2018/0118748 A1 | 5/2018 | Slaugenhaupt et al. |
| 2018/0161456 A1 | 6/2018 | Naryshkin et al. |
| 2018/0282347 A1 | 10/2018 | Arlt et al. |
| 2019/0264267 A1 | 8/2019 | Yang et al. |
| 2020/0056173 A1 | 2/2020 | Vargeese et al. |
| 2020/0080083 A1 | 3/2020 | Vargeese et al. |

FOREIGN PATENT DOCUMENTS

| | | | |
|---|---|---|---|
| CN | 103533835 A | | 1/2014 |
| CN | 101426772 A | | 5/2014 |
| CN | 104768960 B | | 3/2017 |
| DE | 2345064 A1 | | 4/1974 |
| EP | 1227084 A1 | | 7/2002 |
| EP | 2560008 A2 | | 2/2013 |
| EP | 2841428 B1 | | 8/2018 |
| FR | 2914188 A1 | | 10/2008 |
| GB | 1047935 A | | 11/1966 |
| GB | 1383409 | | 2/1975 |
| JP | S58-52307 A | | 3/1983 |
| JP | S61-36282 | | 2/1986 |
| JP | 2006219453 A | * | 8/2006 |
| JP | 2009-508957 A | | 3/2009 |
| JP | 2009-545540 | | 12/2009 |
| JP | 2012-530071 A | | 11/2012 |
| JP | 2013-40945 | | 2/2013 |
| JP | 2017-512834 | | 5/2017 |
| JP | 2017-533237 A | | 11/2017 |
| WO | 1993/023398 A1 | | 11/1993 |
| WO | 1994/026877 A1 | | 11/1994 |
| WO | 1996/039407 A1 | | 12/1996 |
| WO | 1998/025930 A1 | | 6/1998 |
| WO | 2001/053266 A1 | | 7/2001 |
| WO | 2002/062290 A2 | | 8/2002 |
| WO | 2002/087589 A1 | | 11/2002 |
| WO | 2004/009558 A1 | | 1/2004 |
| WO | 2004/019002 A2 | | 3/2004 |
| WO | 2004/029053 A1 | | 4/2004 |
| WO | 2004/043458 A1 | | 5/2004 |
| WO | 2004/113335 A2 | | 12/2004 |
| WO | 2005/012288 A1 | | 2/2005 |
| WO | 2005/019215 A1 | | 3/2005 |
| WO | 2005/061513 A1 | | 7/2005 |
| WO | 2005/066166 A2 | | 7/2005 |
| WO | 2005/072720 A1 | | 8/2005 |
| WO | 2005/105801 A1 | | 11/2005 |
| WO | 2006/131835 A2 | | 12/2006 |
| WO | 2006/138418 A2 | | 12/2006 |
| WO | 2007/003604 A2 | | 1/2007 |
| WO | 2007/016392 A2 | | 2/2007 |
| WO | 2007/018738 A1 | | 2/2007 |
| WO | 2007/047913 A2 | | 4/2007 |
| WO | 2007/056580 A2 | | 5/2007 |
| WO | 2007/065892 A1 | | 6/2007 |
| WO | 2007/071055 A1 | | 6/2007 |
| WO | 2007/089584 A2 | | 8/2007 |
| WO | 2007/089611 A2 | | 8/2007 |
| WO | 2007/090073 A2 | | 8/2007 |
| WO | 2007/109211 A2 | | 9/2007 |
| WO | 2007/110364 A1 | | 10/2007 |
| WO | 2007/130383 A2 | | 11/2007 |
| WO | 2007/133561 A2 | | 11/2007 |
| WO | 2007/133756 A2 | | 11/2007 |
| WO | 2007/135121 A1 | | 11/2007 |
| WO | 2008/011109 A2 | | 1/2008 |
| WO | 2008/014822 A1 | | 2/2008 |
| WO | 2008/020302 A2 | | 2/2008 |
| WO | 2008/049864 A1 | | 5/2008 |
| WO | 2008/077188 A1 | | 7/2008 |
| WO | 2009/042907 A1 | | 4/2009 |
| WO | 2009/085945 A1 | | 7/2009 |
| WO | 2009/114874 A2 | | 9/2009 |
| WO | 2009/126635 A1 | | 10/2009 |
| WO | 2009/151546 A2 | | 12/2009 |
| WO | 2009/156861 A2 | | 12/2009 |
| WO | 2010/000032 A1 | | 1/2010 |
| WO | 2010/019236 A1 | | 2/2010 |
| WO | 2010/024903 A1 | | 3/2010 |
| WO | 2010/045303 A2 | | 4/2010 |
| WO | 2010/071819 A1 | | 6/2010 |
| WO | 2010/093425 A1 | | 8/2010 |
| WO | 2010/130934 A2 | | 11/2010 |
| WO | 2010/145208 A1 | | 12/2010 |
| WO | 2011/032045 A1 | | 3/2011 |
| WO | 2011/050245 A1 | | 4/2011 |
| WO | 2011/057204 A1 | | 5/2011 |
| WO | 2011/062853 A1 | | 5/2011 |
| WO | 2011/085990 A1 | | 7/2011 |
| WO | 2011/097641 A1 | | 8/2011 |
| WO | 2011/097643 A1 | | 8/2011 |
| WO | 2011/097644 A2 | | 8/2011 |
| WO | 2012/012467 A2 | | 1/2012 |
| WO | 2012/019106 A2 | | 2/2012 |

(56) References Cited

FOREIGN PATENT DOCUMENTS

| | | |
|---|---|---|
| WO | 2012/075393 A2 | 6/2012 |
| WO | 2012/103806 A1 | 8/2012 |
| WO | 2012/104823 A2 | 8/2012 |
| WO | 2012/109395 A1 | 8/2012 |
| WO | 2012/116965 A1 | 9/2012 |
| WO | 2013/019938 A1 | 2/2013 |
| WO | 2013/020993 A1 | 2/2013 |
| WO | 2013/022990 A1 | 2/2013 |
| WO | 2013/033223 A1 | 3/2013 |
| WO | 2013/059606 A1 | 4/2013 |
| WO | 2013/068769 A1 | 5/2013 |
| WO | 2013/101974 A1 | 7/2013 |
| WO | 2013/112788 A1 | 8/2013 |
| WO | 2013/119916 A1 | 8/2013 |
| WO | 2013/130689 A1 | 9/2013 |
| WO | 2013/142236 A1 | 9/2013 |
| WO | 2013/151877 A1 | 10/2013 |
| WO | 2013/163190 A1 | 10/2013 |
| WO | 2014/012050 A2 | 1/2014 |
| WO | 2014/028459 A1 | 2/2014 |
| WO | 2014/059341 A2 | 4/2014 |
| WO | 2014/059356 A2 | 4/2014 |
| WO | 2014/066836 A1 | 5/2014 |
| WO | 2014/069675 A1 | 5/2014 |
| WO | 2014/116845 A1 | 7/2014 |
| WO | 2014/121287 A2 | 8/2014 |
| WO | 2014/135244 A1 | 9/2014 |
| WO | 2014/184163 A1 | 11/2014 |
| WO | 2014/209841 A2 | 12/2014 |
| WO | 2015/024876 A2 | 12/2014 |
| WO | 2015/017589 A1 | 2/2015 |
| WO | 2015/095446 A1 | 6/2015 |
| WO | 2015/095449 A1 | 6/2015 |
| WO | 2015/105657 A1 | 7/2015 |
| WO | 2015/107425 A2 | 7/2015 |
| WO | 2015/107494 A1 | 7/2015 |
| WO | 2015/110446 A1 | 7/2015 |
| WO | 2017/080967 A1 | 7/2015 |
| WO | 2015/143185 A1 | 9/2015 |
| WO | 2015/173181 A1 | 11/2015 |
| WO | 2015/197503 A1 | 12/2015 |
| WO | 2016/071283 A1 | 5/2016 |
| WO | 2016/087417 A1 | 6/2016 |
| WO | 2016/128343 A1 | 8/2016 |
| WO | 2016/131776 A1 | 8/2016 |
| WO | 2016/144351 A1 | 9/2016 |
| WO | WO-2016170163 A1 * 10/2016 ........... C07D 487/04 |
| WO | 2016/184832 A1 | 11/2016 |
| WO | 2017/023987 A1 | 2/2017 |
| WO | 2017/081111 A1 | 5/2017 |
| WO | 2017/097728 A1 | 6/2017 |
| WO | 2017/100726 A1 | 6/2017 |
| WO | 2017/153601 A1 | 9/2017 |
| WO | 2017/175068 A1 | 10/2017 |
| WO | 2017/189829 A1 | 11/2017 |
| WO | 2017/210134 A1 | 12/2017 |
| WO | 2018/013770 A1 | 1/2018 |
| WO | 2018/081091 A1 | 5/2018 |
| WO | 2018/187209 A1 | 10/2018 |
| WO | 2018/218133 A1 | 11/2018 |
| WO | 2018/226622 A1 | 12/2018 |
| WO | 2019/005980 A1 | 1/2019 |
| WO | 2019/005993 A1 | 1/2019 |
| WO | 2019/028440 A1 | 2/2019 |
| WO | 2019/165073 A1 | 8/2019 |
| WO | 2019/183364 A1 | 9/2019 |
| WO | 2019/183367 A1 | 9/2019 |
| WO | 2019/191092 A1 | 10/2019 |
| WO | 2019/191229 A1 | 10/2019 |
| WO | 2020/005873 A1 | 1/2020 |
| WO | 2020/005877 A1 | 1/2020 |
| WO | 2020/005882 A1 | 1/2020 |
| WO | 2020/190793 A1 | 9/2020 |
| WO | 2020/231977 A1 | 11/2020 |
| WO | 2021/007378 A1 | 1/2021 |
| WO | 2021/084495 A1 | 5/2021 |
| WO | 2021/174163 A1 | 9/2021 |
| WO | 2021/207453 A1 | 10/2021 |
| WO | 2022/103980 A1 | 5/2022 |
| WO | 2023/009816 A1 | 2/2023 |
| WO | 2023/244996 A2 | 12/2023 |

OTHER PUBLICATIONS

Brunhilde Wirth et al., "Moving towards treatments for spinal muscular atrophy: hopes and limits", Expert Opinion on Emerging drugs, 20(3):353-356, Apr. 28, 2015.

Cheung et al., "Discovery of Small Molecule Splicing Modulators of Survival Motor Neuron-2 (SMN2) for the Treatment of Spinal Muscular Atrophy (SMA)", J. Med. Chem. vol. 61(24):11021-11036, Nov. 8, 2018 (published), pp. A-P.

Chiara Zanetta et al., "Molecular Therapeutic Strategies for Spinal Muscular Atrophies: Current and Future Clinical Trials", Clinical Therapeutics, 36(1):128-140, Dec. 17, 2013.

Coady et al., 2010, "Trans-splicing-mediated improvement in a severe mouse model of spinal muscular atrophy", J. Neurosci., vol. 30(1), pp. 126-130, 2010.

Combrink et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.

European Patent Office, Communication pursuant to Article 94(3) EPC, European Application No. 14877918.4, date of mailing Mar. 23, 2018.

Greene, Protective Groups in Organic Syntehsis, 1991, Wiley, New York, pp. v-xxi and 1-17.

H. Kubinyi, "3D QSAR in Drug Design—Theory Methods and Applications", pp. vii-ix and pp. 243-244, 1998.

Higuchi and V. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).

Hua et al., "Peripheral SMN restoration is essential for long-term rescue of a severe SMA mouse model", Nature, vol. 478(7367), pp. 123-126, 2012.

Jarecki et al., "Diverse small-molecule modulators of SMN expression found by high-throughput compound screening: early leads towards a therapeutic for spinal muscular atrophy", Human molecular genetics, 14(14):2003-2018, 2005.

Knight et al., "Isoform-specific phosphoinositide 3-kinase inhibitors from an arylmorpholine scaffold", *Bioorganic & Medicinal Chemistry*, vol. 12(17):4749-4759, 2004.

Kocar, Transformations of 3-aminopyridazines. Synthesis of 4-oxo-4H-pyrimido [1,2-b]pyridazine and 1-(substituted pyridazin-3-yl)-1H-1,2,3-triazole derivatives, Arkivoc, vol. 8, 2002, 143-156.

Lazarev et al., "Factors Affecting Aggregate Formation in Cell Models of Huntington's Disease and Amyotrophic Lateral Sclerosis", *Acta Naturae*, vol. 5(2):81-89, Apr. 2013.

Le et al., "SMND7, the major product of the centromeric survival motor neuron (SMN2) gene, extends survival in mice with spinal muscular atrophy and associates with full-length SMN", Human Molecular Genetics, vol. 14(5), pp. 845-857, 2005.

Liu et al., "A novel nuclear structure containing the survival of motor neurons protein", EMBO J. vol. 15(14), pp. 3555-3565 (1996).

MacDonald et al., "Quantification Assays for Total and Polyglutamine-Expanded Huntington Proteins", PLOS One, 2014, vol. 9(5), published May 9, 2014, pp. 1-17.

Makhortova et al., "A screen for regulators of survival of motor neuron proteins levels", Nature chemical biology, vol. 7(8):544-552, 2011.

Markus Riessland et al., "The benzamide M344, a novel histone deacetylase inhibitor, significantly increases SMN2 RNA/protein levels in spinal muscular atrophy cells", Hum Genet 120:101-110, May 26, 2006.

(56) References Cited

OTHER PUBLICATIONS

Naryshkin et al., "SMN2 splicing modifiers improve motor function and longevity in mice with spinal muscular atrophy", Science, vol. 345(6197):688-693, 2014 (including supplementary materials).
Palacino et al., "SMN2 splice modulators enhance U1-pre-mRNA association and rescue SMA mice", Nature: Chemical Biology, pp. 511-517 and 5 Supplemental pp. +S1-S20, vol. 11, Jun. 1, 2015.
Passini et al., "Antisense Oligonucleotides delivered to the mouse CNS ameliorate symptoms of severe spinal muscular atrophy", Sci Transl. Med., vol. 3(72), 2001.
Peng, Lijie et al., "Identification of pyrido[1,2-alpha]pyrimidine-4-ones as new molecules improving the transcriptional functions of estrogen-related receptor alpha", Journal of medicinal chemistry, vol. 54(21):7729-7733, 2011.
Potkin et al., "New directions in therapeutics for Huntington disease", Future Neurology, vol. 13(2):101-121, May 2018.
Pryor et al., "Huntingtin promotes mTORC1 signaling in the pathogenesis of Huntington's disease", Sci. Signal, dated Oct. 28, 2014, 2014, vol. 7, Issue 349, ra103, pp. 1-12.
PubChem/NCBI Database accession No. CID 377422 [online], 2005, retrieved on Jul. 4, 2016, URL http://pubchem.nci.nlm.nih.gov/compound/377422.
Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.
Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.
Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19(16):4857-4862, Aug. 15, 2009.
Yuo et al., 2008, "5-(N-ethyl-N-isopropyl)-amiloride enhances SMN2 exon 7 inclusion and protein expression in spinal muscular atrophy cells", Annals of neurology, vol. 63(1):26-34, 2008.
Wermuth, "The Practice of Medicinal Chemistry", 2nd ed., 2003, Chapters 9-10.
Pubchem, Substance Record for SID 249779947, Mar. 31, 2015, "4H-Quinolizin-4one1; Hydrobromide".
International Search Report for PCT/EP2012/065499, mailed Sep. 28, 2012.
Written Opinion of the International Searching Authority in PCT/EP2012/065499, mailed Sep. 28, 2012.
International Search Report for PCT/EP2014/059699, mailed Aug. 25, 2014.
Written Opinion of the International Searching Authority in PCT/EP2014/059699, mailed Aug. 25, 2014.
International Search Report for PCT/EP2015/051066, mailed Feb. 19, 2015.
Written Opinion of the International Searching Authority in PCT/EP2015/051066, mailed Feb. 19, 2015.
International Search Report for PCT/EP2015/060343, mailed Jul. 13, 2015.
Written Opinion of the International Searching Authority in PCT/EP2015/060343, mailed Jul. 13, 2015.
International Search Report for PCT/EP2016/060952, mailed Jun. 29, 2016.
Written Opinion of the International Searching Authority in PCT/EP2016/060952, mailed Jun. 29, 2016.
International Search Report for PCT/EP2016/076905, mailed Feb. 9, 2017.
Written Opinion of the International Searching Authority in PCT/EP2016/076905, Feb. 9, 2017.
Written Opinion of the International Searching Authority in PCT/EP2016/077190, mailed Mar. 1, 2017.
International Search Report for PCT/EP2016/077190, mailed Mar. 1, 2017.
International Search Report for PCT/EP2016/079816, mailed Jan. 19, 2017.
Written Opinion of the International Searching Authority in PCT/EP2016/079816, mailed Jan. 19, 2017.
International Search Report for PCT/US2013/025292, mailed Aug. 30, 2013.
Written Opinion of the International Searching Authority in PCT/US2013/025292, mailed Aug. 30, 2013.
International Search Report for PCT/US2016/066042, mailed Mar. 16, 2017.
Written Opinion of the International Searching Authority in PCT/US2016/066042, mailed Mar. 16, 2017.
International Search Report for PCT/US2018/035954, mailed Oct. 1, 2018.
Written Opinion of the International Searching Authority in PCT/US2018/035954, mailed Oct. 1, 2018.
International Search Report for PCT/US2018/039775, mailed Oct. 29, 2018.
Written Opinion of the International Searching Authority in PCT/US2018/039775, mailed Oct. 29, 2018.
International Search Report for PCT/US2018/039794, mailed Oct. 25, 2018.
Written Opinion of the International Searching Authority in PCT/US2018/039794, mailed Oct. 25, 2018.
International Search Report for PCT/US2019/024068, mailed Jul. 10, 2019.
Written Opinion of the International Searching Authority in PCT/US2019/024068, mailed Jul. 10, 2019.
International Search Report for PCT/US2019/024278, mailed May 28, 2019.
Written Opinion of the International Searching Authority in PCT/US2019/024278, mailed May 28, 2019.
Andreassi, C. et al. 2001. Human Molecular Genetics 10, 2841-2849. "Aclarubicin treatment restores SMN levels to cells derived from type I spinal muscular atrophy patients."
Artursson P., et al. 1991. Biochem Biophys Res Comm 175, 880-5. "Correlation between oral drug absorption in humans and apparent drug permeability coefficients in human intestinal epithelial (Caco-2) cells."
Baldo, B. et al. 2012. J. Biol. Chem. 287, 1406-1414. "A screen for enhancers of clearance identifies huntingtin as a heat shock protein 90 (Hsp90) client protein."
Barbaro, B.A. et al. 2015. Human Molecular Genetics 24, 913-925 (published online Oct. 9, 2014). "Comparative study of naturally occurring huntingtin fragments in *Drosophila* points to exon 1 as the most pathogenic species in Huntington's disease."
Bates, G.P. et al. 2015. Nature Reviews, Disease Primers 1, 15005 (published online Apr. 23, 2015). "Huntington disease."
Bengart, P. et al. 2004. Nucleic Acids Res. 32, W154-W159. "Riboswitch finder—a tool for indentification of riboswitch RNAs."
Bhattacharyya, A. et al. 2007 Drug Discovery Today 12, 553-560. "Mining the GEMS—a novel platform technology targeting post-transcriptional control mechanisms."
Bibillo, A and Eickbush, T.H. 2002. J. Biol. Chem. 277, 34836-34845. "High Processivity of the Reverse Transcriptase from a Non-long Terminal Repeat Retrotransposon."
Carroll, J.B. et al. 2015. Lancet Neurol 14, 1135-1142 (No. 11—Nov. 2015). "Treating the whole body in Huntington's disease."
Cartegni, L. et al. 2003. Nucleic Acids Res. 31, 3568-3571. "ESEfinder: a web resource to identify exonic splicing enhancers."
Crooks, G. E., et al. 2004. Genome Research 14, 1188-1190. "WebLogo: a sequence logo generator."
Daguenet et al. 2015. EMBO reports 16, 1640-1655 (published online Nov. 13, 2015). "The pathogenicity of splicing defects: mechanistic insights into pre-mRNA processing inform novel therapeutic approaches."
DiFiglia, et al 1997. Science 277, 1990-1993. "Aggregation of Huntingtin in Neuronal Intranuclear Inclusions and Dystrophic Neurites in Brain".
Dobin, A. et al. 2013. Bioinformatics 29, 15-21. "STAR: ultrafast universal RNA-seq aligner."

(56) References Cited

OTHER PUBLICATIONS

Evers, M.M. et al. 2015. Molecular Neurodegeneration 10, Article No. 21 (published online Apr. 28, 2015). "Making (anti-) sense out of huntingtin levels in Huntington disease."
Fardaei, M. et al. 2002. Human Molecular Genetics 11, 805-814. "Three proteins, MBNL, MBLL and MBXL, co-localize in vivo with nuclear foci of expanded-repeat transcripts in DM1 and DM2 cells."
Fernandez-Nogales, M. et al. 2014. Nature Medicine 20, 881-885. "Huntington's disease is a four-repeat tauopathy with tau nuclear rods."
Gipson, T. A. et al. 2013. RNA Biology 10, 1647-1652. "Aberrantly spliced HTT, a new player in Huntington's disease pathogenesis."
Gray, M. et al. 2008. J. Neurosci. 28, 6182-6195. "Full-length human mutant huntingtin with a stable polyglutamine repeat can elicit progressive and selective neuropathogenesis in BACHD mice."
Griffiths-Jones, S. et al. 2005. Nucleic Acids Res. 33, D121-D124. "Rfam: annotating non-coding RNAs in complete genomes."
Griffiths-Jones, S. et al. 2006. Nucleic Acids Res. 34, D140-D144. "miRBase: microRNA sequences, targets and gene nomenclature."
Grillo, G. et al. 2003. Nucleic Acids Res. 31, 3608-3612. "PatSearch: a program for the detection of patterns and structural motifs in nucleotide sequences."
Grimson, A. et al. 2007. Molecular Cell 27, 91-105. "MicroRNA Targeting Specificity in Mammals: Determinants beyond Seed Pairing."
Heemskerk, J. et al. 2002. Nature Neuroscience Supplement 5, 1027-1029. "From chemical to drug: neurodegeneration drug screening and the ethics of clinical trials."
Heemskerk, J, et al. 2002. Trends Neurosci. 25, 494-496. "Teaching old drugs new tricks."
Heemskerk, J. et al. 2005. Chapter 16—"Therapeutics Development for Hereditary Disorders" in ed. Waxman, S. From Neuroscience to Neurology: Neuroscience, Molecular Medicine, and the Therapeutic Transformation of Neurology, pp. 285-291.
Hernandez-Imas, E. et al. 2015. PLoS One 10, e141735 (published online Oct. 28, 2015). "Functional Analysis of Mutations in Exon 9 of NF1 Revales the Presence of Several Elements Regulating Splicing."
Hodges, A. et al. 2006. Human Molecular Genetics 15, 965-977. "Regional and cellular gene expression changes in human Huntington's disease brain."
Hua et al. 2007. PLoS Biol 5, e73. Enhancement of SMN2 Exon 7 "Inclusion by Antisense Oligonucleotides Targeting the Exon."
Hua et al. 2008. American J. of Human Genetics 82, 834-848. "Antisense Masking of an hnRNP A1/A2 Intronic Splicing Silencer Corrects SMN2 Splicing in Transgenic Mice."
The Huntington's Disease Collaborative Research Group, 1993, Cell, 72, pp. 971-983 (1993). "A novel gene containing a trinucleotide repeat that is expanded and unstable on Huntington's Disease chromosomes."
Janas, A. M. 2015. "A Stem Cell Model of the Motor Circuit Reveals Distinct Requirements for SMN in Motor Neuron Survival and Function."
Jacobs, G.H. et al. 2006. Nucleic Acids Res. 34, suppl_1, D37-D40. "Transterm—extended search facilities and improved integration with other databases."
Kanadia, R.N. et al. 2003. Science 302, 1978-1980. "A Muscleblind Knockout Model for Myotonic Dystrophy."
Kaplan, A. et al. 2012. Prog. Neurobiol. 99(3), 262-280. "Therapeutic approaches to preventing cell death in Huntington disease."
Kim, D. et al. 2013. Genome Biology 14, Article No. R36. "TopHat2: accurate alignment of transcriptomes in the presence of insertions, deletions and gene fusions."
Kordasiewicz, H.B. et al. 2012. Neuron, 74, 1031-1044. "Sustained Therapeutic Reversal of Huntington's Disease by Transient Repression of Huntingtin Synthesis".
Kuhn, A. et al. 2007. Human Molecular Genetics 16, 1845-1861. "Mutant huntingtin's effects on striatal gene expression in mice recapitulate changes observed in human Huntington's disease brain and do not differ with mutant huntingtin length or wild-type huntingtin dosage."
Labadorf, A.T. et al. 2015. Plos One 10(10): e0141298 (published online Oct. 23, 2015). "Evidence of Extensive Alternative Splicing in Post Mortem Human Brain HTT Transcription by mRNA Sequencing." (including supplemental information).
Labadorf, A. et al. 2015. PLoS One 10(12): e0143563 (published online Dec. 4, 2015). "RNA Sequence Analysis of Human Huntington Disease Brain Reveals an Extensive Increase in Inflammatory and Developmental Gene Expression."
Labbadia, J. et al. 2013. Trends Biochem. Sci. 38, 378-385. "Huntington's disease: underlying molecular mechanisms and emerging concepts."
Landles, C. et al. 2010. J. Bio. Chem. 285, 8808-8823. "Protoelysis of Mutant Huntington Produces an Exon 1 Fragment That Accumulates as an Aggregated Protein in Neuronal Nuclei in Huntington Disease."
Lei, et al. 2005. Nucleic Acids Res 33, 3897-3909. "Exonization of AluYa5 in the human ACE gene requires mutations in both 3' and 5' splice sites and is facilitated by a conserved splicing enhancer."
Liang, Y. et al. 2009. Brain Res. 2009 1286, 221-229. "ATF3 plays a protective role against toxicity by N-terminal fragment of mutant huntingtin in stable PC12 cell line."
Love, M. I. et al. 2014. Genome Biology 15, 550. "Moderated estimation of fold change and dispersion for RNA-seq data with DESeq2."
Lunkes, A. et al. 2002. Molecular Cell 10, 259-269. "Proteases Acting on Mutant Huntingtin Generate Cleaved Products that Differentially Build Up Cytoplasmic and Nuclear Inclusions."
Macke, T.J. 2001. Nucleic Acids Res. 29, 4724-4735. "RNAMotif, an RNA secondary structure definition and search algorithm."
Mahmood, I. et al. 1996. Xenobiotica 26, 887-895. "Interspecies scaling: predicting clearance of drugs in humans. Three different approaches."
Mahmood, I. 2006. Pharm. Sci. 95, 1810-1821. "Prediction of human drug clearance from animal data: Application of the rule of exponents and 'fu corrected intercept method' (FCIM)."
Mahmoudi, S et al. 2010. PLoS Biology 8(11), e10000521. "WRAP53 is Essential for Cajal Body and for Targeting the Survival of Motor Neuron Complex to Cajal Bodies."
Mangiarini, L. 1996. Cell 87, 493-506. "Exon 1 of the HD Gene with an Expanded CAG Repeat Is Sufficient to Cause a Progressive Neurological Phenotype in Transgenic Mice."
Mantione, K.J. et al. 2014. Med. Sci. Monit. Basic Res. 20, 138-141. "Comparing Bioinformation Gene Expression Profiling Methods: Microarray and RNA-Seq."
Mendoza, L.G. et al. 1999. BioTechniques 27, 778-788. "Hight-Throughput Microarray-Based Enzyme-Linked Immunosorbent Assay (ELISA)."
Mielcarek, M. et al. 2014. PLOS Genetics 10: 8 e1004550. "Dysfunction of the CNS-Heart Axis in Mouse Models of Huntington's Disease."
Mignone, F. et al. 2005. Nucleic Acids Res. 33, D141-D146. "UTRdb and UTRsite: a collection of sequences and regulatory motifs of the untranslated regions of eukaryotic mRNAs."
Mort, M. et al. 2015. J. of Huntington's Disease 4(2 of 4), 161-171. "Huntingtin Exists as Multiple Splice Forms in Human Brain."
Neuder, A. et al. 2014. BMC Medical Genomics 7:60. "A common gene expression signature in Huntington's disease patient brain regions."
Paganetti, P. et al. 2009. ChemBioChem 10, 1678-1688. "Development of Method for the High-Throughput Quantification of Cellular Proteins."
Pouladi, M. et al. 2013. Nature Review Neuroscience 14, 709-721. "Choosing an animal model for the study of Huntington's disease."
Ratovitski, T. et al. 2012. Cell Cycle 11, 2006-2021. "Huntingtin protein interactions altered by polyglutamine expansion as determined by quantitative proteomic analysis."
Reiner, A. et al. 2011. International Review of Neurobiology 98, 325-372. "Genetics and neuropathology of Huntington's disease."

(56) References Cited

OTHER PUBLICATIONS

Ruzo, A. et al. 2015. PLoS One 10, e0127678 (published online May 26, 2015). "Discovery of Novel Isoforms of Huntingtin Reveals a New Hominid-Specific Exon."
Sadeghian, H. et al. 2011. Arch. Neurol. 68, 650-652. "Huntington Chorea Presenting with Motor Neuron Disease."
Sathasivam, K. et al. 2013. Proc. Natl. Acad. Sci. 110, 2366-2370. "Aberrant splicing of HTT generates the pathogenic exon 1 protein in Huntington disease."
Schilling, G. et al. 2007. J Neuropathol. Exp. Neurol. 66, 313-320. "Characterization of Huntingtin Pathologic Fragments in Human Huntington Disease, Transgenic Mice, and Cell Models."
Schwab, C. et al. 2008. J. Neuropathol Exp Neurol 67, 1159-1165. "Colocalization of Transactivation-Responsive DNA-Binding Protein 43 and Huntingtin in Inclusions of Huntington Disease."
Shlyakhtenko, L.S. et al. 2007. Nanomedicine: Nanotech., Bio., and Med. 3, 192-197. "Single-molecule selection and recovery of structure-specific antibodies using atomic force microscopy."
Southwell, A.L. et al. 2013. Hum. Mol. Genet. 22, 18-34. "A fully humanized transgenic mouse model of Huntington disease."
Stanek, L.M. et al. 2014. Human Gene Therapy 25, 461-474. "Silencing Mutant Huntingtin by Adeno-Associated Virus-Mediated RNA Interference Ameliorates Disease Manifestations in the YAC128 Mouse Model of Huntington's Disease."
Stoilov, P. et al. 2008. Proc. Natl. Acad. Sci. 105, 11218-11223. "A high-throughput screening strategy identifies cardiotonic steroids as alternative splicing modulators."
Taylor et al. 1999. Nat. Biotechnol. 17, 1097-1100 "Induction of endogenous Bcl-xS through the control of Bcl-x pre-mRNA splicing by antisense oligonucleotides."
Van der Burg, J.M.M. et al. 2009. The Lancet (Neurology) 8, 765-774. "Beyond the brain: widespread pathology in Huntington's disease."
Varma, H. et al. 2008. Comb Chem High Throughput Screen 11, 238-248. "High Throughput Screening for Neurodegeneration and Complex Disease Phenotypes."
Vickers et al., 2006. J. Immunol. 176, 3652-3661 "Modification of MyD88 mRNA splicing and inhibition of IL-1beta signaling in cell culture and in mice with a 2'-O-methoxyethyl-modified oligonucleotide."
Wachter, A. 2014. Trends in Genetics 30, 172-181. "Gene regulation by structured mRNA elements."
Weiland, M. et al. 2012. Methods 56, 351-357. "Engineering of ribozyme-based riboswitches for mammalian cells."
Wild, E.J. et al. 2014. Movement Disorders 29, 1434-1445. "Targets for Future Clinical Trials in Huntington's Disease: What's in the Pipeline?"
Wilton et al. 1999. Neuromuscul. Disord. 9, 330-338. "Specific removal of the nonsense mutation from the mdx dystrophin mRNA using antisense oligonucleotides."
Xiong, H.Y. et al. 2015. Science 347, 1254806 (published online Dec. 18, 2014.) "The human splicing code reveals new insights into the genetic determinants of disease."
Yeo, G. et al. 2004. J. Comput. Biol. 11, 377-394. "Maximum entropy modeling of short sequence motifs with applications to RNA splicing signals."
Younis et al. 2010. Molecular and Cellular Biology 30, 1718-1728. "Rapid-Response Splicing Reporter Screens Identify Differential Regulators of Constitutive and Alternative Splicing."
Yu, S. et al. 2014. Trends in Pharmacological Sci. 35, 53-62. "Drugging unconventional targets: insights from Huntington's disease."
Zona, S. et al. 2014. Biochimica et Biophysica Acta 1839, 1316-1322. "FOXM1: An emerging master regulator of DNA damage response and genotoxic agent resistance."
Nair, A.B. et al. 2016. J. Basic and Clinical Pharmacy 7, 27-31. "A simple and practical guide for dose conversion between animals and human."
Neuder, A. et al. 2017. Scientific Reports 7, 1307 (published online May 2, 2017). "The pathogenic exon 1 HTT protein is produced by incomplete splicing in Huntington's disease patients."
Nopoulos, P. C. 2016. Dialogues Clin Neurosci 18, 91-98. "Huntington disease: a single-gene degenerative disorder of the striatum."
Ratni, H. et al. 2016. J. Med. Chem. 59, 6086-6100. "Specific Correction of Alternative Survival Motor Neuron 2 Splicing by Small Molecules: Discovery of a Potential Novel Medicine To Treat Spinal Muscular Atrophy."
Rüb, U. et al. 2016. Brain Pathol. 26, 726-740. "Huntington's disease (HD): the neuropathology of a multisystem neurodegenerative disorder of the human brain."
Saudou, F. et al. 2016. Neuron 89, 910-926. "The Biology of Huntingtin."
Wang, G. et al. 2016. Proc. Natl. Acad. Sci. 113, 3359-3364. "Ablation of huntingtin in adult neurons is nondeleterious but its depletion in young mice causes acute pancreatitis."
Woll, M.G. et al. 2016. J. Med. Chem. 59, 6070-6085. "Discovery and Optimization of Small Molecule Splicing Modifiers of Survival Motor Neuron 2 as a Treatment for Spinal Muscular Atrophy."
International Search Report for PCT/EP2015/063894, mailed Aug. 6, 2015.
Written Opinion of the International Searching Authority in PCT/EP2015/063894, mailed Aug. 6, 2015.
Nair et al., "Synthesis and fluorescence properties of 3-benzoxa- and thiazol-2-ylquinoline-5 or 7-maleimides," Indian Journal of Chemistry, Sep. 2004, vol. 43B, pp. 1944-1949.
Naik et al., "Studies in the Vilsmeier-Haack Reaction: Part XVI—Synthesis of 7-Amino-3-hetrarylquinoline Fluorophore & Derivatives," Indian Journal of Chemistry, Jun. 1977, pp. 506-508.
International Search Report for PCT/US19/38889, mailed Aug. 8, 2019.
Written Opinion of the International Searching Authority in PCT/US19/38889, mailed Aug. 8, 2019.
International Search Report for PCT/US19/38895, mailed Aug. 14, 2019.
Written Opinion of the International Searching Authority in PCT/US19/38895, mailed Aug. 14, 2019.
Written Opinion of the International Searching Authority in PCT/US19/38900, mailed Aug. 20, 2019.
International Search Report for PCT/US20/32446, mailed Jul. 7, 2020.
Written Opinion of the International Searching Authority in PCT/US20/32446, mailed Jul. 7, 2020.
International Search Report for PCT/US20/41300, mailed Oct. 16, 2020.
Written Opinion of the International Searching Authority in PCT/US20/41300, mailed Oct. 16, 2020.
Abdul Khader K K et al., "Regioselective synthesis of C-2 substituted imidazo[4,5-b]pyridines utilizing palladium catalysed C—N bond forming reactions with enolizable heterocycles", Tetrahedron Letters, Elsevier, Amsterdam, NL, vol. 55, No. 10, Feb. 1, 2014, p. 1778-1783.
Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, No. 23, Oct. 18, 2014, p. 6616-6624.
Ingo Knepper et al, "3-Acylindoles as versatile starting materials for pyridine ring annulation: synthesis of 1-deazapurine isosteres", Tetrahedron, vol. 67, No. 29, May 14, 2011, p. 5293-5303.
Chloé Copin et al, "S N Ar versus Buchwald-Hartwig Amination/Amidation in the Imidazo[2,1-b][1,3,4]thiadiazole Series : S N Ar versus Buchwald-Hartwig Amination/Amidation", European Journal of Organic Chemistry, vol. 2015, No. 31, Sep. 29, 2015, p. 6932-6942.
Patel Harun M et al, "2,5,6-Trisubstituted imidazo[2,1-b][1,3,4]thiadiazoles: Search for antihyperlipidemic agents", European Journal of Medicinal Chemistry, Editions Scientifique Elsevier, Paris, FR, vol. 65, Apr. 18, 2013, p. 119-133.
Mazzone G et al, "Sintesi e valutazione biologica preliminare di imidazo[2,1-b]-1,3-4-tiadiazoli-2,6-diarilsostituti", Farmaco, Edizione Scientifica, Societa Chimica Italiana, Pavia, IT, vol. 39, No. 7, Jan. 1, 1984, p. 585-598. English abstract only.

(56) References Cited

OTHER PUBLICATIONS

Fascio Mirta L et al, "Synthesis and antiviral activity of some imidazo[1,2-b][1,3,4]thiadiazole carbohydrate derivatives", Carbohydrate Research, vol. 480, May 21, 2019, p. 61-66.
Database Registry [Online], Chemical Abstracts Service, Columbus, Ohio, US; Feb. 22, 2018, Database accession No. 2178867-25-7.
Database Registry [Online], Chemical Abstracts Service, Columbus, Ohio, US; Sep. 25, 2017, Database accession No. 2130694-60-7.
Database Registry [Online], Chemical Abstracts Service, Columbus, Ohio, US; Sep. 24, 2017, Database accession No. 2130300-22-8.
Database Registry [Online], Chemical Abstracts Service, Columbus, Ohio, US; Sep. 18, 2017, Database accession No. 2128311-64-6.
Chemical Abstracts Registry No. 2107242-04-04, indexed in the Registry file on STN CAS Online Aug. 2, 2017. (Year: 2017).
USPTO, Office Action dated Feb. 4, 2021 in U.S. Appl. No. 16/617,450; see whole document in general and compounds on pp. 10-14 and 15-18 in particular.
Daldin et al., "Polyglutamine expansion affects huntingtin conformation in multiple Huntington's disease models", Scientific Reports, vol. 7, 15 pages, 2017.
Gleave et al., "Synthesis and evaluation of 3-amino-6-arylpyridazines as selective CB2 agonists for the treatment of inflammatory pain", Bioorganic & Medicinal Chemistry Letters, vol. 20, pp. 465-468, 2010.
Kaida et al., "U1 snRNP protects pre-mRNAs from premature cleavage and polyadenylation"; Nature, vol. 468, pp. 664-669; Dec. 2, 2010.
Ross & Tabrizi, "Huntington's disease: from molecular pathogenesis to clinical treatment"; The Lancet Neurology, vol. 10, pp. 83-98, Jan. 2011.
Wang et al., "Mechanism of alternative splicing and its regulation (Review)", Biomedical Reports, vol. 3, pp. 152-158, 2015.
Berg, J.M., Tymoczko, J.L., & Stryer, L., *Biochemistry* (5th ed.), p. 798, 2002.
Opposition in European Patent No. 3,386,511, Feb. 25, 2022, 29 pages.
Bhattacharyya et al., Small molecule splicing modifiers with systemic HTT-lowering activity Nature Communications 12(7299), 2021.
Boudreau et al., 2009. "Nonallele-Specific Silencing of Mutant and Wild-Type Huntingtin Demonstrates Therapeutic Efficacy in Huntington's Disease Mice." Molecular Therapy: The Journal of the American Society of Gene Therapy 17 (6): 1053-63.
Campagne et al., 2019. "Structural Basis of a Small Molecule Targeting RNA for a Specific Splicing Correction." Nature Chemical Biology 15 (12): 1191-98, 2019.
Connelly et al., 2016. "The Emerging Role of RNA as a Therapeutic Target for Small Molecules." Cell Chemical Biology 23 (9): 1077-90.
Effenberger et al., 2016. "Modulating Splicing with Small Molecular Inhibitors of the Spliceosome." Wiley Interdisciplinary Reviews. RNA 8 (2).
Marxreiter et al., 2020. "Huntington Lowering Strategies." International Journal of Molecular Sciences 21 (6).
Mount et al., A catalogue of splice junction sequences Nucleic Acids Research 10(2):459-472 (Jan. 22, 1982).
Nishigaki et al., Syntheses of 9-Deazatheophyllines and 6-Deoxy-9-deazatheophyllines Chemical and Pharmaceutical Bulletin 28(5):1636-1641 (1980).
Ratni et al., Discovery of Risdiplam, a Selective Survival of Motor Neuron-2 (SMN2) Gene Splicing Modifier . . . , Journal of Medicinal Chemistry, 61(15), 6501-6517 (2018).
Ritz et al., Dose-Response Analysis Using R PLos ONE 10(12) (Dec. 30, 2015).
Romo et al., 2018. "A Fresh Look at Huntington mRNA Processing in Huntington"s Disease." Journal of Huntington"s Disease 7 (2): 101-8.
Schilling Judith, Meike Broemer, Ilian Atanassov, Yvonne Duernberger, Ina Vorberg, Christoph Dieterich, Alina Dagane, et al. 2019. "Deregulated Splicing Is a Major Mechanism of RNA-Induced Toxicity in Huntington"s Disease." Journal of Molecular Biology 431 (9): 1869-77.
Sibley et al., 2016. "Lessons from Non-Canonical Splicing." Nature Reviews. Genetics 17 (7): 407-21.
Sivaramakrishnan et al., Binding to SMN2 pre-mRNA-protein complex elicits specificity for small molecule splicing modifiers Nature Communications 8(1) (Nov. 2017).
Southwell et al. 2018. "Huntingtin Suppression Restores Cognitive Function in a Mouse Model of Huntington"s Disease." Science Translational Medicine (10) 1-12.
Southwell et al. 2017. "A Novel Humanized Mouse Model of Huntington Disease for Preclinical Development of Therapeutics Targeting Mutant Huntingtin Alleles." Human Molecular Genetics 26 (6): 1115-32.
Tabrizi et al., Huntington Lowering Strategies for Disease Modification in Huntington's Disease J. Neuron 101(5):801-819 (Mar. 6, 2019).
Wild et al., 2017. "Therapies Targeting DNA and RNA in Huntington"s Disease." Lancet Neurology 16 (10): 837-47.
International Search Report in PCT/US2021/059010, dated Apr. 26, 2022.
Written Opinion of the International Searching Authority in PCT/US2021/059010, dated Apr. 26, 2022.
Reply to Opposition in European Patent No. 3,386,511, Jul. 7, 2022, 427 pages.
EPO Board Communication in Opposition in European Patent No. 3,386,511, Oct. 18, 2022, 12 pages.
International Search Report in PCT/US2021/026316, dated Aug. 5, 2021.
Written Opinion of the International Searching Authority in PCT/US2021/026316, dated Aug. 5, 2021.
Burli et al., "Design, Synthesis, and Biological Evaluation of Potent and Selective Class IIa Histone Deacetylase (HDAC) Inhibitors as a Potential Therapy for Huntington's Disease", Journal of Medicinal Chemistry, vol. 56, pp. 9934-9954, 2013.
Chemical Abstracts Registry No. 1381103-87-2, indexed in the Registry file on STN CAS Online Jul. 4, 2012. (Year: 2012).
Chemical Abstracts Registry No. 1381109-95-0, indexed in the Registry file on STN CAS Online Jul. 4, 2012. (Year: 2012).
Chemical Abstracts Registry No. 1381103-06-5, indexed in the Registry file on STN CAS Online Jul. 4, 2012. (Year: 2012).
Chemical Abstracts Registry No. 1381085-12-6, indexed in the Registry file on STN CAS Online Jul. 4, 2012. (Year: 2012).
Chemical Abstracts Registry No. 1381084-38-3, indexed in the Registry file on STN CAS Online Jul. 4, 2012. (Year: 2012).
Chemical Abstracts Registry No. 1381084-19-0, indexed in the Registry file on STN CAS Online Jul. 4, 2012. (Year: 2012).
Chemical Abstracts Registry No. 1381069-02-8, indexed in the Registry file on STN CAS Online Jul. 4, 2012. (Year: 2012).
Chemical Abstracts Registry No. 1381060-23-6, indexed in the Registry file on STN CAS Online Jul. 4, 2012. (Year: 2012).
Chemical Abstracts Registry No. 1381036-73-2, indexed in the Registry file on STN CAS Online Jul. 4, 2012. (Year: 2012).
Chemical Abstracts Registry No. 1381033-11-9, indexed in the Registry file on STN CAS Online Jul. 4, 2012. (Year: 2012).
Chemical Abstracts Registry No. 1381016-89-2, indexed in the Registry file on STN CAS Online Jul. 4, 2012. (Year: 2012).
Chemical Abstracts Registry No. 1381016-41-6, indexed in the Registry file on STN CAS Online Jul. 4, 2012. (Year: 2012).
Chemical Abstracts Registry No. 1381013-97-3, indexed in the Registry file on STN CAS Online Jul. 4, 2012. (Year: 2012).
Chemical Abstracts Registry No. 1380991-96-7, indexed in the Registry file on STN CAS Online Jul. 4, 2012. (Year: 2012).
Chemical Abstracts Registry No. 1380991-09-2, indexed in the Registry file on STN CAS Online Jul. 4, 2012. (Year: 2012).
Chemical Abstracts Registry No. 1380955-66-7, indexed in the Registry file on STN CAS Online Jul. 4, 2012. (Year: 2012).

(56) References Cited

OTHER PUBLICATIONS

Chemical Abstracts Registry No. 1380889-28-0, indexed in the Registry file on STN CAS Online Jul. 3, 2012. (Year: 2012).
Chemical Abstracts Registry No. 1380857-75-9, indexed in the Registry file on STN CAS Online Jul. 3, 2012. (Year: 2012).
Chemical Abstracts Registry No. 1350420-68-6, indexed in the Registry file on STN CAS Online Dec. 7, 2011. (Year: 2011).
Chemical Abstracts Registry No. 1350191-80-8, indexed in the Registry file on STN CAS Online Dec. 7, 2011. (Year: 2011).
Chemical Abstracts Registry No. 919610-78-9, indexed in the Registry file on STN CAS Online Feb. 6, 2007. (Year: 2007).
Chemical Abstracts Registry No. 919610-77-8, indexed in the Registry file on STN CAS Online Feb. 6, 2007. (Year: 2007).
Chemical Abstracts Registry No. 919610-71-2, indexed in the Registry file on STN CAS Online Feb. 6, 2007. (Year: 2007).
Chemical Abstracts Registry No. 919610-70-1, indexed in the Registry file on STN CAS Online Feb. 6, 2007. (Year: 2007).
Chemical Abstracts Registry No. 919610-69-8, indexed in the Registry file on STN CAS Online Feb. 6, 2007. (Year: 2007).
Chemical Abstracts Registry No. 919494-40-9, indexed in the Registry file on STN CAS Online Feb. 6, 2007. (Year: 2007).
Chemical Abstracts Registry No. 919494-38-5, indexed in the Registry file on STN CAS Online Feb. 6, 2007. (Year: 2007).
Chemical Abstracts Registry No. 919494-22-7, indexed in the Registry file on STN CAS Online Feb. 6, 2007. (Year: 2007).
Chemical Abstracts Registry No. 1348577-48-9, indexed in the Registry file on STN CAS Online Dec. 4, 2011. (Year: 2011).
Chemical Abstracts Registry No. 1380990-95-3, indexed in the Registry file on STN CAS Online Jul. 4, 2012. (Year: 2012).
Chemical Abstracts Registry No. 1380944-26-2, indexed in the Registry file on STN CAS Online Jul. 4, 2012. (Year: 2012).
Chemical Abstracts Registry No. 1380879-49-1, indexed in the Registry file on STN CAS Online Jul. 3, 2012. (Year: 2012).
Chemical Abstracts Registry No. 1380858-18-3, indexed in the Registry file on STN CAS Online Jul. 3, 2012. (Year: 2012).
Chemical Abstracts Registry No. 1381109-36-9, indexed in the Registry file on STN CAS Online Jul. 4, 2012. (Year: 2012).
Chemical Abstracts Registry No. 1381106-70-2, indexed in the Registry file on STN CAS Online Jul. 4, 2012. (Year: 2012).
Chemical Abstracts Registry No. 1380864-49-2, indexed in the Registry file on STN CAS Online Jul. 3, 2012. (Year: 2012).
Chemical Abstracts Registry No. 1380859-62-0, indexed in the Registry file on STN CAS Online Jul. 3, 2012. (Year: 2012).
Chemical Abstracts Registry No. 1381035-24-0, indexed in the Registry file on STN CAS Online Jul. 4, 2012. (Year: 2012).
Chemical Abstracts Registry No. 2059673-20-8, indexed in the Registry file on STN CAS Online Jan. 26, 2017. (Year: 2017).
Chemical Abstracts Registry No. 2224380-48-5, indexed in the Registry file on STN CAS Online May 20, 2018.
Chemical Abstracts Registry No. 2055492-51-6, indexed in the Registry file on STN CAS Online Jan. 5, 2017.
Chemical Abstracts Registry No. 1608159-30-3, indexed in the Registry file on STN CAS Online May 22, 2014.
Chemical Abstracts Registry No. 1349790-59-5, indexed in the Registry file on STN CAS Online Dec. 6, 2011.
Chemical Abstracts Registry No. 1349075-20-2, indexed in the Registry file on STN CAS Online Dec. 5, 2011.
Chemical Abstracts Registry No. 1348522-09-7, indexed in the Registry file on STN CAS Online Dec. 4, 2011.
Chemical Abstracts Registry No. 1348048-78-1, indexed in the Registry file on STN CAS Online Dec. 4, 2011.
Chemical Abstracts Registry No. 1347905-79-6, indexed in the Registry file on STN CAS Online Dec. 4, 2011.
Chemical Abstracts Registry No. 1347641-28-4, indexed in the Registry file on STN CAS Online Dec. 2, 2011.
Chemical Abstracts Registry No. 1347614-67-8, indexed in the Registry file on STN CAS Online Dec. 2, 2011.
Chemical Abstracts Registry No. 1347467-65-5, indexed in the Registry file on STN CAS Online Dec. 2, 2011.
Chemical Abstracts Registry No. 2213453-82-6, indexed in the Registry file on STN CAS Online Apr. 16, 2018.
Chemical Abstracts Registry No. 2170880-44-9, indexed in the Registry file on STN CAS Online Jan. 24, 2018.
Chemical Abstracts Registry No. 2170880-30-3, indexed in the Registry file on STN CAS Online Jan. 24, 2018.
Chemical Abstracts Registry No. 2170880-29-0, indexed in the Registry file on STN CAS Online Jan. 24, 2018.
Chemical Abstracts Registry No. 2170876-00-1, indexed in the Registry file on STN CAS Online Jan. 24, 2018.
Chemical Abstracts Registry No. 2170875-99-5, indexed in the Registry file on STN CAS Online Jan. 24, 2018.
Chemical Abstracts Registry No. 2138484-61-2, indexed in the Registry file on STN CAS Online Nov. 3, 2017.
Chemical Abstracts Registry No. 2117679-02-2, indexed in the Registry file on STN CAS Online Aug. 21, 2017.
Chemical Abstracts Registry No. 2098833-57-7, indexed in the Registry file on STN CAS Online Jun. 21, 2017.
Chemical Abstracts Registry No. 2096985-34-9, indexed in the Registry file on STN CAS Online May 23, 2017.
Chemical Abstracts Registry No. 1957192-78-7, indexed in the Registry file on STN CAS Online Jul. 21, 2016.
Chemical Abstracts Registry No. 1579964-39-8, indexed in the Registry file on STN CAS Online Apr. 3, 2014.
Chemical Abstracts Registry No. 1381102-22-2, indexed in the Registry file on STN CAS Online Jul. 4, 2012.
Chemical Abstracts Registry No. 1381055-52-2, indexed in the Registry file on STN CAS Online Jul. 4, 2012.
Chemical Abstracts Registry No. 1380859-69-7, indexed in the Registry file on STN CAS Online Jul. 4, 2012.
Chemical Abstracts Registry No. 1283718-58-0, indexed in the Registry file on STN CAS Online Apr. 21, 2011.
Chemical Abstracts Registry No. 919610-72-3, indexed in the Registry file on STN CAS Online Feb. 6, 2007.
Chemical Abstracts Registry No. 919496-89-2, indexed in the Registry file on STN CAS Online Feb. 6, 2007.
Chemical Abstracts Registry No. 919494-45-4, indexed in the Registry file on STN CAS Online Feb. 6, 2007.
Chemical Abstracts Registry No. 919494-44-3, indexed in the Registry file on STN CAS Online Feb. 6, 2007.
Chemical Abstracts Registry No. 919494-39-6, indexed in the Registry file on STN CAS Online Feb. 6, 2007.
Chemical Abstracts Registry No. 919494-26-1, indexed in the Registry file on STN CAS Online Feb. 6, 2007.
Chemical Abstracts Registry No. 919494-23-8, indexed in the Registry file on STN CAS Online Feb. 6, 2007.
Chemical Abstracts Registry No. 919494-19-2, indexed in the Registry file on STN CAS Online Feb. 6, 2007.
Chemical Abstracts Registry No. 919493-72-4, indexed in the Registry file on STN CAS Online Feb. 6, 2007.
Chemical Abstracts Registry No. 919493-71-3, indexed in the Registry file on STN CAS Online Feb. 6, 2007.
Chemical Abstracts Registry No. 848953-00-4, indexed in the Registry file on STN CAS Online Apr. 21, 2005.
Chemical Abstracts Registry No. 848952-99-8, indexed in the Registry file on STN CAS Online Apr. 21, 2005.
Chemical Abstracts Registry No. 120821-79-6, indexed in the Registry file on STN CAS Online May 26, 1989.
Chemical Abstracts Registry No. 1369171-97-0, indexed in the Registry file on STN CAS Online Apr. 16, 2012.
Chemical Abstracts Registry No. 1330263-81-4, indexed in the Registry file on STN CAS Online Sep. 9, 2011.
Alessandro Stella et. al., A short and straightforward approach towards 6-amino and 6-aminoalkyl thiazolo[4,5-c]pyridazines, Tetrahedron Letters, 54(8) (2013) pp. 830-833.
Thuraya Al-Harthy et al., "Design, synthesis and antimicrobial evaluation of novel 2-arylbenzothiazole analogs bearing fluorine and piperazine moieties," Monatshefte fur Chemie (2018) 149(3) pp. 645-651.
Hye Ri Park et al., "Oxazolopyridines and thiazolopyridines as monoamine oxidase B inhibitors for the treatment of Parkinson's disease," Bioorganic & Medicinal Chemistry, 21(17) (2013) pp. 5480-5487.

(56) References Cited

OTHER PUBLICATIONS

Chemical Abstracts Registry No. 1368225-46-0, indexed in the Registry file on STN CAS Online Apr. 15, 2012.
Chemical Abstracts Registry No. 1330013-08-5, indexed in the Registry file on STN CAS Online Sep. 8, 2011.
Chemical Abstracts Registry No. 1329755-78-3, indexed in the Registry file on STN CAS Online Sep. 8, 2011.
Chemical Abstracts Registry No. 1329572-44-2, indexed in the Registry file on STN CAS Online Sep. 7, 2011.
Chemical Abstracts Registry No. 1329511-91-2, indexed in the Registry file on STN CAS Online Sep. 7, 2011.
Chemical Abstracts Registry No. 1327110-38-2, indexed in the Registry file on STN CAS Online Sep. 2, 2011.
Chemical Abstracts Registry No. 1310217-40-3, indexed in the Registry file on STN CAS Online Jun. 23, 2011.
Chemical Abstracts Registry No. 1310089-22-5, indexed in the Registry file on STN CAS Online Jun. 23, 2011.
Chemical Abstracts Registry No. 1267789-60-5, indexed in the Registry file on STN CAS Online Mar. 10, 2011.
Chemical Abstracts Registry No. 1267620-08-5, indexed in the Registry file on STN CAS Online Mar. 9, 2011.
Chemical Abstracts Registry No. 1267544-92-2, indexed in the Registry file on STN CAS Online Mar. 9, 2011.
Chemical Abstracts Registry No. 1267173-86-3, indexed in the Registry file on STN CAS Online Mar. 9, 2011.
Chemical Abstracts Registry No. 1267173-76-1, indexed in the Registry file on STN CAS Online Mar. 9, 2011.
Chemical Abstracts Registry No. 1266786-33-7, indexed in the Registry file on STN CAS Online Mar. 8, 2011.
"Chemical Encyclopedia", scientific publishing house "Great Russian Encyclopedia," Moskva, vol. 4, pp. 499-501, 1995.
V.V. Boltromeyuk, "General Chemistry", Minsk, Graduate School, Grodno State Medical University, Department of General and Bioorganic Chemistry, p. 65, 2012 (textbook).
Chemical Abstracts Registry No. 1202076-20-7, indexed in the Registry file on STN CAS Online Jan. 13, 2010.
Chemical Abstracts Registry No. 1202076-21-8, indexed in the Registry file on STN CAS Online Jan. 13, 2010.
Chemical Abstracts Registry No. 1202076-22-9, indexed in the Registry file on STN CAS Online Jan. 13, 2010.
Chemical Abstracts Registry No. 889062-91-3, indexed in the Registry file on STN CAS Online Jun. 23, 2006.
Chemical Abstracts Registry No. 667457-86-5, indexed in the Registry file on STN CAS Online Mar. 25, 2004.
Chemical Abstracts Registry No. 1691540-69-8, indexed in the Registry file on STN CAS Online Apr. 26, 2015.
Chemical Abstracts Registry No. 1691540-67-6, indexed in the Registry file on STN CAS Online Apr. 26, 2015.
Chemical Abstracts Registry No. 1691538-20-1, indexed in the Registry file on STN CAS Online Apr. 26, 2015.
Chemical Abstracts Registry No. 1691538-17-6, indexed in the Registry file on STN CAS Online Apr. 26, 2015.
International Search Report in PCT/US2022/038870, dated Nov. 9, 2022.
Written Opinion of the International Searching Authority in PCT/US2022/038870, dated Nov. 9, 2022.
Glenn Noronha, et al. Discovery of [7-(2,6-Dichlorophenyl)-5-methylbenzo[1,2,4]triazin-3-yl]-[4-(2-pyrrolidin-1-ylethoxy)phenyl]amine—A Potent, Orally Active Src Kinase Inhibitor with Antitumor Activity in Preclinical Assays. Bioorg. Med. Chem. Lett., vol. 17, No. 3, pp. 602-608, 2007.
Sara D. Reis et al., "Modulation of Molecular Chaperones in Huntington's Disease and Other Polyglutamine Disorders," Molecular Neurobiology, vol. 54, pp. 5829-5854, (2016) (Sep. 22, 2016).
Hideshi Nakamura et al., Synthesis and Chemiluminescence of 5-[(2-Pyridyl)-, (2-Pyrazinyl)-, and (Substituted 2-pyrazinyl)amino]-1,2,4-trioxanes, The Chemical Society of Japan, vol. 61, No. 10, (1988) pp. 3776-3778.
Written Opinion of the International Searching Authority in PCT/US2021/059139, mailed Mar. 14, 2022.
International Search Report for PCT/US2021/059139, mailed Mar. 14, 2022.
Hughes, A.C. et al. 2014. J. Mol. Biol. 426, 1428-1438. "Identification of Novel Alternative Splicing Events in the Huntingtin Gene and Assessment of the Functional Consequences Using Structural Protein Homology Modelling."
Yen, L. et al. 2004. Nature 431, 471-6. "Exogenous control of mammalian gene expression through modulation of RNA self-cleavage."
International Search Report for PCT/US19/38900, mailed Aug. 20, 2019.
Holste et al., 2008. "Strategies for Identifying RNA Splicing Regulatory Motifs and Predicting Alternative Splicing Events." PLoS Computational Biology 4 (1): e21.
Stephen M. Berge, et al., "Pharmaceutical Salts," Journal of Pharmaceutical Sciences, vol. 66, No. 1, pp. 1-19 (1977).
Chemical Abstracts Registry No. 1207531-45-0, indexed in the Registry file on STN CAS Online Mar. 1, 2010.
"Drug Structure-Activity Relationship", edited by Li Renli, China Medical Science and Technology Press, 1st edition, Jan. 2004, 1st printing, pp. 182-183).
Written Opinion of the International Searching Authority in PCT/US23/68335, mailed Dec. 20, 2023.
International Search Report for PCT/US23/68335, mailed Dec. 20, 2023.

* cited by examiner

COMPOUNDS FOR TREATING HUNTINGTON'S DISEASE

CROSS-REFERENCE TO RELATED APPLICATIONS

This application is a continuation of U.S. patent application Ser. No. 16/617,450, filed Nov. 26, 2019, which in turn is a U.S. National Stage filing under 35 U.S.C. § 371 of International Application No. PCT/US2018/035954, filed Jun. 5, 2018, which in turn claims priority to U.S. Provisional Application No. 62/514,999, filed Jun. 5, 2017, the entire contents of which are incorporated by reference herein.

An aspect of the present description relates to compounds, forms, and pharmaceutical compositions thereof and methods of using such compounds, forms, or compositions thereof useful for treating or ameliorating Huntington's disease. In particular, another aspect of the present description relates to substituted bicyclic heteroaryl compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100,000 in populations of western European descent. In North America, an estimated 30,000 people have HD, while an additional 200,000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

An aspect of the present description includes compounds comprising, a compound of Formula (I):

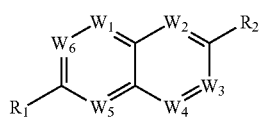

or a form thereof, wherein $R_1$, $R_2$, $W_1$, $W_2$, $W_3$, $W_4$, $W_5$ and $W_6$ are as defined herein.

An aspect of the present description includes a method for treating or ameliorating HD in a subject in need thereof comprising, administering to the subject an effective amount of a compound of Formula (I) or a form thereof.

An aspect of the present description includes a method for use of a compound of Formula (I) or a form or composition thereof for treating or ameliorating HD in a subject in need thereof comprising, administering to the subject an effective amount of the compound of Formula (I) or a form or composition thereof.

An aspect of the present description includes a use for a compound of Formula (I) or a form thereof for treating or ameliorating HD in a subject in need thereof comprising, administering to the subject an effective amount of the compound of Formula (I) or a form thereof.

An aspect of the present description includes a use for a compound of Formula (I) or a form thereof in the manufacture of a medicament for treating or ameliorating HD in a subject in need thereof comprising, administering to the subject an effective amount of the medicament.

An aspect of the present description includes a use for a compound of Formula (I) or a form thereof in a combination product with one or more therapeutic agents for treating or ameliorating HD in a subject in need thereof comprising, administering to the subject an effective amount of the compound of Formula (I) or a form thereof in combination with an effective amount of the one or more agents.

DETAILED DESCRIPTION

An aspect of the present description relates to compounds comprising, a compound of Formula (I):

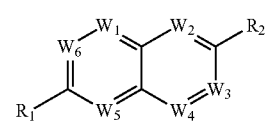

or a form thereof, wherein:

$W_1$, $W_2$, $W_3$, $W_4$, $W_5$ and $W_6$ are independently C—$R_a$, C—$R_b$ or N, wherein, when one, two or three of $W_1$, $W_5$ and $W_6$ are N, then $W_2$, $W_3$ and $W_4$ are C—$R_a$ or C—$R_b$, and wherein, when one, two or three of $W_2$, $W_3$ and $W_4$ are N, then $W_1$, $W_5$ and $W_6$ are C—$R_a$ or C—$R_b$; $R_1$ is aryl, heterocyclyl, heterocyclyl-amino, (heterocyclyl)($C_{1-8}$alkyl)amino or heteroaryl, wherein, each instance of heterocyclyl is optionally substituted with one, two or three $R_3$ substituents and optionally, with one additional $R_4$ substituent, or, wherein, alternatively, each instance of heterocyclyl is optionally substituted with one, two, three or four $R_3$ substituents;

$R_2$ is aryl, heteroaryl, heteroaryl-amino or (heteroaryl)($C_{1-8}$alkyl)amino, wherein, each instance of aryl and heteroaryl is optionally substituted with one, two or three $R_6$ substituents and optionally, with one additional $R_7$ substituent;

$R_a$ is, in each instance, independently selected from hydrogen, halogen or $C_{1-8}$alkyl;

$R_b$ is, in each instance, independently selected from hydrogen, halogen or $C_{1-8}$alkyl;

$R_3$ is, in each instance, independently selected from cyano, halogen, hydroxy, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$ alkoxy-carbonyl, amino, $C_{1-8}$alkyl-amino, ($C_{1-8}$ alkyl)$_2$-amino, amino-$C_{1-8}$alkyl, $C_{1-8}$alkyl-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl)$_2$-amino-$C_{1-8}$alkyl-amino, [($C_{1-8}$alkyl)$_2$-amino-$C_{1-8}$alkyl]$_2$-amino, ($C_{1-8}$alkyl-amino-$C_{1-8}$alkyl)($C_{1-8}$alkyl)amino, [($C_{1-8}$alkyl)$_2$-amino-$C_{1-8}$alkyl]$C_{1-8}$alkyl)amino, $C_{1-8}$alkoxy-$C_{1-8}$alkyl-amino, ($C_{1-8}$alkoxy-$C_{1-8}$ alkyl)$_2$-amino, ($C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$Cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl, heterocyclyl-$C_{1-8}$alkyl, heteroaryl or heteroaryl-$C_{1-8}$alkyl; wherein, each instance of $C_{3-14}$cycloalkyl, aryl, heterocyclyl and heteroaryl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, cyano-$C_{1-8}$alkyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, $C_{1-8}$alkoxy-$C_{1-8}$alkoxy, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl, $C_{1-8}$ alkyl)amino or $C_{1-8}$alkyl-thio; and, $R_7$ is $C_{3-14}$cycloalkyl, $C_{3-14}$cycloalkyl-oxy, aryl, heterocyclyl, heteroaryl or heteroaryl-$C_{1-8}$alkoxy;

wherein a form of the compound is selected from the group consisting of a prodrug, salt, hydrate, solvate, clathrate, isotopologue, racemate, enantiomer, diastereomer, stereoisomer, polymorph and tautomer form thereof.

ASPECTS OF THE DESCRIPTION

Another aspect of the present description includes a compound of Formula (I) comprising, a compound of Formula (I.1):

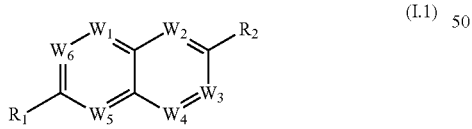

(I.1)

or a form thereof, wherein:

$W_1$, $W_2$, $W_3$, $W_4$, $W_5$ and $W_6$ are independently $C$—$R_a$, $C$—$R_b$ or N, wherein, when one, two or three of $W_1$, $W_5$ and $W_6$ are N, then $W_2$, $W_3$ and $W_4$ are $C$—$R_a$ or $C$—$R_b$, and wherein, when one, two or three of $W_2$, $W_3$ and $W_4$ are N, then $W_1$, $W_5$ and $W_6$ are $C$—$R_a$ or $C$—$R_b$;

$R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$ alkyl)$_2$-amino, ($C_{1-8}$ alkoxy-$C_{1-8}$alkyl)($C_{1-8}$alkyl)amino, amino-$C_{1-8}$ alkyl, $C_{1-8}$alkyl-amino-$C_{1-8}$alkyl, ($C_{1-8}$alkoxy-$C_{1-8}$alkyl)$_2$-amino-$C_{1-8}$alkyl, $C_{1-8}$ alkoxy-$C_{1-8}$ alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$ alkyl-amino-$C_{1-8}$alkyl) ($C_{1-8}$ alkyl)amino, ($C_{1-8}$ alkyl)$_2$-amino-$C_{1-8}$alkyl-amino, [($C_{1-8}$alkyl)$_2$-amino-$C_{1-8}$alkyl]$C_{1-8}$alkyl) amino, amino-$C_{1-8}$ alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$ alkyl-amino, (hydroxy-$C_{1-8}$alkyl-amino-$C_{1-8}$alkyl)$_2$-amino, (hydroxy-$C_{1-8}$alkyl)amino-$C_{1-8}$ alkyl-amino, (hydroxy-$C_{1-8}$alkyl-amino-$C_{1-8}$alkyl)($C_{1-8}$alkyl) amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$ alkyl)amino, [(hydroxy-$C_{1-8}$alkyl)($C_{1-8}$alkyl) amino-$C_{1-8}$alkyl]($C_{1-8}$alkyl)amino, $C_{3-14}$cycloalkyl, aryl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$ alkyl, (aryl-$C_{1-8}$alkyl)$_2$-amino-$C_{1-8}$ alkyl, (aryl-$C_{1-8}$alkyl)($C_{1-8}$alkyl)amino-$C_{1-8}$alkyl, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$ alkyl)$_2$-amino, (heterocyclyl-$C_{1-8}$alkyl)($C_{1-8}$ alkyl)amino, heterocyclyl-$C_{1-8}$alkyl-amino-$C_{1-8}$alkyl, (heterocyclyl-$C_{1-8}$alkyl)$_2$-amino-$C_{1-8}$ alkyl, (heterocyclyl-$C_{1-8}$ alkyl)($C_{1-8}$ heterocyclyl-oxy, heterocyclyl-carbonyl, heterocyclyl-carbonyl-oxy, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$ alkyl)($C_{1-8}$alkyl)amino-$C_{1-8}$ alkyl, wherein, each instance of $C_{3-14}$cycloalkyl, aryl, heterocyclyl and heteroaryl is optionally substituted with one, two or three $R_3$ substituents and optionally, with one additional $R_4$ substituent, or, wherein, alternatively, each instance of $C_{3-14}$cycloalkyl, aryl, heterocyclyl and heteroaryl is optionally substituted with one, two, three or four $R_3$ substituents;

$R_2$ is aryl, heteroaryl, heteroaryl-amino or (heterocyclyl)($C_{1-8}$alkyl)amino, wherein, each instance of aryl and heteroaryl is optionally substituted with one, two or three $R_6$ substituents and optionally, with one additional $R_7$ substituent;

$R_a$ is, in each instance, independently selected from hydrogen, or $C_{1-8}$alkyl;

$R_b$ is, in each instance, independently selected from hydrogen, or halogen;

$R_3$ is, in each instance, independently selected from cyano, halogen, hydroxy, halo-$C_{1-8}$alkyl, $C_{1-8}$alkyl-carbonyl, $C_{1-8}$alkoxy, halo-$C_{1-8}$alkoxy, $C_{1-8}$ alkoxy-$C_{1-8}$alkyl, $C_{1-8}$ alkoxy-carbonyl, amino, $C_{1-8}$ alkyl-amino, amino-$C_{1-8}$ alkyl, $C_{1-8}$ alkyl-amino-$C_{1-8}$alkyl, amino-$C_{1-8}$alkyl-amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino, $[(C_{1-8}$alkyl$)_2$-amino-$C_{1-8}$alkyl$]_2$-amino, $(C_{1-8}$ alkyl-amino-$C_{1-8}$alkyl)($C_{1-8}$ alkyl)amino, $[(C_{1-8}$alkyl$)_2$-amino-$C_{1-8}$alkyl]($C_{1-8}$alkyl)amino, $C_{1-8}$alkoxy-$C_{1-8}$alkyl-amino, $(C_{1-8}$ alkoxy-$C_{1-8}$ alkyl$)_2$-amino, $(C_{1-8}$ alkoxy-$C_{1-8}$ alkyl)($C_{1-8}$ alkyl)amino, $C_{1-8}$ alkyl-carbonyl-amino, $C_{1-8}$alkoxy-carbonyl-amino, hydroxy-$C_{1-8}$ alkyl, hydroxy-$C_{1-8}$ alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino;

$R_4$ is $C_{3-14}$cycloalkyl, $C_{3-14}$Cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl, heterocyclyl-$C_{1-8}$alkyl, heteroaryl or heteroaryl-$C_{1-8}$ alkyl; wherein, each instance of $C_{3-14}$cycloalkyl, aryl, heterocyclyl and heteroaryl is optionally substituted with one, two or three $R_5$ substituents;

$R_5$ is, in each instance, independently selected from halogen, hydroxy, cyano, nitro, $C_{1-8}$alkyl, halo-$C_{1-8}$ alkyl, $C_{1-8}$alkoxy, halo-$C_{1-8}$ alkoxy, hydroxy-$C_{1-8}$ alkyl, amino, $C_{1-8}$ alkyl-amino, $(C_{1-8}$alkyl$)_2$-amino, $(C_{1-8}$ alkyl$)_2$-amino-$C_{1-8}$alkyl, $C_{1-8}$alkyl-thio or heteroaryl-$C_{1-8}$alkyl;

$R_6$ is, in each instance, independently selected from halogen, hydroxy, cyano, nitro, $C_{1-8}$alkyl, $C_{2-8}$alkenyl, cyano-$C_{1-8}$alkyl, halo-$C_{1-8}$alkyl, hydroxy-$C_{1-8}$alkyl, $C_{1-8}$alkoxy, halo-$C_{1-8}$alkoxy, $C_{1-8}$alkyl$)_2$-amino-$C_{1-8}$alkoxy, $C_{1-8}$alkoxy-$C_{1-8}$alkyl, $C_{1-8}$alkoxy-$C_{1-8}$alkoxy, amino, $C_{1-8}$alkyl-amino, $C_{1-8}$alkyl$)_2$-amino, $C_{1-8}$alkoxy-$C_{1-8}$alkyl-amino, $(C_{1-8}$alkoxy-$C_{1-8}$alkyl, $C_{1-8}$alkyl)amino or $C_{1-8}$alkyl-thio; and, $R_7$ is $C_{1-14}$cycloalkyl, $C_{1-14}$cycloalkyl-oxy, aryl, heterocyclyl, heteroaryl or heteroaryl-$C_{1-8}$alkoxy.

One aspect includes a compound of Formula (I), wherein $W_1$ is N.

Another aspect includes a compound of Formula (I), wherein $W_1$ is N, $W_4$ is C—$R_b$ and $W_2$, $W_3$, $W_5$ and $W_6$ are C—$R_a$.

One aspect includes a compound of Formula (I), wherein $W_2$ is N.

Another aspect includes a compound of Formula (I), wherein $W_2$ is N, $W_4$ is C—$R_b$ and $W_1$, $W_3$, $W_5$ and $W_6$ are C—$R_a$.

One aspect includes a compound of Formula (I), wherein $W_3$ is N.

Another aspect includes a compound of Formula (I), wherein $W_3$ is N, $W_4$ is C—$R_b$ and $W_1$, $W_2$, $W_5$ and $W_6$ are C—$R_a$.

One aspect includes a compound of Formula (I), wherein $W_4$ is N.

Another aspect includes a compound of Formula (I), wherein $W_4$ is N and $W_1$, $W_2$, $W_3$, $W_5$ and $W_6$ are independently C—$R_a$.

One aspect includes a compound of Formula (I), wherein $W_5$ is N.

Another aspect includes a compound of Formula (I), wherein $W_5$ is N, $W_4$ is C—$R_b$ and $W_1$, $W_2$, $W_3$ and $W_6$ are C—$R_a$.

One aspect includes a compound of Formula (I), wherein $W_6$ is N.

Another aspect includes a compound of Formula (I), wherein $W_6$ is N, $W_4$ is C—$R_b$ and $W_1$, $W_2$, $W_3$ and $W_5$ are C—$R_a$.

Another aspect includes a compound of Formula (I), wherein $R_1$ is aryl, heterocyclyl, heterocyclyl-amino, (heterocyclyl)($C_{1-8}$alkyl)amino, or heteroaryl.

Another aspect includes a compound of Formula (I), wherein $R_1$ is aryl or heteroaryl.

Another aspect includes a compound of Formula (I), wherein $R_1$ is aryl.

Another aspect includes a compound of Formula (I), wherein $R_1$ is heteroaryl.

Another aspect includes a compound of Formula (I), wherein $R_1$ is heterocyclyl, heterocyclyl-amino or (heterocyclyl)($C_{1-8}$alkyl)amino.

Another aspect includes a compound of Formula (I), wherein $R_1$ is heterocyclyl.

Another aspect includes a compound of Formula (I), wherein $R_1$ is heterocyclyl-amino.

Another aspect includes a compound of Formula (I), wherein $R_1$ is (heterocyclyl)($C_{1-8}$alkyl)amino.

Another aspect includes a compound of Formula (I), wherein $R_a$ is hydrogen or $C_{1-8}$alkyl.

Another aspect includes a compound of Formula (I), wherein $R_b$ is hydrogen or halogen.

Another aspect includes a compound of Formula (I), wherein $R_4$ is heterocyclyl-$C_{1-8}$alkyl or heteroaryl-$C_{1-8}$alkyl.

Another aspect includes a compound of Formula (I), wherein $R_5$ is hydroxy-$C_{1-8}$alkyl, $(C_{1-8}$alkyl$)_2$-amino-$C_{1-8}$alkyl, or heteroaryl-$C_{1-8}$alkyl.

Another aspect includes a compound of Formula (I), wherein $R_6$ is halogen, hydroxy, cyano, $C_{1-8}$alkyl, cyano-$C_{1-8}$alkyl, halo-$C_{1-8}$alkyl, hydroxy-$C_{1-8}$alkyl, $C_{1-8}$alkoxy, $(C_{1-8}$alkyl$)_2$-amino-$C_{1-8}$alkoxy-$C_{1-8}$alkoxy-$C_{1-8}$alkoxy, or $C_{1-8}$alkoxy-$C_{1-8}$alkyl-amino.

Another aspect includes a compound of Formula (I), wherein $R_7$ is $C_{3-14}$cycloalkyl, heterocyclyl, or heteroaryl-$C_{1-8}$alkoxy.

One aspect includes a compound of Formula (I), wherein $W_1$ and $W_5$ are N.

Another aspect includes a compound of Formula (I), wherein $W_1$ and $W_5$ are N, $W_4$ is C—$R_b$ and $W_2$, $W_3$ and $W_6$ are C—$R_a$.

One aspect includes a compound of Formula (I), wherein $W_1$ and $W_6$ are N.

Another aspect includes a compound of Formula (I), wherein $W_1$ and $W_6$ are N, $W_4$ is C—$R_b$ and $W_2$, $W_3$ and $W_5$ are C—$R_a$.

One aspect includes a compound of Formula (I), wherein $W_2$ and $W_3$ are N.

Another aspect includes a compound of Formula (I), wherein $W_2$ and $W_3$ are N, $W_4$ is C—$R_b$ and $W_1$, $W_5$ and $W_6$ are C—$R_a$.

One aspect includes a compound of Formula (I), wherein $W_2$ and $W_4$ are N.

Another aspect includes a compound of Formula (I), wherein $W_2$ and $W_4$ are N, and $W_1$, $W_3$, $W_5$ and $W_6$ are independently C—$R_a$.

One aspect includes a compound of Formula (I), wherein $W_3$ and $W_4$ are N.

Another aspect includes a compound of Formula (I), wherein $W_3$ and $W_4$ are N, and $W_1$, $W_2$, $W_5$ and $W_6$ are independently C—$R_a$.

One aspect includes a compound of Formula (I), wherein $W_5$ and $W_6$ are N.

Another aspect includes a compound of Formula (I), wherein $W_5$ and $W_6$ are N, $W_4$ is C—$R_b$ and $W_1$, $W_2$ and $W_3$ are C—$R_a$.

Another aspect includes a compound of Formula (I), wherein $W_5$ and $W_6$ are N, $W_2$ is C—$R_b$ and $W_1$, $W_3$ and $W_4$ are C—$R_a$.

Another aspect includes a compound of Formula (I), wherein $W_5$ and $W_6$ are N, $W_3$ is C—$R_b$ and $W_1$, $W_2$ and $W_4$ are C—$R_a$.

One aspect includes a compound of Formula (I), wherein $W_1$, $W_5$ and $W_6$ are N.

Another aspect includes a compound of Formula (I), wherein $W_1$, $W_5$ and $W_6$ are N, $W_4$ is C—$R_b$ and $W_2$ and $W_3$ are C—$R_a$.

One aspect includes a compound of Formula (I), wherein $W_2$, $W_3$ and $W_4$ are N.

Another aspect includes a compound of Formula (I), wherein $W_2$, $W_3$ and $W_4$ are N, and $W_1$, $W_5$ and $W_6$ are independently C—$R_a$.

One aspect includes a compound of Formula (I), wherein $R_1$ is heterocyclyl selected from azetidinyl, tetrahydrofuranyl, pyrrolidinyl, piperidinyl, piperazinyl, azepanyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-c]pyrazin-(2H)-one, hexahydropyrrolo[1,2-c]pyrazin-(1H)-yl, (7R,8aS)-hexahydropyrrolo[1,2-c]pyrazin-(1H)-yl, (8aS)-hexahydropyrrolo[1,2-a]pyrazin-(1H)-yl, (8aR)-hexahydropyrrolo[1,2-a]pyrazin-(1H)-yl, hexahydro-1H-cyclobuta[1,2-c:1,4-c']dipyrrol-(3H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 1,4-diazabicyclo[3.1.1]heptyl, 3,6-diazabicyclo[3.2.0]heptyl, 2,5-diazabicyclo[2.2.2]octyl, 1,4-diazabicyclo[3.2.1]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 4,7-diazaspiro[2.5]octanyl, 2,6-diazaspiro[3.3]heptyl, 2,6-diazaspiro[3.4]octanyl, 1,7-diazaspiro[4.4]nonyl, 2,6-diazaspiro[3.5]nonyl, 2,7-diazaspiro[3.5]nonyl, 5,8-diazaspiro[3.5]nonyl, 2,7-diazaspiro[4.4]nonyl, 2,7-diazaspiro[4.5]decanyl or 6,9-diazaspiro[4.5]decyl; wherein, each instance of heterocyclyl is optionally substituted with $R_3$ and $R_4$ substituents.

Another aspect includes a compound of Formula (I), wherein $R_1$ is heterocyclyl selected from azetidin-1-yl, tetrahydrofuran-3-yl, pyrrolidin-1-yl, pyrrolidin-3-yl, piperidin-1-yl, piperidin-4-yl, piperazin-1-yl, azepan-4-yl, 1,4-diazepan-1-yl, 1,2,5,6-tetrahydropyridin-5-yl, 1,2,3,6-tetrahydropyridin-4-yl, hexahydropyrrolo[3,4-b]pyrrol-1(2H)-yl, (3aS,6aS)-hexahydropyrrolo[3,4-h]pyrrol-1(2H)-yl, (3aS,6aS)-hexahydropyrrolo[3,4-h]pyrrol-5(1H)-yl, (3aR,6aR)-hexahydropyrrolo[3,4-b]pyrrol-5(1H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, (3aR,6aS)-hexahydropyrrolo[3,4-c]pyrrol-2(1H)-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, hexahydro-1H-cyclobuta[1,2-c:1,4-c']dipyrrol-2(3H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, 3-azabicyclo[3.1.0]hexan-3-yl, 8-azabicyclo[3.2.1]octan-3-yl, (1R,5S)-8-azabicyclo[3.2.1]octan-3-yl, 8-azabicyclo[3.2.1]oct-2-en-3-yl, (1R,5S)-8-azabicyclo[3.2.1]oct-2-en-3-yl, 9-azabicyclo[3.3.1]nonan-3-yl, (1R,5S)-9-azabicyclo[3.3.1]nonan-3-yl, 2,5-diazabicyclo[2.2.1]heptan-2-yl, (1S,4S)-2,5-diazabicyclo[2.2.1]heptan-2-yl, 1,4-diazabicyclo[3.1.1]hepant-4-yl, 3,6-diazabicyclo[3.2.0]heptan-3-yl, 3,6-diazabicyclo[3.2.0]hepant-6-yl, 2,5-diazabicyclo[2.2.2]octan-2-yl, 1,4-diazabicyclo[3.2.1]octan-4-yl, 3,8-diazabicyclo[3.2.1]octan-3-yl, (1R,5S)-3,8-diazabicyclo[3.2.1]ocant-3-yl, 1,4-diazabicyclo[3.2.2]nonan-4-yl, azaspiro[3.3]hepant-2-yl, 4,7-diazaspiro[2.5]octan-4-yl, 4,7-diazaspiro[2.5]octan-7-yl, 2,6-diazaspiro[3.3]heptanan-2-yl, 2,6-diazaspiro[3.4]octan-2-yl, 2,6-diazaspiro[3.4]octan-6-yl, 1,7-diazaspiro[4.4]nonan-1-yl, 1,7,-diazaspiro[4.4]nonan-7-yl, 2,6-diazaspiro[3.5]nonan-2-yl, 2,6-diazaspiro[3.5]nonan-6-yl, 2,7-diazaspiro[3.5]nonan-2-yl, 2,7-diazaspiro[3.5]nonan-7-yl, 5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl or 6,9-diazaspiro[4.5]decan-9-yl; wherein, each instance of heterocyclyl is optionally substituted with $R_3$ and $R_4$ substituents.

Another aspect includes a compound of Formula (I), wherein $R_1$ is heterocyclyl selected from pyrrolidinyl, piperidinyl, piperazinyl, azepanyl, 1,2,5,6-tetrahydropyridinyl, 1,2,3,6-tetrahydropyridinyl, 3-azabicyclo[3.1.0]hexyl, 8-azabicyclo[3.2.1]octyl, 2,5-diazabicyclo[2.2.1]heptyl, 2,6-diazaspiro[3.4]octanyl, 2,6-diazaspiro[3.5]nonyl, 2,7-diazaspiro[3.5]nonyl.

Another aspect includes a compound of Formula (I), wherein $R_1$ is heterocyclyl selected from pyrrolidin-3-yl, piperidin-4-yl, piperazin-1-yl, azepan-4-yl, 1,2,5,6-tetrahydropyridin-5-yl, 1,2,3,6-tetrahydropyridin-4-yl, 3-azabicyclo[3.1.0]hexan-3-yl, 8-azabicyclo[3.2.1]octan-3-yl, 2,5-diazabicyclo[2.2.1]heptan-2-yl, 2,6-diazaspiro[3.4]octan-2-yl, 2,6-diazaspiro[3.4]octan-6-yl, 2,6-diazaspiro[3.5]nonan-2-yl, 2,7-diazaspiro[3.5]nonan-2-yl, and 2,7-diazaspiro[3.5]nonan-7-yl.

Another aspect includes a compound of Formula (I), wherein $R_1$ is substituted heterocyclyl selected from N,N-dimethylpyrrolidin-3-amine, N,N-dimethylpiperidin-4-amine, N,N-4-trimethylpiperidin-4-amine, 1-methylpiperidin-4-yl, 1-ethylpiperidin-4-yl, 1-(propan-2-yl)piperidin-4-yl, 2-hydroxyethylpiperidin-4-yl, 2-fluoroethylpiperidin-4-yl, 2,2-difluoroethylpiperidin-4-yl, N,N-dimethyl-2-(piperidin-1-yl)ethan-1-amine, N,N-dimethyl-2-(piperidin-1-yl)propan-1-amine, (2S,6S)-2,6-dimethylpiperidin-4-yl, (2R,6S)-2,6-dimethylpiperidin-4-yl, (2S,6S)-2,6-diethylpiperidin-4-yl, (2S,6S)-(2,6- diethyl-1-methyl)piperidin-4-yl, (2S,6S)-1,2,6-trimethylpiperidin-4-yl, (2R,6S)-1,2,6-trimethylpiperidin-4-yl, (2S,4R,6R)-1,2,6-trimethylpiperidin-4-yl, (2R,6R)-1-ethyl-2,6-dimethylpiperidin-4-yl, (2R,6S)-[1-(2-fluoroethyl)-2,6-dimethyl]piperidin-4-yl, (ethyl-1-ol)piperidin-1-yl, 2,6-dimethylpiperidin-1-yl-ethan-1-ol, 3-(1H-pyrazol-1-yl)propyl]piperidin-4-yl, 3-(1H-benzimidazol-1-yl)propyl]piperidin-4-yl, 2-(1H-benzimidazol-1-yl)ethyl]piperidin-4-yl, 1-ethyl-1,2,3,6-tetrahydropyridin-4-yl, 2,2,6,6-tetramethylpiperidin-4-yl, 2,2,6,6-tetramethyl-1,2,3,6-tetrahydropyridin-4-yl, (3R,5S)-3,5-dimethylpiperazin-1-yl, 1-methylazepan-4-yl, 1-ethylazepan-4-yl, 2-fluoroethyl)azepan-4-yl, azepan-1-yl-ethan-1-ol, 4-methyl-1,4-diazepan-1-yl, (3aS,6aS)-1-methylhexahydropyrrolo[3,4-b]pyrrol-5(1H)-yl, (3aS,6aS)-5-methylhexahydropyrrolo[3,4-b]pyrrol-1(2H)-yl, (3aR,6aR)-1-methylhexahydropyrrolo[3,4-b]pyrrol-5(1H)-yl, (3aR,6aS)-5-methylhexahydropyrrolo[3,4-c]pyrrol-2(1H)-yl, (3aR,6aS)-5-(2-hydroxyethyl)hexahydropyrrolo[3,4-c]pyrrol-2(1H)-yl, (3aR,6aS)-5-(propan-2-yl)hexahydropyrrolo[3,4-c]pyrrol-2(1H)-yl, (3aR,6aS)-5-ethylhexahydropyrrolo[3,4-c]pyrrol-2(1H)-yl, (4aR,7aR)-1-methyloctahydro-6H-pyrrolo[3,4-b]pyridin-6-yl, (4aR,7aR)-1-ethyloctahydro-6H-pyrrolo[3,4-b]pyridin-6-yl, (4aR,7aR)-1-(2-hydroxyethyfloctahydro-6H-pyrrolo[3,4-b]pyridin-6-yl, (4aS,7aS)-1-methyloctahydro-6H-pyrrolo[3,4-b]pyridin-6-yl, (4aS,7aS)-1-(2-hydroxyethyfloctahydro-6H-pyrrolo[3,4-b]pyridin-6-yl, (7R,8aS)-7-hydroxyhexahydropyrrolo[1,2-a]pyrazin-2(1H)-yl, (8aS)-8a-methyloctahydropyrrolo[1,2-a]pyrazin-2(1H)-yl, (8aR)-8a-methyloctahydropyrrolo[1,2-c]pyrazin-2(1H)-yl, (1R,5S,6s)-6-(dimethylamino)-3-azabicyclo[3.1.0]hex-3-yl, N,N-dimethyl-3-azabicyclo[3.1.0]hexan-6-amine, (1R,5S)-8-methyl-8-azabicyclo[3.2.1]oct-3-yl, 9-methyl-9-azabicyclo[3.3.1]non-3-yl, (3-exo)-9-methyl-9-azabicyclo[3.3.1]non-3-yl, (1R,5S)-9-methyl-9-azabicyclo[3.3.1]non-3-yl, 5-methyl-2,5-diazabicyclo[2.2.1]heptan-2-yl, (1S,4S)-5-methyl-2,5-diazabicyclo[2.2.1]heptan-2-yl, (1S,4S)-5-methyl-2,5-diazabicyclo[2.2.1]hept-2-yl or (1S,4S)-5-ethyl-2,5-diazabicyclo[2.2.1]hept-2-yl.

Another aspect includes a compound of Formula (I), wherein $R_1$ is substituted heterocyclyl selected from N,N-dimethylpyrrolidin-3-amine, N,N-dimethylpiperidin-4-amine, N,N-4-trimethylpiperidin-4-amine, 1-methylpiperidin-4-yl, 1-ethyl-piperidin-4-yl, 1-(propan-2-yl)piperidin-4-yl, 2-hydroxyethylpiperidin-4-yl, 2-fluoroethylpiperidin-4-yl, 2,2-difluoroethylpiperidin-4-yl, N,N-dimethyl-2-(piperidin-1-yl)ethan-1-amine, N,N-dimethyl-2-(piperidin-1-yl)propan-1-amine, (2S,6S)-2,6-dimethylpiperidin-4-yl, (2R,6S)-2,6-dimethylpiperidin-4-yl, (2S,6S)-2,6-diethylpiperidin-4-yl, (2S,6S)-2,6-diethyl-1-methylpiperidin-4-yl, (2S,6S)-1,2,6-trimethylpiperidin-4-yl, (2R,6S)-1,2,6-trimethylpiperidin-4-yl, (2S,4R,6R)-1,2,6-trimethylpiperidin-4-yl, (2R,6R)-1-ethyl-2,6-dimethylpiperidin-4-yl, (2R,6S)-1-(2-fluoroethyl)-2,6-dimethylpiperidin-4-yl, piperidin-1-yl-ethan-1-ol, 2,6-dimethylpiperidin-1-yl-ethan-1-ol, 3-(1H-pyrazol-1-yl)propyl]piperidin-4-yl, 3-(1H-benzimidazol-1-yl)propyl]piperidin-4-yl, 2-(1H-benzimidazol-1-yl)ethyl]piperidin-4-yl, 1-ethyl-1,2,3,6-tetrahydropyridin-4-yl, 2,2,6,6-tetramethylpiperidin-4-yl, 2,2,6,6-tetramethyl-1,2,3,6-tetrahydropyridin-4-yl, (3R,5S)-3,5-dimethylpiperazin-1-yl, 1-methylazepan-4-yl, 1-ethylazepan-4-yl, 2-fluoroethylazepan-4-yl, azepan-1-yl-ethan-1-ol, N,N-dimethyl-3-azabicyclo[3.1.0]hexan-6-amine, 5-methyl-2,5-diazabicyclo[2.2.1]heptan-2-yl or (1S,4S)-5-methyl-2,5-diazabicyclo[2.2.1]heptan-2-yl.

One aspect includes a compound of Formula (I), wherein $R_1$ is heterocyclyl-amino, wherein heterocyclyl is selected from azetidinyl, pyrrolidinyl, piperidinyl, 9-azabicyclo[3.3.1]nonyl or (1R,5S)-9-azabicyclo[3.3.1]nonyl; and, wherein, each instance of heterocyclyl is optionally substituted with $R_3$ and $R_4$ substituents.

Another aspect includes a compound of Formula (I), wherein $R_1$ is heterocyclyl-amino selected from azetidin-3-yl-amino, pyrrolidin-3-yl-amino, piperidin-4-yl-amino, 9-azabicyclo[3.3.1]non-3-yl-amino, (1R,5S)-9-azabicyclo[3.3.1]non-3-yl-amino, 9-methyl-9-azabicyclo[3.3.1]non-3-yl-amino, (3-exo)-9-methyl-9-azabicyclo[3.3.1]non-3-yl-amino or (1R,5S)-9-methyl-9-azabicyclo[3.3.1]non-3-yl-amino; wherein, each instance of heterocyclyl is optionally substituted with $R_3$ and $R_4$ substituents.

One aspect includes a compound of Formula (I), wherein $R_1$ is (heterocyclyl)($C_{1-8}$alkyl)amino, wherein heterocyclyl is selected from pyrrolidinyl or piperidinyl; and, wherein, each instance of heterocyclyl is optionally substituted with $R_3$ and $R_4$ substituents.

Another aspect includes a compound of Formula (I), wherein $R_1$ is (heterocyclyl)($C_{1-8}$alkyl)amino wherein heterocyclyl is piperidinyl.

Another aspect includes a compound of Formula (I), wherein $R_1$ is (heterocyclyl)($C_{1-8}$alkyl)amino selected from (pyrrolidin-3-yl)(methyl)amino or (piperidin-4-yl)(methyl)amino; wherein, each instance of heterocyclyl is optionally substituted with $R_3$ and $R_4$ substituents.

One aspect includes a compound of Formula (I), wherein $R_3$ is selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$ alkyl-amino, ($C_{1-8}$alkyl)$_2$-amino, amino-$C_{1-8}$ $C_{1-8}$ alkyl-amino-$C_{1-8}$ alkyl, ($C_{1-8}$ alkyl)$_2$-amino-$C_{1-8}$alkyl, amino-$C_{1-8}$ $C_{1-8}$alkyl-amino-$C_{1-8}$ alkyl-amino, ($C_{1-8}$alkyl)$_2$-amino-$C_{1-8}$ alkyl-amino, $C_{1-8}$alkoxy-$C_{1-8}$ alkyl-amino, $C_{1-8}$alkyl-carbonyl-amino, $C_{1-8}$ alkoxy-carbonyl-amino, hydroxy-$C_{1-8}$ alkyl, hydroxy-$C_{1-8}$ alkoxy-$C_{1-8}$alkyl, hydroxy-$C_{1-8}$alkyl-amino, (hydroxy-$C_{1-8}$ alkyl)$_2$-amino or (hydroxy-$C_{1-8}$alkyl)($C_{1-8}$ alkyl)amino.

Another aspect includes a compound of Formula (I), wherein $R_3$ is selected from cyano, halogen, hydroxy, oxo, $C_{1-8}$ alkyl, halo-$C_{1-8}$alkyl, $C_{1-8}$alkoxy, $C_{1-8}$ alkoxy-$C_{1-8}$alkyl, $C_{1-8}$ alkoxy-carbonyl, amino, $C_{1-8}$ alkyl-amino, ($C_{1-8}$alkyl)$_2$-amino, amino-$C_{1-8}$alkyl, $C_{1-8}$ alkyl-amino-$C_{1-8}$ alkyl, ($C_{1-8}$ alkyl)$_2$-amino-$C_{1-8}$alkyl, $C_{1-8}$alkyl-amino-$C_{1-8}$ alkyl-amino, $C_{1-8}$ alkoxy-$C_{1-8}$alkyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino.

Another aspect includes a compound of Formula (I), wherein $R_3$ is $C_{1-8}$alkyl selected from methyl, ethyl, propyl, isopropyl or tert-butyl.

Another aspect includes a compound of Formula (I), $R_3$ is $C_{1-8}$alkyl selected from methyl, ethyl, propyl, isopropyl or tert-butyl.

Another aspect includes a compound of Formula (I), wherein $R_3$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

Another aspect includes a compound of Formula (I), wherein $R_3$ is halo-$C_{1-8}$alkyl selected from trihalo-methyl, dihalo-methyl, halo-methyl, trihalo-ethyl, dihalo-ethyl, trihalo-propyl or dihalo-propyl; wherein, halo is selected from fluoro, chloro, bromo or iodo.

Another aspect includes a compound of Formula (I), wherein $R_3$ is hydroxy-$C_{1-8}$alkyl selected from hydroxy-methyl, hydroxy-ethyl, hydroxy-propyl, dihydroxy-propyl, hydroxy-butyl or dihydroxy-butyl.

Another aspect includes a compound of Formula (I), wherein $R_3$ is hydroxy-$C_{1-8}$alkyl selected from hydroxy-methyl, hydroxy-ethyl, dihydroxy-propyl, hydroxy-butyl or dihydroxy-butyl.

Another aspect includes a compound of Formula (I), wherein $R_3$ is $C_{1-8}$alkoxy selected from methoxy, ethoxy, propoxy or isopropoxy.

Another aspect includes a compound of Formula (I), wherein $R_3$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

Another aspect includes a compound of Formula (I), wherein $R_3$ is $C_{1-8}$alkoxy-carbonyl-amino selected from methoxy-carbonyl-amino, ethoxy-carbonyl-amino, propoxy-carbonyl-amino, isopropoxy-carbonyl-amino, tert-butoxy-carbonyl-amino.

Another aspect includes a compound of Formula (I), wherein $R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$ alkoxy-carbonyl, aryl-sulfonyloxy-$C_{1-8}$ alkyl, heterocyclyl, heterocyclyl-$C_{1-8}$alkyl or heteroaryl; wherein, each instance of $C_{3-14}$cycloalkyl, aryl, heterocyclyl and heteroaryl is optionally substituted with one, two or three $R_5$ substituents.

Another aspect includes a compound of Formula (I), wherein $R_5$ is, in each instance, independently selected from halogen, hydroxy, cyano, nitro, $C_{1-8}$alkyl, halo-$C_{1-8}$alkyl, $C_{1-8}$ alkoxy, halo-$C_{1-8}$ alkoxy, hydroxy-$C_{1-8}$alkyl, amino, $C_{1-8}$ alkyl-amino, ($C_{1-8}$ alkyl)$_2$-amino, ($C_{1-8}$ alkyl)$_2$-amino-$C_{1-8}$alkyl, $C_{1-8}$alkyl-thio or heteroaryl-$C_{1-8}$ alkyl.

One aspect includes a compound of Formula (I), wherein $R_2$ is aryl, heteroaryl, heteroaryl-amino, (heteroaryl)($C_{1-8}$ alkyl)amino or (heterocyclyl)($C_{1-8}$ alkyl)amino.

Another aspect includes a compound of Formula (I), wherein $R_2$ is aryl, heteroaryl, heteroaryl-amino or (heteroaryl)($C_{1-8}$ alkyl)amino.

Another aspect includes a compound of Formula (I), wherein $R_2$ is aryl.

Another aspect includes a compound of Formula (I), wherein $R_2$ is heteroaryl.

Another aspect includes a compound of Formula (I), wherein $R_2$ is heteroaryl-amino.

Another aspect includes a compound of Formula (I), wherein $R_2$ is (heteroaryl)($C_{1-8}$alkyl)amino.

Another aspect includes a compound of Formula (I), wherein $R_2$ is (heterocyclyl)($C_{1-8}$alkyl)amino.

One aspect includes a compound of Formula (I), wherein $R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b] pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 2H-pyrazolo[3,4-c]pyridinyl, 2H-pyrazolo[4,3-b]pyridinyl, 2H-pyrazolo[4,3-c]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,3]oxazolo[4,5-c]pyridinyl, [1,3]thiazolo[4,5-c]pyridinyl, [1,3]thiazolo[5,4-b]pyridinyl, [1,2,4]triazolo[1,5-a]pyridinyl or quinoxalinyl; wherein, each instance of heteroaryl is optionally substituted with $R_6$ and $R_7$ substituents.

Another aspect includes a compound of Formula (I), wherein $R_2$ is heteroaryl selected from thien-2-yl, thien-3-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,2,4-oxadiazol-3-yl, 1,3,4-oxadiazol-2-yl, pyridin-2-yl, pyridin-3-yl, pyridin-4-yl, pyrimidin-4-yl, 1H-indol-3-yl, 1H-indol-4-yl, 1H-indol-5-yl, 1H-indol-6-yl, 1H-indazol-5-yl, 2H-indazol-5-yl, indolizin-2-yl, benzofuran-2-yl, benzofuran-5-yl, benzothien-2-yl, benzothien-3-yl, 1H-benzimidazol-2-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 9H-purin-8-yl, furo[3,2-b]pyridin-2-yl, furo[3,2-c]pyridin-2-yl, furo[2,3-c]pyridin-2-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-2-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, 2H-pyrazolo[3,4-c]pyridin-5-yl, 2H-pyrazolo[4,3-b]pyridin-5-yl, 2H-pyrazolo[4,3-c]pyridin-5-yl, pyrazolo[1,5-a]pyrazin-2-yl, imidazo[1,2-a]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-b]pyridazin-6-yl, imidazo[1,2-a]pyrazin-2-yl, imidazo[1,2-a]pyrazin-6-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,3]oxazolo[4,5-c]pyridin-2-yl, [1,3]thiazolo[5,4-b]pyridin-5-yl, [1,3]thiazolo[5,4-c]pyridin-2-yl, [1,2,4]triazolo[1,5-a]pyridin-6-yl, or quinoxalin-2-yl; wherein, each instance of heteroaryl is optionally substituted with $R_6$ and $R_7$ substituents.

One aspect includes a compound of Formula (I), wherein $R_6$ is selected from halogen, hydroxy, cyano, nitro, $C_{1-8}$alkyl, halo-$C_{1-8}$alkyl, hydroxy-$C_{1-8}$alkyl, $C_{1-8}$alkoxy, halo-$C_{1-8}$ alkoxy, $C_{1-8}$alkoxy-$C_{1-8}$alkyl, $C_{1-8}$alkoxy-$C_{1-8}$alkoxy, ($C_{1-8}$alkyl)$_2$-amino-$C_{1-8}$alkoxy, heteroaryl-$C_{1-8}$ alkoxy, aryl-oxy, ($C_{1-8}$alkyl)$_2$-amino, $C_{1-8}$alkoxy-$C_{1-8}$ alkyl-amino, $C_{1-8}$alkyl-thio, $C_{3-14}$cycloalkyl; wherein, halogen and halo is selected from fluoro, chloro, bromo or iodo.

Another aspect includes a compound of Formula (I), wherein $R_6$ is $C_{1-8}$alkyl selected from methyl, ethyl, propyl, isopropyl or tert-butyl.

Another aspect includes a compound of Formula (I), wherein $R_6$ is $C_{1-8}$alkyl selected from methyl, ethyl, propyl, isopropyl or tert-butyl.

Another aspect includes a compound of Formula (I), wherein $R_6$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

Another aspect includes a compound of Formula (I), wherein $R_7$ is $C_{3-14}$cycloalkyl, $C_{3-14}$cycloalkyl-oxy, aryl, heterocyclyl or heteroaryl.

One aspect includes a compound of Formula (I), wherein $R_a$ is hydrogen or $C_{1-8}$alkyl.

One aspect includes a compound of Formula (I), wherein $R_b$ is hydrogen or $C_{1-8}$alkyl.

Another aspect includes a compound of Formula (I), wherein $R_h$ is halo.

One aspect of the compound of Formula (I) includes a compound selected from Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In):

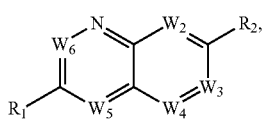
(Ia)

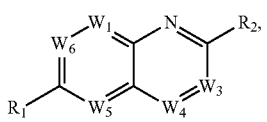
(Ib)

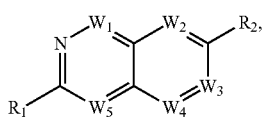
(Ic)

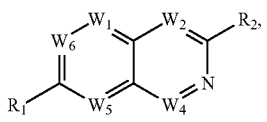
(Id)

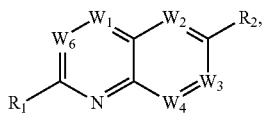
(Ie)

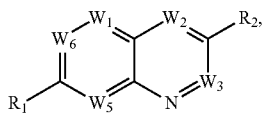
(If)

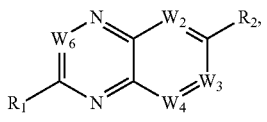
(Ig)

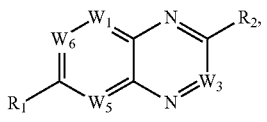
(Ih)

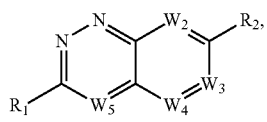
(Ii)

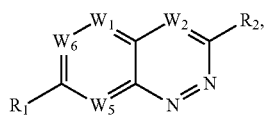
(Ij)

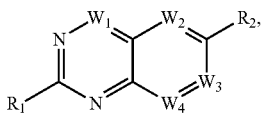
(Ik)

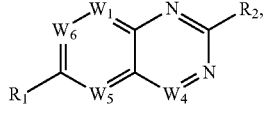
(Il)

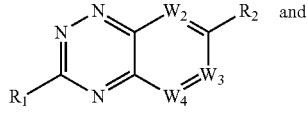
(Im)

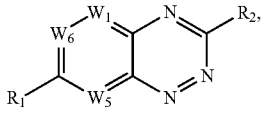
(In)

or a form thereof.

Another aspect of the compound of Formula (I) includes the compound selected from Formula (Ib), Formula (Ic), Formula (Ie), Formula (If), Formula (Ig), Formula (Ii), Formula (Ij), Formula (Ik) Formula (Im) or Formula (In):

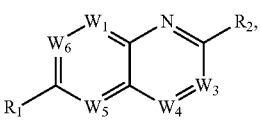
(Ib)

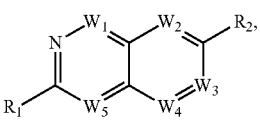
(Ic)

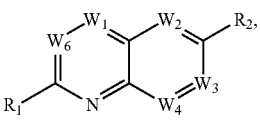
(Ie)

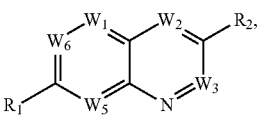
(If)

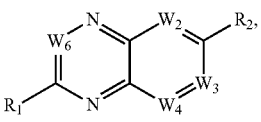
(Ig)

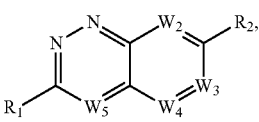
(Ii)

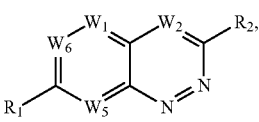
(Ij)

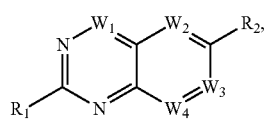
(Ik)
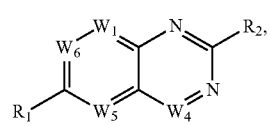
(Il)
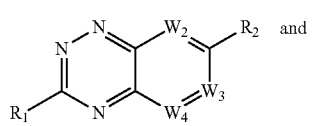
(Im) and
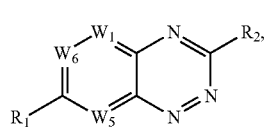
(In)
or a form thereof.
Another aspect of the compound of Formula (I) includes the compound selected from of Formula (Ia1), Formula (Ib 1), Formula (Ic1), Formula (Id1), Formula (Ie1), Formula (If1), Formula (Ig1), Formula (Ih1), Formula (Ii1), Formula (Ij1), Formula (Ik1), Formula (Il1), Formula (Im1) or Formula (In1), respectively:
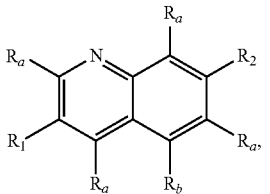
(Ia1)
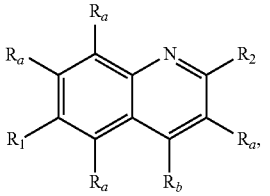
(Ib1)
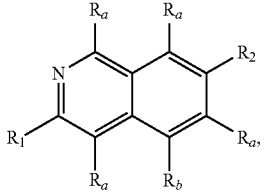
(Ic1)
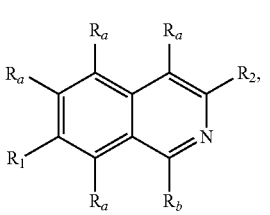
(Id1)
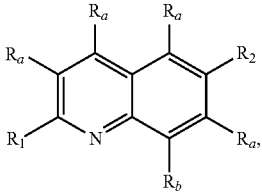
(Ie1)
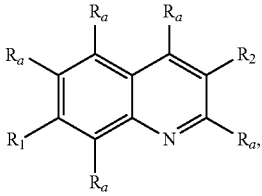
(If1)
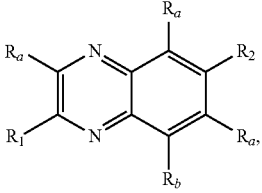
(Ig1)
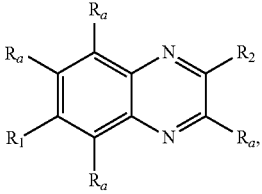
(Ih1)
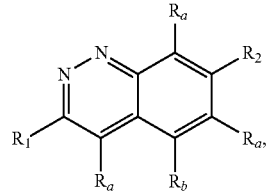
(Ii)
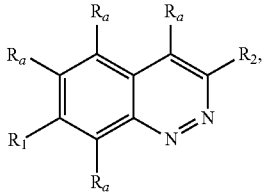
(Ij1)
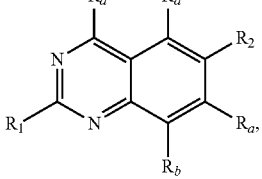
(Ik1)

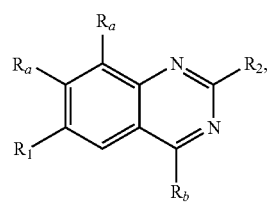
(Il1)
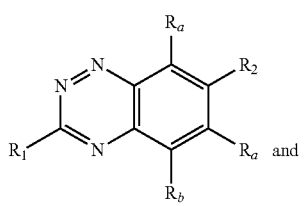
(Im1)
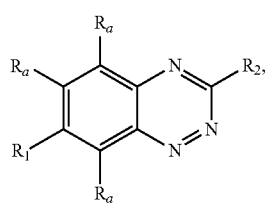
and
(In1)
or a form thereof.
Another aspect of the compound of Formula (I) includes the compound selected from Formula (Ib 1), Formula (Ic1), Formula (Ie1), Formula (If1), Formula (Ig1), Formula (Ii1), Formula (Ij1), Formula (Ik1), Formula (Il1), Formula (Im1) or Formula (In1), respectively:
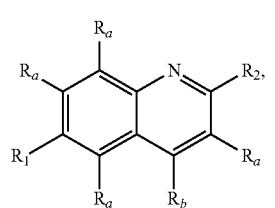
(Ib1)
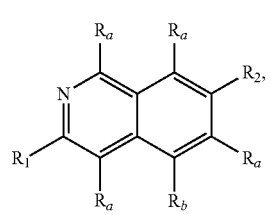
(Ic1)
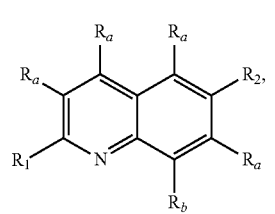
(Ie1)
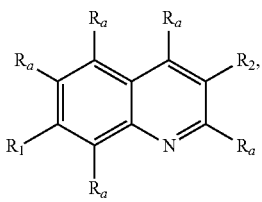
(If1)
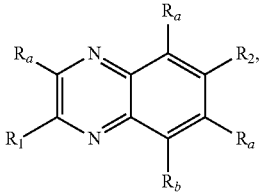
(Ig1)
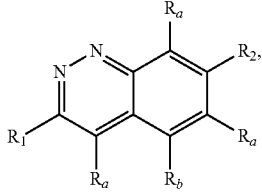
(Ii1)
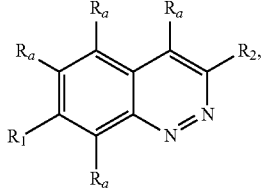
(Ij1)
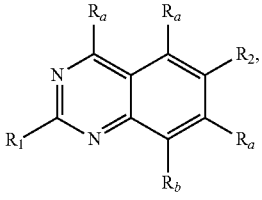
(Ik1)
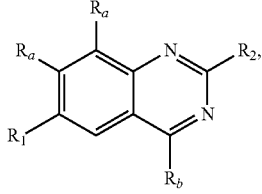
(Il1)
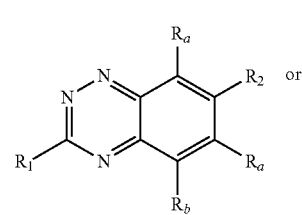
or
(Im1)

-continued

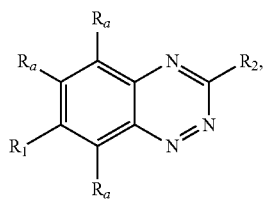
(In1)

or a form thereof.

Another aspect of the compound of Formula (I) includes the compound of Formula (Ia1):

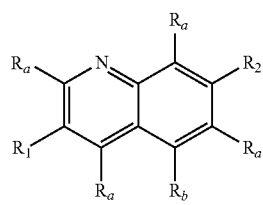
(Ia1)

or a form thereof.

Another aspect of the compound of Formula (I) includes the compound of Formula (Ib 1):

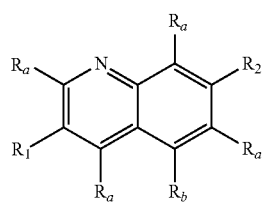
(Ib1)

or a form thereof.

Another aspect of the compound of Formula (I) includes the compound of Formula (Ic1):

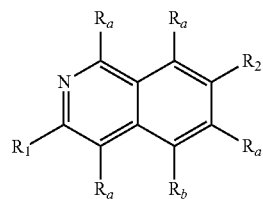
(Ic1)

or a form thereof.

Another aspect of the compound of Formula (I) includes the compound of Formula (Id1):

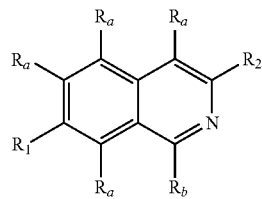
(Id1)

or a form thereof.

Another aspect of the compound of Formula (I) includes the compound of Formula (Ie1):

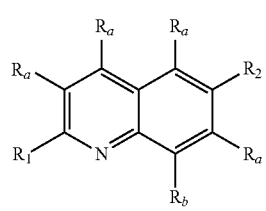
(Ie1)

or a form thereof.

Another aspect of the compound of Formula (I) includes the compound of Formula (If1):

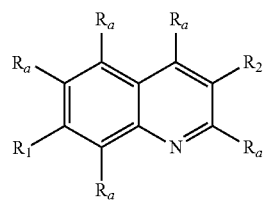
(If1)

or a form thereof.

Another aspect of the compound of Formula (I) includes the compound of Formula (Ig1):

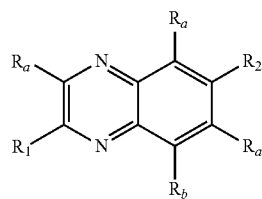
(Ig1)

or a form thereof.

Another aspect of the compound of Formula (I) includes the compound of Formula (Ih1):

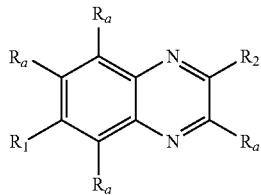

(Ih1)

or a form thereof.

Another aspect of the compound of Formula (I) includes the compound of Formula (Ii1):

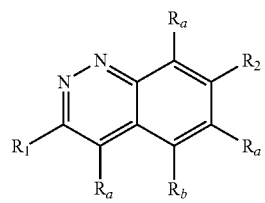

(Ii1)

or a form thereof.

Another aspect of the compound of Formula (I) includes the compound of Formula (Ij1):

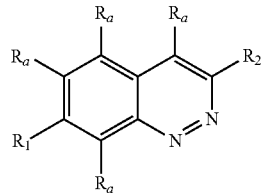

(Ij1)

or a form thereof.

Another aspect of the compound of Formula (I) includes the compound of Formula (Ik1):

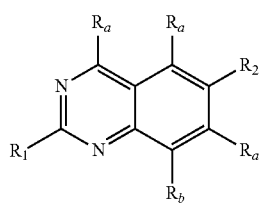

(Ik1)

or a form thereof.

Another aspect of the compound of Formula (I) includes the compound of Formula (Il1):

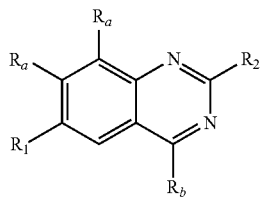

(Il1)

or a form thereof.

Another aspect of the compound of Formula (I) includes the compound of Formula (Im1):

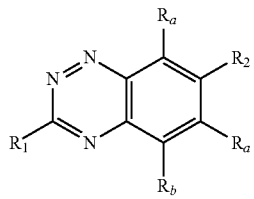

(Im1)

or a form thereof.

Another aspect of the compound of Formula (I) includes the compound of Formula (In1):

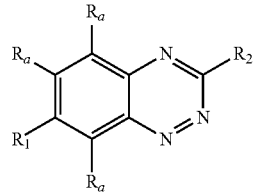

(In1)

or a form thereof.

One aspect of the compound of Formula (I) or a form thereof includes a compound selected from the group consisting of:

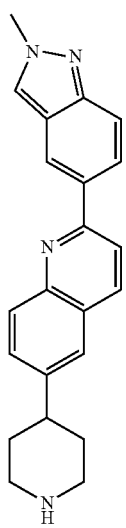

1

2
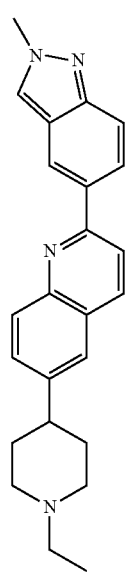
3
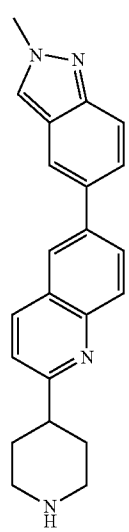
4
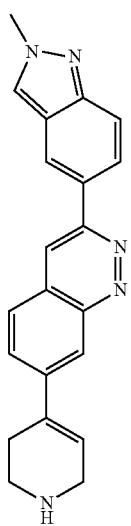
5
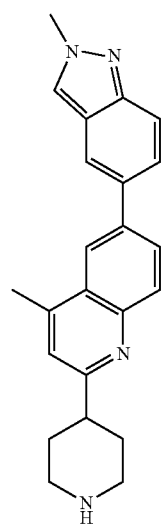
6
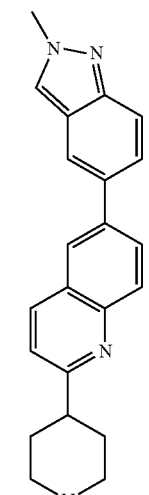
7
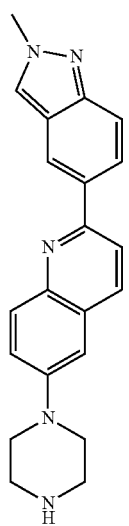

9
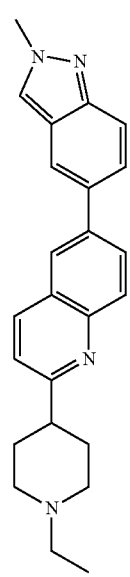
10
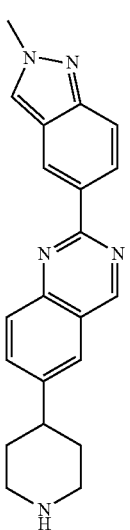
11
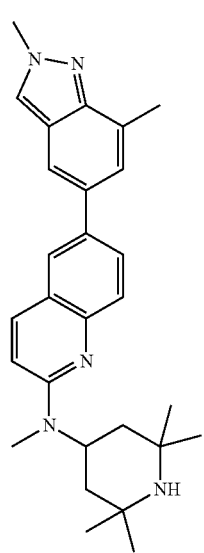
12
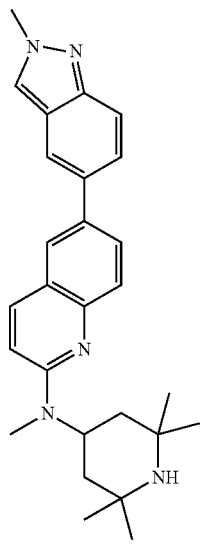
13
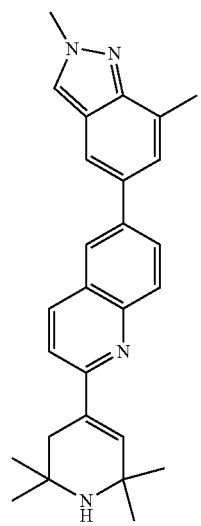
14
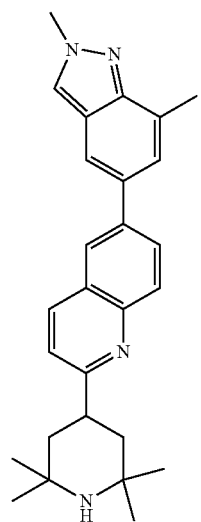

15
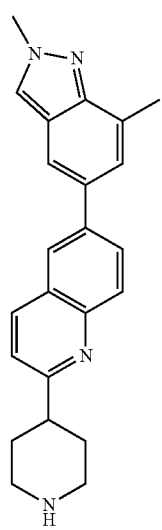
16
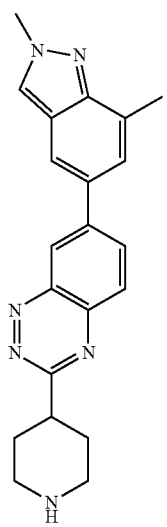
17
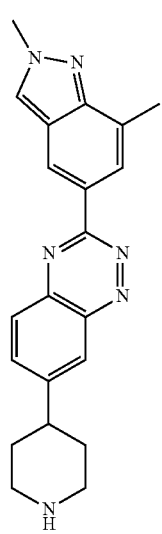
18
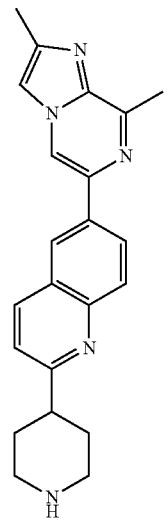
19
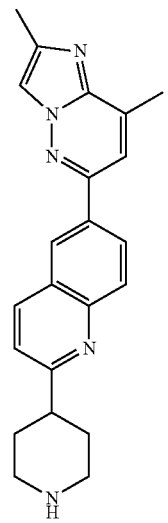
20
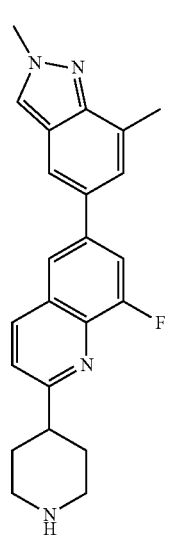

23
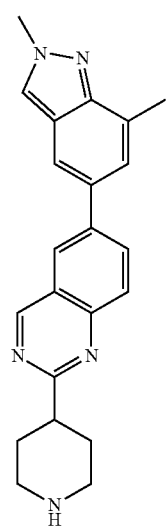
24
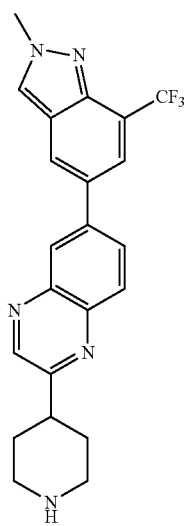
25
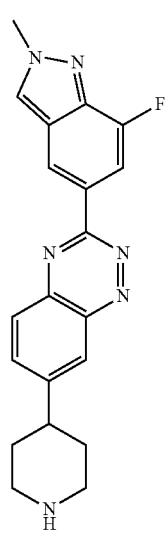
26
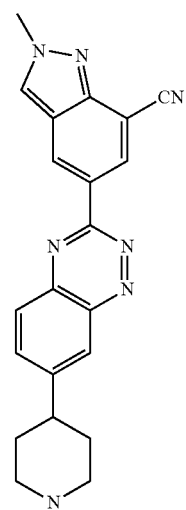
27
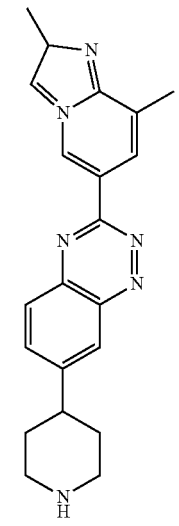
28
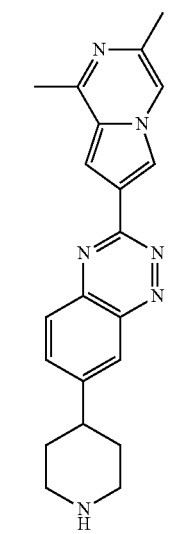

29
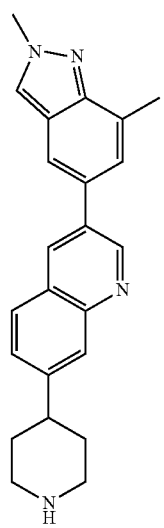
30
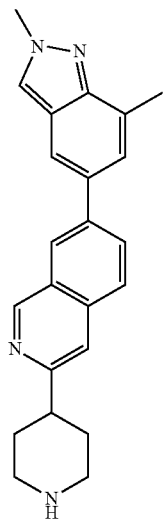
31
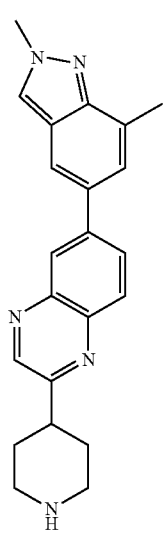
32
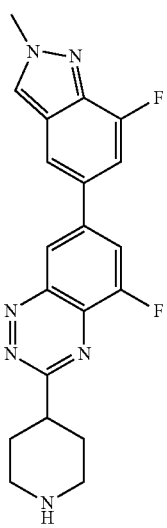
33
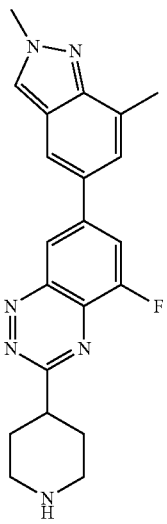
34
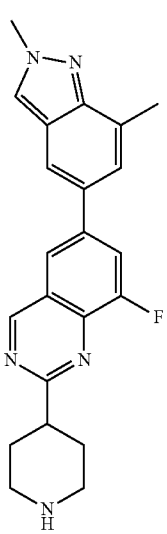

33
-continued
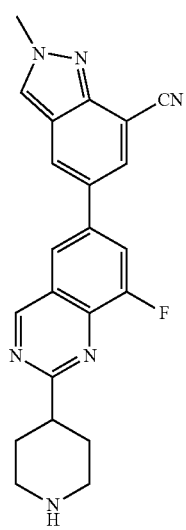
35
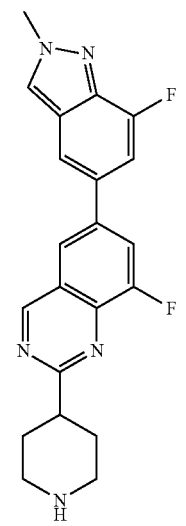
36
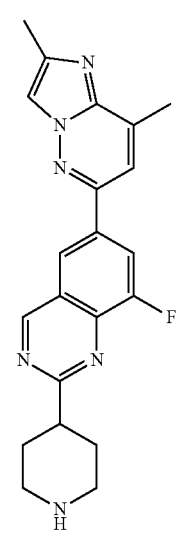
37
34
-continued
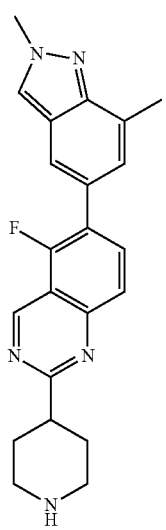
38
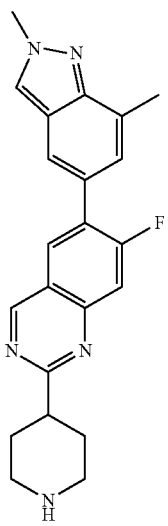
39
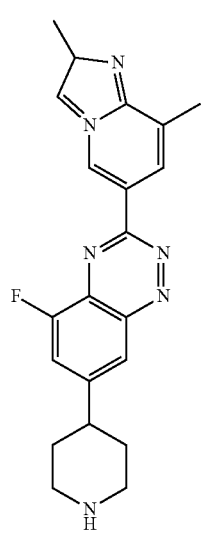
40

41
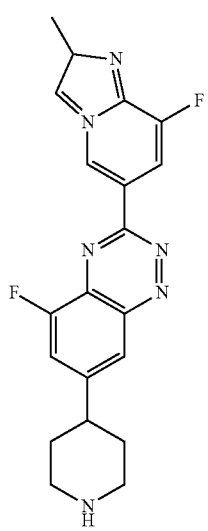
42
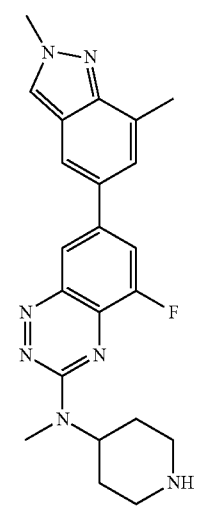
43
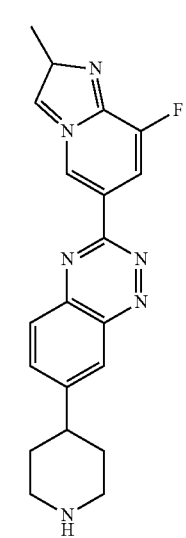
44
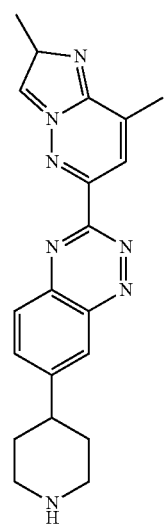
45
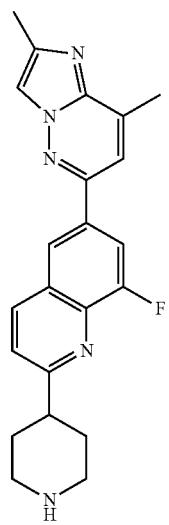
46
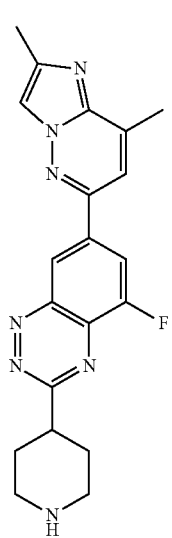

-continued

| 53 | 56 |
|---|---|
| 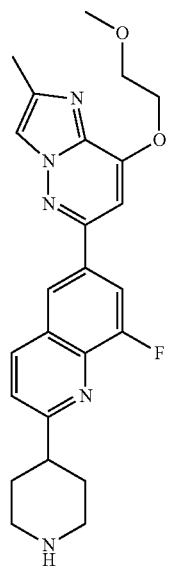 | 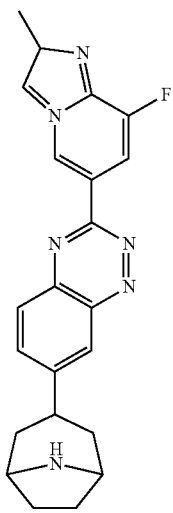 |
| 54 | 57 |
|---|---|
| 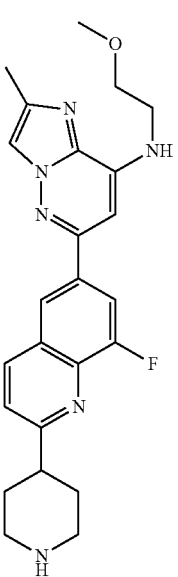 | 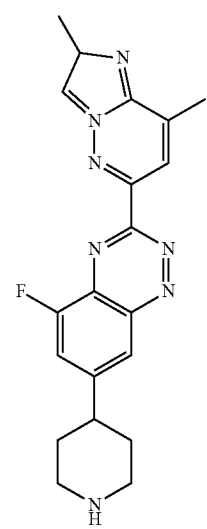 |
| 55 | 58 |
|---|---|
| 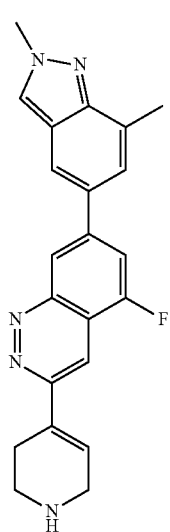 | 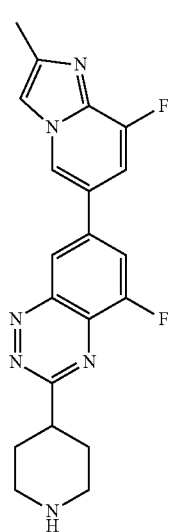 |

-continued
59
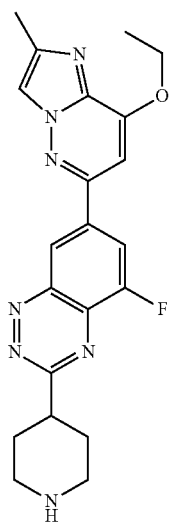
60
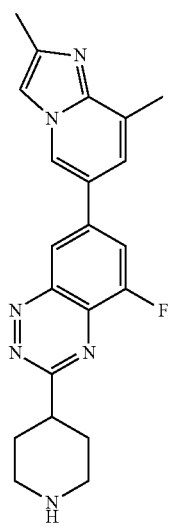
61
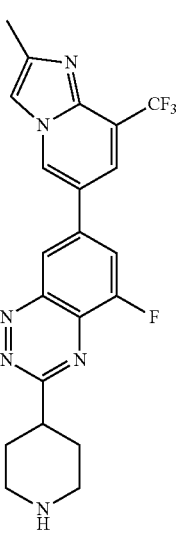
-continued
62
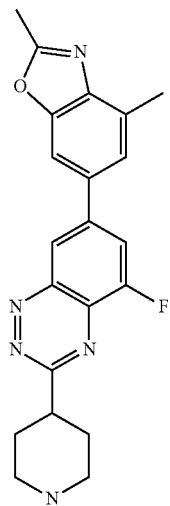
63
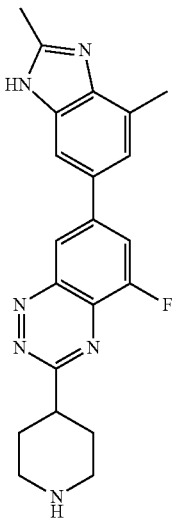
64
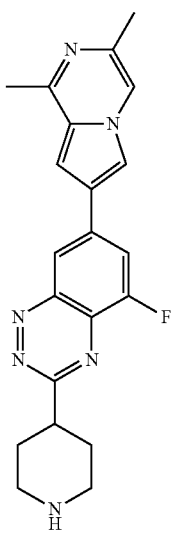

65
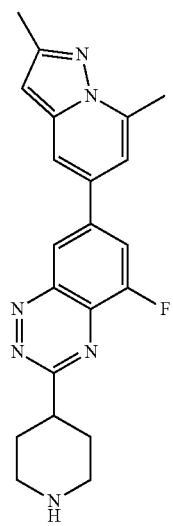
66
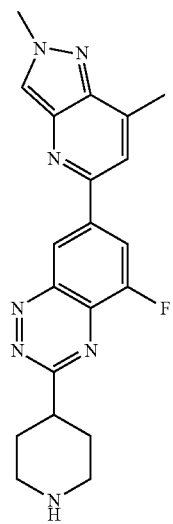
67
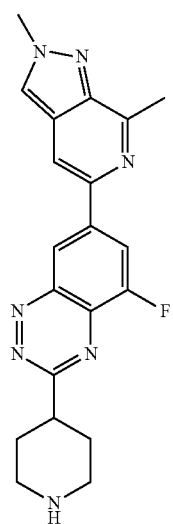
68
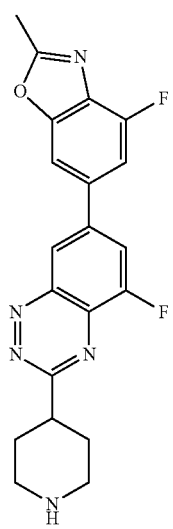
69
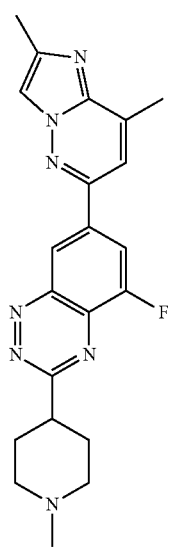
70
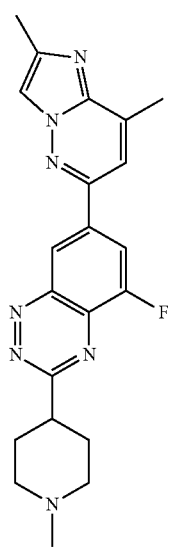

71
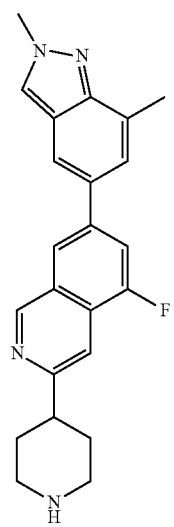
72
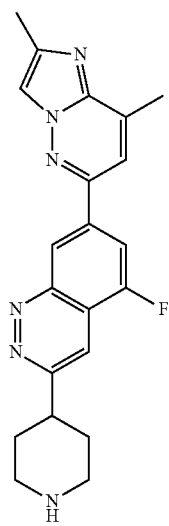
73
74
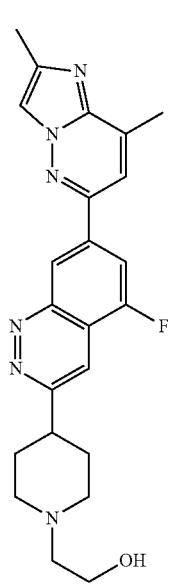
75
76
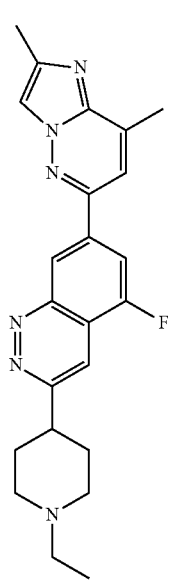

77
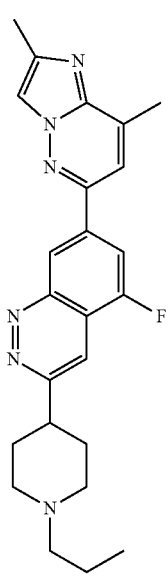
78
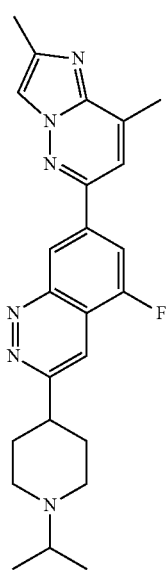
79
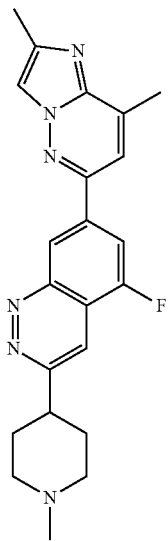
80
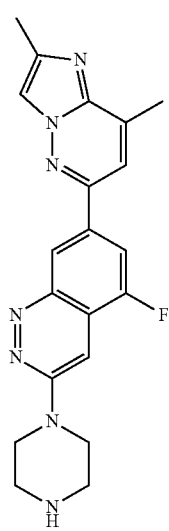
81
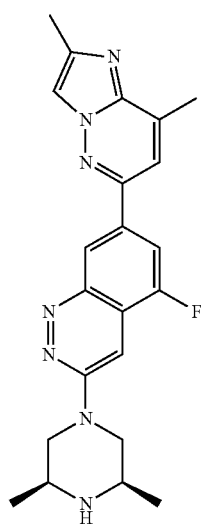
82
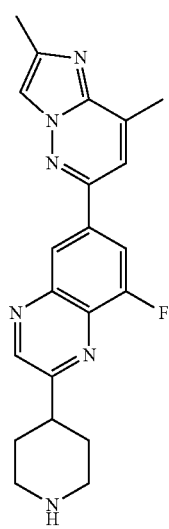

83
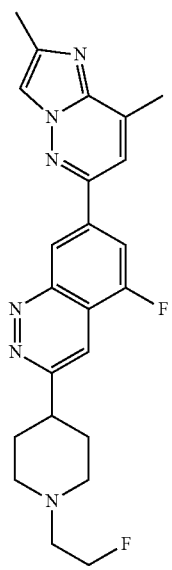
84
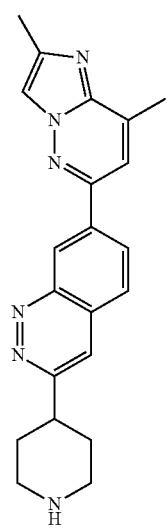
85
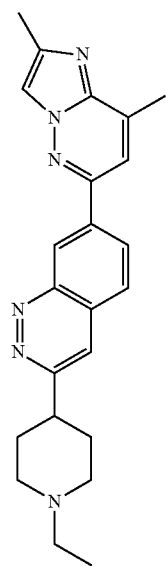
86
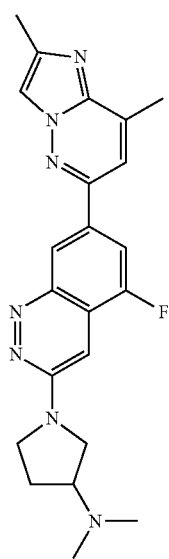
87
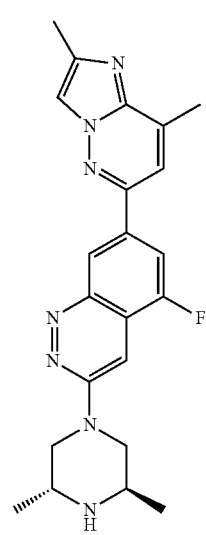
88
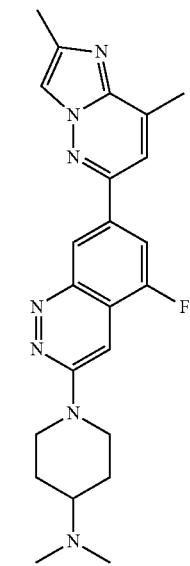

89
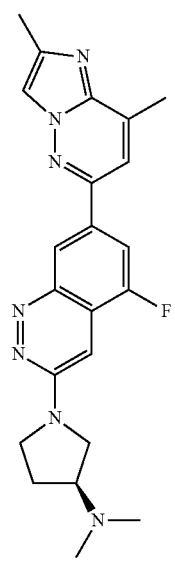
90
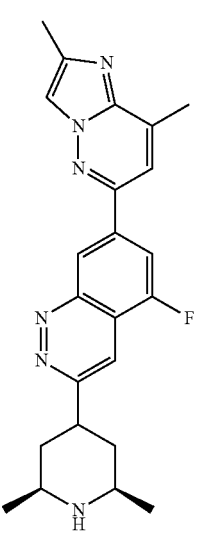
91
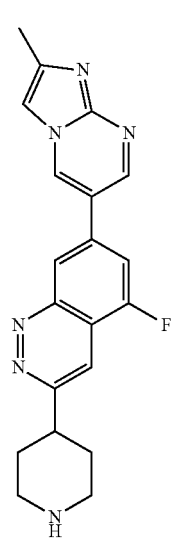
92
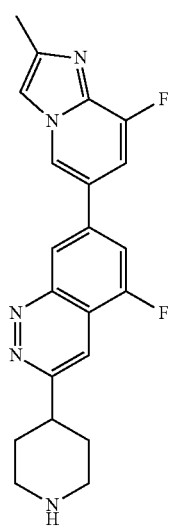
93
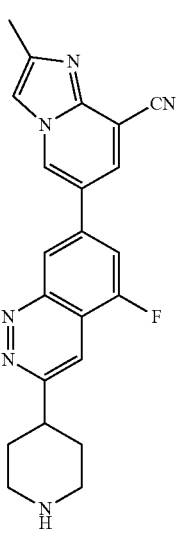
94
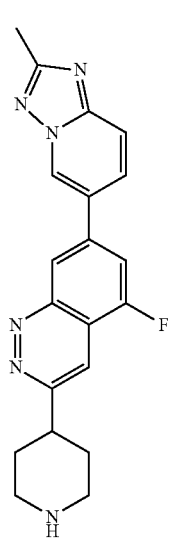

95
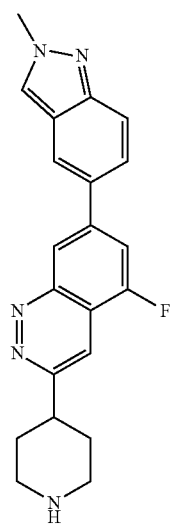
96
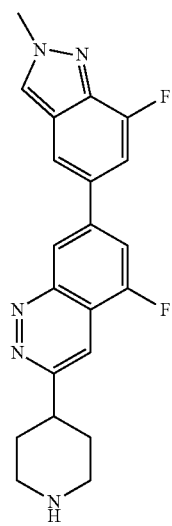
97
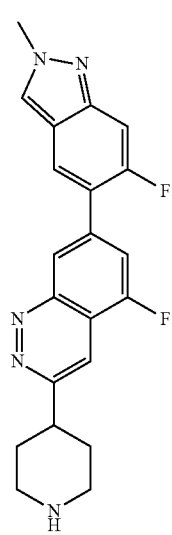
98
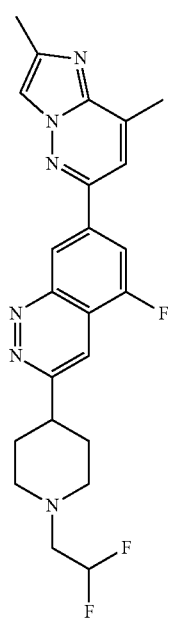
99
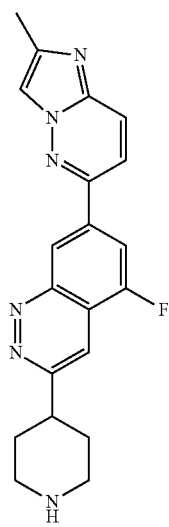

-continued
100
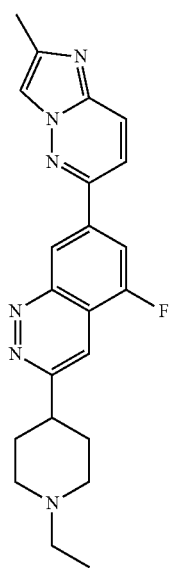
101
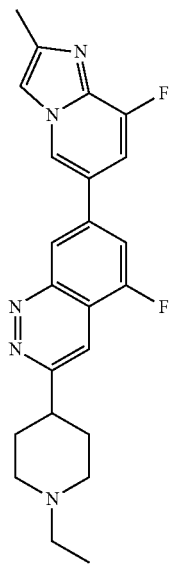
102
-continued
103
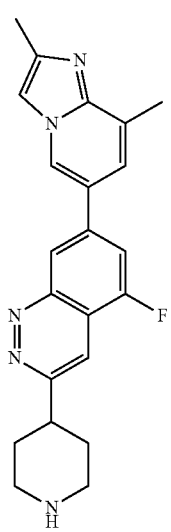
104
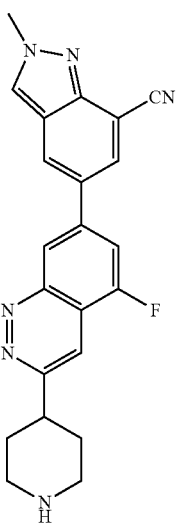
105
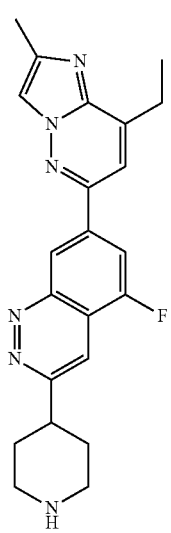

106
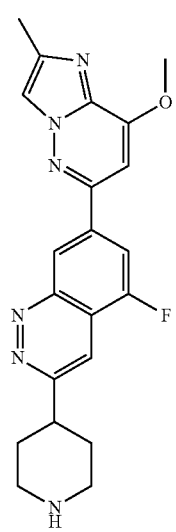
107
108
109
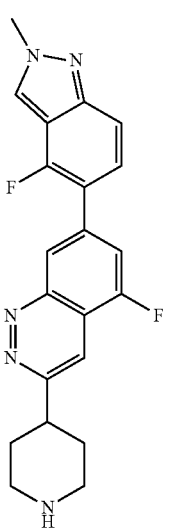
110
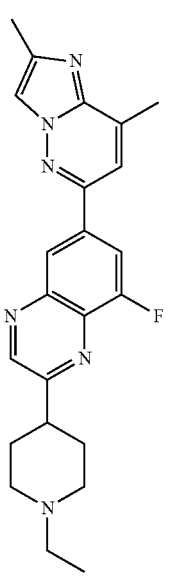
111
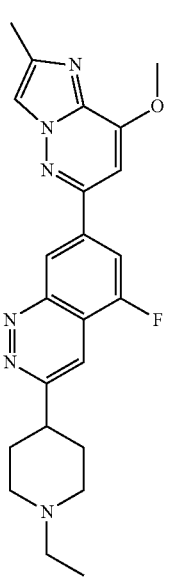

112
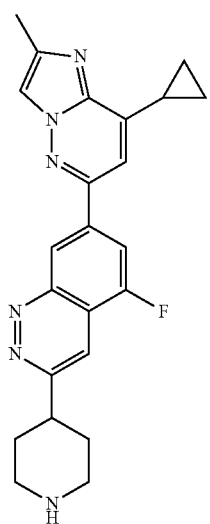
113
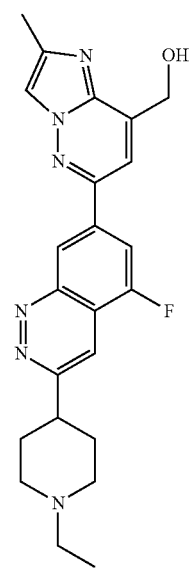
114
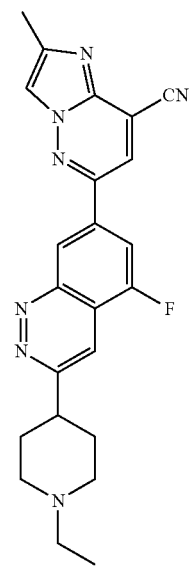
115
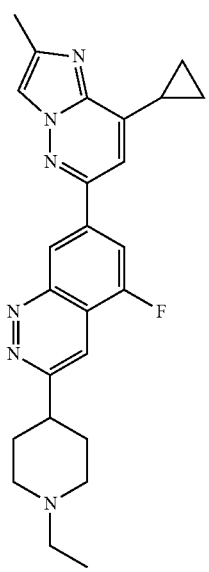
116
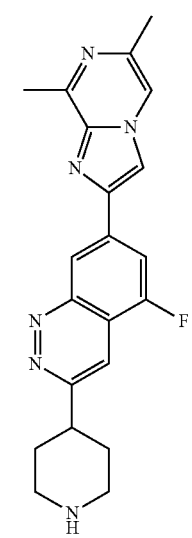
117
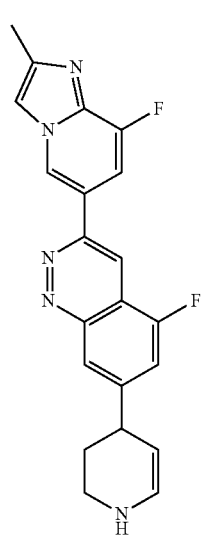

118
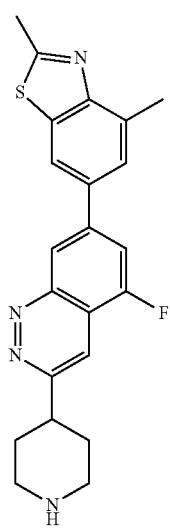
119
120
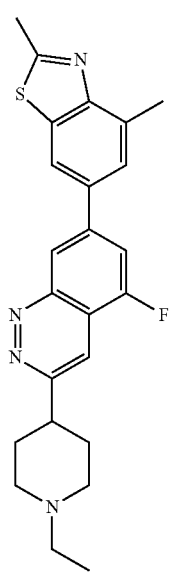
121
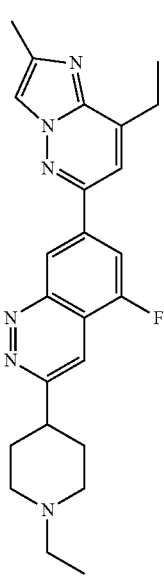
122
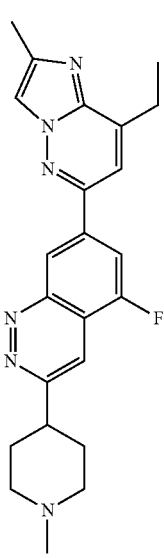

123 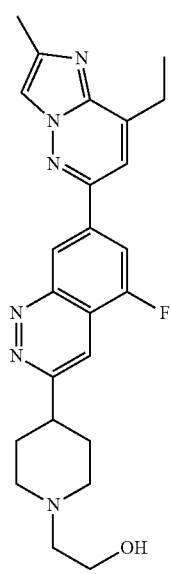
124 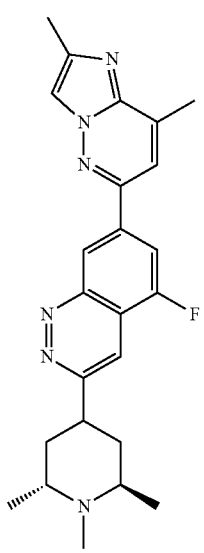
125 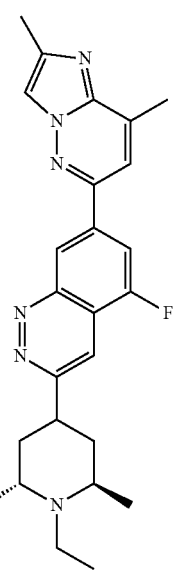
126 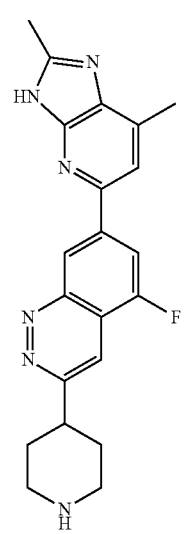
127 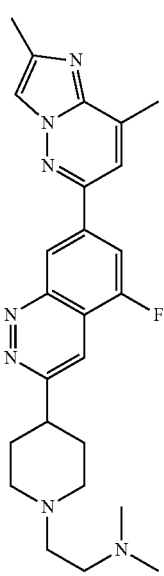

| 128 | 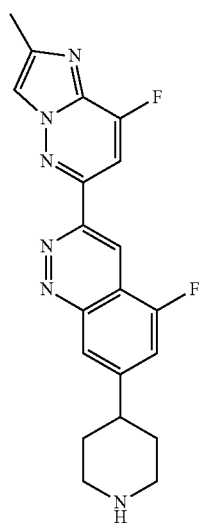 | 131 | 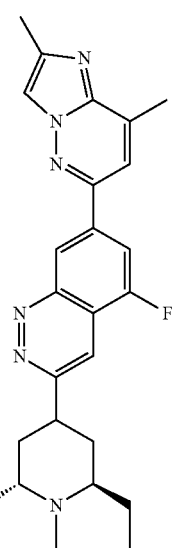 |
| 129 | 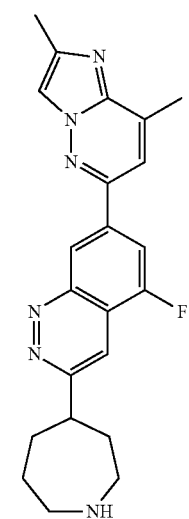 | 132 | 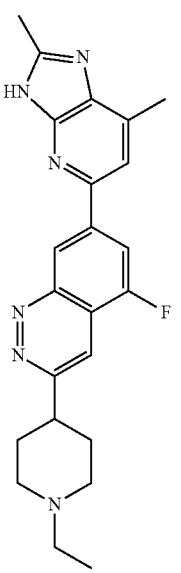 |
| 130 | 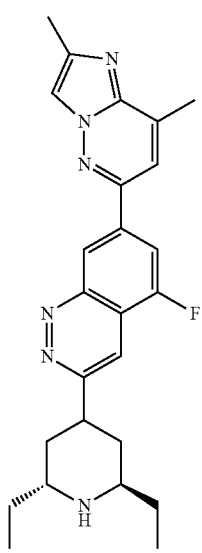 | 133 | 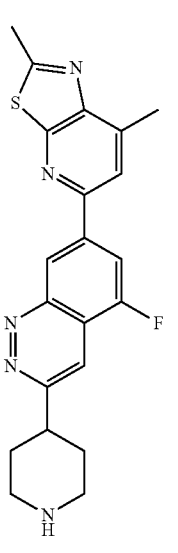 |

134
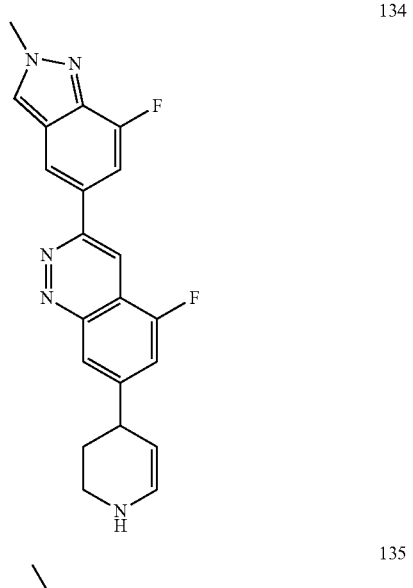
135
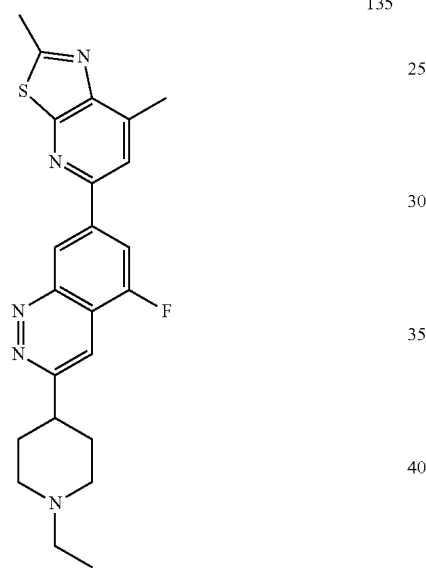
136
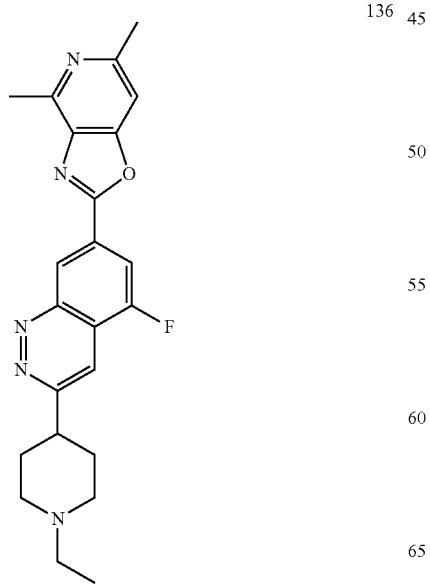
137
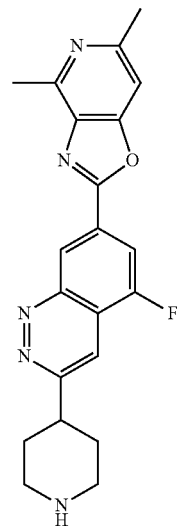
138
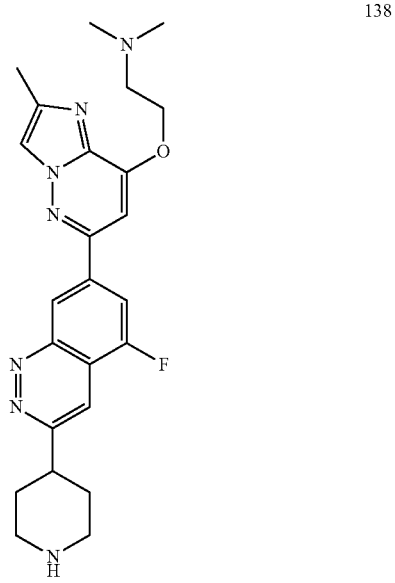

| 69 | 70 |
|---|---|
| 139 | 141 |
| 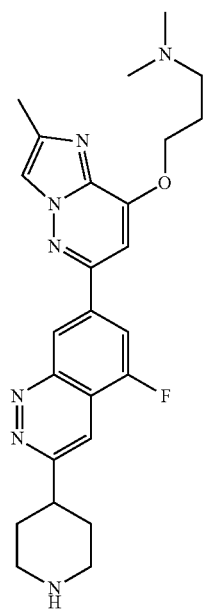 | 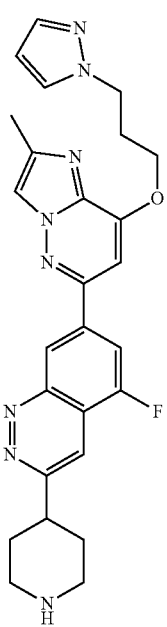 |
| 140 | 142 |

143
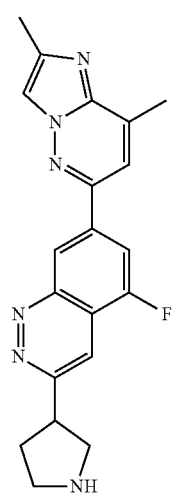
144
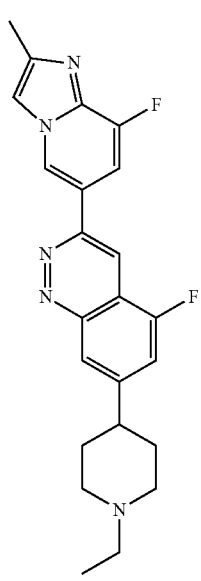
145
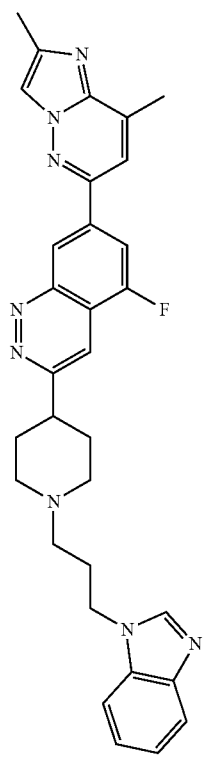
146
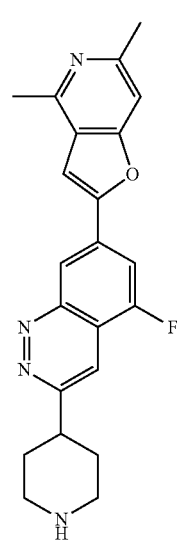

147
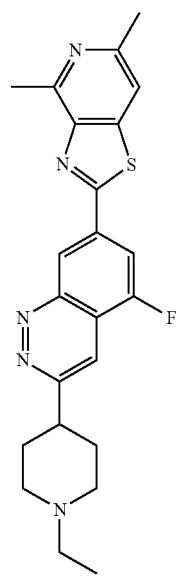
148
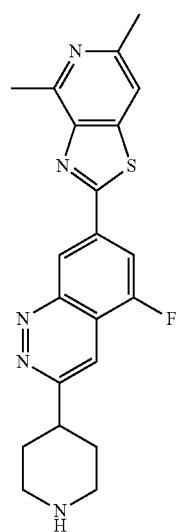
149
150
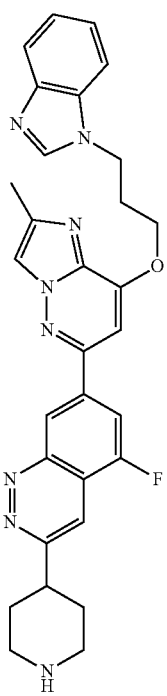
151
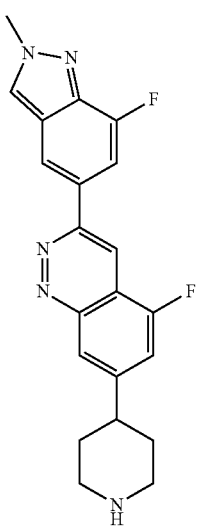

75
-continued
152
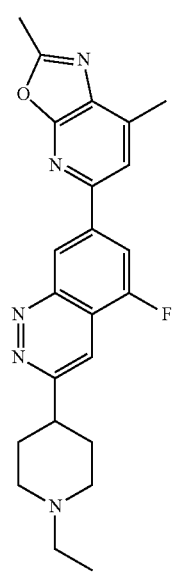
153
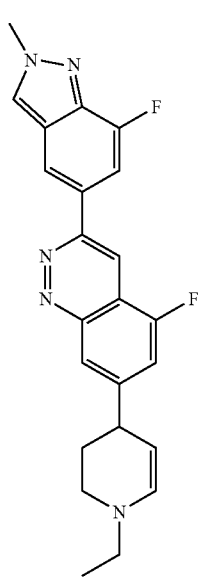
76
-continued
154
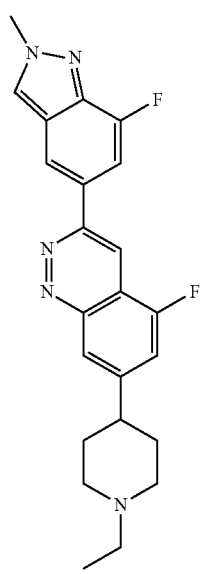
155
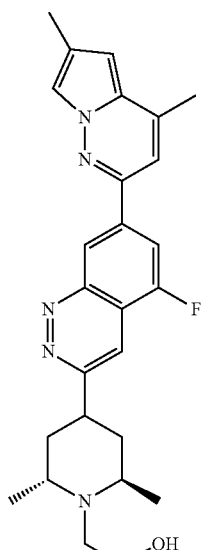
156
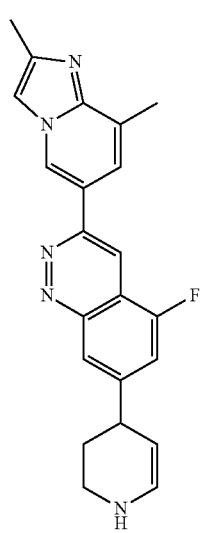

157
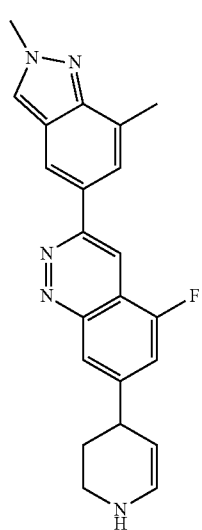
158
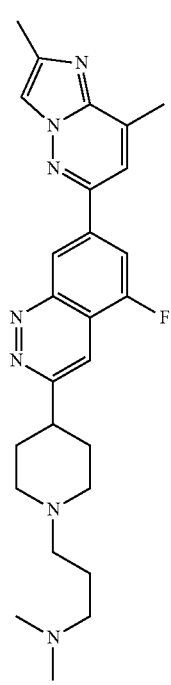
159
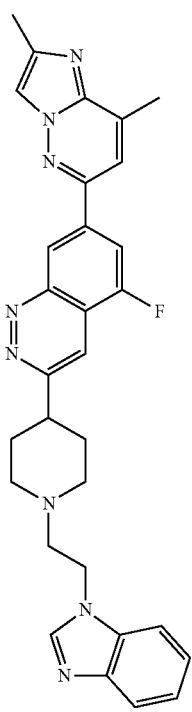
160
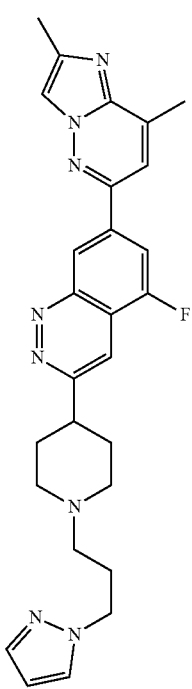

161
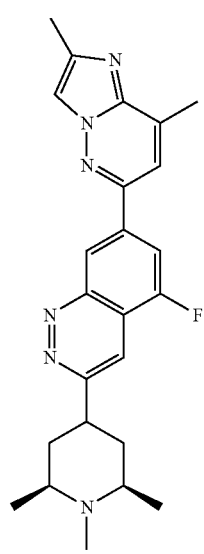
162
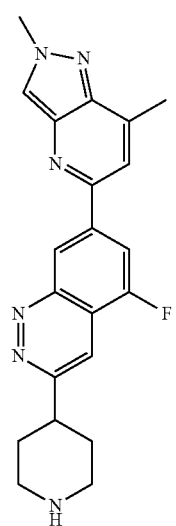
163
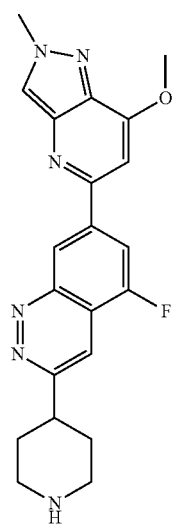
164
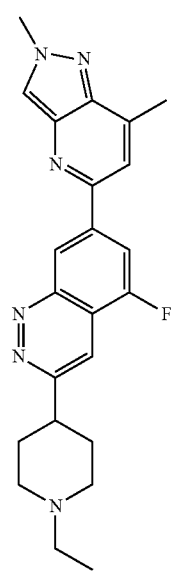
165
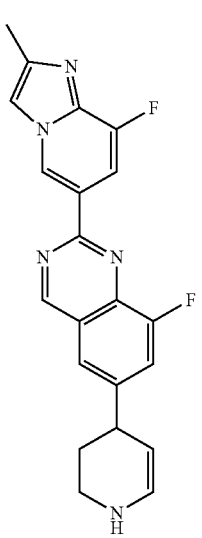
166
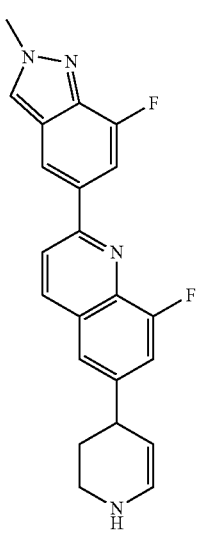

167
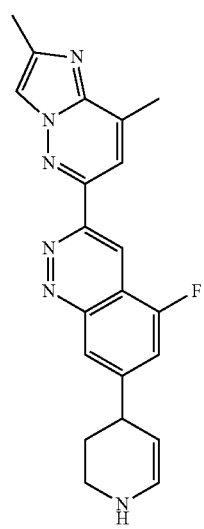
168
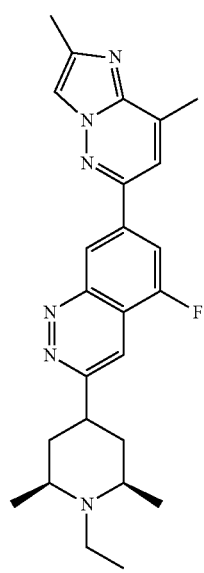
169
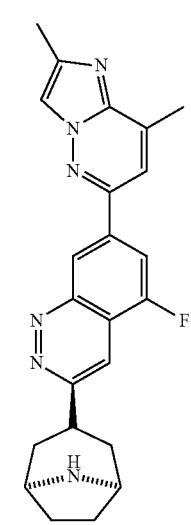
170
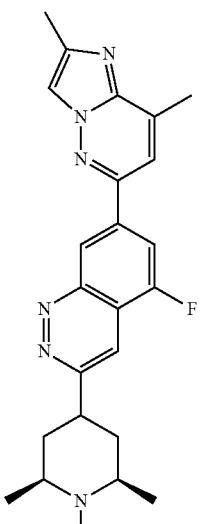
171
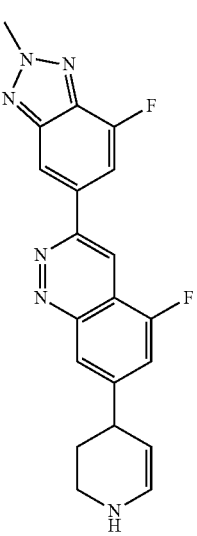
172
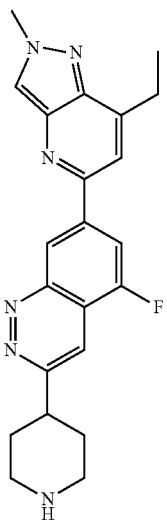

173
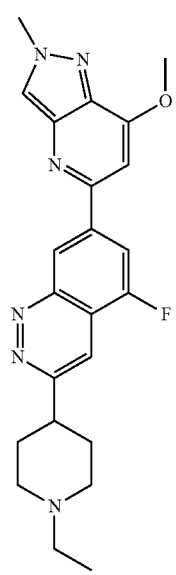
174
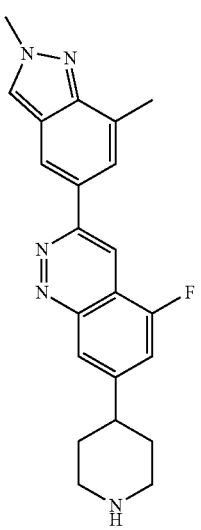
175
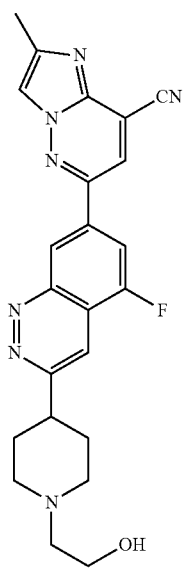
176
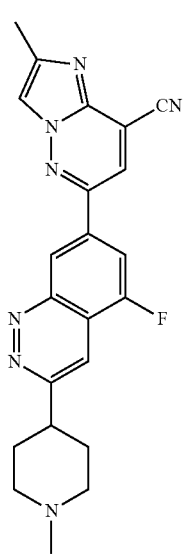
177
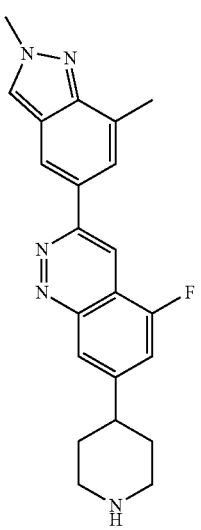
178
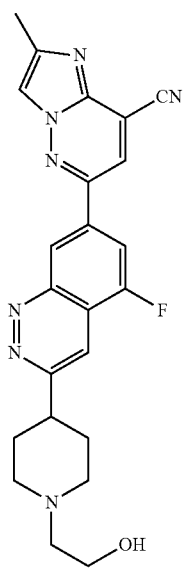

179
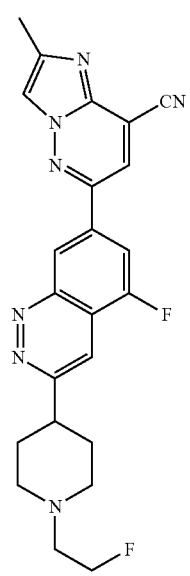
180
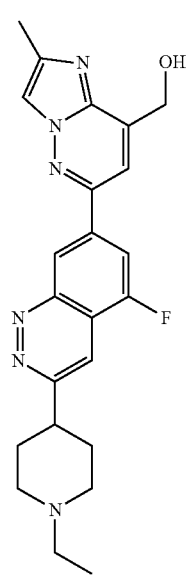
181
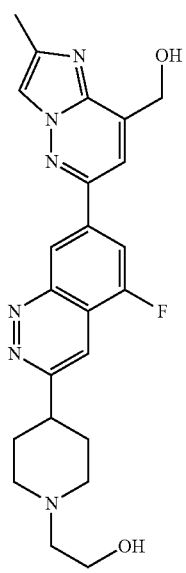
182
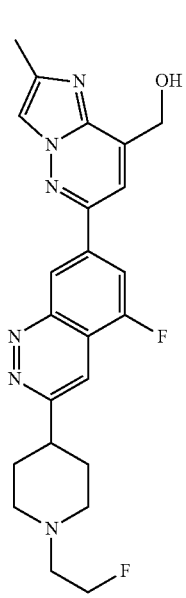

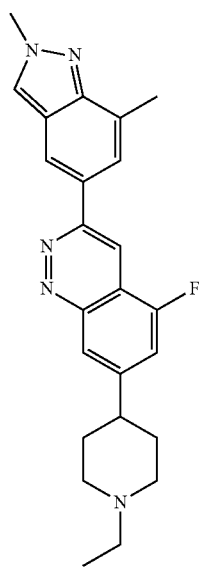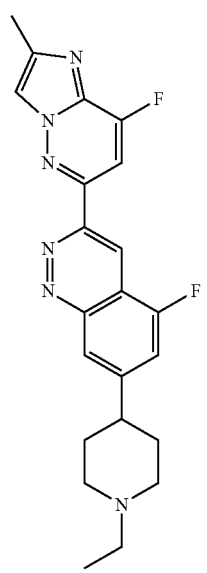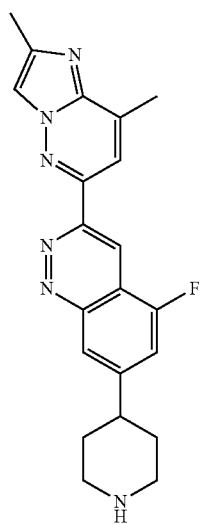

89
-continued
189
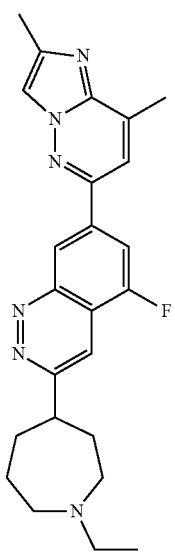
190
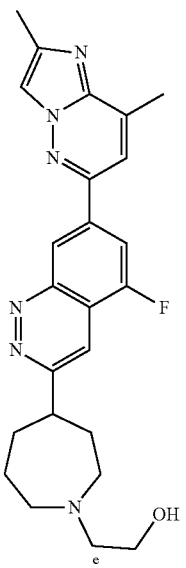
191
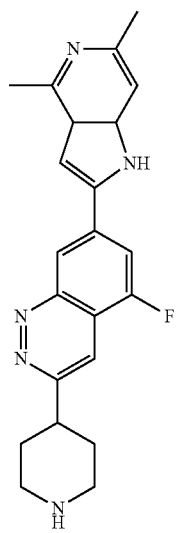
90
-continued
192
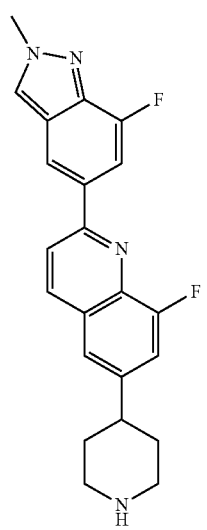
193
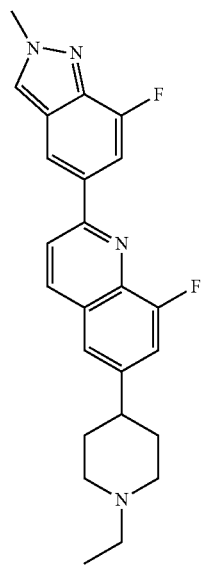
194

195 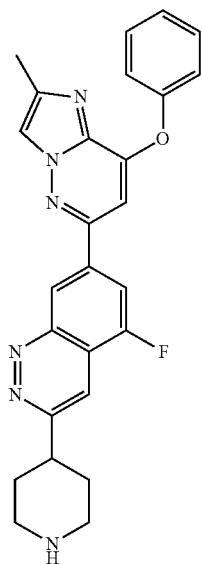
196 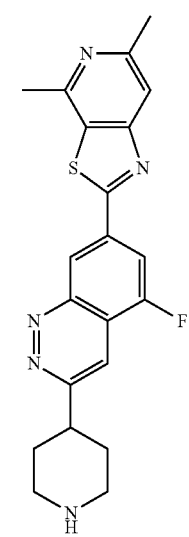
197 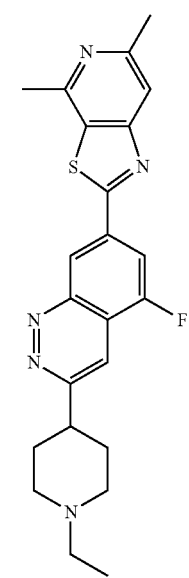
198 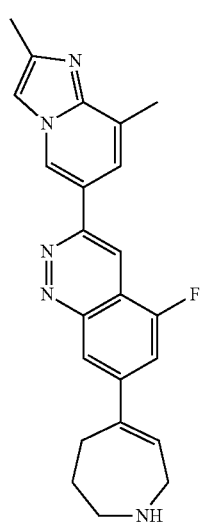
199 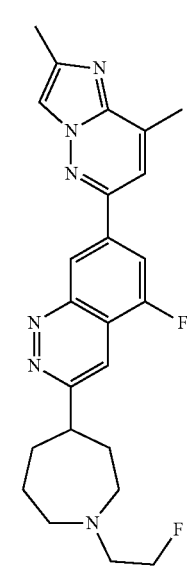

200
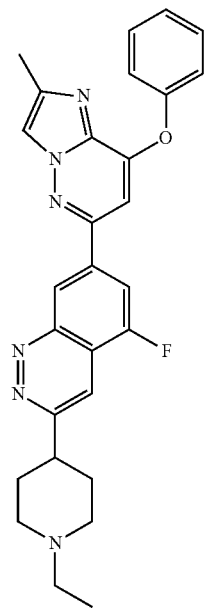
201
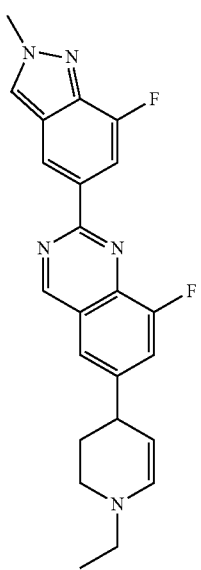
202
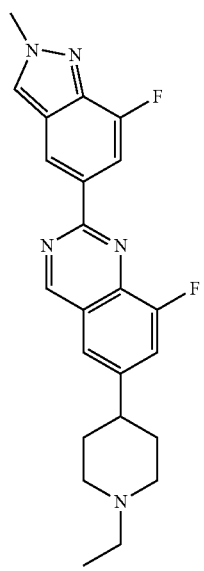
203
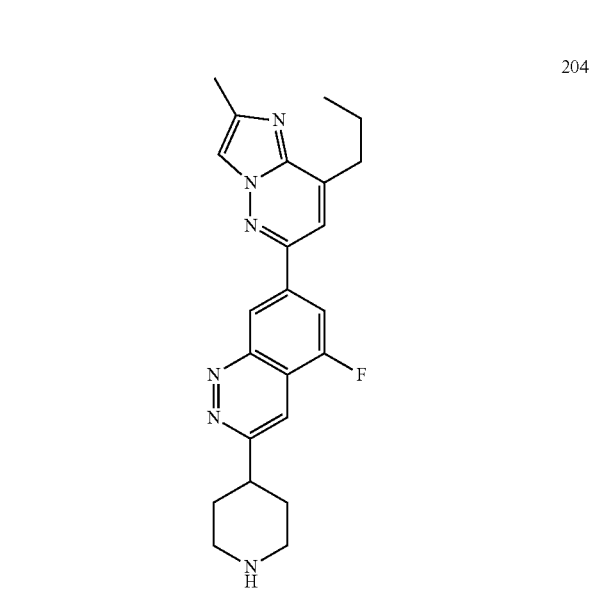
204

| 205 | 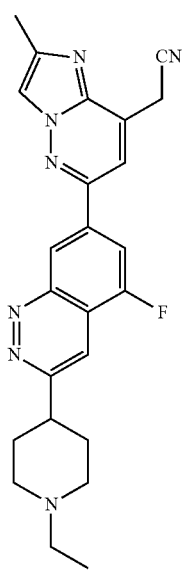 | 208 | 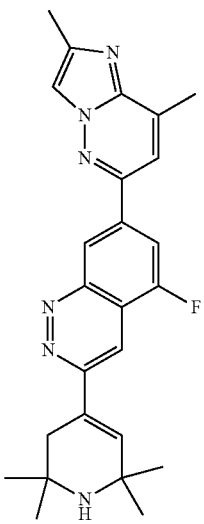 |
| --- | --- | --- | --- |
| 206 | 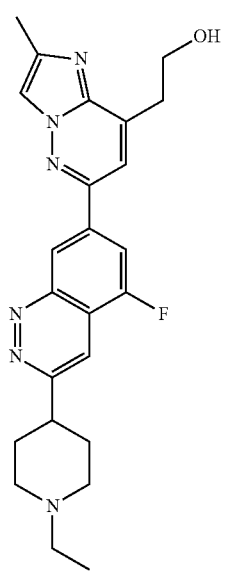 | 209 | 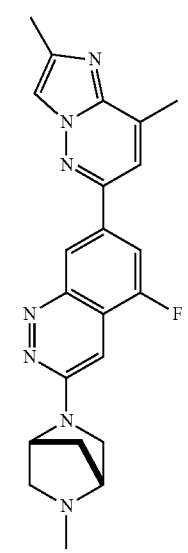 |
| 207 | 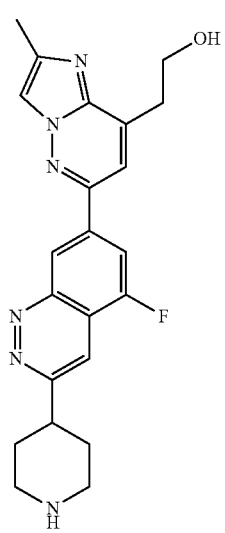 | 210 | 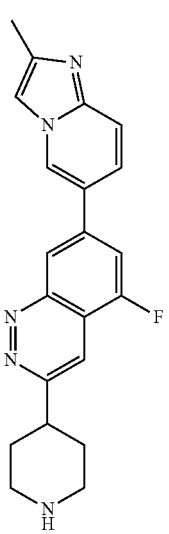 |

| 211 | 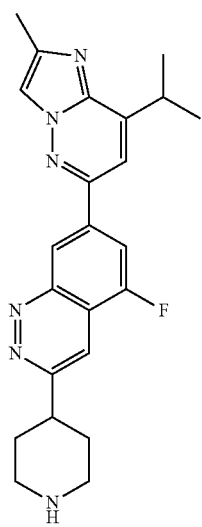 |
| --- | --- |
| 212 | 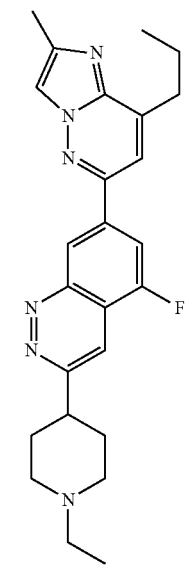 |
| 213 | 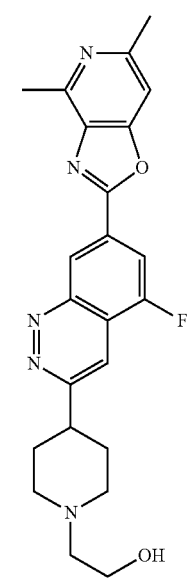 |
| 214 | 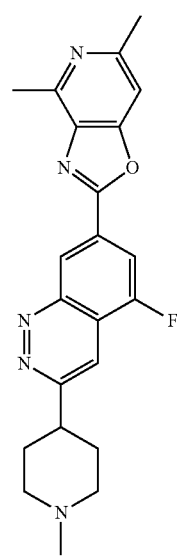 |
| 215 | 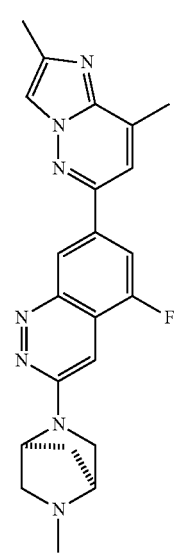 |
| 216 | 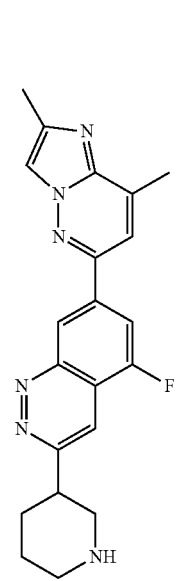 |

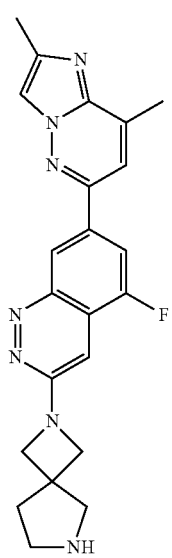
217
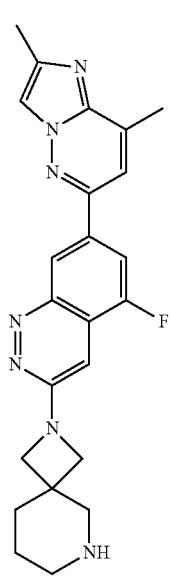
218
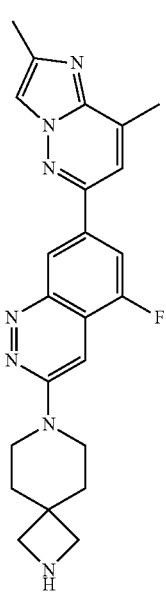
219
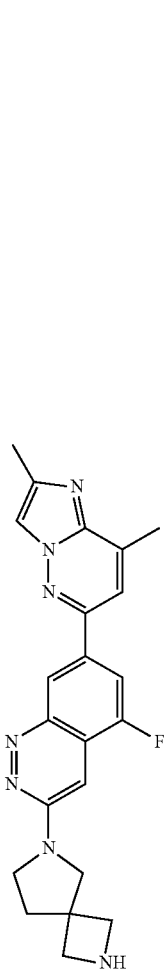
220

221
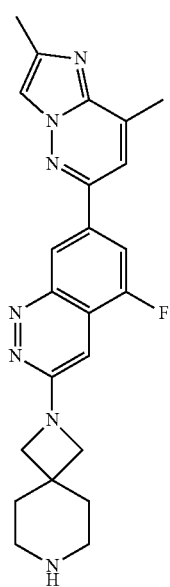
222
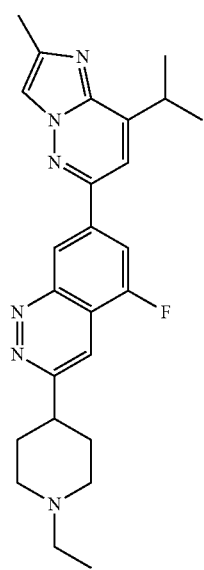
223
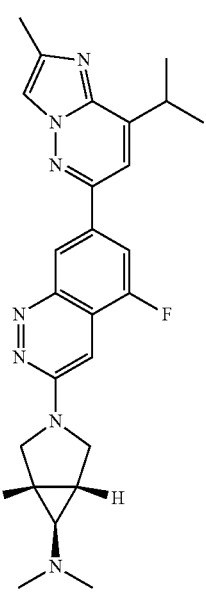
224
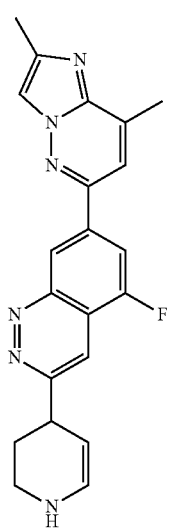
225

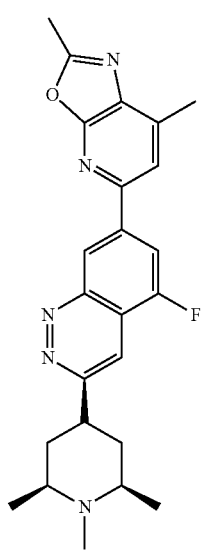

226

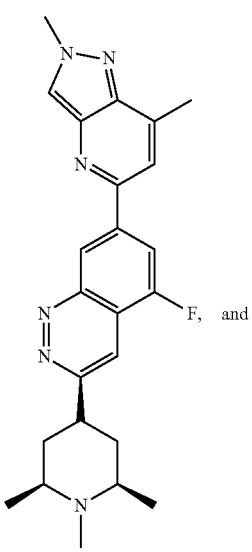

227

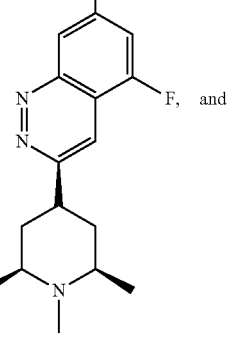

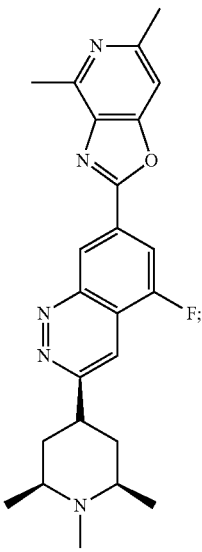

228 wherein the form of the compound is selected from the group consisting of a salt, prodrug, hydrate, solvate, clathrate, isotopologue, racemate, enantiomer, diastereomer, stereoisomer, polymorph and tautomer form thereof.

An aspect the compound of Formula (I) or a form thereof (wherein compound number (#1) indicates that the salt form was isolated) includes a compound selected from the group consisting of:

| Cpd | Name |
|---|---|
| 1[1] | 2-(2-methyl-2H-indazol-5-yl)-6-(piperidin-4-yl)quinoline |
| 2[1] | 6-(1-ethylpiperidin-4-yl)-2-(2-methyl-2H-indazol-5-yl)quinoline |
| 3[1] | 6-(2-methyl-2H-indazol-5-yl)-2-(piperidin-4-yl)quinolone |
| 4[1] | 3-(2-methyl-2H-indazol-5-yl)-7-(1,2,3,6-tetrahydropyridin-4-yl)cinnoline |
| 5[1] | 4-methyl-6-(2-methyl-2H-indazol-5-yl)-2-(piperidin-4-yl)quinoline |
| 6[1] | 6-(2-methyl-2H-indazol-5-yl)-2-(1-methylpiperidin-4-yl)quinoline |
| 7 | 2-(2-methyl-2H-indazol-5-yl)-6-(piperazin-1-yl)quinoline |
| 9[1] | 2-(1-ethylpiperidin-4-yl)-6-(2-methyl-2H-indazol-5-yl)quinoline |
| 10[1] | 2-(2-methyl-2H-indazol-5-yl)-6-(piperidin-4-yl)quinazoline |
| 11 | 6-(2,7-dimethyl-2H-indazol-5-yl)-N-methyl-N-(2,2,6,6-tetramethylpiperidin-4-yl)quinolin-2-amine |
| 12 | N-methyl-6-(2-methyl-2H-indazol-5-yl)-N-(2,2,6,6-tetramethylpiperidin-4-yl)quinolin-2-amine |
| 13 | 6-(2,7-dimethyl-2H-indazol-5-yl)-2-(2,2,6,6-tetramethyl-1,2,3,6-tetrahydropyridin-4-yl)quinoline |
| 14 | 6-(2,7-dimethyl-2H-indazol-5-yl)-2-(2,2,6,6-tetramethylpiperidin-4-yl)quinoline |
| 15 | 6-(2,7-dimethyl-2H-indazol-5-yl)-2-(piperidin-4-yl)quinoline |
| 16 | 7-(2,7-dimethyl-2H-indazol-5-yl)-3-(piperidin-4-yl)-1,2,4-benzotriazine |
| 17 | 3-(2,7-dimethyl-2H-indazol-5-yl)-7-(piperidin-4-yl)-1,2,4-benzotriazine |
| 18 | 6-(2,8-dimethylimidazo[1,2-a]pyrazin-6-yl)-2-(piperidin-4-yl)quinoline |
| 19 | 6-(2,8-dimethylimidazo[1,2-b]pyridazin-6-yl)-2-(piperidin-4-yl)quinoline |
| 20 | 6-(2,7-dimethyl-2H-indazol-5-yl)-8-fluoro-2-(piperidin-4-yl)quinoline |
| 23 | 6-(2,7-dimethyl-2H-indazol-5-yl)-2-(piperidin-4-yl)quinazoline |

-continued

| Cpd | Name |
|---|---|
| 24[1] | 6-[2-methyl-7-(trifluoromethyl)-2H-indazol-5-yl]-2-(piperidin-4-yl)quinoxaline |
| 25[1] | 3-(7-fluoro-2-methyl-2H-indazol-5-yl)-7-(piperidin-4-yl)-1,2,4-benzotriazine |
| 26 | 2-methyl-5-[7-(piperidin-4-yl)-1,2,4-benzotriazin-3-yl]-2H-indazole-7-carbonitrile |
| 27 | 3-(2,8-dimethylimidazo[1,2-a]pyridin-6-yl)-7-(piperidin-4-yl)-1,2,4-benzotriazine |
| 28 | 3-(1,3-dimethylpyrrolo[1,2-a]pyrazin-7-yl)-7-(piperidin-4-yl)-1,2,4-benzotriazine |
| 29 | 3-(2,7-dimethyl-2H-indazol-5-yl)-7-(piperidin-4-yl)quinoline |
| 30 | 7-(2,7-dimethyl-2H-indazol-5-yl)-3-(piperidin-4-yl)isoquinoline |
| 31[1] | 6-(2,7-dimethyl-2H-indazol-5-yl)-2-(piperidin-4-yl)quinoxaline |
| 32 | 5-fluoro-7-(7-fluoro-2-methyl-2H-indazol-5-yl)-3-(piperidin-4-yl)-1,2,4-benzotriazine |
| 33 | 7-(2,7-dimethyl-2H-indazol-5-yl)-5-fluoro-3-(piperidin-4-yl)-1,2,4-benzotriazine |
| 34[1] | 6-(2,7-dimethyl-2H-indazol-5-yl)-8-fluoro-2-(piperidin-4-yl)quinazoline |
| 35[1] | 5-[8-fluoro-2-(piperidin-4-yl)quinazolin-6-yl]-2-methyl-2H-indazole-7-carbonitrile |
| 36[1] | 8-fluoro-6-(7-fluoro-2-methyl-2H-indazol-5-yl)-2-(piperidin-4-yl)quinazoline |
| 37[1] | 6-(2,8-dimethylimidazo[1,2-b]pyridazin-6-yl)-8-fluoro-2-(piperidin-4-yl)quinazoline |
| 38[1] | 6-(2,7-dimethyl-2H-indazol-5-yl)-5-fluoro-2-(piperidin-4-yl)quinazoline |
| 39[1] | 6-(2,7-dimethyl-2H-indazol-5-yl)-7-fluoro-2-(piperidin-4-yl)quinazoline |
| 40 | 3-(2,8-dimethylimidazo[1,2-a]pyridin-6-yl)-5-fluoro-7-(piperidin-4-yl)-1,2,4-benzotriazine |
| 41 | 5-fluoro-3-(8-fluoro-2-methylimidazo[1,2-a]pyridin-6-yl)-7-(piperidin-4-yl)-1,2,4-benzotriazine |
| 42 | 7-(2,7-dimethyl-2H-indazol-5-yl)-5-fluoro-N-methyl-N-(piperidin-4-yl)-1,2,4-benzotriazin-3-amine |
| 43 | 3-(8-fluoro-2-methylimidazo[1,2-a]pyridin-6-yl)-7-(piperidin-4-yl)-1,2,4-benzotriazine |
| 44 | 3-(2,8-dimethylimidazo[1,2-b]pyridazin-6-yl)-7-(piperidin-4-yl)-1,2,4-benzotriazine |
| 45[1] | 6-(2,8-dimethylimidazo[1,2-b]pyridazin-6-yl)-8-fluoro-2-(piperidin-4-yl)quinoline |
| 46 | 7-(2,8-dimethylimidazo[1,2-b]pyridazin-6-yl)-5-fluoro-3-(piperidin-4-yl)-1,2,4-benzotriazine |
| 47[1] | 6-(2,8-dimethylimidazo[1,2-b]pyridazin-6-yl)-8-fluoro-2-(1-methylpiperidin-4-yl)quinoline |
| 48[1] | 6-(2,8-dimethylimidazo[1,2-b]pyridazin-6-yl)-2-(1-ethylpiperidin-4-yl)-8-fluoroquinoline |
| 49[1] | 8-fluoro-6-(7-methoxy-2-methyl-2H-indazol-5-yl)-2-(piperidin-4-yl)quinoline |
| 50[1] | 8-fluoro-6-(8-fluoro-2-methylimidazo[1,2-a]pyridin-6-yl)-2-(piperidin-4-yl)quinoline |
| 51[1] | 8-fluoro-6-(8-methoxy-2-methylimidazo[1,2-b]pyridazin-6-yl)-2-(piperidin-4-yl)quinoline |
| 52 | 3-(7-methoxy-2-methyl-2H-indazol-5-yl)-7-(piperidin-4-yl)-1,2,4-benzotriazine |
| 53[1] | 8-fluoro-6-[8-(2-methoxyethoxy)-2-methylimidazo[1,2-b]pyridazin-6-yl]-2-(piperidin-4-yl)quinoline |
| 54[1] | 6-[8-fluoro-2-(piperidin-4-yl)quinolin-6-yl]-N-(2-methoxyethyl)-2-methylimidazo[1,2-b]pyridazin-8-amine |
| 55[1] | 7-(2,7-dimethyl-2H-indazol-5-yl)-5-fluoro-3-(1,2,3,6-tetrahydropyridin-4-yl)cinnoline |
| 56[1] | 7-(8-azabicyclo[3.2.1]oct-3-yl)-3-(8-fluoro-2-methylimidazo[1,2-a]pyridin-6-yl)-1,2,4-benzotriazine |
| 57[1] | 3-(2,8-dimethylimidazo[1,2-b]pyridazin-6-yl)-5-fluoro-7-(piperidin-4-yl)-1,2,4-benzotriazine |
| 58[1] | 5-fluoro-7-(8-fluoro-2-methylimidazo[1,2-a]pyridin-6-yl)-3-(piperidin-4-yl)-1,2,4-benzotriazine |
| 59[1] | 7-(8-ethoxy-2-methylimidazo[1,2-b]pyridazin-6-yl)-5-fluoro-3-(piperidin-4-yl)-1,2,4-benzotriazine |
| 60[1] | 7-(2,8-dimethylimidazo[1,2-a]pyridin-6-yl)-5-fluoro-3-(piperidin-4-yl)-1,2,4-benzotriazine |
| 61[1] | 5-fluoro-7-[2-methyl-8-(trifluoromethyl)imidazo[1,2-a]pyridin-6-yl]-3-(piperidin-4-yl)-1,2,4-benzotriazine |
| 62[1] | 7-(2,4-dimethyl-1,3-benzoxazol-6-yl)-5-fluoro-3-(piperidin-4-yl)-1,2,4-benzotriazine |
| 63[1] | 7-(2,4-dimethyl-1H-benzimidazol-6-yl)-5-fluoro-3-(piperidin-4-yl)-1,2,4-benzotriazine |
| 64[1] | 7-(1,3-dimethylpyrrolo[1,2-a]pyrazin-7-yl)-5-fluoro-3-(piperidin-4-yl)-1,2,4-benzotriazine |
| 65[1] | 7-(2,7-dimethylpyrazolo[1,5-a]pyridin-5-yl)-5-fluoro-3-(piperidin-4-yl)-1,2,4-benzotriazine |
| 66[1] | 7-(2,7-dimethyl-2H-pyrazolo[4,3-b]pyridin-5-yl)-5-fluoro-3-(piperidin-4-yl)-1,2,4-benzotriazine |
| 67[1] | 7-(2,7-dimethyl-2H-pyrazolo[3,4-c]pyridin-5-yl)-5-fluoro-3-(piperidin-4-yl)-1,2,4-benzotriazine |
| 68 | 5-fluoro-7-(4-fluoro-2-methyl-1,3-benzoxazol-6-yl)-3-(piperidin-4-yl)-1,2,4-benzotriazine |
| 69[1] | 7-(2,8-dimethylimidazo[1,2-b]pyridazin-6-yl)-5-fluoro-3-(1-methylpiperidin-4-yl)-1,2,4-benzotriazine |
| 70 | 7-(2,8-dimethylimidazo[1,2-b]pyridazin-6-yl)-3-(1-ethylpiperidin-4-yl)-5-fluoro-1,2,4-benzotriazine |
| 71[1] | 7-(2,7-dimethyl-2H-indazol-5-yl)-5-fluoro-3-(piperidin-4-yl)isoquinoline |
| 72[1] | 7-(2,8-dimethylimidazo[1,2-b]pyridazin-6-yl)-5-fluoro-3-(piperidin-4-yl)isoquinoline |
| 73[1] | 7-(2,7-dimethyl-2H-indazol-5-yl)-5-fluoro-3-(piperidin-4-yl)cinnoline |
| 74[1] | 7-(2,8-dimethylimidazo[1,2-b]pyridazin-6-yl)-5-fluoro-3-(piperidin-4-yl)cinnoline |
| 75 | 2-{4-[7-(2,8-dimethylimidazo[1,2-b]pyridazin-6-yl)-5-fluorocinnolin-3-yl]piperidin-1-yl}ethanol |
| 76 | 7-(2,8-dimethylimidazo[1,2-b]pyridazin-6-yl)-3-(1-ethylpiperidin-4-yl)-5-fluorocinnoline |

-continued

| Cpd | Name |
|---|---|
| 77 | 7-(2,8-dimethylimidazo[1,2-b]pyridazin-6-yl)-5-fluoro-3-(l-propylpiperidin-4-yl)cinnoline |
| 78 | 7-(2,8-dimethylimidazo[1,2-b]pyridazin-6-yl)-5-fluoro-3-[1-(propan-2-yl)piperidin-4-yl]cinnoline |
| 79 | 7-(2,8-dimethylimidazo[1,2-b]pyridazin-6-yl)-5-fluoro-3-(1-methylpiperidin-4-yl)cinnoline |
| 80[1] | 7-(2,8-dimethylimidazo[1,2-b]pyridazin-6-yl)-5-fluoro-3-(piperazin-1-yl)cinnoline |
| 81[1] | 7-(2,8-dimethylimidazo[1,2-b]pyridazin-6-yl)-3-[(3R,5S)-3,5-dimethylpiperazin-1-yl]-5-fluorocinnoline |
| 82 | 6-(2,8-dimethylimidazo[1,2-b]pyridazin-6-yl)-8-fluoro-2-(piperidin-4-yl)quinoxaline |
| 83[1] | 7-(2,8-dimethylimidazo[1,2-b]pyridazin-6-yl)-5-fluoro-3-[1-(2-fluoroethyl)piperidin-4-yl]cinnoline |
| 84[1] | 7-(2,8-dimethylimidazo[1,2-b]pyridazin-6-yl)-3-(piperidin-4-yl)cinnoline |
| 85 | 7-(2,8-dimethylimidazo[1,2-b]pyridazin-6-yl)-3-(1-ethylpiperidin-4-yl)cinnoline |
| 86 | 1-[7-(2,8-dimethylimidazo[1,2-b]pyridazin-6-yl)-5-fluorocinnolin-3-yl]-N,N-dimethylpyrrolidin-3-amine |
| 87[1] | 7-(2,8-dimethylimidazo[1,2-b]pyridazin-6-yl)-3-[(2S,6S)-2,6-dimethylpiperidin-4-yl]-5-fluorocinnoline |
| 88 | 1-[7-(2,8-dimethylimidazo[1,2-b]pyridazin-6-yl)-5-fluorocinnolin-3-yl]-N,N-dimethylpiperidin-4-amine |
| 89 | (3R)-1-[7-(2,8-dimethylimidazo[1,2-b]pyridazin-6-yl)-5-fluorocinnolin-3-yl]-N,N-dimethylpyrrolidin-3-amine |
| 90 | 7-(2,8-dimethylimidazo[1,2-b]pyridazin-6-yl)-3-[(2R,4r,6S)-2,6-dimethylpiperidin-4-yl]-5-fluorocinnoline |
| 91[1] | 5-fluoro-7-(2-methylimidazo[1,2-a]pyrimidin-6-yl)-3-(piperidin-4-yl)cinnoline |
| 92[1] | 5-fluoro-7-(8-fluoro-2-methylimidazo[1,2-a]pyridin-6-yl)-3-(piperidin-4-yl)cinnoline |
| 93[1] | 6-[5-fluoro-3-(piperidin-4-yl)cinnolin-7-yl]-2-methylimidazo[1,2-a]pyridine-8-carbonitrile |
| 94[1] | 5-fluoro-7-(2-methyl[1,2,4]triazolo[1,5-a]pyridin-6-yl)-3-(piperidin-4-yl)cinnoline |
| 95[1] | 5-fluoro-7-(2-methyl-2H-indazol-5-yl)-3-(piperidin-4-yl)cinnoline |
| 96[1] | 5-fluoro-7-(7-fluoro-2-methyl-2H-indazol-5-yl)-3-(piperidin-4-yl)cinnoline |
| 97[1] | 5-fluoro-7-(6-fluoro-2-methyl-2H-indazol-5-yl)-3-(piperidin-4-yl)cinnoline |
| 98[1] | 3-[1-(2,2-difluoroethyl)piperidin-4-yl]-7-(2,8-dimethylimidazo[1,2-b]pyridazin-6-yl)-5-fluorocinnoline |
| 99[1] | 5-fluoro-7-(2-methylimidazo[1,2-b]pyridazin-6-yl)-3-(piperidin-4-yl)cinnoline |
| 100[1] | 3-(1-ethylpiperidin-4-yl)-5-fluoro-7-(2-methylimidazo[1,2-b]pyridazin-6-yl)cinnoline |
| 101[1] | 7-(1,3-dimethylpyrrolo[1,2-a]pyrazin-7-yl)-5-fluoro-3-(piperidin-4-yl)cinnoline |
| 102[1] | 3-(1-ethylpiperidin-4-yl)-5-fluoro-7-(8-fluoro-2-methylimidazo[1,2-a]pyridin-6-yl)cinnoline |
| 103[1] | 7-(2,8-dimethylimidazo[1,2-a]pyridin-6-yl)-5-fluoro-3-(piperidin-4-yl)cinnoline |
| 104[1] | 5-[5-fluoro-3-(piperidin-4-yl)cinnolin-7-yl]-2-methyl-2H-indazole-7-carbonitrile |
| 105 | 7-(8-ethyl-2-methylimidazo[1,2-b]pyridazin-6-yl)-5-fluoro-3-(piperidin-4-yl)cinnoline |
| 106 | 5-fluoro-7-(8-methoxy-2-methylimidazo[1,2-b]pyridazin-6-yl)-3-(piperidin-4-yl)cinnoline |
| 107 | {6-[5-fluoro-3-(piperidin-4-yl)cinnolin-7-yl]-2-methylimidazo[1,2-b]pyridazin-8-yl}methanol |
| 108 | 6-[5-fluoro-3-(piperidin-4-yl)cinnolin-7-yl]-2-methylimidazo[1,2-b]pyridazine-8-carbonitrile |
| 109[1] | 5-fluoro-7-(4-fluoro-2-methyl-2H-indazol-5-yl)-3-(piperidin-4-yl)cinnoline |
| 110 | 6-(2,8-dimethylimidazo[1,2-b]pyridazin-6-yl)-2-(1-ethylpiperidin-4-yl)-8-fluoroquinoxaline |
| 111 | 3-(1-ethylpiperidin-4-yl)-5-fluoro-7-(8-methoxy-2-methylimidazo[1,2-b]pyridazin-6-yl)cinnoline |
| 112 | 7-(8-cyclopropyl-2-methylimidazo[1,2-b]pyridazin-6-yl)-5-fluoro-3-(piperidin-4-yl)cinnoline |
| 113 | {6-[3-(1-ethylpiperidin-4-yl)-5-fluorocinnolin-7-yl]-2-methylimidazo[1,2-b]pyridazin-8-yl}methanol |
| 114 | 6-[3-(1-ethylpiperidin-4-yl)-5-fluorocinnolin-7-yl]-2-methylimidazo[1,2-b]pyridazine-8-carbonitrile |
| 115[1] | 7-(8-cyclopropyl-2-methylimidazo[1,2-b]pyridazin-6-yl)-3-(1-ethylpiperidin-4-yl)-5-fluorocinnoline |
| 116 | 7-(6,8-dimethylimidazo[1,2-a]pyrazin-2-yl)-5-fluoro-3-(piperidin-4-yl)cinnoline |
| 117[1] | 5-fluoro-3-(8-fluoro-2-methylimidazo[1,2-a]pyridin-6-yl)-7-(1,2,3,6-tetrahydropyridin-4-yl)cinnoline |
| 118 | 7-(2,4-dimethyl-1,3-benzothiazol-6-yl)-5-fluoro-3-(piperidin-4-yl)cinnoline |
| 119 | 7-(6,8-dimethylimidazo[1,2-a]pyrazin-2-yl)-3-(1-ethylpiperidin-4-yl)-5-fluorocinnoline |
| 120[1] | 7-(2,4-dimethyl-1,3-benzothiazol-6-yl)-3-(1-ethylpiperidin-4-yl)-5-fluorocinnoline |
| 121[1] | 7-(8-ethyl-2-methylimidazo[1,2-b]pyridazin-6-yl)-3-(1-ethylpiperidin-4-yl)-5-fluorocinnoline |
| 122[1] | 7-(8-ethyl-2-methylimidazo[1,2-b]pyridazin-6-yl)-5-fluoro-3-(1-methylpiperidin-4-yl)cinnoline |
| 123[1] | 2-{4-[7-(8-ethyl-2-methylimidazo[1,2-b]pyridazin-6-yl)-5-fluorocinnolin-3-yl]piperidin-1-yl}ethan-1-ol |
| 124 | 7-(2,8-dimethylimidazo[1,2-b]pyridazin-6-yl)-5-fluoro-3-[(2S,6S)-1,2,6-trimethylpiperidin-4-yl]cinnoline |
| 125 | 7-(2,8-dimethylimidazo[1,2-b]pyridazin-6-yl)-3-[(2R,6R)-1-ethyl-2,6-dimethylpiperidin-4-yl]-5-fluorocinnoline |

-continued

| Cpd | Name |
|---|---|
| 126 | 7-(2,7-dimethyl-3H-imidazo[4,5-b]pyridin-5-yl)-5-fluoro-3-(piperidin-4-yl)cinnoline |
| 127[1] | 2-{4-[7-(2,8-dimethylimidazo[1,2-b]pyridazin-6-yl)-5-fluorocinnolin-3-yl]piperidin-1-yl}-N,N-dimethylethan-1-amine |
| 128[1] | 5-fluoro-3-(8-fluoro-2-methylimidazo[1,2-a]pyridin-6-yl)-7-(piperidin-4-yl)cinnoline |
| 129 | 3-(azepan-4-yl)-7-(2,8-dimethylimidazo[1,2-b]pyridazin-6-yl)-5-fluorocinnoline |
| 130 | 3-[(2S,6S)-2,6-diethylpiperidin-4-yl]-7-(2,8-dimethylimidazo[1,2-b]pyridazin-6-yl)-5-fluorocinnoline |
| 131 | 3-[(2S,6S)-2,6-diethyl-1-methylpiperidin-4-yl]-7-(2,8-dimethylimidazo[1,2-b]pyridazin-6-yl)-5-fluorocinnoline |
| 132 | 7-(2,7-dimethyl-3H-imidazo[4,5-b]pyridin-5-yl)-3-(1-ethylpiperidin-4-yl)-5-fluorocinnoline |
| 133[1] | 7-(2,7-dimethyl[1,3]thiazolo[5,4-b]pyridin-5-yl)-5-fluoro-3-(piperidin-4-yl)cinnoline |
| 134[1] | 5-fluoro-3-(7-fluoro-2-methyl-2H-indazol-5-yl)-7-(1,2,3,6-tetrahydropyridin-4-yl)cinnoline |
| 135[1] | 7-(2,7-dimethyl[1,3]thiazolo[5,4-b]pyridin-5-yl)-3-(1-ethylpiperidin-4-yl)-5-fluorocinnoline |
| 136 | 7-(4,6-dimethyl[1,3]oxazolo[4,5-c]pyridin-2-yl)-3-(1-ethylpiperidin-4-yl)-5-fluorocinnoline |
| 137 | 7-(4,6-dimethyl[1,3]oxazolo[4,5-c]pyridin-2-yl)-5-fluoro-3-(piperidin-4-yl)cinnoline |
| 138[1] | 2-({6-[5-fluoro-3-(piperidin-4-yl)cinnolin-7-yl]-2-methylimidazo[1,2-b]pyridazin-8-yl}oxy)-N,N-dimethylethan-1-amine |
| 139[1] | 3-({6-[5-fluoro-3-(piperidin-4-yl)cinnolin-7-yl]-2-methylimidazo[1,2-b]pyridazin-8-yl}oxy)-N,N-dimethylpropan-1-amine |
| 140[1] | 5-fluoro-7-{2-methyl-8-[2-(1H-pyrazol-1-yl)ethoxy]imidazo[1,2-b]pyridazin-6-yl}-3-(piperidin-4-yl)cinnoline |
| 141[1] | 5-fluoro-7-{2-methyl-8-[3-(1H-pyrazol-1-yl)propoxy]imidazo[1,2-b]pyridazin-6-yl}-3-(piperidin-4-yl)cinnoline |
| 142[1] | 5-fluoro-7-{8-[3-(1H-imidazol-1-yl)propoxy]-2-methylimidazo[1,2-b]pyridazin-6-yl}-3-(piperidin-4-yl)cinnoline |
| 143 | 7-(2,8-dimethylimidazo[1,2-b]pyridazin-6-yl)-5-fluoro-3-(pyrrolidin-3-yl)cinnoline |
| 144 | 7-(1-ethylpiperidin-4-yl)-5-fluoro-3-(8-fluoro-2-methylimidazo[1,2-a]pyridin-6-yl)cinnoline |
| 145[1] | 3-{1-[3-(1H-benzimidazol-1-yl)propyl]piperidin-4-yl}-7-(2,8-dimethylimidazo[1,2-b]pyridazin-6-yl)-5-fluorocinnoline |
| 146[1] | 7-(5,7-dimethylfuro[2,3-c]pyridin-2-yl)-5-fluoro-3-(piperidin-4-yl)cinnoline |
| 147 | 7-(4,6-dimethyl[1,3]thiazolo[4,5-c]pyridin-2-yl)-3-(1-ethylpiperidin-4-yl)-5-fluorocinnoline |
| 148 | 7-(2,7-dimethyl[1,3]oxazolo[5,4-b]pyridin-5-yl)-5-fluoro-3-(piperidin-4-yl)cinnoline |
| 149 | 7-(4,6-dimethyl[1,3]thiazolo[4,5-c]pyridin-2-yl)-5-fluoro-3-(piperidin-4-yl)cinnoline |
| 150[1] | 7-{8-[3-(1H-benzimidazol-1-yl)propoxy]-2-methylimidazo[1,2-b]pyridazin-6-yl}-5-fluoro-3-(piperidin-4-yl)cinnoline |
| 151[1] | 5-fluoro-3-(7-fluoro-2-methyl-2H-indazol-5-yl)-7-(piperidin-4-yl)cinnoline |
| 152 | 7-(2,7-dimethyl[1,3]oxazolo[5,4-b]pyridin-5-yl)-3-(1-ethylpiperidin-4-yl)-5-fluorocinnoline |
| 153[1] | 7-(1-ethyl-1,2,3,6-tetrahydropyridin-4-yl)-5-fluoro-3-(7-fluoro-2-methyl-2H-indazol-5-yl)cinnoline |
| 154 | 7-(1-ethylpiperidin-4-yl)-5-fluoro-3-(7-fluoro-2-methyl-2H-indazol-5-yl)cinnoline |
| 155 | 2-{(2S,6S)-4-[7-(2,8-dimethylimidazo[1,2-b]pyridazin-6-yl)-5-fluorocinnolin-3-yl]-2,6-dimethylpiperidin-1-yl}ethan-1-ol |
| 156[1] | 3-(2,8-dimethylimidazo[1,2-a]pyridin-6-yl)-5-fluoro-7-(1,2,3,6-tetrahydropyridin-4-yl)cinnoline |
| 157[1] | 3-(2,7-dimethyl-2H-indazol-5-yl)-5-fluoro-7-(1,2,3,6-tetrahydropyridin-4-yl)cinnoline |
| 158 | 3-{4-[7-(2,8-dimethylimidazo[1,2-b]pyridazin-6-yl)-5-fluorocinnolin-3-yl]piperidin-1-yl}-N,N-dimethylpropan-1-amine |
| 159 | 3-{1-[2-(1H-benzimidazol-1-yl)ethyl]piperidin-4-yl}-7-(2,8-dimethylimidazo[1,2-b]pyridazin-6-yl)-5-fluorocinnoline |
| 160 | 7-(2,8-dimethylimidazo[1,2-b]pyridazin-6-yl)-5-fluoro-3-{1-[3-(1H-pyrazol-1-yl)propyl]piperidin-4-yl}cinnoline |
| 161 | 7-(2,8-dimethylimidazo[1,2-b]pyridazin-6-yl)-5-fluoro-3-[(2R,6S)-1,2,6-trimethylpiperidin-4-yl]cinnoline |
| 162 | 7-(2,7-dimethyl-2H-pyrazolo[4,3-b]pyridin-5-yl)-5-fluoro-3-(piperidin-4-yl)cinnoline |
| 163[1] | 5-fluoro-7-(7-methoxy-2-methyl-2H-pyrazolo[4,3-b]pyridin-5-yl)-3-(piperidin-4-yl)cinnoline |
| 164 | 7-(2,7-dimethyl-2H-pyrazolo[4,3-b]pyridin-5-yl)-3-(1-ethylpiperidin-4-yl)-5-fluorocinnoline |
| 165[1] | 8-fluoro-2-(7-fluoro-2-methyl-2H-indazol-5-yl)-6-(1,2,3,6-tetrahydropyridin-4-yl)quinazoline |
| 166[1] | 8-fluoro-2-(7-fluoro-2-methyl-2H-indazol-5-yl)-6-(1,2,3,6-tetrahydropyridin-4-yl)quinoline |
| 167[1] | 3-(2,8-dimethylimidazo[1,2-b]pyridazin-6-yl)-5-fluoro-7-(1,2,3,6-tetrahydropyridin-4-yl)cinnoline |
| 168 | 7-(2,8-dimethylimidazo[1,2-b]pyridazin-6-yl)-3-[(2R,6S)-1-ethyl-2,6-dimethylpiperidin-4-yl]-5-fluorocinnoline |
| 169 | 3-[(1R,3r,5S)-8-azabicyclo[3.2.1]octan-3-yl]-7-(2,8-dimethylimidazo[1,2-b]pyridazin-6-yl)-5-fluorocinnoline |
| 170 | 7-(2,8-dimethylimidazo[1,2-b]pyridazin-6-yl)-5-fluoro-3-[(2R,6S)-1-(2-fluoroethyl)-2,6-dimethylpiperidin-4-yl]cinnoline |

-continued

| Cpd | Name |
|---|---|
| 171[1] | 5-fluoro-3-(7-fluoro-2-methyl-2H-benzotriazol-5-yl)-7-(1,2,3,6-tetrahydropyridin-4-yl)cinnoline |
| 172 | 7-(7-ethyl-2-methyl-2H-pyrazolo[4,3-b]pyridin-5-yl)-5-fluoro-3-(piperidin-4-yl)cinnoline |
| 173[1] | 3-(1-ethylpiperidin-4-yl)-5-fluoro-7-(7-methoxy-2-methyl-2H-pyrazolo[4,3-b]pyridin-5-yl)cinnoline |
| 174 | 7-(7-ethyl-2-methyl-2H-pyrazolo[4,3-b]pyridin-5-yl)-3-(1-ethylpiperidin-4-yl)-5-fluorocinnoline |
| 175[1] | 5-[5-fluoro-7-(1,2,3,6-tetrahydropyridin-4-yl)cinnolin-3-yl]-2-methyl-2H-indazole-7-carbonitrile |
| 176[1] | 6-[5-fluoro-3-(1-methylpiperidin-4-yl)cinnolin-7-yl]-2-methylimidazo[1,2-b]pyridazine-8-carbonitrile |
| 177[1] | 3-(2,7-dimethyl-2H-indazol-5-yl)-5-fluoro-7-(piperidin-4-yl)cinnoline |
| 178[1] | 6-{5-fluoro-3-[1-(2-hydroxyethyl)piperidin-4-yl]cinnolin-7-yl}-2-methylimidazo[1,2-b]pyridazine-8-carbonitrile |
| 179[1] | 6-{5-fluoro-3-[1-(2-fluoroethyl)piperidin-4-yl]cinnolin-7-yl}-2-methylimidazo[1,2-b]pyridazine-8-carbonitrile |
| 180 | {6-[5-fluoro-3-(1-methylpiperidin-4-yl)cinnolin-7-yl]-2-methylimidazo[1,2-b]pyridazin-8-yl}methanol |
| 181[1] | 2-(4-{5-fluoro-7-[8-(hydroxymethyl)-2-methylimidazo[1,2-b]pyridazin-6-yl]cinnolin-3-yl}piperidin-1-yl)ethan-1-ol |
| 182[1] | (6-{5-fluoro-3-[1-(2-fluoroethyl)piperidin-4-yl]cinnolin-7-yl}-2-methylimidazo[1,2-b]pyridazin-8-yl)methanol |
| 183 | 3-(2,7-dimethyl-2H-indazol-5-yl)-7-(1-ethylpiperidin-4-yl)-5-fluorocinnoline |
| 184[1] | 6-(1-ethyl-1,2,3,6-tetrahydropyridin-4-yl)-8-fluoro-2-(7-fluoro-2-methyl-2H-indazol-5-yl)quinoline |
| 185[1] | 3-(2,8-dimethylimidazo[1,2-b]pyridazin-6-yl)-5-fluoro-7-(piperidin-4-yl)cinnoline |
| 186 | 3-(2,8-dimethylimidazo[1,2-b]pyridazin-6-yl)-7-(1-ethylpiperidin-4-yl)-5-fluorocinnoline |
| 187 | {6-[5-fluoro-3-(piperidin-4-yl)cinnolin-7-yl]-2-methylimidazo[1,2-b]pyridazin-8-yl}acetonitrile |
| 188 | 7-(2,8-dimethylimidazo[1,2-b]pyridazin-6-yl)-5-fluoro-3-(1-methylazepan-4-yl)cinnoline |
| 189 | 7-(2,8-dimethylimidazo[1,2-b]pyridazin-6-yl)-3-(1-ethylazepan-4-yl)-5-fluorocinnoline |
| 190 | 2-{4-[7-(2,8-dimethylimidazo[1,2-b]pyridazin-6-yl)-5-fluorocinnolin-3-yl]azepan-1-yl}ethan-1-ol |
| 191[1] | 7-(5,7-dimethyl-1H-pyrrolo[2,3-c]pyridin-2-yl)-5-fluoro-3-(piperidin-4-yl)cinnoline |
| 192[1] | 8-fluoro-2-(7-fluoro-2-methyl-2H-indazol-5-yl)-6-(piperidin-4-yl)quinoline |
| 193[1] | 6-(1-ethylpiperidin-4-yl)-8-fluoro-2-(7-fluoro-2-methyl-2H-indazol-5-yl)quinoline |
| 194[1] | 5-fluoro-7-[8-(1H-imidazol-1-yl)-2-methylimidazo[1,2-b]pyridazin-6-yl]-3-(piperidin-4-yl)cinnoline |
| 195[1] | 5-fluoro-7-(2-methyl-8-phenoxyimidazo[1,2-b]pyridazin-6-yl)-3-(piperidin-4-yl)cinnoline |
| 196[1] | 7-(4,6-dimethyl[1,3]thiazolo[5,4-c]pyridin-2-yl)-5-fluoro-3-(piperidin-4-yl)cinnoline |
| 197 | 7-(4,6-dimethyl[1,3]thiazolo[5,4-c]pyridin-2-yl)-3-(1-ethylpiperidin-4-yl)-5-fluorocinnoline |
| 198 | 3-(2,7-dimethyl-2H-indazol-5-yl)-5-fluoro-7-(2,3,6,7-tetrahydro-1H-azepin-4-yl)cinnoline |
| 199 | 7-(2,8-dimethylimidazo[1,2-b]pyridazin-6-yl)-5-fluoro-3-[1-(2-fluoroethyl)azepan-4-yl]cinnoline |
| 200 | 3-(1-ethylpiperidin-4-yl)-5-fluoro-7-(2-methyl-8-phenoxyimidazo[1,2-b]pyridazin-6-yl)cinnoline |
| 201[1] | 6-(1-ethyl-1,2,3,6-tetrahydropyridin-4-yl)-8-fluoro-2-(7-fluoro-2-methyl-2H-indazol-5-yl)quinazoline |
| 202[1] | 6-(1-ethylpiperidin-4-yl)-8-fluoro-2-(7-fluoro-2-methyl-2H-indazol-5-yl)quinazoline |
| 203 | (3S,4S)-4-[3-(2,7-dimethyl-2H-indazol-5-yl)-5-fluorocinnolin-7-yl]piperidine-3,4-diol |
| 204 | 5-fluoro-7-(2-methyl-8-propylimidazo[1,2-b]pyridazin-6-yl)-3-(piperidin-4-yl)cinnoline |
| 205[1] | {6-[3-(1-ethylpiperidin-4-yl)-5-fluorocinnolin-7-yl]-2-methylimidazo[1,2-b]pyridazin-8-yl}acetonitrile |
| 206 | 2-{6-[3-(1-ethylpiperidin-4-yl)-5-fluorocinnolin-7-yl]-2-methylimidazo[1,2-b]pyridazin-8-yl}ethan-1-ol |
| 207 | 2-{6-[5-fluoro-3-(piperidin-4-yl)cinnolin-7-yl]-2-methylimidazo[1,2-b]pyridazin-8-yl}ethan-1-ol |
| 208 | 7-(2,8-dimethylimidazo[1,2-b]pyridazin-6-yl)-5-fluoro-3-(2,2,6,6-tetramethyl-1,2,3,6-tetrahydropyridin-4-yl)cinnoline |
| 209 | 7-(2,8-dimethylimidazo[1,2-b]pyridazin-6-yl)-5-fluoro-3-(5-methyl-2,5-diazabicyclo[2.2.1]heptan-2-yl)cinnoline |
| 210[1] | 5-fluoro-7-(2-methylimidazo[1,2-a]pyridin-6-yl)-3-(piperidin-4-yl)cinnoline |
| 211 | 5-fluoro-7-[2-methyl-8-(propan-2-yl)imidazo[1,2-b]pyridazin-6-yl]-3-(piperidin-4-yl)cinnoline |
| 212 | 3-(1-ethylpiperidin-4-yl)-5-fluoro-7-(2-methyl-8-propylimidazo[1,2-b]pyridazin-6-yl)cinnoline |
| 213 | 2-{4-[7-(4,6-dimethyl[1,3]oxazolo[4,5-c]pyridin-2-yl)-5-fluorocinnolin-3-yl]piperidin-1-yl}ethan-1-ol |
| 214 | 7-(4,6-dimethyl[1,3]oxazolo[4,5-c]pyridin-2-yl)-5-fluoro-3-(1-methylpiperidin-4-yl)cinnoline |

| Cpd | Name |
|---|---|
| 215 | 7-(2,8-dimethylimidazo[1,2-b]pyridazin-6-yl)-5-fluoro-3-[(1S,4S)-5-methyl-2,5-diazabicyclo[2.2.1]heptan-2-yl]cinnoline |
| 216[1] | 7-(2,8-dimethylimidazo[1,2-b]pyridazin-6-yl)-5-fluoro-3-(piperidin-3-yl)cinnoline |
| 217[1] | 3-(2,6-diazaspiro[3.4]octan-2-yl)-7-(2,8-dimethylimidazo[1,2-b]pyridazin-6-yl)-5-fluorocinnoline |
| 218[1] | 3-(2,6-diazaspiro[3.5]nonan-2-yl)-7-(2,8-dimethylimidazo[1,2-b]pyridazin-6-yl)-5-fluorocinnoline |
| 219[1] | 3-(2,7-diazaspiro[3.5]nonan-7-yl)-7-(2,8-dimethylimidazo[1,2-b]pyridazin-6-yl)-5-fluorocinnoline |
| 220[1] | 3-(2,6-diazaspiro[3.4]octan-6-yl)-7-(2,8-dimethylimidazo[1,2-b]pyridazin-6-yl)-5-fluorocinnoline |
| 221[1] | 3-(2,7-diazaspiro[3.5]nonan-2-yl)-7-(2,8-dimethylimidazo[1,2-b]pyridazin-6-yl)-5-fluorocinnoline |
| 222 | 3-(1-ethylpiperidin-4-yl)-5-fluoro-7-[2-methyl-8-(propan-2-yl)imidazo[1,2-b]pyridazin-6-yl]cinnoline |
| 223 | (1R,5S,6s)-3-[7-(2,8-dimethylimidazo[1,2-b]pyridazin-6-yl)-5-fluorocinnolin-3-yl]-N,N-dimethyl-3-azabicyclo[3.1.0]hexan-6-amine |
| 224 | 1-[7-(2,8-dimethylimidazo[1,2-b]pyridazin-6-yl)-5-fluorocinnolin-3-yl]-N,N,4-trimethylpiperidin-4-amine |
| 225[1] | 7-(2,8-dimethylimidazo[1,2-b]pyridazin-6-yl)-5-fluoro-3-(1,2,3,6-tetrahydropyridin-4-yl)cinnoline |
| 226 | 5-(5-fluoro-3-((2S,4R,6R)-1,2,6-trimethylpiperidin-4-yl)cinnolin-7-yl)-2,7-dimethyloxazolo[5,4-b]pyridine |
| 227 | 7-(2,7-dimethyl-2H-pyrazolo[4,3-b]pyridin-5-yl)-5-fluoro-3-((2S,4R,6R)-1,2,6-trimethylpiperidin-4-yl)cinnoline and |
| 228 | 7-(4,6-dimethyloxazolo[4,5-c]pyridin-2-yl)-5-fluoro-3-((2S,4R,6R)-1,2,6-trimethylpiperidin-4-yl)cinnoline; | wherein the form of the compound is selected from the group consisting of a salt, prodrug, hydrate, solvate, clathrate, isotopologue, racemate, enantiomer, diastereomer, stereoisomer, polymorph and tautomer form thereof.

Another aspect of the compound of Formula (I) or a form thereof is a compound salt selected from the group consisting of:

| Cpd | Name |
|---|---|
| 1 | 2-(2-methyl-2H-indazol-5-yl)-6-(piperidin-4-yl)quinoline hydrochloride |
| 2 | 6-(1-ethylpiperidin-4-yl)-2-(2-methyl-2H-indazol-5-yl)quinoline hydrochloride |
| 3 | 6-(2-methyl-2H-indazol-5-yl)-2-(piperidin-4-yl)quinoline hydrochloride |
| 4 | 3-(2-methyl-2H-indazol-5-yl)-7-(1,2,3,6-tetrahydropyridin-4-yl)cinnoline hydrochloride |
| 5 | 4-methyl-6-(2-methyl-2H-indazol-5-yl)-2-(piperidin-4-yl)quinoline hydrochloride |
| 6 | 6-(2-methyl-2H-indazol-5-yl)-2-(1-methylpiperidin-4-yl)quinoline hydrochloride |
| 9 | 2-(1-ethylpiperidin-4-yl)-6-(2-methyl-2H-indazol-5-yl)quinoline hydrochloride |
| 10 | 2-(2-methyl-2H-indazol-5-yl)-6-(piperidin-4-yl)quinazoline hydrochloride |
| 24 | 6-[2-methyl-7-(trifluoromethyl)-2H-indazol-5-yl]-2-(piperidin-4-yl)quinoxaline hydrochloride |
| 25 | 3-(7-fluoro-2-methyl-2H-indazol-5-yl)-7-(piperidin-4-yl)-1,2,4-benzotriazine dihydrochloride |
| 31 | 6-(2,7-dimethyl-2H-indazol-5-yl)-2-(piperidin-4-yl)quinoxaline hydrochloride |
| 34 | 6-(2,7-dimethyl-2H-indazol-5-yl)-8-fluoro-2-(piperidin-4-yl)quinazoline dihydrochloride |
| 35 | 5-[8-fluoro-2-(piperidin-4-yl)quinazolin-6-yl]-2-methyl-2H-indazole-7-carbonitrile dihydrochloride |
| 36 | 8-fluoro-6-(7-fluoro-2-methyl-2H-indazol-5-yl)-2-(piperidin-4-yl)quinazoline dihydrochloride |
| 37 | 6-(2,8-dimethylimidazo[1,2-b]pyridazin-6-yl)-8-fluoro-2-(piperidin-4-yl)quinazoline dihydrochloride |
| 38 | 6-(2,7-dimethyl-2H-indazol-5-yl)-5-fluoro-2-(piperidin-4-yl)quinazoline dihydrochloride |
| 39 | 6-(2,7-dimethyl-2H-indazol-5-yl)-7-fluoro-2-(piperidin-4-yl)quinazoline dihydrochloride |
| 45 | 6-(2,8-dimethylimidazo[1,2-b]pyridazin-6-yl)-8-fluoro-2-(piperidin-4-yl)quinoline hydrochloride |
| 47 | 6-(2,8-dimethylimidazo[1,2-b]pyridazin-6-yl)-8-fluoro-2-(1-methylpiperidin-4-yl)quinoline hydrochloride |
| 48 | 6-(2,8-dimethylimidazo[1,2-b]pyridazin-6-yl)-2-(1-ethylpiperidin-4-yl)-8-fluoroquinoline hydrochloride |
| 49 | 8-fluoro-6-(7-methoxy-2-methyl-2H-indazol-5-yl)-2-(piperidin-4-yl)quinoline hydrochloride |

-continued

| Cpd | Name |
|---|---|
| 50 | 8-fluoro-6-(8-fluoro-2-methylimidazo[1,2-a]pyridin-6-yl)-2-(piperidin-4-yl)quinoline hydrochloride |
| 51 | 8-fluoro-6-(8-methoxy-2-methylimidazo[1,2-b]pyridazin-6-yl)-2-(piperidin-4-yl)quinoline hydrochloride |
| 53 | 8-fluoro-6-[8-(2-methoxyethoxy)-2-methylimidazo[1,2-b]pyridazin-6-yl]-2-(piperidin-4-yl)quinoline hydrochloride |
| 54 | 6-[8-fluoro-2-(piperidin-4-yl)quinolin-6-yl]-N-(2-methoxyethyl)-2-methylimidazo[1,2-b]pyridazin-8-amine hydrochloride |
| 55 | 7-(2,7-dimethyl-2H-indazol-5-yl)-5-fluoro-3-(1,2,3,6-tetrahydropyridin-4-yl)cinnoline hydrochloride |
| 56 | 7-(8-azabicyclo[3.2.1]oct-3-yl)-3-(8-fluoro-2-methylimidazo[1,2-a]pyridin-6-yl)-1,2,4-benzotriazine hydrochloride |
| 57 | 3-(2,8-dimethylimidazo[1,2-b]pyridazin-6-yl)-5-fluoro-7-(piperidin-4-yl)-1,2,4-benzotriazine hydrochloride |
| 58 | 5-fluoro-7-(8-fluoro-2-methylimidazo[1,2-a]pyridin-6-yl)-3-(piperidin-4-yl)-1,2,4-benzotriazine hydrochloride |
| 59 | 7-(8-ethoxy-2-methylimidazo[1,2-b]pyridazin-6-yl)-5-fluoro-3-(piperidin-4-yl)-1,2,4-benzotriazine hydrochloride |
| 60 | 7-(2,8-dimethylimidazo[1,2-a]pyridin-6-yl)-5-fluoro-3-(piperidin-4-yl)-1,2,4-benzotriazine hydrochloride |
| 61 | 5-fluoro-7-[2-methyl-8-(trifluoromethyl)imidazo[1,2-a]pyridin-6-yl]-3-(piperidin-4-yl)-1,2,4-benzotriazine hydrochloride |
| 62 | 7-(2,4-dimethyl-1,3-benzoxazol-6-yl)-5-fluoro-3-(piperidin-4-yl)-1,2,4-benzotriazine hydrochloride |
| 63 | 7-(2,4-dimethyl-1H-benzimidazol-6-yl)-5-fluoro-3-(piperidin-4-yl)-1,2,4-benzotriazine hydrochloride |
| 64 | 7-(1,3-dimethylpyrrolo[1,2-a]pyrazin-7-yl)-5-fluoro-3-(piperidin-4-yl)-1,2,4-benzotriazine hydrochloride |
| 65 | 7-(2,7-dimethylpyrazolo[1,5-a]pyridin-5-yl)-5-fluoro-3-(piperidin-4-yl)-1,2,4-benzotriazine hydrochloride |
| 66 | 7-(2,7-dimethyl-2H-pyrazolo[4,3-b]pyridin-5-yl)-5-fluoro-3-(piperidin-4-yl)-1,2,4-benzotriazine dihydrochloride |
| 67 | 7-(2,7-dimethyl-2H-pyrazolo[3,4-c]pyridin-5-yl)-5-fluoro-3-(piperidin-4-yl)-1,2,4-benzotriazine dihydrochloride |
| 69 | 7-(2,8-dimethylimidazo[1,2-b]pyridazin-6-yl)-5-fluoro-3-(1-methylpiperidin-4-yl)-1,2,4-benzotriazine dihydrochloride |
| 71 | 7-(2,7-dimethyl-2H-indazol-5-yl)-5-fluoro-3-(piperidin-4-yl)isoquinoline hydrochloride |
| 72 | 7-(2,8-dimethylimidazo[1,2-b]pyridazin-6-yl)-5-fluoro-3-(piperidin-4-yl)isoquinoline hydrochloride |
| 73 | 7-(2,7-dimethyl-2H-indazol-5-yl)-5-fluoro-3-(piperidin-4-yl)cinnoline hydrochloride |
| 74 | 7-(2,8-dimethylimidazo[1,2-b]pyridazin-6-yl)-5-fluoro-3-(piperidin-4-yl)cinnoline dihydrochloride |
| 80 | 7-(2,8-dimethylimidazo[1,2-b]pyridazin-6-yl)-5-fluoro-3-(piperazin-1-yl)cinnoline dihydrochloride |
| 81 | 7-(2,8-dimethylimidazo[1,2-b]pyridazin-6-yl)-3-[(3R,5S)-3,5-dimethylpiperazin-1-yl]-5-fluorocinnoline dihydrochloride |
| 83 | 7-(2,8-dimethylimidazo[1,2-b]pyridazin-6-yl)-5-fluoro-3-[1-(2-fluoroethyl)piperidin-4-yl]cinnoline dihydrochloride |
| 84 | 7-(2,8-dimethylimidazo[1,2-b]pyridazin-6-yl)-3-(piperidin-4-yl)cinnoline dihydrochloride |
| 87 | 7-(2,8-dimethylimidazo[1,2-b]pyridazin-6-yl)-3-[(2S,6S)-2,6-dimethylpiperidin-4-yl]-5-fluorocinnoline hydrochloride |
| 91 | 5-fluoro-7-(2-methylimidazo[1,2-a]pyrimidin-6-yl)-3-(piperidin-4-yl)cinnoline dihydrochloride |
| 92 | 5-fluoro-7-(8-fluoro-2-methylimidazo[1,2-a]pyridin-6-yl)-3-(piperidin-4-yl)cinnoline dihydrochloride |
| 93 | 6-[5-fluoro-3-(piperidin-4-yl)cinnolin-7-yl]-2-methylimidazo[1,2-a]pyridine-8-carbonitrile dihydrochloride |
| 94 | 5-fluoro-7-(2-methyl[1,2,4]triazolo[1,5-a]pyridin-6-yl)-3-(piperidin-4-yl)cinnoline dihydrochloride |
| 95 | 5-fluoro-7-(2-methyl-2H-indazol-5-yl)-3-(piperidin-4-yl)cinnoline hydrochloride |
| 96 | 5-fluoro-7-(7-fluoro-2-methyl-2H-indazol-5-yl)-3-(piperidin-4-yl)cinnoline hydrochloride |
| 97 | 5-fluoro-7-(6-fluoro-2-methyl-2H-indazol-5-yl)-3-(piperidin-4-yl)cinnoline hydrochloride |
| 98 | 3-[1-(2,2-difluoroethyl)piperidin-4-yl]-7-(2,8-dimethylimidazo[1,2-b]pyridazin-6-yl)-5-fluorocinnoline dihydrochloride |
| 99 | 5-fluoro-7-(2-methylimidazo[1,2-b]pyridazin-6-yl)-3-(piperidin-4-yl)cinnoline dihydrochloride |
| 100 | 3-(1-ethylpiperidin-4-yl)-5-fluoro-7-(2-methylimidazo[1,2-b]pyridazin-6-yl)cinnoline dihydrochloride |
| 101 | 7-(1,3-dimethylpyrrolo[1,2-a]pyrazin-7-yl)-5-fluoro-3-(piperidin-4-yl)cinnoline dihydrochloride |
| 102 | 3-(1-ethylpiperidin-4-yl)-5-fluoro-7-(8-fluoro-2-methylimidazo[1,2-a]pyridin-6-yl)cinnoline dihydrochloride |
| 103 | 7-(2,8-dimethylimidazo[1,2-a]pyridin-6-yl)-5-fluoro-3-(piperidin-4-yl)cinnoline dihydrochloride |

-continued

| Cpd | Name |
|---|---|
| 104 | 5-[5-fluoro-3-(piperidin-4-yl)cinnolin-7-yl]-2-methyl-1H-indazole-7-carbonitrile hydrochloride |
| 109 | 5-fluoro-7-(4-fluoro-2-methyl-2H-indazol-5-yl)-3-(piperidin-4-yl)cinnoline hydrochloride |
| 115 | 7-(8-cyclopropyl-2-methylimidazo[1,2-b]pyridazin-6-yl)-3-(1-ethylpiperidin-4-yl)-5-fluorocinnoline formate |
| 117 | 5-fluoro-3-(8-fluoro-2-methylimidazo[1,2-a]pyridin-6-yl)-7-(1,2,3,6-tetrahydropyridin-4-yl)cinnoline hydrochloride |
| 120 | 7-(2,4-dimethyl-1,3-benzothiazol-6-yl)-3-(1-ethylpiperidin-4-yl)-5-fluorocinnoline formate |
| 121 | 7-(8-ethyl-2-methylimidazo[1,2-b]pyridazin-6-yl)-3-(1-ethylpiperidin-4-yl)-5-fluorocinnoline dihydrochloride |
| 122 | 7-(8-ethyl-2-methylimidazo[1,2-b]pyridazin-6-yl)-5-fluoro-3-(1-methylpiperidin-4-yl)cinnoline dihydrochloride |
| 123 | 2-{4-[7-(8-ethyl-2-methylimidazo[1,2-b]pyridazin-6-yl)-5-fluorocinnolin-3-yl]piperidin-1-yl}ethan-1-ol dihydrochloride |
| 127 | 2-{4-[7-(2,8-dimethylimidazo[1,2-b]pyridazin-6-yl)-5-fluorocinnolin-3-yl]piperidin-1-yl}-N,N-dimethylethan-1-amine trihydrochloride |
| 128 | 5-fluoro-3-(8-fluoro-2-methylimidazo[1,2-a]pyridin-6-yl)-7-(piperidin-4-yl)cinnoline dihydrochloride |
| 133 | 7-(2,7-dimethyl[1,3]thiazolo[5,4-b]pyridin-5-yl)-5-fluoro-3-(piperidin-4-yl)cinnoline formate |
| 134 | 5-fluoro-3-(7-fluoro-2-methyl-2H-indazol-5-yl)-7-(1,2,3,6-tetrahydropyridin-4-yl)cinnoline hydrochloride |
| 135 | 7-(2,7-dimethyl[1,3]thiazolo[5,4-b]pyridin-5-yl)-3-(1-ethylpiperidin-4-yl)-5-fluorocinnoline formate |
| 138 | 2-({6-[5-fluoro-3-(piperidin-4-yl)cinnolin-7-yl]-2-methylimidazo[1,2-b]pyridazin-8-yl}oxy)-N,N-dimethylethan-1-amine trihydrochloride |
| 139 | 3-({6-[5-fluoro-3-(piperidin-4-yl)cinnolin-7-yl]-2-methylimidazo[1,2-b]pyridazin-8-yl}oxy)-N,N-dimethylpropan-1-amine trihydrochloride |
| 140 | 5-fluoro-7-{2-methyl-8-[2-(1H-pyrazol-1-yl)ethoxy]imidazo[1,2-b]pyridazin-6-yl}-3-(piperidin-4-yl)cinnoline dihydrochloride |
| 141 | 5-fluoro-7-{2-methyl-8-[3-(1H-pyrazol-1-yl)propoxy]imidazo[1,2-b]pyridazin-6-yl}-3-(piperidin-4-yl)cinnoline trihydrochloride |
| 142 | 5-fluoro-7-{8-[3-(1H-imidazol-1-yl)propoxy]-2-methylimidazo[1,2-b]pyridazin-6-yl}-3-(piperidin-4-yl)cinnoline trihydrochloride |
| 145 | 3-{1-[3-(1H-benzimidazol-1-yl)propyl]piperidin-4-yl}-7-(2,8-dimethylimidazo[1,2-b]pyridazin-6-yl)-5-fluorocinnoline trihydrochloride |
| 146 | 7-(5,7-dimethylfuro[2,3-c]pyridin-2-yl)-5-fluoro-3-(piperidin-4-yl)cinnoline hydrochloride |
| 150 | 7-{8-[3-(1H-benzimidazol-1-yl)propoxy]-2-methylimidazo[1,2-b]pyridazin-6-yl}-5-fluoro-3-(piperidin-4-yl)cinnoline trihydrochloride |
| 151 | 5-fluoro-3-(7-fluoro-2-methyl-2H-indazol-5-yl)-7-(piperidin-4-yl)cinnoline hydrochloride |
| 153 | 7-(1-ethyl-1,2,3,6-tetrahydropyridin-4-yl)-5-fluoro-3-(7-fluoro-2-methyl-2H-indazol-5-yl)cinnoline hydrochloride |
| 156 | 3-(2,8-dimethylimidazo[1,2-a]pyridin-6-yl)-5-fluoro-7-(1,2,3,6-tetrahydropyridin-4-yl)cinnoline hydrochloride |
| 157 | 3-(2,7-dimethyl-2H-indazol-5-yl)-5-fluoro-7-(1,2,3,6-tetrahydropyridin-4-yl)cinnoline hydrochloride |
| 163 | 5-fluoro-7-(7-methoxy-2-methyl-2H-pyrazolo[4,3-b]pyridin-5-yl)-3-(piperidin-4-yl)cinnoline formate |
| 165 | 8-fluoro-2-(7-fluoro-2-methyl-2H-indazol-5-yl)-6-(1,2,3,6-tetrahydropyridin-4-yl)quinazoline hydrochloride |
| 166 | 8-fluoro-2-(7-fluoro-2-methyl-2H-indazol-5-yl)-6-(1,2,3,6-tetrahydropyridin-4-yl)quinoline hydrochloride |
| 167 | 3-(2,8-dimethylimidazo[1,2-b]pyridazin-6-yl)-5-fluoro-7-(1,2,3,6-tetrahydropyridin-4-yl)cinnoline hydrochloride |
| 171 | 5-fluoro-3-(7-fluoro-2-methyl-2H-benzotriazol-5-yl)-7-(1,2,3,6-tetrahydropyridin-4-yl)cinnoline hydrochloride |
| 173 | 3-(1-ethylpiperidin-4-yl)-5-fluoro-7-(7-methoxy-2-methyl-2H-pyrazolo[4,3-b]pyridin-5-yl)cinnoline formate |
| 175 | 5-[5-fluoro-7-(1,2,3,6-tetrahydropyridin-4-yl)cinnolin-3-yl]-2-methyl-2H-indazole-7-carbonitrile hydrochloride |
| 176 | 6-[5-fluoro-3-(1-methylpiperidin-4-yl)cinnolin-7-yl]-2-methylimidazo[1,2-b]pyridazine-8-carbonitrile trihydrochloride |
| 177 | 3-(2,7-dimethyl-2H-indazol-5-yl)-5-fluoro-7-(piperidin-4-yl)cinnoline hydrochloride |
| 178 | 6-{5-fluoro-3-[1-(2-hydroxyethyl)piperidin-4-yl]cinnolin-7-yl}-2-methylimidazo[1,2-b]pyridazine-8-carbonitrile trihydrochloride |
| 179 | 6-{5-fluoro-3-[1-(2-fluoroethyl)piperidin-4-yl]cinnolin-7-yl}-2-methylimidazo[1,2-b]pyridazine-8-carbonitrile trihydrochloride |
| 181 | 2-(4-{5-fluoro-7-[8-(hydroxymethyl)-2-methylimidazo[1,2-b]pyridazin-6-yl]cinnolin-3-yl}piperidin-1-yl)ethan-1-ol trihydrochloride |
| 182 | (6-{5-fluoro-3-[1-(2-fluoroethyl)piperidin-4-yl]cinnolin-7-yl}-2-methylimidazo[1,2-b]pyridazin-8-yl)methanol trihydrochloride |
| 184 | 6-(1-ethyl-1,2,3,6-tetrahydropyridin-4-yl)-8-fluoro-2-(7-fluoro-2-methyl-2H-indazol-5-yl)quinoline hydrochloride |

| Cpd | Name |
| --- | --- |
| 185 | 3-(2,8-dimethylimidazo[1,2-b]pyridazin-6-yl)-5-fluoro-7-(piperidin-4-yl)cinnoline hydrochloride |
| 191 | 7-(5,7-dimethyl-1H-pyrrolo[2,3-c]pyridin-2-yl)-5-fluoro-3-(piperidin-4-yl)cinnoline dihydrochloride |
| 192 | 8-fluoro-2-(7-fluoro-2-methyl-2H-indazol-5-yl)-6-(piperidin-4-yl)quinoline hydrochloride |
| 193 | 6-(1-ethylpiperidin-4-yl)-8-fluoro-2-(7-fluoro-2-methyl-2H-indazol-5-yl)quinoline hydrochloride |
| 194 | 5-fluoro-7-[8-(1H-imidazol-1-yl)-2-methylimidazo[1,2-b]pyridazin-6-yl]-3-(piperidin-4-yl)cinnoline formate |
| 195 | 5-fluoro-7-(2-methyl-8-phenoxyimidazo[1,2-b]pyridazin-6-yl)-3-(piperidin-4-yl)cinnoline formate |
| 196 | 7-(4,6-dimethyl[1,3]thiazolo[5,4-c]pyridin-2-yl)-5-fluoro-3-(piperidin-4-yl)cinnoline formate |
| 201 | 6-(1-ethyl-1,2,3,6-tetrahydropyridin-4-yl)-8-fluoro-2-(7-fluoro-2-methyl-2H-indazol-5-yl)quinazoline hydrochloride |
| 202 | 6-(1-ethylpiperidin-4-yl)-8-fluoro-2-(7-fluoro-2-methyl-2H-indazol-5-yl)quinazoline hydrochloride |
| 205 | {6-[3-(1-ethylpiperidin-4-yl)-5-fluorocinnolin-7-yl]-2-methylimidazo[1,2-b]pyridazin-8-yl}acetonitrile formate |
| 210 | 5-fluoro-7-(2-methylimidazo[1,2-a]pyridin-6-yl)-3-(piperidin-4-yl)cinnoline dihydrochloride |
| 216 | 7-(2,8-dimethylimidazo[1,2-b]pyridazin-6-yl)-5-fluoro-3-(piperidin-3-yl)cinnoline dihydrochloride |
| 217 | 3-(2,6-diazaspiro[3.4]octan-2-yl)-7-(2,8-dimethylimidazo[1,2-b]pyridazin-6-yl)-5-fluorocinnoline trihydrochloride |
| 218 | 3-(2,6-diazaspiro[3.5]nonan-2-yl)-7-(2,8-dimethylimidazo[1,2-b]pyridazin-6-yl)-5-fluorocinnoline trihydrochloride |
| 219 | 3-(2,7-diazaspiro[3.5]nonan-7-yl)-7-(2,8-dimethylimidazo[1,2-b]pyridazin-6-yl)-5-fluorocinnoline ditrifluoroacetate |
| 220 | 3-(2,6-diazaspiro[3.4]octan-6-yl)-7-(2,8-dimethylimidazo[1,2-b]pyridazin-6-yl)-5-fluorocinnoline ditrifluoroacetate |
| 221 | 3-(2,7-diazaspiro[3.5]nonan-2-yl)-7-(2,8-dimethylimidazo[1,2-b]pyridazin-6-yl)-5-fluorocinnoline ditrifluoroacetate and |
| 225 | 7-(2,8-dimethylimidazo[1,2-b]pyridazin-6-yl)-5-fluoro-3-(1,2,3,6-tetrahydropyridin-4-yl)cinnoline dihydrochloride; | wherein the form of the compound salt is selected from the group consisting of a prodrug, hydrate, solvate, clathrate, isotopologue, racemate, enantiomer, diastereomer, stereoisomer, polymorph and tautomer form thereof.

An aspect of the present description includes a method for preventing, treating or ameliorating HD in a subject in need thereof comprising, administering to the subject an effective amount of a compound of Formula (I) or a form thereof.

An aspect of the present description includes a method for treating or ameliorating HD in a subject in need thereof comprising, administering to the subject an effective amount of a compound of Formula (I) or a form thereof.

Another aspect of the present description includes a method for treating or ameliorating HD in a subject in need thereof comprising, administering to the subject an effective amount of a compound salt of Formula (I) or a form thereof.

An aspect of the present description includes a method for use of a compound of Formula (I) or a form or composition thereof for treating or ameliorating HD in a subject in need thereof comprising, administering to the subject an effective amount of the compound of Formula (I) or a form or composition thereof.

Another aspect of the present description includes a method for use of a compound salt of Formula (I) or a form or composition thereof for treating or ameliorating HD in a subject in need thereof comprising, administering to the subject an effective amount of the compound salt of Formula (I) or a form thereof.

An aspect of the present description includes a use for a compound of Formula (I) or a form thereof for treating or ameliorating HD in a subject in need thereof comprising, administering to the subject an effective amount of the compound of Formula (I) or a form thereof.

Another aspect of the present description includes a use for a compound salt of Formula (I) or a form thereof for treating or ameliorating HD in a subject in need thereof comprising, administering to the subject an effective amount of the compound salt of Formula (I) or a form thereof.

An aspect of the present description includes a use for a compound of Formula (I) or a form thereof in the manufacture of a medicament for treating or ameliorating HD in a subject in need thereof comprising, administering to the subject an effective amount of the medicament.

Another aspect of the present description includes a use for a compound salt of Formula (I) or a form thereof in the manufacture of a medicament for treating or ameliorating HD in a subject in need thereof comprising, administering to the subject an effective amount of the medicament.

An aspect of the present description includes a use for a compound of Formula (I) or a form thereof in a combination product with one or more therapeutic agents for treating or ameliorating HD in a subject in need thereof comprising, administering to the subject an effective amount of the compound of Formula (I) or a form thereof in combination with an effective amount of the one or more agents.

Another aspect of the present description includes a use for a compound salt of Formula (I) or a form thereof in a combination product with one or more therapeutic agents for treating or ameliorating HD in a subject in need thereof comprising, administering to the subject an effective amount of the compound salt of Formula (I) or a form thereof in combination with an effective amount of the one or more agents.

Chemical Definitions

The chemical terms used above and throughout the description herein, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butynyl), isobutyl, sec-butyl, tert-butyl, n-pentyl (also referred to as pentyl or pentanyl), n-hexyl (also referred to as hexyl or hexanyl), n-heptyl (also referred to as heptyl or heptanyl), n-octyl and the like. In certain aspects, $C_{1-8}$alkyl includes, but is not limited to, $C_{1-6}$alkyl, $C_{1-4}$alkyl and the like. A $C_{1-8}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In certain aspects, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In certain aspects, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In certain aspects, $C_{1-8}$alkoxy includes, but is not limited to, $C_{1-6}$alkoxy, $C_{1-4}$alkoxy and the like. A $C_{1-8}$alkoxy radical is optionally substituted with substituent species as described herein where allowed by available valences.

As used herein, the term "$C_{3-14}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In certain aspects, $C_{3-14}$cycloalkyl includes, but is not limited to, $C_{3-8}$cycloalkyl, $C_{5-8}$cycloalkyl, $C_{3-14}$cycloalkyl and the like. A $C_{3-14}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thienyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothienyl, benzoimidazolyl, 1,3-benzothiazolyl, 1,3-benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thienyl may also be referred to as thiophenyl, pyridinyl may also be referred to as pyridyl, benzothienyl may also be referred to as benzothiophenyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl, 2,3-dihydro-1,4-benzodioxinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

In certain aspects, the nomenclature for a heterocyclyl radical may differ, such as in non-limiting examples where 1,3-benzodioxolyl may also be referred to as benzo[d][1,3]dioxolyl and 2,3-dihydro-1,4-benzodioxinyl may also be referred to as 2,3-dihydrobenzo[b][1,4]dioxinyl.

As used herein, the term "heteroaryl-$C_{1-8}$alkyl" refers to a radical of the formula: —$C_{1-8}$alkyl-heteroaryl.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$alkyl.

As used herein, the term "($C_{1-8}$alkoxy-$C_{1-8}$alkyl)$_2$-amino" refers to a radical of the formula: —N($C_{1-8}$alkyl-O—$C_{1-8}$alkyl)$_2$.

As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkoxy" refers to a radical of the formula: —O—$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkoxy" refers to a radical of the formula: —O—$C_{1-8}$alkyl-N($C_{1-8}$alkyl)($C_{1-8}$alkyl-O—$C_{1-8}$alkyl).

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-O—$C_{1-8}$alkyl).

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{2-8}$alkenyl" refers to a radical of the formula: —$C_{2-8}$alkenyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "heteroaryl-$C_{1-8}$alkoxy" refers to a radical of the formula: —O—$C_{1-8}$alkyl-heteroaryl.

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{2-8}$alkenyl" refers to a radical of the formula: —$C_{2-8}$alkenyl-NH—$C_{1-8}$alkyl.

As used herein, the term "($C_{1-8}$alkyl)$_2$-amino-$C_{2-8}$alkenyl" refers to a radical of the formula: —$C_{2-8}$alkenyl-N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$alkyl.

As used herein, the term "($C_{1-8}$alkyl)$_2$-amino-$C_{1-8}$alkoxy" refers to a radical of the formula: —O—$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "($C_{1-8}$alkyl-amino-$C_{1-8}$alkyl)$_2$-amino" refers to a radical of the formula: —N($C_{1-8}$alkyl-NH—$C_{1-8}$alkyl)$_2$.

As used herein, the term "[($C_{1-8}$alkyl)$_2$-amino-$C_{1-8}$alkyl]$_2$-amino" refers to a radical of the formula: —N[$C_{1-8}$alkyl-N($C_{1-8}$alkyl)$_2$]$_2$.

As used herein, the term "($C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl).

As used herein, the term "[($C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl)$_2$].

As used herein, the term "$C_{1-8}$alkyl-amino-$C_{2-8}$alkynyl" refers to a radical of the formula: —$C_{2-8}$alkynyl-NH—$C_{1-8}$alkyl.

As used herein, the term "($C_{1-8}$alkyl)$_2$-amino-$C_{2-8}$alkynyl" refers to a radical of the formula: —$C_{2-8}$alkynyl-N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "$C_{1-8}$alkyl-thio" refers to a radical of the formula: —S—$C_{1-8}$alkyl.

As used herein, the term "amino-$C_{2-8}$alkenyl" refers to a radical of the formula: —$C_{2-8}$alkenyl-NH$_2$.

As used herein, the term "amino-$C_{1-8}$alkoxy" refers to a radical of the formula: —O—$C_{1-8}$alkyl-NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino" refers to a radical of the formula: —NH—$C_{1-8}$ alkyl-$NH_2$.

As used herein, the term "(amino-$C_{1-8}$alkyl)$_2$-amino" refers to a radical of the formula: —N($C_{1-8}$alkyl-$NH_2$).

As used herein, the term "(amino-$C_{1-8}$alkyl)($C_{1-8}$alkyl) amino" refers to a radical of the formula: —N($C_{1-8}$alkyl)($C_{1-8}$alkyl-$NH_2$).

As used herein, the term "amino-$C_{2-8}$alkynyl" refers to a radical of the formula: —$C_{2-8}$alkynyl-$NH_2$.

As used herein, the term "aryl-$C_{1-8}$alkoxy-carbonyl" refers to a radical of the formula: —C(O)—O—$C_{1-8}$ alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N($C_{1-8}$ alkyl-aryl)$_2$.

As used herein, the term "(aryl-$C_{1-8}$alkyl)($C_{1-8}$alkyl) amino" refers to a radical of the formula: —N($C_{1-8}$alkyl)($C_{1-8}$alkyl-aryl).

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$ alkyl-N($C_{1-8}$ alkyl-aryl)$_2$.

As used herein, the term "(aryl-$C_{1-8}$alkyl)($C_{1-8}$alkyl) amino-$C_{1-8}$alkyl" refers to a radical of the formula: —$C_{1-8}$alkyl-N($C_{1-8}$alkyl)($C_{1-8}$alkyl-aryl).

As used herein, the term "aryl-amino" refers to a radical of the formula: —NH-aryl.

As used herein, the term "aryl-amino-carbonyl" refers to a radical of the formula: —C(O)—NH-aryl.

As used herein, the term "aryl-sulfonyloxy-$C_{1-8}$alkyl" refers to a radical of the formula: —$C_{1-8}$alkyl-O—$SO_2$-aryl.

As used herein, the term "benzoxy-carbonyl" refers to a radical of the formula: —C(O)—O—$CH_2$-phenyl.

As used herein, the term "$C_{3-14}$cycloalkyl-$C_{1-8}$alkyl" refers to a radical of the formula: —$C_{1-8}$ alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-oxy" refers to a radical of the formula: —O—$C_{3-14}$cycloalkyl.

As used herein, the term "aryl-oxy" refers to a radical of the formula: —O-aryl.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl is partially or completely substituted with one or more halogen atoms where allowed by available valences.

As used herein, the term "halo-$C_{1-8}$alkyl" refers to a radical of the formula: —$C_{1-8}$alkyl-halo, wherein $C_{1-8}$alkyl is partially or completely substituted with one or more halogen atoms where allowed by available valences.

As used herein, the term "halo-$C_{1-8}$alkyl-amino" refers to a radical of the formula: —NH—$C_{1-8}$alkyl-halo.

As used herein, the term "(halo-$C_{1-8}$alkyl)($C_{1-8}$alkyl) amino" refers to a radical of the formula: —N($C_{1-8}$alkyl)($C_{1-8}$ alkyl-halo).

As used herein, the term "(halo-$C_{1-8}$alkyl)$_2$-amino" refers to a radical of the formula: —N($C_{1-8}$alkyl-halo)$_2$.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$ alkyl-heteroaryl.

As used herein, the term "heteroaryl-$C_{1-8}$alkyl-amino" refers to a radical of the formula: —NH—$C_{1-8}$alkyl-heteroaryl.

As used herein, the term "(heteroaryl-$C_{1-8}$alkyl)$_2$-amino" refers to a radical of the formula: —N($C_{1-8}$alkyl-heteroaryl)$_2$.

As used herein, the term "(heteroaryl-$C_{1-8}$alkyl)($C_{1-8}$alkyl)amino" refers to a radical of the formula: —N($C_{1-8}$alkyl)($C_{1-8}$alkyl-heteroaryl).

As used herein, the term "heteroaryl-$C_{1-8}$alkyl-amino-$C_{1-8}$alkyl" refers to a radical of the formula: —$C_{1-8}$ alkyl-NH—$C_{1-8}$alkyl-heteroaryl.

As used herein, the term "(heteroaryl-$C_{1-8}$alkyl)$_2$-amino-$C_{1-8}$alkyl" refers to a radical of the formula: —$C_{1-8}$alkyl-N($C_{1-8}$alkyl-heteroaryl)$_2$.

As used herein, the term "(heteroaryl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heteroaryl).

As used herein, the term "heteroaryl-amino" refers to a radical of the formula: —NH-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —C alkyl-heterocyclyl.

As used herein, the term "heterocyclyl-$C_{1-8}$alkyl-amino" refers to a radical of the formula: —NH—$C_{1-8}$alkyl-heterocyclyl.

As used herein, the term "(heterocyclyl-$C_{1-8}$alkyl)$_2$-amino" refers to a radical of the formula: —N($C_{1-8}$alkyl-heterocyclyl)$_2$.

As used herein, the term "(heterocyclyl-$C_{1-8}$alkyl)($C_{1-8}$alkyl)amino" refers to a radical of the formula: —N($C_{1-8}$alkyl)($C_{1-8}$alkyl-heterocyclyl).

As used herein, the term "heterocyclyl-$C_{1-8}$alkyl-amino-$C_{1-8}$alkyl" refers to a radical of the formula: —$C_8$alkyl-NH—$C_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N($C_{1-8}$alkyl-heterocyclyl)$_2$.

As used herein, the term "(heterocyclyl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heterocyclyl).

As used herein, the term "heterocyclyl-amino" refers to a radical of the formula: —NH-heterocyclyl.

As used herein, the term "(heterocyclyl)($C_{1-8}$alkyl) amino" refers to a radical of the formula: —N($C_{1-8}$alkyl)(heterocyclyl).

As used herein, the term "heterocyclyl-amino-$C_{1-8}$alkyl" refers to a radical of the formula: —$C_{1-8}$alkyl-NH-heterocyclyl.

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "hydroxy" refers to a radical of the formula: —OH.

As used herein, the term "hydroxy-$C_{1-8}$alkoxy-$C_{1-8}$alkyl" refers to a radical of the formula: —$C_{1-8}$ alkyl-O—$C_{1-8}$ alkyl-OH.

As used herein, the term "hydroxy-$C_{1-8}$alkyl" refers to a radical of the formula: —$C_{1-8}$alkyl-OH, wherein $C_{1-8}$alkyl is partially or completely substituted with one or more hydroxy radicals where allowed by available valences.

As used herein, the term "hydroxy-$C_{1-8}$alkyl-amino" refers to a radical of the formula: —NH—$C_{1-8}$alkyl-OH.

As used herein, the term "(hydroxy-$C_{1-8}$alkyl)$_2$-amino" refers to a radical of the formula: —N($C_{1-8}$alkyl-OH)$_2$.

As used herein, the term "(hydroxy-$C_{1-8}$alkyl)($C_{1-8}$alkylamino" refers to a radical of the formula: —N($C_{1-8}$alkyl)($C_{1-8}$alkyl-OH).

As used herein, the term "hydroxy-$C_{1-8}$alkyl-amino-$C_{1-8}$alkyl" refers to a radical of the formula: —$C_{1-8}$alkyl-NH—$C_{1-8}$alkyl-OH.

As used herein, the term "(hydroxy-$C_{1-8}$alkyl)$_2$-amino-$C_{1-8}$alkyl" refers to a radical of the formula: —$C_{1-8}$ alkyl-N($C_{1-8}$ alkyl-OH)$_2$.

As used herein, the term "(hydroxy-$C_{1-8}$alkyl)($C_{1-8}$alkyl) amino-$C_{1-8}$alkyl" refers to a radical of the formula: —$C_{1-8}$alkyl-N($C_{1-8}$ alkyl)($C_{1-8}$ alkyl-OH).

As used herein, the term "hydroxy-$C_{1-8}$alkyl-amino-$C_{1-8}$alkoxy" refers to a radical of the formula: —O—$C_{1-8}$alkyl-NH—$C_{1-8}$alkyl-OH.

As used herein, the term "(hydroxy-$C_{1-8}$alkyl)$_2$-amino-$C_{1-8}$alkoxy" refers to a radical of the formula: —O—$C_{1-8}$alkyl-N($C_{1-8}$alkyl-OH)$_2$.

As used herein, the term "(hydroxy-$C_{1-8}$alkyl)($C_{1-8}$alkyl) amino-$C_{1-8}$alkoxy" refers to a radical of the formula: —O—$C_{1-8}$alkyl-N($C_{1-8}$alkyl)($C_{1-8}$ alkyl-OH).

As used herein, the term "hydroxy-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "(hydroxy-$C_{1-8}$alkyl)$_2$-amino-$C_{1-8}$alkyl)$_2$-amino" refers to a radical of the formula: —N($C_{1-8}$ alkyl-NH—$C_{1-8}$alkyl-OH)$_2$.

As used herein, the term "(hydroxy-$C_{1-8}$alkyl)$_2$-amino-$C_{1-8}$alkyl-amino" refers to a radical of the formula: —NH—$C_{1-8}$alkyl-N($C_{1-8}$alkyl-OH)$_2$.

As used herein, the term "(hydroxy-$C_{1-8}$alkyl-amino-$C_{1-8}$alkyl)($C_{1-8}$alkyl)amino" refers to a radical of the formula: —N($C_{1-8}$alkyl)($C_{1-8}$ alkyl-NH—$C_{1-8}$alkyl-OH).

As used herein, the term "[(hydroxy-$C_{1-8}$alkyl)$_2$-amino-$C_{1-8}$ alkyl]($C_{1-8}$alkyl)amino" refers to a radical of the formula: —N($C_{1-8}$alkyl)[$C_{1-8}$alkyl-N($C_{1-8}$alkyl-OH)$_2$].

As used herein, the term "(hydroxy-$C_{1-8}$alkyl)($C_{1-8}$alkyl) amino-$C_{1-8}$alkyl-amino" refers to a radical of the formula: —NH—$C_{1-8}$alkyl-N($C_{1-8}$alkyl,$C_{1-8}$alkyl-OH).

As used herein, the term "[(hydroxy-$C_{1-8}$alkyl)($C_{1-8}$alkyl) amino-$C_{1-8}$alkyl]($C_{1-8}$alkyl)amino" refers to a radical of the formula: —N($C_{1-8}$alkyl) [$C_{1-8}$ alkyl-N($C_{1-8}$ alkyl)($C_{1-8}$alkyl-OH)].

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or a form thereof encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{1-14}$cycloalkyl, $C_{1-14}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{1-14}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) having a form selected from the group consisting of a free acid, free base, prodrug, salt, hydrate, solvate, clathrate, isotopologue, racemate, enantiomer, diastereomer, stereoisomer, polymorph and tautomer form thereof.

In certain aspects described herein, the form of the compound of Formula (I) is a free acid, free base or salt thereof.

In certain aspects described herein, the form of the compound of Formula (I) is a salt thereof.

In certain aspects described herein, the form of the compound of Formula (I) is an isotopologue thereof.

In certain aspects described herein, the form of the compound of Formula (I) is a stereoisomer, racemate, enantiomer or diastereomer thereof.

In certain aspects described herein, the form of the compound of Formula (I) is a tautomer thereof.

In certain aspects described herein, the form of the compound of Formula (I) is a pharmaceutically acceptable form.

In certain aspects described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in organic Synthesis (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) can form salts, which are intended to be included within the scope of this description. Reference to a compound of Formula (I) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain particular aspects of acid addition salts include chloride or dichloride.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J.* of *Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, $^{35}C$ and $^{36}Cl$, respectively, each of which are also within the scope of this description.

Certain isotopically-enriched compounds described herein (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I) and of the salts, solvates, hydrates, esters and prodrugs of the compounds of Formula (I) are further intended to be included in the present description.

Compound Uses

In accordance with the intended scope of the present description, aspects of the present description include compounds that have been identified and have been demonstrated to be useful in selectively preventing, treating or ameliorating HD and have been provided for use for preventing, treating or ameliorating HD.

An aspect of the present description includes a method for preventing, treating or ameliorating HD in a subject in need thereof comprising, administering to the subject an effective amount of a compound of Formula (I) or a form thereof.

An aspect of the present description includes a method for treating or ameliorating HD in a subject in need thereof comprising, administering to the subject an effective amount of a compound of Formula (I) or a form thereof.

An aspect of the present description includes a method for preventing HD in a subject in need thereof comprising, administering to the subject an effective amount of a compound of Formula (I) or a form thereof.

An aspect of the present description includes a method for treating HD in a subject in need thereof comprising, administering to the subject an effective amount of a compound of Formula (I) or a form thereof.

An aspect of the present description includes a method for ameliorating HD in a subject in need thereof comprising, administering to the subject an effective amount of a compound of Formula (I) or a form thereof.

Another aspect of the present description includes a method for treating or ameliorating HD in a subject in need thereof comprising, administering to the subject an effective amount of a compound salt of Formula (I) or a form thereof.

An aspect of the present description includes a method for use of a compound of Formula (I) or a form or composition thereof for treating or ameliorating HD in a subject in need thereof comprising, administering to the subject an effective amount of the compound of Formula (I) or a form or composition thereof.

Another aspect of the present description includes a method for use of a compound salt of Formula (I) or a form or composition thereof for treating or ameliorating HD in a subject in need thereof comprising, administering to the subject an effective amount of the compound salt of Formula (I) or a form thereof.

An aspect of the present description includes a use for a compound of Formula (I) or a form thereof for treating or ameliorating HD in a subject in need thereof comprising, administering to the subject an effective amount of the compound of Formula (I) or a form thereof.

Another aspect of the present description includes a use for a compound salt of Formula (I) or a form thereof for treating or ameliorating HD in a subject in need thereof comprising, administering to the subject an effective amount of the compound salt of Formula (I) or a form thereof.

An aspect of the present description includes a use for a compound of Formula (I) or a form thereof in the manufacture of a medicament for treating or ameliorating HD in a subject in need thereof comprising, administering to the subject an effective amount of the medicament.

Another aspect of the present description includes a use for a compound salt of Formula (I) or a form thereof in the manufacture of a medicament for treating or ameliorating HD in a subject in need thereof comprising, administering to the subject an effective amount of the medicament.

An aspect of the present description includes in vitro or in vivo use of the compound of Formula (I) or a form thereof having activity toward HD.

An aspect of the present description includes a use of the compound of Formula (I) or a form thereof in a combination therapy to provide additive or synergistic activity, thus enabling the development of a combination product for treating or ameliorating HD.

Another aspect of the present description includes a combination therapy comprising compounds described herein in combination with one or more known drugs or one or more known therapies may be used to treat HD regardless of whether HD is responsive to the known drug.

An aspect of the present description includes a use for a compound of Formula (I) or a form thereof in a combination product with one or more therapeutic agents for treating or ameliorating HD in a subject in need thereof comprising, administering to the subject an effective amount of the compound of Formula (I) or a form thereof in combination with an effective amount of the one or more agents.

Another aspect of the present description includes a use for a compound salt of Formula (I) or a form thereof in a combination product with one or more therapeutic agents for treating or ameliorating HD in a subject in need thereof comprising, administering to the subject an effective amount of the compound salt of Formula (I) or a form thereof in combination with an effective amount of the one or more agents.

In an aspect of a use or method provided herein, compounds of Formula (I) or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I) or a form thereof and an additional agent(s) can be administered to a subject or contacted with a cell in single composition or different compositions. In a specific aspect, a compound(s) of Formula (I) or a form thereof is used in combination with gene therapy to inhibit HTT expression (using, e.g., viral delivery vectors) or the administration of another small molecule HTT inhibitor. In another specific aspect, a compound(s) of Formula (I) or a form thereof are used in combination with cell replacement using differentiated non-mutant HTT stem cells. In another specific aspect, a compound(s) of Formula (I) or a form thereof are used in combination with cell replacement using differentiated HTT stem cells.

In one aspect, provided herein is the use of compounds of Formula (I) or a form thereof in combination with supportive standard of care therapies, including palliative care.

An aspect of the present description includes a use for a compound of Formula (I) or a form thereof in the preparation of a kit for treating or ameliorating HD in a subject in need thereof comprising, the compound of Formula (I) or a form thereof and instructions for administering an effective amount of the compound of Formula (I) or a form thereof.

An aspect of the present description includes a use for a compound of Formula (I) or a form thereof in the preparation of a kit for treating or ameliorating HD in a subject in need thereof comprising, the compound of Formula (I) or a form thereof and instructions for administering an effective amount of the compound of Formula (I) or a form thereof; and optionally, for administering to the subject an effective amount of the compound of Formula (I) or a form thereof in a combination product with an effective amount of one or more therapeutic agents.

An aspect of the present description includes a use for a compound of Formula (I) or a form thereof in the preparation of a kit for treating or ameliorating HD in a subject in need thereof comprising, the compound of Formula (I) or a form thereof and instructions for administering an effective amount of the compound of Formula (I) or a form thereof;

and optionally, for administering to the subject an effective amount of the compound of Formula (I) or a form thereof in a combination product with an effective amount of the one or more therapeutic agents; and optionally, for administering to the subject an effective amount of the compound of Formula (I) or a form thereof in a combination product with an effective amount of the one or more therapeutic agents in a combination therapy with a standard of care supportive therapy, wherein the standard of care supportive therapy is palliative care.

In one respect, for each of such aspects, the subject is treatment naive. In another respect, for each of such aspects, the subject is not treatment naive.

As used herein, the term "preventing" refers to keeping a disease, disorder or condition from occurring in a subject that may be predisposed to the disease, disorder and/or condition but has not yet been diagnosed as having the disease, disorder and/or condition.

As used herein, the term "treating" refers to inhibiting the progression of a disease, disorder or condition in a subject already exhibiting the symptoms of the disease, disorder and/or condition, i.e., arresting the development of a disease, disorder and/or condition that has already affected the subject.

As used herein, the term "ameliorating" refers to relieving the symptoms of a disease, disorder or condition in a subject already exhibiting the symptoms of the disease, disorder and/or condition, i.e., causing regression of the disease, disorder and/or condition that has already affected the subject.

As used herein, the term "subject" refers to an animal or any living organism having sensation and the power of voluntary movement, and which requires oxygen and organic food. Nonlimiting examples include members of the human, primate, equine, porcine, bovine, murine, rattus, canine and feline specie. In certain aspects, the subject is a mammal or a warm-blooded vertebrate animal. In other aspects, the subject is a human. As used herein, the term "patient" may be used interchangeably with "subject" and "human".

As used herein, the terms "effective amount" or "therapeutically effective amount" mean an amount of compound of Formula (I) or a form, composition or medicament thereof that achieves a target plasma concentration that is effective in treating or ameliorating HD as described herein and thus producing the desired therapeutic, ameliorative, inhibitory or preventative effect in a subject in need thereof. In one aspect, the effective amount may be the amount required to treat HD in a subject or patient, more specifically, in a human.

In another aspect, the concentration-biological effect relationships observed with regard to a compound of Formula (I) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., "q.d."), twice (once in approximately a 12 hour period; i.e., "b.i.d." or "q.12h"), thrice (once in approximately an 8 hour period; i.e., "t.i.d." or "q.8h"), or four times (once in approximately a 6 hour period; i.e., "q.d.s.", or "q.6h") daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intravenous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmacological procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

In one aspect, provided herein are methods for modulating the amount of HTT (huntingtin protein), comprising contacting a human cell with a compound of Formula (I) or a form thereof. In a specific aspect, provided herein are methods for modulating the amount of HTT, comprising contacting a human cell with a compound of Formula (I) or a form thereof that modulates the expression of HTT. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I).

In a specific aspect, provided herein is a method for enhancing the inhibition of mutant HTT transcribed from the Htt gene, comprising contacting a human cell with a compound of Formula (I) or a form thereof. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of wild-type "normal" HTT expression and/or function. In another aspect, the human cell is from a human with HD. In another aspect, the human cell is in a human with HD. In one aspect, the compound is a form of the compound of Formula (I).

In another aspect, provided herein is a method for modulating the inhibition of mutant HTT transcribed from the Htt gene, comprising administering to a non-human animal model for HD a compound of Formula (I) or a form thereof. In a specific aspect, provided herein is a method for modulating the inhibition of mutant HTT transcribed from the Htt gene, comprising administering to a non-human animal model for HD a compound of Formula (I) or a form thereof. In a specific aspect, the compound is a form of the compound of Formula (I).

In another aspect, provided herein is a method for decreasing the amount of mutant HTT, comprising contacting a human cell with a compound of Formula (I) or a form thereof. In a specific aspect, provided herein is a method for decreasing the amount of mutant HTT, comprising contacting a human cell with a compound of Formula (I) that inhibits the transcription of mutant HTT (huntingtin mRNA) from the Htt gene. In another specific aspect, provided herein is a method for decreasing the amount of HTT, comprising contacting a human cell with a compound of Formula (I) that inhibits the expression of mutant HTT transcribed from the Htt gene. The human cell can be contacted with a compound of Formula (I) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I).

In certain aspects, treating or ameliorating HD with a compound of Formula (I) or a form thereof (alone or in combination with an additional agent) has a therapeutic effect and/or beneficial effect. In a specific aspect, treating HD with a compound of Formula (I) or a form thereof (alone or in combination with an additional agent) results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^{3}H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

In accordance with the intended scope of the present description, aspects of the present description include compounds that have been identified and have been demonstrated to be useful in selectively preventing, treating or ameliorating HD and have been provided for use as one or more pharmaceutical compositions for preventing, treating or ameliorating HD.

An aspect of the present description includes a use for a compound of Formula (I) or a form thereof in the preparation of a pharmaceutical composition for treating or ameliorating HD in a subject in need thereof comprising, administering to the subject an effective amount of the compound of Formula (I) or a form thereof in admixture with one or more pharmaceutically acceptable excipients.

An aspect of the present description includes a use for a pharmaceutical composition of the compound of Formula (I) or a form thereof in the preparation of a kit for treating or ameliorating HD in a subject in need thereof comprising, the pharmaceutical composition of the compound of Formula (I) or a form thereof and instructions for administering the pharmaceutical composition.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In certain aspects, the pharmaceutical composition is formulated to achieve a pH of from about pH 3 to about pH 7. In other aspects, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other aspects, pharmaceutical compositions described herein may be formulated as suspensions comprising a compound of Formula (I) or a form thereof in admixture with one or more pharmaceutically acceptable excipients suitable for the manufacture of a suspension. In yet other aspects, pharmaceutical compositions described herein may be formulated as dispersible powders and granules suitable for preparation of a suspension by the addition of one or more excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In certain aspects, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween® 80, respectively) or polyoxyl 40 hydrogenated castor oil.

In other aspects, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative aspects, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In certain aspects, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Methods

As disclosed herein, general methods for preparing the compounds of Formula (I) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Compounds of Formula (I), wherein $R_1$ and $R_2$ are monocyclic or bicyclic heterocyclyl or heteroaryl ring systems, may be prepared as described in Scheme A below.

Scheme A

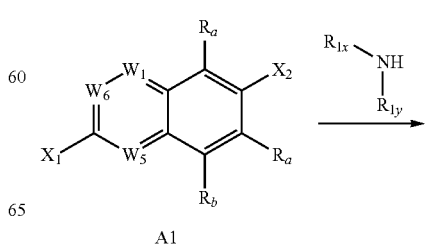

A1

Scheme C

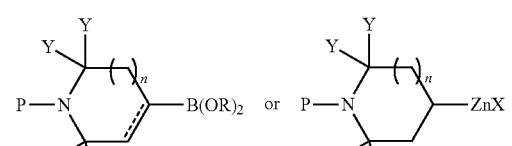

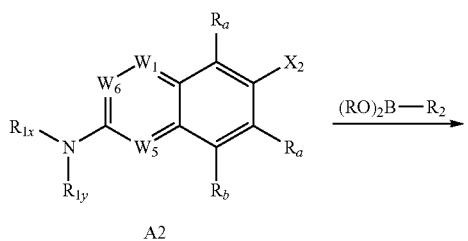

A2

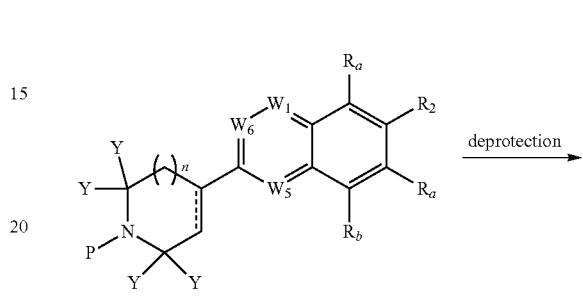

C1

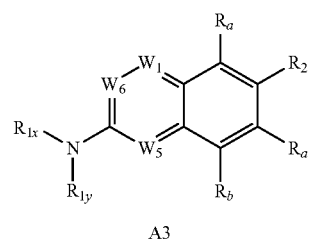

A3

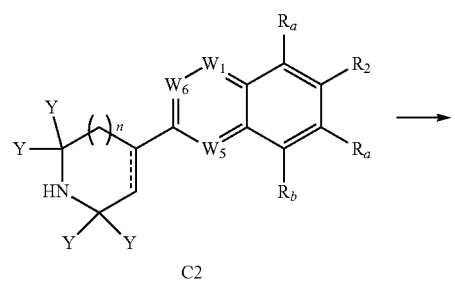

C2

Compound A1 (where $X_1$ and $X_2$ are independently bromine, chlorine and the like) is converted to Compound A2 by a nucleophilic substitution with a primary or secondary amine in the presence of a suitable base (such as $K_2CO_3$ and the like) in a suitable solvent (such as DMF and the like). Alternatively, Compound A1 is converted to Compound A2 via cross coupling with a primary or secondary amine (i.e., an $R_1$ substituent base) in the presence of a suitable catalyst (such as RuPhos Pd G2 and the like) and base (such as sodium tert-butoxide and the like) in an appropriate solvent (such as 1,4-dioxane and the like). Compound A2 is converted to Compound A3 by a Suzuki coupling with an aryl- or heteroaryl-boronic acid (or pinacol boronic ester) (i.e., an $R_2$ substituted-boronic acid or ester) in the presence of a catalyst (such as Pd(dppf)Cl$_2$ and the like) and base (such as aqueous $K_2CO_3$ and the like) in a suitable solvent (such as 1,4-dioxane and the like).

Compounds of Formula (I), wherein $R_1$ and $R_2$ are monocyclic or bicyclic heterocyclyl or heteroaryl ring systems, may be prepared as described in Scheme B below.

Scheme B

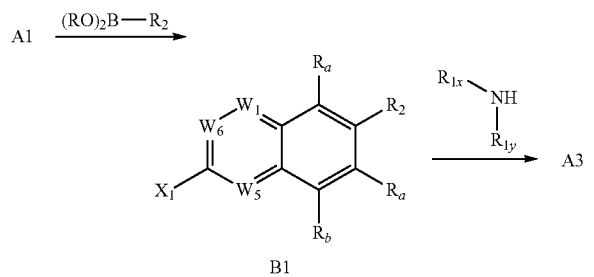

B1

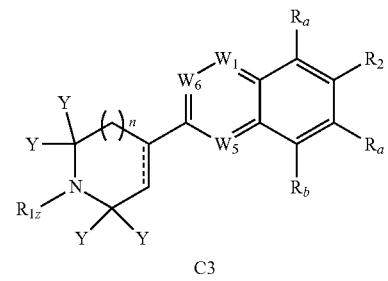

C3

Following conditions described in Scheme A, but switching the order of steps 1 and 2, compound B1 can be converted to compound A3.

Compounds of Formula (I), wherein $R_1$ and $R_2$ are monocyclic or bicyclic heterocyclyl or heteroaryl ring systems, may be prepared as described in Scheme C below.

Compound B1 (where $X_1$ is bromine, chlorine and the like) is converted to Compound C1 by a Suzuki coupling with an optionally substituted and appropriately protected amino-containing cycloalkyl/cycloalkenyl pinacol boronic ester (where Y is hydrogen or an optionally substituted alkyl group and P is a protecting group such as Boc and the like) (i.e., an $R_1$ substituted-boronic ester) in the presence of a catalyst (such as Pd(dppf)Cl$_2$ and the like) and base (such as aqueous $K_2CO_3$ and the like) in a suitable solvent (such as 1,4-dioxane and the like). Alternatively, Compound B1 is converted to Compound C1 by a Negishi coupling with an optionally substituted and appropriately protected amino-containing cycloalkyl zinc halide (i.e., an $R_1$ substituted-zinc halide) in the presence of a catalyst (such as Pd(dppf)Cl$_2$ and the like) in a suitable solvent (such as 1,4-dioxane and the like). Upon treatment with a deprotecting agent appropriate for the protecting group (such as HCl in dioxane for a Boc protecting group), Compound C1 is converted to Compound C2. Compound C2 is converted to Compound C3 by reductive amination with a suitable aldehyde and reducing agent (such as NaBH(OAc)$_3$ and the like) in a suitable solvent (such as 1,2-dichloroethane and the like). Alternatively, Compound C2 is converted to Compound C3 by alkylation with an alkyl halide (such as 2-iodopropane and the like) in the presence of an appropriate base (such as K$_2$CO$_3$ and the like). In cases where unsaturation exists in the ring containing the basic amino group, the compound may be converted to the fully saturated analog under an atmosphere of H$_2$ in a suitable solvent (such as methanol and the like) and in the presence of catalyst (such as 10% Pd/C and the like).

Compounds of Formula (I), wherein R$_1$ and R$_2$ are monocyclic or bicyclic heterocyclyl or heteroaryl ring systems, may be prepared as described in Scheme D below.

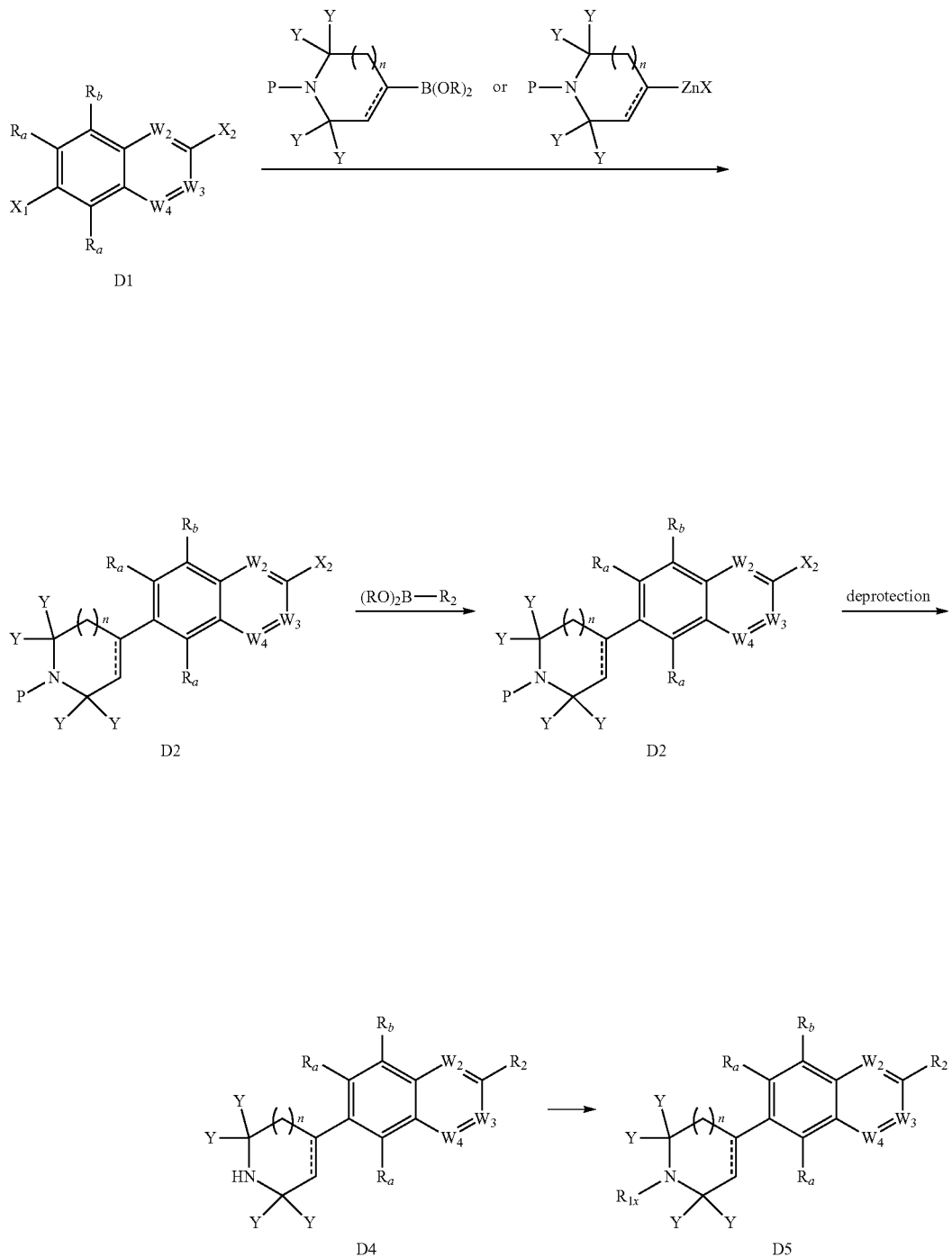

Following the general conditions described in Scheme C, compound D1 can be converted to compound D5.

Compounds of Formula (I), wherein $R_1$ and $R_2$ are monocyclic or bicyclic heterocyclyl or heteroaryl ring systems, may be prepared as described in Scheme E below.

Scheme E

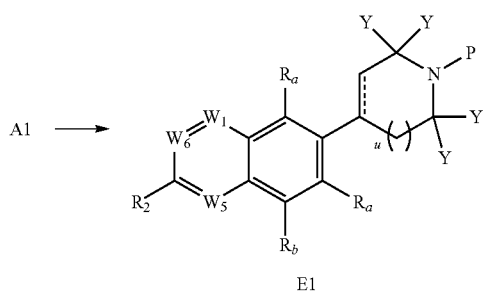

Following the general conditions described in Scheme A and/or Scheme C, compound A1 can be converted to compound E1.

Compounds of Formula (I), wherein $R_1$ and $R_2$ are monocyclic or bicyclic heterocyclyl or heteroaryl ring systems, may be prepared as described in Scheme F below.

Scheme F

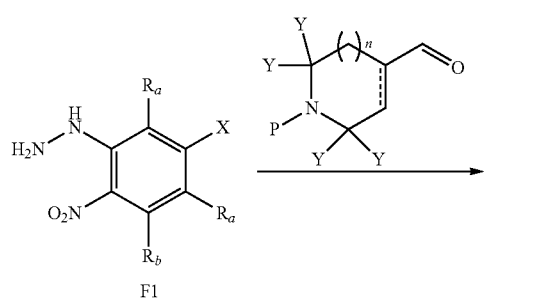

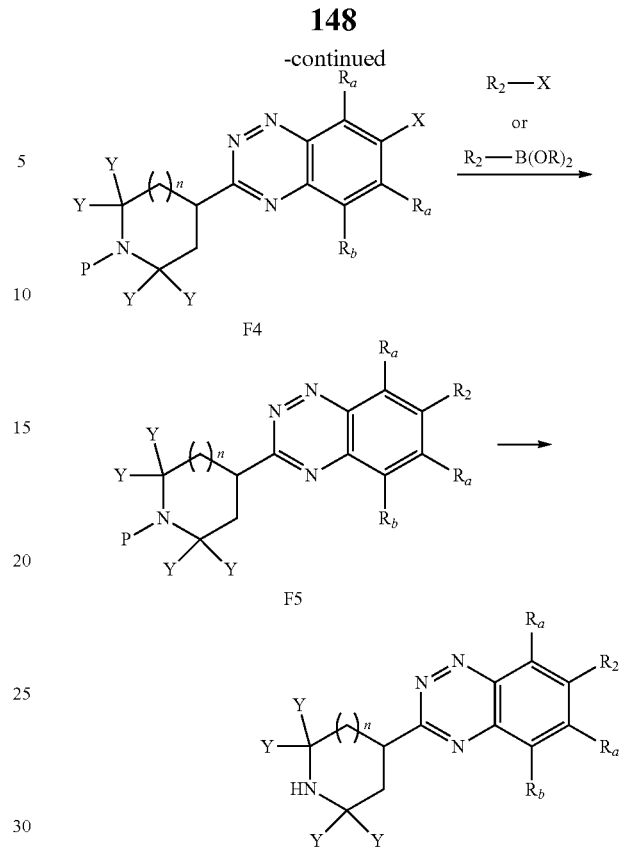

Compound F1 (where X is bromine, chlorine and the like) is converted to Compound F2 through a condensation with an optionally substituted N-Boc-piperidine-4-aldehyde (where Y is hydrogen or an optionally substituted alkyl group and P is a protecting group such as Boc and the like) in a suitable solvent (such as EtOH and the like). Compound F2 is converted to Compound F3 by reducing the nitro group with $H_2$ in the presence of a catalyst (such as $PtO_2$ and the like) in an appropriate solvent (such as EtOH and the like). Compound F3 is converted to Compound F4 through a cyclization/oxidation reaction with an appropriate oxidant (such as DDQ and the like) in an appropriate solvent (such as $CH_3CN$ and the like). Compound F4 is converted to Compound F5 by a Suzuki coupling with an aryl- or heteroaryl-boronic acid (or pinacol boronic ester) (i.e., an $R_2$ substituted-boronic acid or ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound F4 is converted to Compound F5 by treatment with pinacolatodiboron and a base (such as KOAc and the like) in the presence of a catalyst (such as $Pd(dppf)Cl_2$ and the like) in an appropriate solvent (such as 1,4-dioxane and the like), followed by addition of an aryl- or heteroaryl-halide (i.e., an $R_2$ substituted-halide). Compound F5 is converted to Compound F6 upon treatment with conditions appropriate to the removal of the protecting group (such as TFA or HCl in dioxane for a Boc protecting group). Additional modification to the basic amino group can be achieved according to methods described in Scheme C.

Compounds of Formula (I), wherein $R_1$ and $R_2$ are monocyclic or bicyclic heterocyclyl or heteroaryl ring systems, may be prepared as described in Scheme G below.

Scheme G

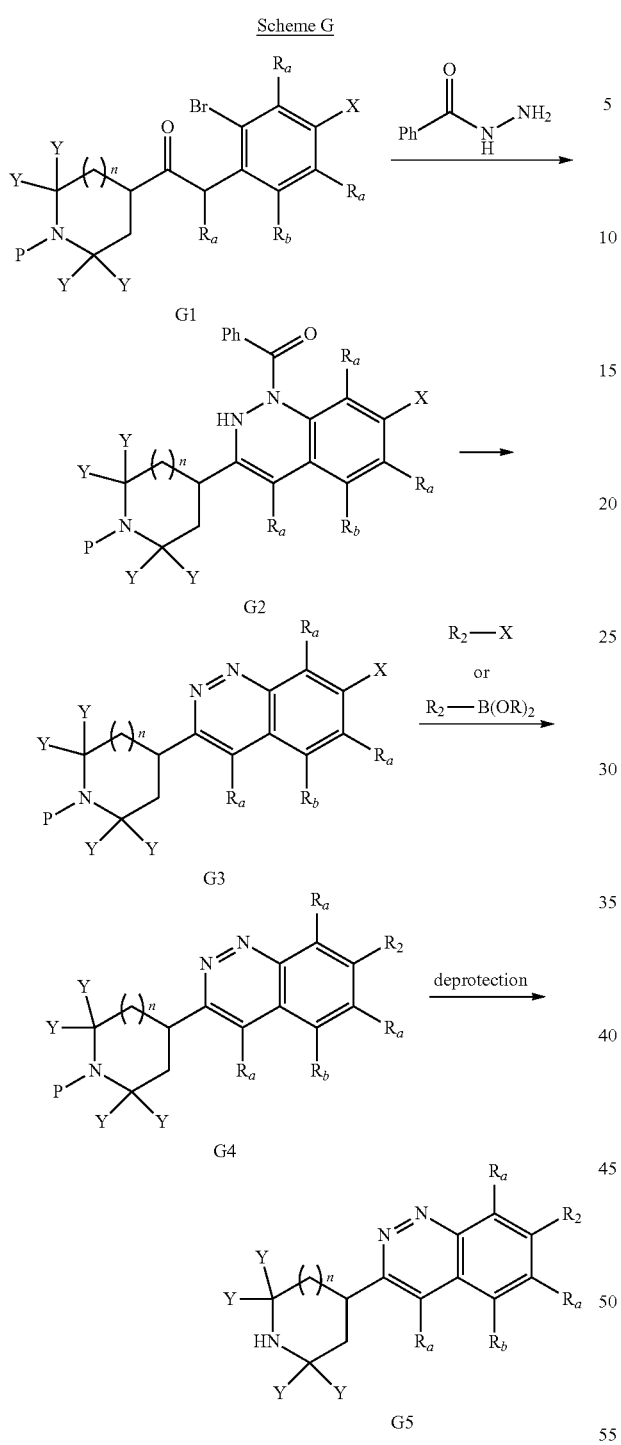

Compound G1 (where X is bromine, chlorine and the like; Y is hydrogen or optionally substituted alkyl; and P is an appropriate protecting group) is converted to Compound G2 through a condensation/cyclization sequence in the presence of catalyst (such as CuI and the like), ligand (such as 1,10-phenanthroline and the like) and base (such as NaOt-Bu and the like) in an appropriate solvent (such as DMF and the like). Compound G2 is converted to Compound G3 by treatment with strong acid (conc. HCl and the like) in the presence of oxygen. Compound G3 is converted to Compound G4 by a Suzuki coupling with an aryl- or heteroaryl- boronic acid (or pinacol boronic ester) (i.e., an $R_2$ substituted-boronic acid or ester) in the presence of a catalyst (such as Pd(dppf)Cl$_2$ and the like) and base (such as aqueous K$_2$CO$_3$ and the like) in a suitable solvent (such as 1,4-dioxane and the like). Alternatively, Compound G3 is converted to Compound G4 by treatment with pinacolatodiboron and a base (such as KOAc and the like) in the presence of a catalyst (such as Pd(dppf)Cl$_2$ and the like) in an appropriate solvent (such as 1,4-dioxane and the like), followed by addition of an aryl- or heteroaryl-halide (i.e., an $R_2$ substituted-halide). Compound G4 is converted to Compound G5 upon treatment with conditions appropriate to the removal of the protecting group (such as TFA or HCl in dioxane for a Boc protecting group). Additional modification to the basic amino group can be achieved according to methods described in Scheme C.

Compounds of Formula (I), wherein $R_1$ and $R_2$ are monocyclic or bicyclic heterocyclyl or heteroaryl ring systems, may be prepared as described in Scheme H below.

Scheme H

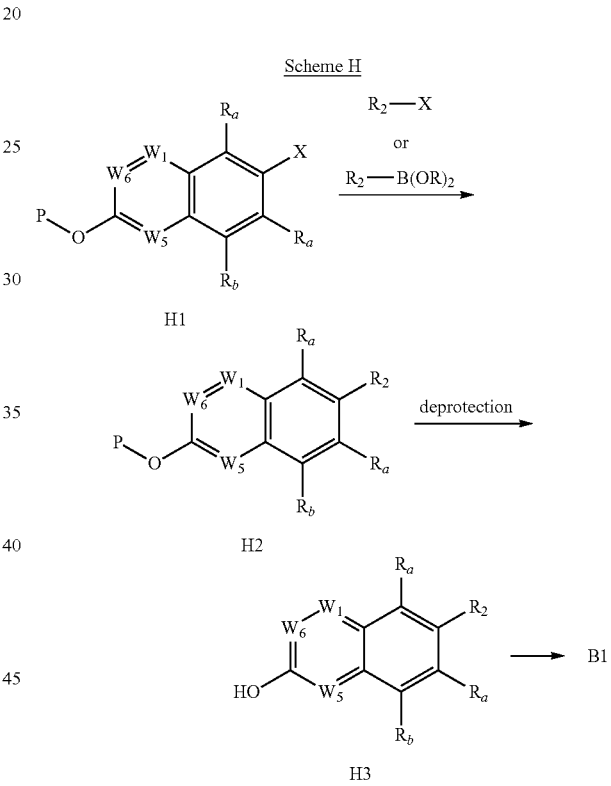

Compound H1 (where $X_2$ is bromine, chlorine and the like; and P is a protecting group such as tert-butyl and the like) is converted to Compound H2 by a Suzuki coupling with an aryl- or heteroaryl-boronic acid or ester (i.e., an $R_2$ substituted-boronic acid or ester) in the presence of a catalyst (such as Pd(dppf)Cl$_2$ and the like) and base (such as aqueous K$_2$CO$_3$ and the like) in a suitable solvent (such as 1,4-dioxane and the like). Upon treatment with acid (such as TFA or HCl in dioxane and the like) Compound H2 is converted to Compound H3. Compound H3 is converted to Compound B1 (where $X_1$ is triflate and the like) by treatment with an activated triflate (such as Tf$_2$O or Tf$_2$NPh and the like) in the presence of base (such as K$_2$CO$_3$ or NaH and the like) in an appropriate solvent (such as THF or DMF and the like). Alternatively, Compound H3 can be converted to Compound B1 (where $X_1$ is Cl and the like) by treatment with a dehydrative halogenating agent (such as POCl$_3$ and the like). Additional modification to the basic amino group can be achieved according to methods described in Scheme C.

Compounds of Formula (I), wherein $R_1$ and $R_2$ are monocyclic or bicyclic heterocyclyl or heteroaryl ring systems, may be prepared as described in Scheme I below.

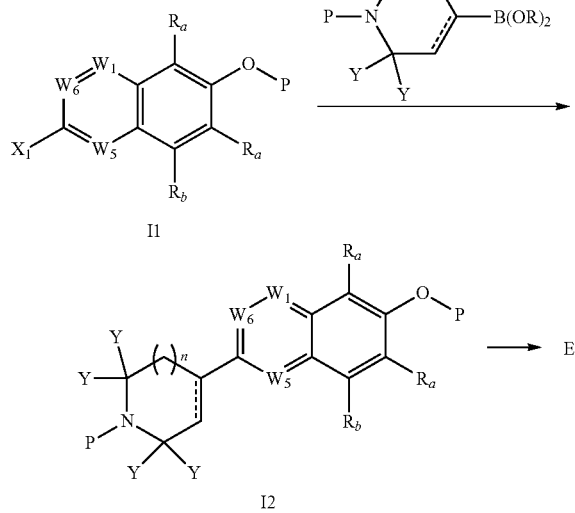

Scheme I

Compound I1 (where $X_1$ is bromine, chlorine and the like; and P is a protecting group such as methyl and the like) is converted to Compound I2 by a Suzuki coupling with an optionally substituted and appropriately protected amino-containing cycloalkyl/cycloalkenyl pinacol boronic ester (where Y is hydrogen or an optionally substituted alkyl group and P is a protecting group such as Boc and the like) (i.e., an $R_1$ substituted-boronic ester) in the presence of a catalyst (such as Pd(dppf)Cl$_2$ and the like) and base (such as aqueous $K_2CO_3$ and the like) in a suitable solvent (such as 1,4-dioxane and the like). Compound I2 is converted to Compound E2 (where $X_2$ is triflate and the like) by treatment with an activated triflate (such as Tf$_2$O or Tf$_2$NPh and the like) in the presence of base (such as $K_2CO_3$ or NaH and the like) in an appropriate solvent (such as THF or DMF and the like). Additional modification to the basic amino group can be achieved according to methods described in Scheme C.

Specific Synthetic Examples

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

COMPOUND EXAMPLES

As used above, and throughout the present description, the following abbreviations, unless otherwise indicated, shall be understood to have the following meanings:

| Abbreviation | Meaning |
| --- | --- |
| Δ | heating (chemistry) or deletion (biology) |
| AcOH or HOAc | acetic acid |
| Ac$_2$O | acetic anhydride |
| Ag$_2$SO$_4$ | silver sulfate |
| Ar | argon |
| ACN or CH$_3$CN | acetonitrile |
| atm | atmosphere(s) |
| B$_2$pin$_2$ | bis(pinacolato)diboron |
| Boc | tert-butoxy-carbonyl |
| Boc$_2$O | di-tert-butyl dicarbonate |
| Br$_2$ | bromine |

-continued

| Abbreviation | Meaning |
| --- | --- |
| nBuLi | n-butyl lithium |
| iBuNO | isobutyl nitrite |
| BuOH | n-butanol |
| $Bu_3SnCl$ | Tributylchlorostannane or tributyltin chloride |
| ° C. | degrees Centigrade |
| Celite ® or Celite | diatomaceous earth |
| $CO_2Cl_2$ | oxalyl chloride |
| $Cs_2CO_3$ | cesium carbonate |
| CuI | copper (I) iodide |
| d/h/hr/hrs/min/s | day(d)/hour(h, hr or hrs)/minute(min)/second(s) |
| DCM or $CH_2Cl_2$ | dichloromethane |
| DDQ | 2,3-dichloro-5,6-dicyano-p-benzoquinone |
| DIEA or DIPEA | N,N-diisopropylethylamine |
| DMA | dimethylacetamide |
| DMAP | 4-(dimethylamino)pyridine or N,N-dimethylpyridin-4-amine |
| DMF | dimethylformamide |
| DMSO | dimethylsulfoxide |
| EtOAc | ethyl acetate |
| EtOH | ethanol |
| $Et_2O$ | diethyl ether |
| $Fe(acac)3_2$ | iron(III) acetylacetonate |
| $H_2$ | hydrogen |
| HCl | hydrochloric acid |
| HI | hydriodic acid |
| $H_2SO_4$ | sulfuric acid |
| $K_2CO_3$ | potassium carbonate |
| KOAc | potassium acetate |
| KOtBu | Potassium t-butoxide |
| KOH | potassium hydroxide |
| $K_2OsO_4 \cdot 2H_2O$ | potassium osmate(VI) dihydrate |
| LAH or $LiAlH_4$ | lithium aluminum hydride |
| Lawesson's reagent | 2,4-bis(4-methoxyphenyl)-1,3,2,4-dithiadiphosphetane-2,4-disulfide |
| LC/MS, LCMS or LC-MS | liquid chromatographic mass spectroscopy |
| LiOH | lithium hydroxide |
| MeOH | methanol |
| $MeSO_3H$ | methanesulfonic acid |
| $MgSO_4$ | magnesium sulfate |
| $MnO_2$ | manganese dioxide |
| MS | mass spectroscopy |
| MsCl | methanesulfonyl chloride |
| NBS | N-bromosuccinimide |
| $NEt_3$ | triethylamine |
| $NH_4Cl$ | ammonium chloride |
| $NH_4OAc$ | ammonium acetate |
| $NaBH_4$ | sodium borohydride |
| $NaBH(OAc)_3$ | sodium triacetoxyborohydride |
| NaH | sodium hydride |
| $NaHCO_3$ | sodium bicarbonate |
| NaHMDS | sodium bis(trimethylsilyl)amide or sodium hexamethyldisilazide |
| NaH | sodium hydride |
| NaOH | sodium hydroxide |
| NaOMe | sodium methoxide |
| $NaNO_2$ | sodium nitrite |
| $Na_2SO_4$ | sodium sulfate |
| $N_2$ | nitrogen |
| $NH_4Cl$ | ammoniuim chloride |
| NMO | 4-methylmorpholine N-oxide |
| NMP | methylpyrrolidone |
| NMR | nuclear magnetic resonance |
| $NOBF_4$ | nitrosonium tetrafluoroborate or nitrosyl tetrafluoroborate |
| $Pb(OAc)_4$ | lead(IV) acetate or lead tetracetate |
| Pd | palladium |
| Pd/C | palladium on carbon |
| $Pd(dppf)Cl_2$ or $Pd(dppf)Cl_2$—$CH_2Cl_2$ | [1,1'-bis(diphenylphosphino)ferrocene]dichloropalladium(II), complex with dichloromethane |
| $PHBU_3BF_4$ or $tBu_3PHBF_4$ | tri-tert-butylphosphonium tetrafluoroborate |
| $PhCH_3$ | toluene |
| PhI | iodobenzene |
| $PhI(OTFA)_2$ | [bis(trifluoroacetoxy)iodo]benzene |
| PhMe | toluene |
| Ph—$N(Tf)_2$ or $PhN(Tf)_2$ | N-phenyl triflimide, also referred to as N-phenyl- |

| Abbreviation | Meaning |
|---|---|
| | bis(trifluoromethanesulfonimide) |
| POBr₃ | phosphoryl bromide or phosphorous(V) oxybromide |
| P₂O₅ | phosphorous pentoxide or phosphorous(V) oxide |
| POCl₃ | phosphoryl chloride or phosphorous(V) oxychloride |
| PhMe | toluene |
| Psi | pounds per square inch pressure |
| Pt₂O | Platinum(IV) oxide |
| Rt or rt | room temperature |
| SEMCl | 2-(trimethylsilyl)ethoxymethyl chloride |
| SnCl₂ | tin(II) chloride or stannous chloride |
| SOCl₂ | thionly chloride |
| S-Phos, SPhos or Sphos | 2-dicyclohexylphosphino-2',6'-dimethoxybiphenyl |
| SPhos Pd G2 | chloro(2-dicyclohexylphosphino-2',6'-dimethoxy-1,1'-biphenyl)(2'-amino-1,1'-biphenyl-2-yl) palladium(II) |
| TBAF | tetrabutylamonium fluoride |
| TBSCl | tert-butyldimetylsilyl chloride |
| TEA, Et₃N or NEt₃ | triethylamine |
| TFA | trifluoroacetic acid |
| THF | tetrahydrofuran |
| TIPS | tiisopropylsilane |
| TLC | thin layer chromatography |
| TMEDA | tetramethylethylenediamine |
| TMS | trimethylsilyl |
| TMSCCH | trimethylsilylacetylene |
| t-Bu | tert-butyl |
| Zn(CN)₂ | zinc cyanide |
| ZnMe₂ | dimethyl zinc |

Example 1

Preparation of Compound 11

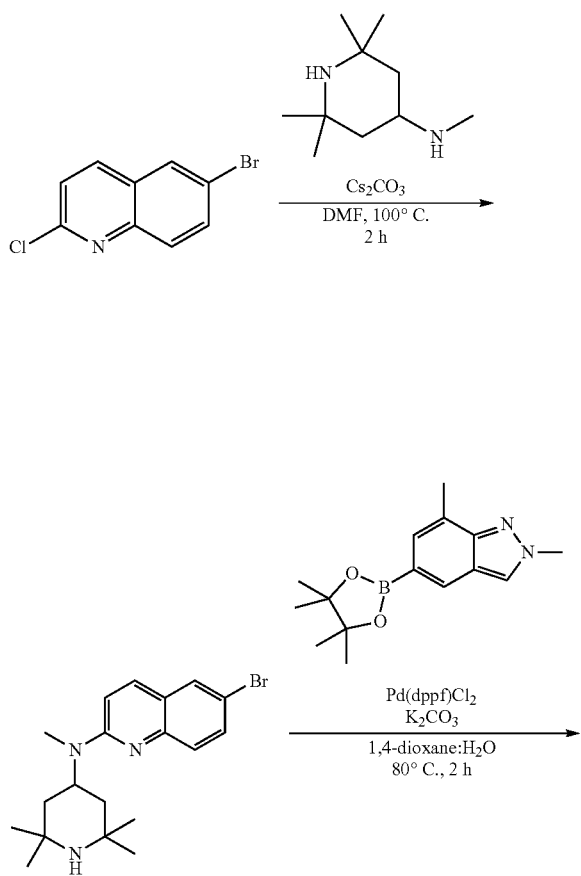

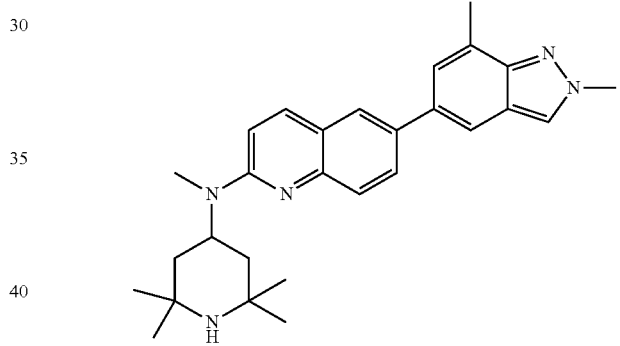

Step A: 6-Bromo-2-chloro-quinoline (121 mg, 0.5 mmol) was combined with N,2,2,6,6-pentamethylpiperidin-4-amine (170 mg, 0.95 mmol) and Cs₂CO₃ (325 mg, 1.0 mmol) in DMF (2 mL) and the mixture was stirred at 100° C. for 2 h. The mixture was partitioned between EtOAc and H₂O. The organic layer was washed with brine, dried over Cs₂SO₄, filtered and concentrated. The residue was chromatographed on silica gel, eluting with 0-5% MeOH in CH₂Cl₂ to yield 6-bromo-N-methyl-N-(2,2,6,6-tetramethylpiperidin-4-yl)quinolin-2-amine (480 mg, 65%). MS m/z 375.9, 377.9 [M+H]⁺.

Step B: 6-Bromo-N-methyl-N-(2,2,6,6-tetramethylpiperidin-4-yl)quinolin-2-amine (40 mg, 0.11 mmol), 2,7-dimethyl-5-(4,4,5,5-tetramethyl-1,3,2-dioxaborolan-2-yl)-2H-indazole (51 mg, 0.15 mmol), and [1,1'-bis(diphenylphosphino)ferrocene] dichloropalladium(II) complex with dichloromethane (8 mg, 0.01 mmol) were combined with aqueous 1 M K₂CO₃ (0.5 mL, 0.5 mmol) and 1,4-dioxane (1 mL). The mixture was stirred at 80° C. for 2 h. The mixture was partitioned between EtOAc and H₂O. The organic layer was washed with brine, dried over Na₂SO₄, filtered and concentrated. The residue was chromatographed on silica gel, eluting with 0-10% MeOH (2 N NH₃) in CH₂Cl₂ to yield 6-(2,7-dimethyl-2H-indazol-5-yl)-N-methyl-N-(2,2,6,6-tetramethylpiperidin-4-yl)quinolin-2-amine (40 mg, 85%) as an off white solid.

MS m/z 442.1 [M+H]⁺; ¹H NMR (DMSO-d₆) δ: 8.35 (s, 1H), 8.11 (d, J=9.4 Hz, 1H), 8.01 (m, 1H), 7.89 (dd, J=9.0, 1.5 Hz, 1H), 7.83 (s, 1H), 7.58 (d, J=9.0 Hz, 1H), 7.46 (s, 1H), 7.13 (d, J=8.9 Hz, 1H), 5.24 (br, 1H), 4.20 (s, 3H), 2.99 (s, 3H), 2.59 (s, 3H), 1.69-1.01 (m, 16H).

Using the procedure described for Example 1, above, additional compounds described herein were prepared by substituting the appropriate boronic acid in Step B, suitable reagents and reaction conditions, obtaining compounds such as those selected from:

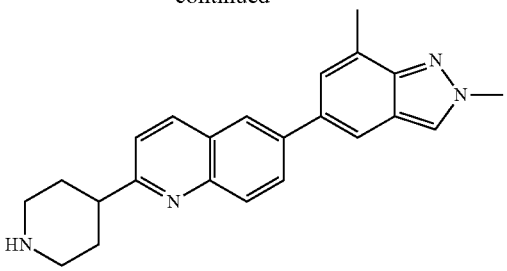

| Cpd | Data |
|---|---|
| 12 | MS m/z 428.5 [M + H]⁺; ¹H NMR (DMSO-d₆) δ: 8.39 (s, 1H), 8.11 (d, J = 9.4 Hz, 1H), 8.00-8.05 (m, 2H), 7.91 (dd, J = 9.0, 1.5 Hz, 1H), 7.71-7.66 (m, 2H), 7.59 (d, J = 9.0 Hz, 1H), 7.13 (d, J = 8.9 Hz, 1H), 5.24 (br, 1H), 4.20 (s, 3H), 2.99 (s, 3H), 1.69-1.01 (m, 16 H). |

Example 2

Preparation of Compound 15

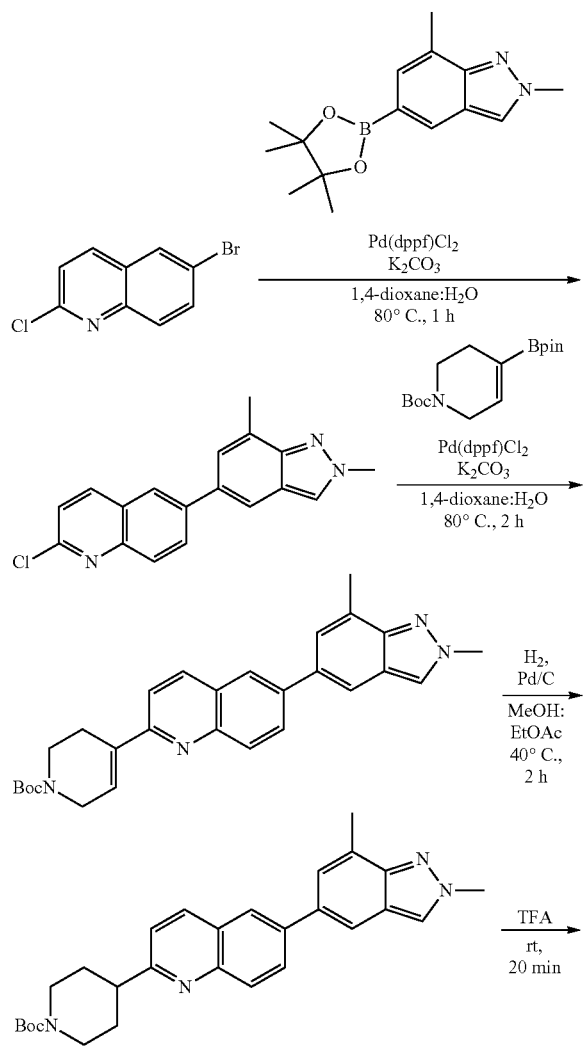

Step A: 6-Bromo-2-chloro-quinoline (242 mg, 1.0 mmol) was combined with 1,1'-bis(diphenylphosphino)ferrocene-palladium(II)dichloride dichloromethane complex (45 mg, 0.05 mmol), 2,7-dimethyl-5-(4,4,5,5-tetramethyl-1,3,2-dioxaborolan-2-yl)-2H-indazole (350 mg, 1.0 mmol), 1,4-dioxane (5 mL) and aqueous 1 M K₂CO₃ (2.5 mL, 2.5 mmol). The mixture was stirred at 80° C. for 1 h. The mixture was partitioned between EtOAc and H₂O. The organic layer was washed with brine, dried over Na₂SO₄, filtered and concentrated. The residue was chromatographed on silica gel, eluting with 10-100% EtOAc in hexanes to yield 2-chloro-6-(2,7-dimethyl-2H-indazol-5-yl)quinoline (150 mg, 49%). MS m/z 308.0, 310.0 [M+H]⁺.

Step B: 2-Chloro-6-(2,7-dimethyl-2H-indazol-5-yl)quinoline (135 mg, 0.30 mmol) was combined with N-Boc-1,2,5,6-tetrahydropyridine-4-boronic acid pinacol ester (193 mg, 0.61 mmol), 1,1'-bis(diphenylphosphino)ferrocene-palladium(II)dichloride dichloromethane complex (40 mg, 0.05 mmol), 1,4-dioxane (2.5 mL), and aqueous 1 M K₂CO₃ (1.2 mL, 1.2 mmol). The mixture was stirred at 90° C. for 2 h. The mixture was partitioned between EtOAc and H₂O. The organic layer was washed with brine, dried over Na₂SO₄, filtered and concentrated. The residue was chromatographed on silica gel, eluting with 0-10% MeOH in EtOAc to yield tert-butyl 4-[6-(2,7-dimethylindazol-5-yl)-2-quinolyl]-3,6-dihydro-2H-pyridine-1-carboxylate (135 mg, 61%). MS m/z 455.1 [M+H]⁺.

Step C: tert-Butyl 4-[6-(2,7-dimethylindazol-5-yl)-2-quinolyl]-3,6-dihydro-2H-pyridine-1-carboxylate (35 mg, 0.08 mmol) was combined with 10% Pd/C (10 mg) in MeOH (3 mL). The mixture was stirred under H₂ (1 atm) for 18 h. The mixture was filtered over Celite®. The filtrate was concentrated to yield tert-butyl 4-[6-(2,7-dimethylindazol-5-yl)-2-quinolyl]piperidine-1-carboxylate (35 mg, 99%). MS m/z 457.2 [M+H]⁺.

Step D: tert-Butyl 4-[6-(2,7-dimethylindazol-5-yl)-2-quinolyl]piperidine-1-carboxylate from Step C (35 mg, 0.077 mmol) was combined with TFA (1 mL). The solution stood for 20 min before the volatiles were removed with a stream of N₂. The residue was partitioned between EtOAc and aqueous 1 M aqueous K₂CO₃. The organic layer was collected and concentrated to yield 6-(2,7-dimethyl-2H-indazol-5-yl)-2-(piperidin-4-yl)quinoline (25 mg, 91%).

MS m/z 357.1 [M+H]⁺; ¹H NMR (DMSO-d₆) δ: 8.40 (s, 1H), 8.33 (d, J=8.5 Hz, 1H), 8.23 (d, J=2.2 Hz, 1H), 8.09

(dd, J=8.8, 2.2 Hz, 1H), 7.99 (d, J=8.8 Hz, 1H), 7.93-7.97 (m, 1H), 7.50-7.57 (m, 1H), 7.48 (d, J=8.5 Hz, 1H), 4.21 (s, 3H), 3.05-3.11 (m, 2H), 2.92-2.99 (m, 1H), 2.61-2.68 (m, 2H), 2.61 (s, 3H), 1.81-1.88 (m, 2H), 1.69-1.79 (m, 2H), NH proton not observed.

Using the procedure described for Example 2, above, additional compounds described herein were prepared by substituting the appropriate starting material, suitable reagents and reaction conditions, obtaining compounds such as those selected from:

| Cpd | Data |
|---|---|
| 3 | MS m/z 343.2 [M + H]+; 1H NMR (DMSO-d6) δ: 9.29 (br s, 1H), 9.19 (br s, 1H), 8.81 (br s, 1H), 8.47-8.52 (m, 2H), 8.33-8.40 (m, 2H), 8.21 (m, 1H), 7.73-7.80 (m, 3H), 4.22 (s, 3H), 3.54 (br s, 1H), 3.41-3.48 (m, 2H), 3.02-3.12 (m, 2H), 2.14-2.25 (m, 4H). |

Example 3

Preparation of Compound 13

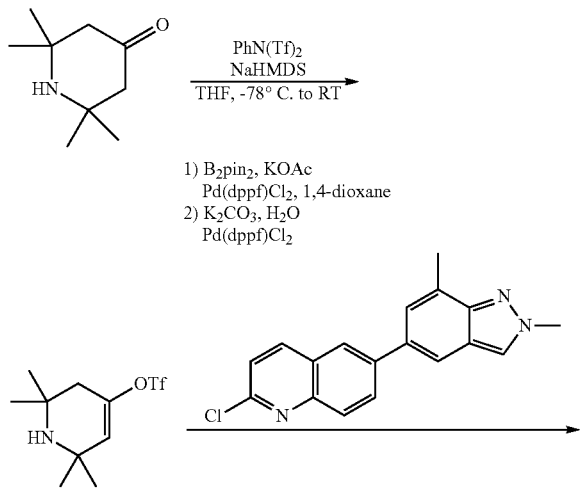

filtered and concentrated to yield 2,2,6,6-tetramethyl-1,2,3,6-tetrahydropyridin-4-yl trifluoromethanesulfonate (6.0 g, 100%).

1H NMR (acetone-d6) δ: 10.28 (br s, 1H), 6.13 (s, 1H), 2.85 (br s, 2H), 1.76 (s, 6H), 1.68 (s, 6H).

Step B: (2,2,6,6-Tetramethyl-1,3-dihydropyridin-4-yl) trifluoromethanesulfonate (100 mg, 0.35 mmol) was combined with bis(pinacolato)diboron (125 mg, 0.50 mmol), potassium acetate (100 mg, 1.0 mmol), 1,1'-bis(diphenylphosphino)ferrocene-palladium(II)dichloride dichloromethane complex (12 mg, 0.015 mmol) and 1,4-dioxane (2.4 mL). The mixture was stirred at 90° C. for 2 h. The mixture was cooled to room temperature. To the mixture was added aqueous 1 M K2CO3 (1 mL, 1 mmol), 2-chloro-6-(2,7-dimethylindazol-5-yl)quinoline (100 mg, 0.30 mmol, prepared according to Example 2, Step A) and 1,1'-bis(diphenylphosphino)ferrocene-palladium(II)dichloride dichloromethane complex (12 mg, 0.015 mmol). The mixture was stirred at 80° C. for 1 h. The mixture was partitioned between EtOAc and H2O. The organic layer was washed with brine, dried over Na2SO4, filtered and concentrated. The residue was chromatographed on silica gel, eluting with 0-10% MeOH (2 N NH3) in CH2Cl2 to yield 6-(2,7-dimethyl-2H-indazol-5-yl)-2-(2,2,6,6-tetramethyl-1,2,3,6-tetrahydropyridin-4-yl)quinoline (90 mg, 46%).

MS m/z 411.5 [M+H]+; 1H NMR (DMSO-d6) δ: 8.41 (s, 1H), 8.34 (d, J=8.5 Hz, 1H), 8.24 (d, J=2.2 Hz, 1H), 8.10 (dd, J=8.8, 2.2 Hz, 1H), 8.02 (d, J=8.8 Hz, 1H), 7.93-7.97 (m, 1H), 7.88 (d, J=8.8 Hz, 1H), 7.54 (t, J=1.6 Hz, 1H), 6.78-6.82 (m, 1H), 4.21 (s, 3H), 2.61 (s, 3H), 2.50 (m, 2H), 1.49 (s, 1H), 1.26 (s, 6H), 1.17 (s, 6H).

Example 4

Preparation of Compound 14

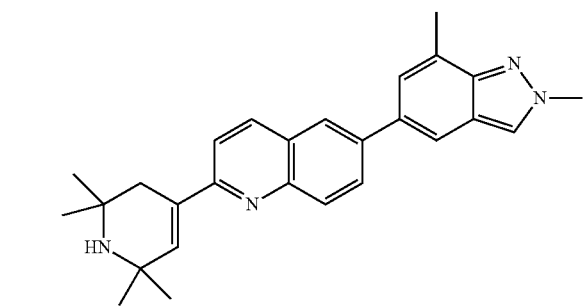

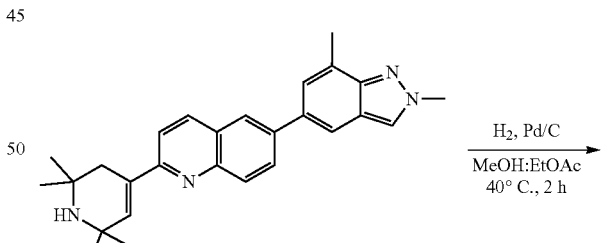

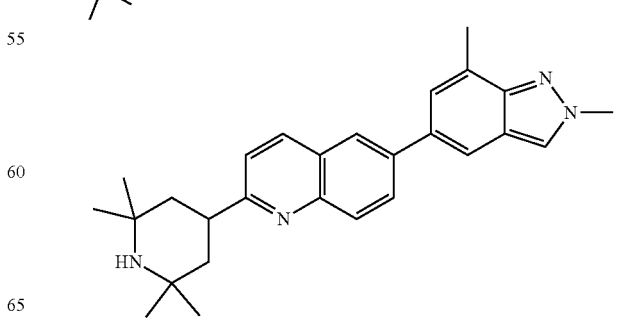

Step A: 2,2,6,6-Tetramethylpiperidin-4-one (3.1 g, 20 mmol) was dissolved in THF (100 mL) and cooled to −78° C. NaHMDS (21 mL, 21 mmol, 1.0 M in THF) was added to the solution. The mixture was stirred for 15 min at −78° C. N,N-bis(trifluoromethylsulfonyl)aniline (7.8 g, 22 mmol) was added to the mixture as a solid. The mixture was allowed to warm to room temperature before being quenched with aqueous saturated NaHCO3. The mixture was partitioned between EtOAc and H2O. The organic layer was washed with aqueous 2 M KOH, dried over Na2SO4, 6-(2,7-Dimethylindazol-5-yl)-2-(2,2,6,6-tetramethyl-1,3-dihydropyridin-4-yl)quinoline (20 mg, 0.05 mmol) was combined with 10% Pd/C (10 mg) in MeOH (2 mL). The mixture was stirred under H₂ (1 atm) at room temperature for 6 h. The mixture was then filtered over Celite. The filtrate was concentrated to yield 6-(2,7-dimethyl-2H-indazol-5-yl)-2-(2,2,6,6-tetramethylpiperidin-4-yl)quinoline (20 mg, 99%).

MS m/z 413.5 [M+H]⁺; ¹H NMR (DMSO-d₆) δ: 8.40 (s, 1H), 8.34 (d, J=8.5 Hz, 1H), 8.23 (d, J=2.2 Hz, 1H), 8.09 (dd, J=8.8, 2.2 Hz, 1H), 8.01 (d, J=8.8 Hz, 1H), 7.93-7.95 (m, 1H), 7.49-7.53 (m, 2H), 4.21 (s, 3H), 2.61 (s, 3H), 1.73-1.79 (m, 2H), 1.47-1.55 (m, 2H), 1.27 (s, 6H), 1.11 (s, 6H), NH proton not observed.

Example 5

Preparation of Compound 20

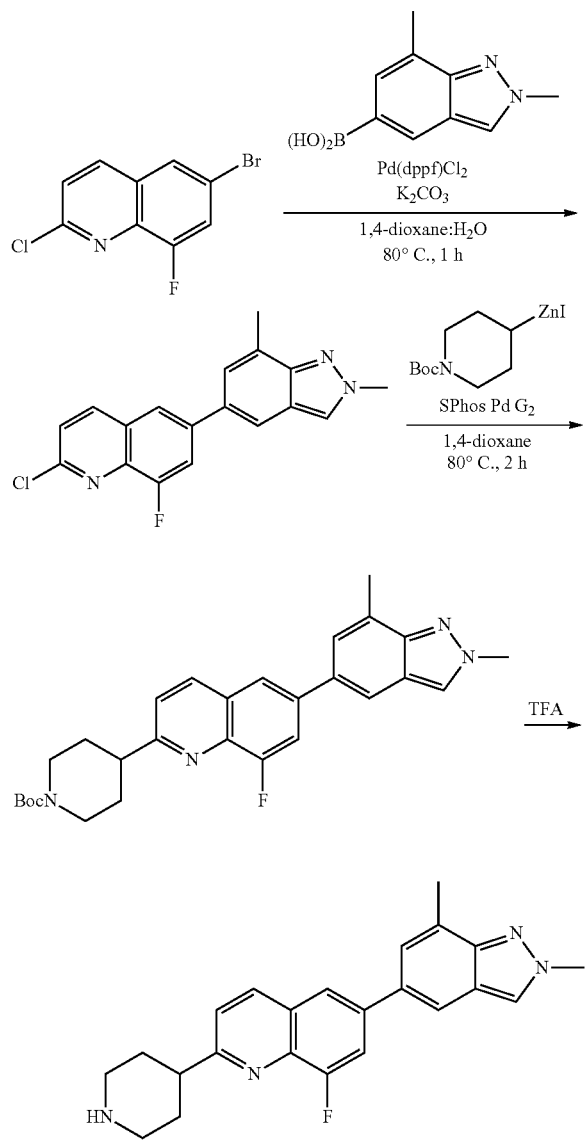

Step A: 6-Bromo-2-chloro-8-fluoro-quinoline (52 mg, 0.2 mmol) was combined with 1,1'-bis(diphenylphosphino)ferrocene-palladium(II)dichloride dichloromethane complex (8 mg, 0.01 mmol), 2,7-dimethyl-5-(4,4,5,5-tetramethyl-1,3,2-dioxaborolan-2-yl)indazole (54 mg, 0.2 mmol), 1,4-dioxane (1 mL) and aqueous 1 M K₂CO₃ (0.5 mL, 0.5 mmol). The mixture was stirred at 80° C. for 1 h. The mixture was partitioned between EtOAc and H₂O. The organic layer was washed with brine, dried over Na₂SO₄, filtered and concentrated. The residue was chromatographed on silica gel, eluting with 10-100% EtOAc in hexanes to yield 2-chloro-6-(2,7-dimethyl-2H-indazol-5-yl)-8-fluoroquinoline (25 mg, 38%). MS m/z 326.2, 328.2 [M+H]⁺.

Step B: Zinc powder (5 g, 76 mmol) was suspended in N,N-dimethylacetamide (10 mL) under argon. A mixture of 1,2-dibromoethane (520 µL, 6.02 mmol) and chlorotrimethylsilane (730 µL, 5.74 mmol) was added dropwise over 10 min. Over the course of the addition the internal temperature rose to 50° C. The reaction mixture was allowed to cool to room temperature. A solution of tert-butyl 4-iodopiperidine-1-carboxylate (16.5 g, 53.0 mmol) in N,N-dimethylacetamide (26 mL) was added dropwise over 20 min. The reaction mixture was filtered through Celite in a Schlenk filter to yield roughly 50 mL of ~1M (1-tert-butoxycarbonyl-4-piperidyl)-iodo-zinc solution. 2-Chloro-6-(2,7-dimethyl-2H-indazol-5-yl)-8-fluoroquinoline (25 mg, 0.077 mmol) was combined with the 1-Cert-butoxycarbonylpiperidin-4-ylzinc iodide solution (0.25 mL, 0.25 mmol), chloro(2-dicyclohexylphosphino-2',6'-dimethoxy-1,1'-biphenyl)(2'-amino-1,1'-biphenyl-2-yl) palladium(II) (4 mg, 0.005 mmol) and 1,4-dioxane (1 mL). The mixture was stirred at 80° C. for 2 h. The mixture was cooled to room temperature. The mixture was partitioned between EtOAc and H₂O. The organic layer was washed with brine, dried over Na₂SO₄, filtered and concentrated. The residue was chromatographed on silica gel, eluting with 0-10% MeOH in EtOAc to yield tert-butyl 4-[6-(2,7-dimethylindazol-5-yl)-8-fluoro-2-quinolyl]piperidine-1-carboxylate (30 mg, 82%). MS m/z 475.4 [M+H]⁺.

Step C: tert-Butyl 4-[6-(2,7-dimethylindazol-5-yl)-8-fluoro-2-quinolyl]piperidine-1-carboxylate (30 mg, 0.06 mmol) was combined with TFA (1 mL). After 10 min, the volatiles were removed. The mixture was partitioned between CH₂Cl₂ and aqueous 1 M K₂CO₃. The organic layer was loaded onto silica gel, eluting with 0-10% MeOH (2 N NH₃) in CH₂Cl₂ to yield 6-(2,7-dimethyl-2H-indazol-5-yl)-8-fluoro-2-(piperidin-4-yl)quinoline (20 mg, 85%).

MS m/z 375.3 [M+H]⁺; ¹H NMR (acetone-d₆) δ: 8.22 (dd, J=8.7, 1.7 Hz, 1H), 8.14 (s, 1H), 7.88 (d, J=2.2 Hz, 1H), 7.79-7.81 (m, 1H), 7.70 (dd, J=12.5, 2.0 Hz, 1H), 7.42 (d, J=8.5 Hz, 1H), 7.36-7.40 (m, 1H), 4.12 (s, 3H), 2.99-3.06 (m, 2H), 2.87-2.93 (m, 1H), 2.58-2.65 (m, 2H), 2.52 (s, 3H), 1.67-1.81 (m, 4H), NH proton not observed.

Using the procedure described for Example 5, above, additional compounds described herein were prepared by substituting the indicated starting material in Step A, suitable reagents and reaction conditions, obtaining compounds such as those selected from:

| Cpd | Starting Material and Data |
|---|---|
| 23 | Starting material: 6-bromo-2-chloroquinazoline<br>MS m/z 358.3 [M + H]+; $^1$H NMR (DMSO-$d_6$) δ: 9.59 (s, 1H), 8.43 (s, 1H), 8.40 (s, 1H), 8.36 (dd, J = 8.5, 1.9 Hz, 1H), 7.98-8.02 (m, 2H), 7.54 (s, 1H), 4.22 (s, 3H), 3.29-3.35 (m, 2H), 2.86-2.94 (m, 1H), 3.01-3.09 (m, 2H), 2.61 (s, 3H), 1.90-1.96 (m, 2H), 1.75-1.84 (m, 2H), NH proton not observed. |
| 30 | Starting material: 7-bromo-3-chloroisoquinoline<br>MS m/z 357.3 [M + H]+; $^1$H NMR (DMSO-$d_6$) δ: 9.32 (s, 1H), 8.41 (s, 1H), 8.38 (s, 1H), 8.13 (dd, J = 8.5, 1.9 Hz, 1H), 7.98 (d, J = 8.8 Hz, 1H), 7.96-7.97 (m, 1H), 7.64 (s, 1H), 7.54 (t, J = 1.6 Hz, 1H), 4.21 (s, 3H), 3.09-3.15 (m, 2H), 2.86-2.94 (m, 1H), 2.66-2.74 (m, 2H), 2.61 (s, 3H), 1.87-1.93 (m, 2H), 1.69-1.78 (m, 2H), NH proton not observed. |

Example 6

Preparation of Compound 72

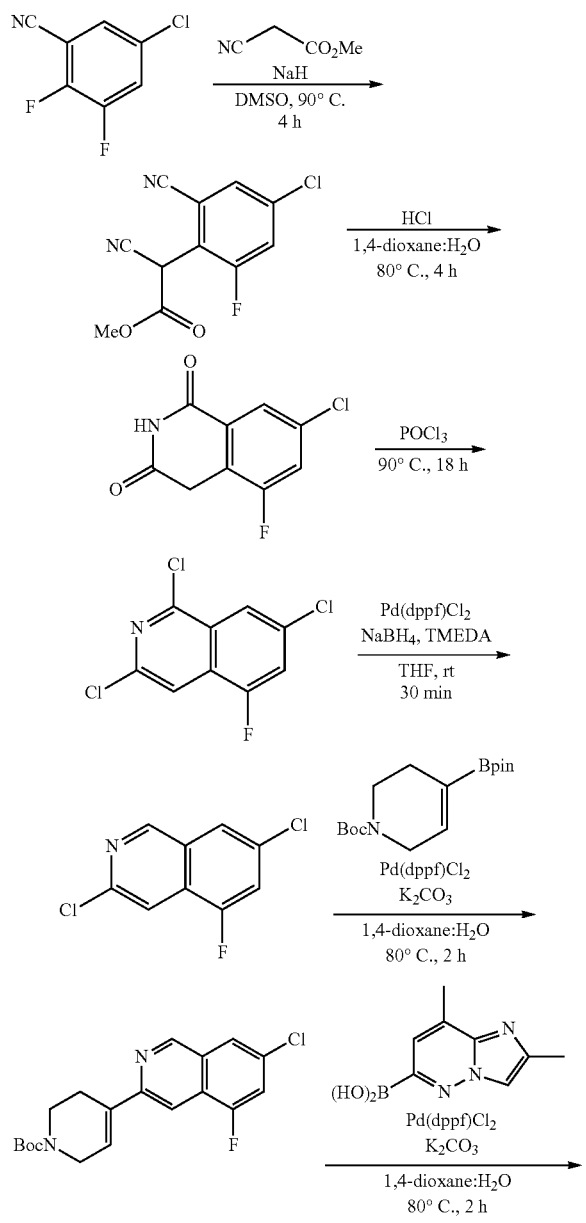

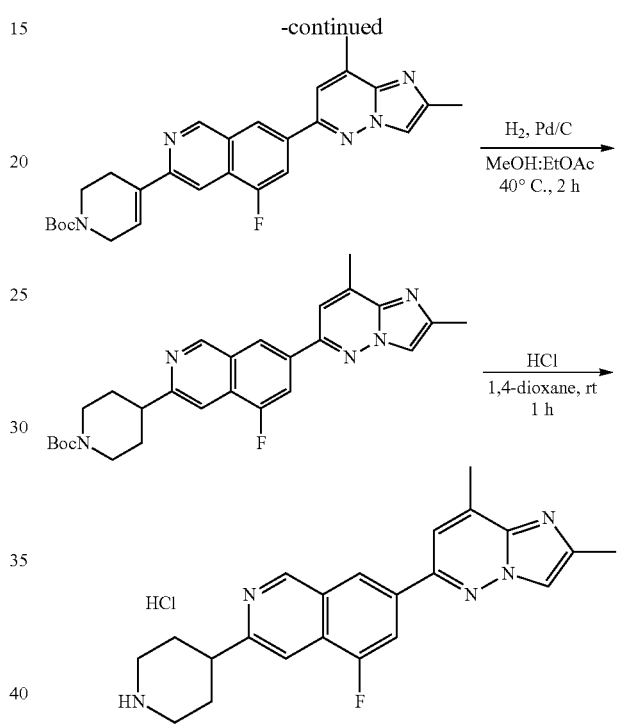

Step A: Methyl cyanoacetate (5.71 g, 57.6 mmol) was added to a mixture of DMSO (30 mL) and NaH (60 mass %) in mineral oil (2.3 g, 57.6 mmol) at 0° C. The mixture was stirred at 0° C. for 15 min. 5-Chloro-2,3-difluoro-benzonitrile (5.0 g, 28.8 mmol) in DMSO (5 mL) was added to the mixture. The mixture was stirred at room temperature for 30 min and then heated to 90° C. for 4 h. The mixture was cooled to room temperature and diluted with H$_2$O (200 mL), brine (100 mL) and EtOAc (200 mL). A precipitate formed and was collected by vacuum filtration. The solid was washed with H$_2$O and dried to yield methyl 2-(4-chloro-2-cyano-6-fluoro-phenyl)-2-cyano-acetate (6 g, 82%) as a tan powder. MS m/z 251.1, 253.1 [M−H]$^-$.

Step B: Methyl 2-(4-chloro-2-cyano-6-fluoro-phenyl)-2-cyano-acetate (5.5 g, 22 mmol) was combined with aqueous concentrated HCl (40 mL) and 1,4-dioxane (20 mL). The mixture was heated at 80° C. for 4 h. The mixture was cooled to room temperature and filtered. The solid was washed with H$_2$O and CH$_3$CN, and then dried to yield 7-chloro-5-fluoro-4H-isoquinoline-1,3-dione (3.0 g, 65%) as an off white solid. MS m/z 214.1, 216.1 [M+H]$^+$.

Step C: 7-Chloro-5-fluoro-4H-isoquinoline-1,3-dione (3.0 g, 14.0 mmol) was combined with POCl$_3$ (20 mL, 212 mmol). The mixture was heated at 110° C. for 2 h and then 90° C. overnight. The mixture was cooled to room temperature and then poured onto ice with vigorous stirring. The solid material was collected by vacuum filtration, dried, and chromatographed on silica gel, eluting with $CH_2Cl_2$ to afford 1,3,7-trichloro-5-fluoro-isoquinoline (1.3 g, 37%) as a white powder. MS m/z 250.2, 252.2, 254.2 $[M+H]^+$.

Step D: 1,3,7-Trichloro-5-fluoro-isoquinoline (1.3 g, 5.2 mmol) was combined with [1,1'-bis(diphenylphosphino)ferrocene]dichloropalladium(II) complex with dichloromethane (210 mg, 0.26 mmol), TMEDA (0.77 mL, 5.2 mmol) and THF (20 mL). To the mixture was added sodium borohydride (378 mg, 10 mmol). The mixture was stirred at room temperature for 30 min, and then was partitioned between EtOAc and $H_2O$. The organic layer was washed with brine, dried over $Na_2SO_4$, filtered and concentrated. The residue was chromatographed on silica gel, eluting with 0-10% EtOAc in $CH_2Cl_2$ to yield 3,7-dichloro-5-fluoro-isoquinoline (870 mg, 78%) as a white solid.

MS m/z 216.2, 218.2, 220.2 $[M+H]^+$; $^1H$ NMR (acetone-$d_6$) δ: 9.26 (m, 1H), 8.16 (m, 1H), 8.00 (s, 1H), 7.72 (dd, J=9.8, 1.9 Hz, 1H).

Step E: 3,7-Dichloro-5-fluoro-isoquinoline (432 mg, 2.0 mmol) was combined with N-Boc-1,2,5,6-tetrahydropyridine-4-boronic acid pinacol ester (610 mg, 2.4 mmol), 1,1'-bis(diphenylphosphino)ferrocene-palladium(II)dichloride dichloromethane complex (50 mg, 0.06 mmol), 1,4-dioxane (6 mL) and aqueous 1 M $K_2CO_3$ (4 mL, 4 mmol). The mixture was stirred at 80° C. for 1 h. The mixture was partitioned between EtOAc and $H_2O$. The organic layer was concentrated. The residue was chromatographed on silica gel, eluting with 0-30% EtOAc in hexanes to yield tert-butyl 4-(7-chloro-5-fluoro-3-isoquinolyl)-3,6-dihydro-2H-pyridine-1-carboxylate (370 mg, 51%) as an off-white solid. MS m/z 362.2, 364.2 $[M-F1-1]^+$.

Step F: 6-Chloro-2,8-dimethyl-imidazo[1,2-b]pyridazine hydrochloride (62 mg, 0.28 mmol, prepared according to the procedure in Example 11) was combined with KOAc (83 mg, 0.85 mmol), 1,1'-bis(diphenylphosphino) ferrocene-palladium(II)dichloride dichloromethane complex (23 mg, 0.03 mmol), bis(pinacolato)diboron (91 mg, 0.36 mmol) and 1,4-dioxane (1.5 mL). The mixture was stirred under $N_2$ at 100° C. for 2 h. To the mixture was added 1 M $K_2CO_3$ (aq) (0.75 mL, 0.75 mmol), followed by 1,1'-bis(diphenylphosphino)ferrocene-palladium(II)dichloride dichloromethane complex (11 mg, 0.014 mmol) and tert-butyl 4-(7-chloro-5-fluoro-3-isoquinolyl)-3,6-dihydro-2H-pyridine-1-carboxylate (100 mg, 0.28 mmol). The mixture was stirred under $N_2$ for 1 h at 80° C. The mixture was partitioned between EtOAc and $H_2O$. The organic layer was concentrated. The residue was chromatographed on silica gel, eluting with 10-100% EtOAc in $CH_2Cl_2$ then 5% MeOH in EtOAc to yield tert-butyl 4-[7-(2,8-dimethylimidazo[1,2-b]pyridazin-6-yl)-5-fluoro-3-isoquinolyl]-3,6-dihydro-2H-pyridine-1-carboxylate (90 mg, 69%) as a white solid. MS m/z 474.5 $[M+H]^+$.

Step G: tert-Butyl 4-[7-(2,8-dimethylimidazo[1,2-b]pyridazin-6-yl)-5-fluoro-3-isoquinolyl]-3,6-dihydro-2H-pyridine-1-carboxylate (90 mg, 0.19 mmol) was combined with 10% Pd/C (20 mg) in MeOH (3 mL). The mixture was stirred under $H_2$ (1 atm) for 2 h at 40° C. The mixture was filtered through a syringe filter. The filtrate was concentrated. The residue was chromatographed on silica gel, eluting with 40-100% EtOAc in hexanes to yield tert-butyl 4-[7-(2,8-dimethylimidazo[1,2-b]pyridazin-6-yl)-5-fluoro-3-isoquinolyl]piperidine-1-carboxylate (52 mg, 57%) as an off-white solid. MS m/z 476.3 $[M+H]^+$.

Step H: tert-Butyl 4-[7-(2,8-dimethylimidazo[1,2-b]pyridazin-6-yl)-5-fluoro-3-isoquinolyl]piperidine-1-carboxylate (52 mg, 0.11 mmol) was combined with 4 N HCl in 1,4-dioxane (2 mL, 8 mmol). The mixture was stirred and sonicated and room temperature. After 1 h, the volatiles were removed. The residue was suspended in $CH_3CN$, sonicated and filtered. The solid was dried to give 7-(2,8-dimethylimidazo[1,2-b]pyridazin-6-yl)-5-fluoro-3-(4-piperidyl)isoquinoline hydrochloride (36 mg, 46%) as a yellow solid.

MS m/z 376.5 $[M+H]^+$; $^1H$ NMR (DMSO-$d_6$) δ: 9.58 (s, 1H), 9.14-9.22 (br, 1H), 8.96-9.05 (br, 1H), 8.89 (s, 1H), 8.48-8.53 (m, 2H), 8.34 (dd, J=11.6, 1.5 Hz, 1H), 7.84 (s, 1H), 3.39-3.45 (m, 2H), 3.25-3.31 (m, 1H), 3.02-3.12 (m, 2H), 2.79 (s, 3H), 2.60 (s, 3H), 2.07-2.17 (m, 4H).

Using the procedure described for Example 6, above, additional compounds described herein were prepared by substituting the appropriate boronic acid in Step F, suitable reagents and reaction conditions, obtaining compounds such as those selected from:

| Cpd | Data |
| --- | --- |
| 71 | MS m/z 375.4 $[M + H]^+$; $^1H$ NMR (DMSO-$d_6$) δ: 9.56 (s, 1H), 9.12-9.20 (br, 1H), 8.89-8.98 (br, 1H), 8.89 (s, 1H), 8.43-8.48 (m, 2H), 8.34 (d, J = 12.2 Hz, 1H), 7.84 (s, 1H), 7.58 (s, 1H), 4.22 (s, 3H), 3.39-3.46 (m, 2H), 3.27-3.34 (m, 1H), 3.02-3.12 (m, 2H), 2.61 (s, 3H), 2.05-2.20 (m, 4H). |

Using the procedure described for Example 6, Steps E-H, above, additional compounds described herein were prepared by substituting the appropriate starting material in Step E, appropriate boronic acid in Step F, suitable reagents and reaction conditions, obtaining compounds such as those selected from:

| Cpd | Starting Material and Data |
| --- | --- |
| 1 | Starting material: 6-bromo-2-chloroquinoline<br>MS m/z 343.2 $[M + H]^+$; $^1H$ NMR (DMSO-$d_6$) δ: 8.75-8.80 (br, 2H), 8.64 (s, 1H), 8.54 (s, 1H), 8.47-8.50 (m, 1H), 8.22-8.26 (m, 2H), 8.07-8.10 (m, 1H), 7.83 (s, 1H), 7.70-7.76 (m, 2H), 4.22 (s, 3H), 3.42-3.48 (m, 2H), 3.05-3.14 (m, 3H), 2.07-2.12 (m, 2H), 1.87-1.95 (m, 2H). |
| 10 | Starting material: 6-bromo-2-chloroquinazoline<br>MS m/z 344.1 $[M + H]^+$; $^1H$ NMR (DMSO-$d_6$) δ: 9.67 (s, 1H), 9.03-9.12 (br s, 2H), 9.00 (s, 1H), 8.55 (s, 1H), 8.44-8.47 (m, 1H), 8.02-8.05 (m, 1H), 7.91-7.96 (m, |

| Cpd | Starting Material and Data |
|---|---|
| | 2H), 7.71-7.74 (m, 1H), 4.21 (s, 3H), 3.40-3.44 (m, 2H), 3.03-3.11 (m, 3H), 1.98-2.09 (m, 4H). |

Example 7

Preparation of Compound 74

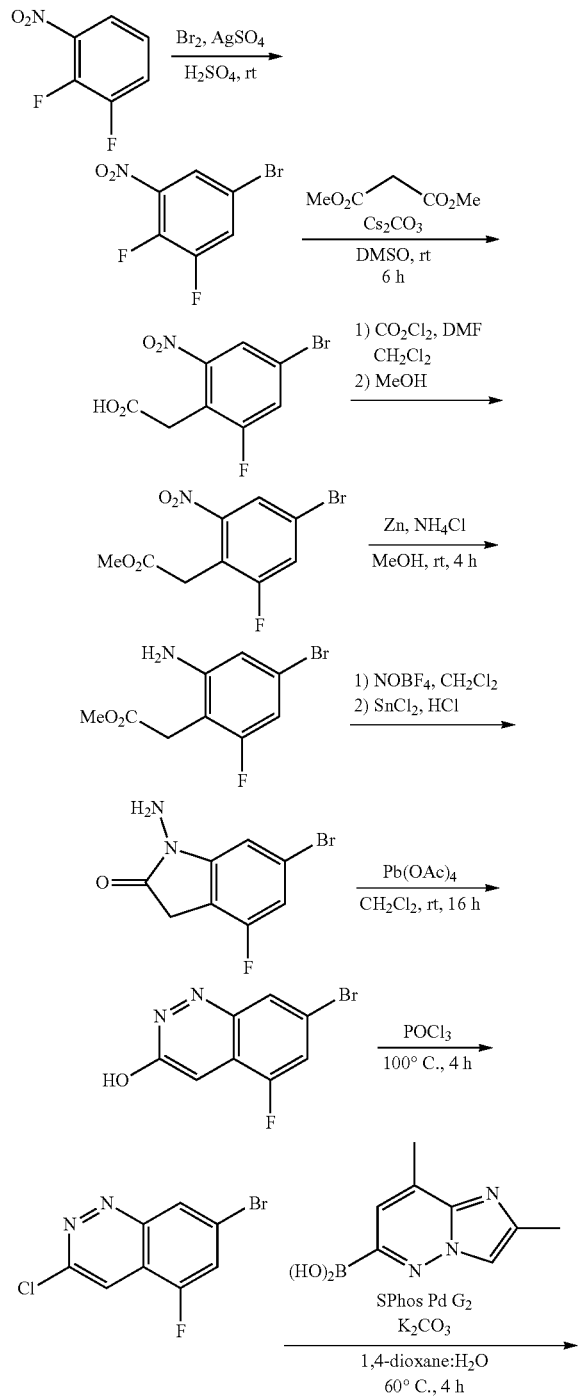

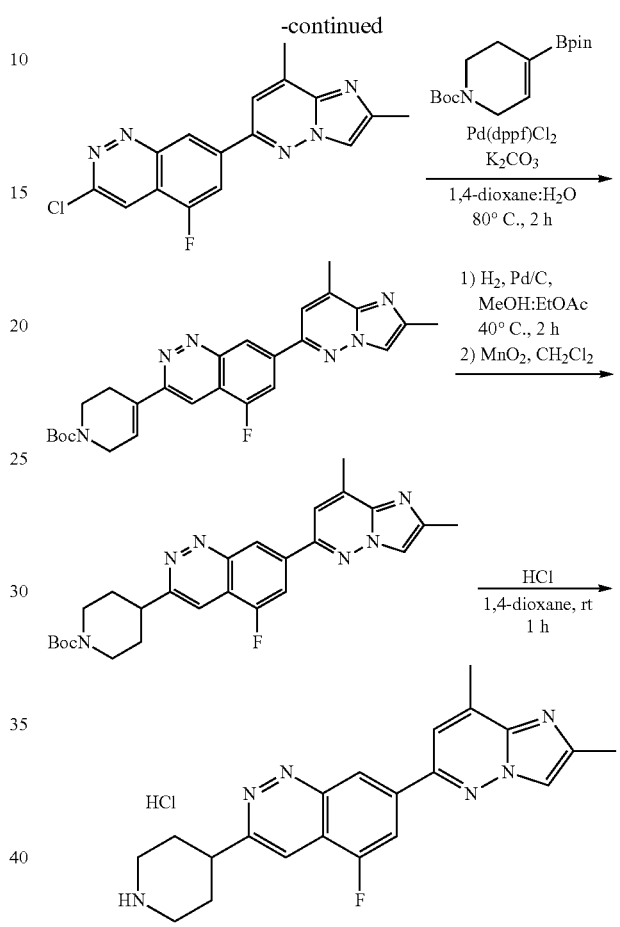

Step A: 1,2-Difluoro-3-nitro-benzene (23 g, 145 mmol) was combined with $Ag_2SO_4$ (45.2 g, 145 mmol) in $H_2SO_4$ (150 mL). The mixture was stirred for 5 min at room temperature. To the mixture was added $Br_2$ (11.2 mL, 217 mmol). The mixture was stirred at room temperature for 16 h, and then was poured into ice water (800 mL). The mixture was extracted with $Et_2O$ (3×500 mL). The combined organics were dried, filtered and concentrated. The residue was chromatographed on silica gel, eluting with 10-30% $CH_2Cl_2$ in hexanes to yield 5-bromo-1,2-difluoro-3-nitro-benzene (18.8 g, 55%) as a white crystalline solid.

$^1$H NMR (acetone-$d_6$) δ: 8.20 (ddd, J=5.8, 2.4, 2.2 Hz, 1H), 8.12 (ddd, J=9.2, 6.5, 2.2 Hz, 1H).

Step B: 5-Bromo-1,2-difluoro-3-nitro-benzene (15 g, 63 mmol), dimethyl malonate (12.5 g, 95 mmol), $Cs_2CO_3$ (41.1 g, 126 mmol), and DMF (63 mL) were stirred at rt for 6 h. The reaction mixture was partitioned between aqueous 1 M HCl and EtOAc. The organic layer was washed with brine, dried over $Na_2SO_4$ and concentrated. The residue was combined with AcOH (30 mL) and conc. HCl (30 mL) and heated at 110° C. for 16 h. The mixture was diluted with $H_2O$ to form a precipitate. The solid was collected by vacuum filtration, washed with $H_2O$, washed with 1:1 hexane/ether and dried to afford 2-(4-bromo-2-fluoro-6-nitro-phenyl)acetic acid (14.5 g, 83%) as a white solid.

$^1$H NMR (acetone-d$_6$) δ: 11.28 (br s, 1H), 8.16 (t, J=1.5 Hz, 1H), 7.92 (dd, J=9.0, 1.5 Hz, 1H), 4.06 (s, 2H).

Step C: 2-(4-Bromo-2-fluoro-6-nitro-phenyl)acetic acid (14.5 g, 52 mmol) was suspended in CH$_2$Cl$_2$ (250 mL). Oxalyl chloride (7 mL, 79 mmol) was added to the mixture followed by DMF (0.1 mL, 1 mmol). The mixture was stirred at room temperature for 1 h, and then added dropwise to MeOH at 0° C. The volatiles were removed under vacuum to yield methyl 2-(4-bromo-2-fluoro-6-nitro-phenyl)acetate (15 g, 98%) as an off-white solid.

$^1$H NMR (acetone-d$_6$) δ: 8.16 (t, J=1.5 Hz, 1H), 7.93 (dd, J=9.0, 1.5 Hz, 1H), 4.05 (s, 2H), 3.71 (s, 3H).

Step D: Methyl 2-(4-bromo-2-fluoro-6-nitro-phenyl)acetate (15 g, 51 mmol) was suspended in a mixture of MeOH (200 mL) and NH$_4$Cl (55 g, 1.03 mol) at 0° C. Zinc powder (16.8 g, 257 mmol) was added in one portion. The mixture was stirred at room temperature for 4 h, and then was filtered through Celite. The filtrate was concentrated and then partitioned between EtOAc and H$_2$O. The organic layer was washed with brine, dried over Na$_2$SO$_4$, filtered and concentrated to yield methyl 2-(2-amino-4-bromo-6-fluoro-phenyl) acetate (12.6 g, 94%) as a white solid. MS m/z 262.0, 264.0 [M+H]$^+$.

Step E: Methyl 2-(2-amino-4-bromo-6-fluoro-phenyl)acetate (12.6 g, 48 mmol) was suspended in CH$_2$Cl$_2$ (150 mL) at 0° C. Nitrosonium tetrafluoroborate (8.4 g, 72 mmol) was added in one portion to the mixture. The mixture was stirred at 0° C. for 1 h. The mixture was added directly to a vigorously stirred mixture of SnCl$_2$ dihydrate (43.8 g, 194 mmol) in conc. HCl (200 mL) at 0° C. The mixture was allowed to slowly warm to room temperature with stirring. After 24 h, the mixture was filtered. The solid was washed with H$_2$O and ether, and then dried to yield 1-amino-6-bromo-4-fluoro-indolin-2-one (9.0 g, 76%) as a white solid. MS m/z 244.9, 246.9 [Mal]$^+$.

Step F: 1-Amino-6-bromo-4-fluoro-indolin-2-one (9.0 g, 37 mmol) was suspended in CH$_2$Cl$_2$ (500 mL) at 0° C. Pb(OAc)$_4$ (22.8 g, 51.4 mmol) was added to the mixture in one portion. The mixture was stirred at room temperature for 16 h. MeOH (50 mL) was added to the mixture, and the mixture was eluted through a pad of silica gel. The filtrate was concentrated and chromatographed on silica gel, eluting with 0-100% EtOAc in CH$_2$Cl$_2$ to yield 7-bromo-5-fluoro-cinnolin-3-ol (3.5 g, 39%) as a yellow powder. MS m/z 241.1, 243.1 [M−H]$^-$.

Step G: 7-Bromo-5-fluoro-cinnolin-3-ol (3.5 g, 14 mmol) was suspended in POCl$_3$ (28 mL, 300 mmol). The mixture was stirred at 100° C. for 4 h in a sealed tube. The mixture was cooled to room temperature and quenched onto ice. The ice water was extracted with CH$_2$Cl$_2$ (2×). The organic layer was washed with brine, dried over Na$_2$SO$_4$, filtered and concentrated. The residue was chromatographed on silica gel, eluting with 0-10% EtOAc in CH$_2$Cl$_2$ to yield 7-bromo-3-chloro-5-fluorocinnoline (2.6 g, 69%) as an off white powder. MS m/z 261.1, 263.1, 265.1 [M+H]$^+$.

Step H: 7-Bromo-3-chloro-5-fluoro-cinnoline (785 mg, 3.00 mmol) was combined with (2,8-dimethylimidazo[1,2-b]pyridazin-6-yl)boronic acid (3.6 mmol, prepared according to the procedure in Example 11), chloro(2-dicyclohexylphosphino-2',6'-dimethoxy-1,1'-biphenyl)(2'-amino-1,1'-biphenyl-2-yl) palladium(II) (108 mg, 0.15 mmol), 1,4-dioxane and aqueous 1 M K$_2$CO$_3$ (10 mL, 10 mmol). The mixture was stirred at 50° C. for 2 h. The mixture was partitioned between EtOAc and H$_2$O, then filtered through Celite. The organic layer was concentrated. The residue was chromatographed on silica gel, eluting with 40-100% EtOAc in hexanes followed by 5% MeOH in EtOAc to yield 3-chloro-7-(2,8-dimethylimidazo[1,2-b]pyridazin-6-yl)-5-fluoro-cinnoline (605 mg, 62%) as a tan solid. MS m/z 328.2, 330.2 [M+H]$^+$.

Step I: 3-Chloro-7-(2,8-dimethylimidazo[1,2-b]pyridazin-6-yl)-5-fluoro-cinnoline (400 mg, 1.2 mmol) was combined with 1,1'-bis(diphenylphosphino)ferrocene-palladium(II)dichloride dichloromethane complex (50 mg, 0.06 mmol), N-Boc-1,2,5,6-tetrahydropyridine-4-boronic acid pinacol ester (462 mg, 1.47 mmol), 1,4-dioxane (6 mL) and aqueous 1 M K$_2$CO$_3$ (3 mL, 3.0 mmol). The mixture was stirred at 80° C. for 1 h. The mixture was partitioned between EtOAc and H$_2$O. The organic layer was concentrated. The residue was chromatographed on silica gel, eluting with 40-100% EtOAc in hexanes, then 5% MeOH in EtOAc to yield tert-butyl 4-[7-(2,8-dimethylimidazo[1,2-b]pyridazin-6-yl)-5-fluoro-cinnolin-3-yl]-3,6-dihydro-2H-pyridine-1-carboxylate (430 mg, 74%) as a tan solid. MS m/z 475.5 [M+H]$^+$.

Step J: tert-Butyl 4-[7-(2,8-dimethylimidazo[1,2-b]pyridazin-6-yl)-5-fluoro-cinnolin-3-yl]-3,6-dihydro-2H-pyridine-1-carboxylate (430 mg, 0.91 mmol) was combined with 10% Pd/C (500 mg) in MeOH:EtOAc (1:1) (25 mL). The mixture was stirred under H$_2$ (1 atm) for 3 h at 40° C. The mixture was filtered through a syringe filter and the filtrate was concentrated. The residue was dissolved in CH$_2$Cl$_2$ (2 mL). MnO$_2$ (20 equiv.) was added to the solution. The mixture was stirred at room temperature for 30 min and then filtered through Celite. The filtrate was concentrated. The residue was chromatographed on silica gel, eluting with 40-100% EtOAc in hexanes to yield tert-butyl 4-[7-(2,8-dimethylimidazo[1,2-b]pyridazin-6-yl)-5-fluoro-cinnolin-3-yl]piperidine-1-carboxylate (200 mg, 46%) as an off-white solid. MS m/z 477.5 [M+H]$^+$.

Step K: tert-Butyl 4-[7-(2,8-dimethylimidazo[1,2-b]pyridazin-6-yl)-5-fluoro-cinnolin-3-yl]piperidine-1-carboxylate (200 mg, 0.42 mmol) was combined with 4 N HCl in 1,4-dioxane (1 mL, 4 mmol). The mixture was stirred at room temperature for 1 h. The volatiles were removed with a stream of N$_2$. The residue was suspended in CH$_3$CN, sonicated and filtered. The solid was dried to give 7-(2,8-dimethylimidazo[1,2-b]pyridazin-6-yl)-5-fluoro-3-(4-piperidyl)cinnoline hydrochloride (190 mg, quant.) as an off white solid.

MS m/z 377.3 [M+H]$^+$; $^1$H NMR (DMSO-d$_6$) δ: 9.13 (s, 1H), 8.84 (br, 1H), 8.58 (br, 1H), 8.32-8.41 (m, 3H), 8.20 (s, 1H), 3.55-3.62 (m, 1H), 3.47-3.53 (m, 2H), 3.11-3.20 (m, 2H), 2.71 (s, 3H), 2.52 (s, 3H), 2.16-2.30 (m, 4H).

Using the procedure described for Example 7, above, additional compounds described herein were prepared by substituting the appropriate boronic acid or boronic acid equivalent in Step H or I, suitable reagents and reaction conditions, obtaining compounds such as those selected from:

| Cpd | Data |
|---|---|
| 73 | MS m/z 376.4 [M + H]+; 1H NMR (DMSO-d6) δ: 9.02-9.10 (br, 1H), 8.75-8.84 (br, 1H), 8.64 (s, 1H), 8.48 (s, 1H), 8.34 (dd, J = 11.4, 1.4 Hz, 1H), 8.16-8.19 (m, 1H), 8.10 (s, 1H), 7.68 (s, 1H), 4.23 (s, 3H), 3.51-3.59 (m, 1H), 3.43-3.50 (m, 2H), 3.08-3.18 (m, 2H), 2.62 (s, 3H), 2.18-2.28 (m, 4H). |
| 84 | MS m/z 359.3 [M + H]+; 1H NMR (methanol-d4) δ: 9.26 (s, 1H), 8.71 (dd, J = 8.5, 1.5 Hz, 1H), 8.58 (s, 1H), 8.44 (s, 1H), 8.40 (s, 1H), 8.32 (d, J = 8.5 Hz, 1H), 3.61-3.69 (m, 3H), 2.45-2.55 (m, 2H - overlaps with residual solvent peak), 2.88 (s, 3H), 2.72 (s, 3H), 2.30-2.50 (m, 4H). NH proton not observed. |
| 87 | MS m/z 405.3 [M + H]+; 1H NMR (methanol-d4) δ: 9.13 (s, 1H), 8.59 (s, 1H), 8.40-8.45 (m, 2H), 8.32 (s, 1H), 4.04 (m, 1H), 3.91 (t, J = 12.5 Hz, 1H), 3.79 (br s, 1H), 2.87 (s, 3H), 2.70 (s, 3H), 2.38-2.50 (m, 2H), 2.24 (d, J = 14 Hz, 1H), 2.06 (q, J = 14 Hz, 1H), 1.65 (d, J = 7 Hz, 3H), 1.45 (d, J = 6 Hz, 3H). NH and HCl protons not observed. |
| 90 | MS m/z 405.5 [M + H]+; 1H NMR (methanol-d4) δ: 8.88 (s, 1H), 8.28 (d, J = 10 Hz, 1H), 8.14 (s, 1H), 7.98 (s, 1H), 7.85 (s, 1H), 3.48 (tt, J = 10, 3 Hz, 1H), 2.98-3.04 (m, 2H), 2.71 (s, 3H), 2.51 (s, 3H), 2.13 (d, J = 15 Hz, 2H), 1.55 (q, J = 12 Hz, 2H), 1.26 (d, J = 7 Hz, 6H). NH proton not observed. |
| 129 | MS m/z 391.5 [M + H]+; 1H NMR (methanol-d4) δ: 8.96 (s, 1H), 8.36 (dd, J = 11 Hz, 1H), 8.23 (s, 1H), 8.02 (s, 1H), 7.90 (s, 1H), 3.60-3.71 (m, 2H), 3.37-3.52 (m, 3H), 2.74 (s, 3H), 2.42-2.55 (m, 5H), 2.30-2.40 (m, 1H), 2.05-2.30 (m, 3H), NH proton not observed. |
| 130 | MS m/z 433.5 [M + H]+; 1H NMR (methanol-d4) δ: 8.91 (s, 1H), 8.30 (dd, J = 11, 1.5 Hz, 1H), 8.18 (s, 1H), 8.00 (s, 1H), 7.88 (s, 1H), 3.62-3.71 (m, 1H), 3.16-3.20 (m, 1H), 2.95-3.02 (m, 1H), 2.73 (s, 3H), 2.51 (s, 3H), 2.21 (d, J = 12.5 Hz, 1H), 2.07-2.16 (m, 2H), 1.89 (pentet, J = 7.5 Hz, 2H), 1.46-1.60 (m, 3H), 1.00-1.08 (m, 6H). NH proton not observed. |
| 143 | MS m/z 363.4 [M + H]+; 1H NMR (methanol-d4) δ: 9.00 (s, 1H), 8.39 (d, J = 11 Hz, 1H), 8.34 (s, 1H), 8.03 (s, 1H), 7.92 (s, 1H), 4.24 (septet, J = 7.5 Hz, 1H), 3.91 (d, J = 7.5 Hz, 2H), 3.68-3.75 (m, 1H), 3.54-3.61 (m, 1H), 2.70-2.78 (m, 4H), 2.53 (s, 3H), 2.45-2.52 (m, 1H), NH proton not observed. |
| 169 | MS m/z 403.5 [M + H]+; 1H NMR (methanol-d4) δ: 9.13 (s, 1H), 8.56 (s, 1H), 8.52 (s, 1H), 8.40 (m, 2H), 4.18 (br s, 2H), 3.87 (m, 1H), 3.12 (d, J = 15 Hz, 2H), 2.85 (s, 3H), 2.60-2.70 (m, 5H), 1.96 (m, 2H), 1.80-1.84 (m, 2H). |
| 210 | MS m/z 362.3 [M + H]+; 1H NMR (methanol-d4) δ: 9.76 (s, 1H), 8.88 (s, 1H), 8.83-8.86 (m, 1H), 8.30 (s, 1H), 8.14 (s, 1H), 8.07 (d, J = 9.5 Hz, 1H), 7.72 (d, J = 9.5 Hz, 1H), 3.61-3.64 (m, 2H), 3.23-3.31 (m, 3H), 2.63 (s, 3H), 2.28-2.35 (m, 2H), 2.07-2.18 (m, 2H), NH and HCl protons not observed. |
| 216 | MS m/z 377.3 [M + H]+; 1H NMR (methanol-d) δ 9.15 (s, 1 H), 8.55 (s, 1 H), 8.44 (br d, J = 10.8 Hz, 1 H), 8.41 (s, 1 H), 8.39 (s, 1 H), 3.83-3.45 (m, 5 H), 2.86 (s, 3 H) 2.69 (s, 3 H) 2.33-2.42 (m, 1 H) 2.02-2.19 (m, 3 H), NH and HCl protons not observed. |

Boronic acid or bornic acid equivalents for use in Step H or I were prepared according to the following procedures:

Example 7-1 rac-(2R,6R)-1-Benzyl-2,6-dimethyl-1,2,3,6-tetrahydropyridin-4-yl trifluoromethanesulfonate and rac-(2S,6R)-1-benzyl-2,6-dimethyl-1,2,3,6-tetrahydropyridin-4-yl trifluoromethanesulfonate Step A: 3-Oxopentanedioic acid (20.5 g, 140 mmol) and acetaldehyde (15.7 mL, 279 mmol) were suspended in $H_2O$ (50 mL). The mixture was stirred with a strong stir bar at room temperature for 10 min. The mixture was then cooled in an ice bath. Benzylamine (15.3 mL, 140 mmol) was added dropwise. The mixture became thick. Stirring was continued at room temperature for 5 days. Aqueous 6N HCl was added. The mixture was stirred at room temperature for 1 h. The mixture was then made basic with aqueous $K_2CO_3$ and washed 3 times with $CH_2Cl_2$. The organic layer was dried over $MgSO_4$, filtered, and concentrated under vacuum. Purification by silica gel chromatography (10-20% EtOAc in hexanes) yielded 6.6 g (17% total yield) of a mixture of rac-(2R,6R)-1-benzyl-2,6-dimethylpiperidin-4-one and (2S,6R)-1-benzyl-2,6-dimethylpiperidin-4-one. These two components readily interconvert one to the other.

Step B: A roughly 2:3 ratio of rac-(2R,6R)-1-benzyl-2,6-dimethylpiperidin-4-one and (2S,6R)-1-benzyl-2,6-dimethylpiperidin-4-one (4.45 g, 18.4 mmol) was dissolved in THF (12.8 mL) at −78° C. NaHMDS (2M in THF, 13.1 mL, 26.2 mmol) was added dropwise. The mixture was stirred at −78° C. for 3 h. N,N-Bis(trifluoromethylsulfonyl)aniline (9.25 g, 25.9 mmol) was added to the mixture in one portion. The mixture was slowly warmed to room temperature over 15 h. THF was removed from the mixture under vacuum. The product mixture was diluted with $CH_2Cl_2$ and was filtered through a plug of silica to remove solid impurities. The filtrate was concentrated under vacuum. The residue was dissolved in EtOAc. This solution was washed with dilute aqueous NaOH (ca. 800 mL) and then with brine. The organic layer was dried over $MgSO_4$, filtered, and concentrated under vacuum. The residue was purified by silica gel chromatography (50-100% $CH_2Cl_2$ in hexanes) yielding trans-isomer rac-(2R,6R)-1-benzyl-2,6-dimethyl-1,2,3,6-tetrahydropyridin-4-yl trifluoromethanesulfonate (1.5 g, 23%) as the higher Rf component. 1H NMR (acetone-d4) δ: 7.37-7.40 (m, 2H), 7.30-7.35 (m, 2H), 7.22-7.27 (m, 1H), 5.87 (s, 1H), 3.76 (d, J=14.5 Hz, 1H), 3.58 (d, J=14.5 Hz, 1H), 3.30-3.42 (m, 2H), 2.41-2.50 (m, 1H), 2.24-2.30 (m, 1H), 1.20-1.25 (m, 6H). The cis-isomer rac-(2S,6R)-1-benzyl-2,6-dimethyl-1,2,3,6-tetrahydropyridin-4-yl trifluoromethanesulfonate (2.1 g, 33%) was collected as the lower Rf component.

1H NMR (acetone-d4) δ: 7.37-7.40 (m, 2H), 7.30-7.35 (m, 2H), 7.20-7.25 (m, 1H), 5.85 (s, 1H), 3.87 (d, J=16 Hz, 1H), 3.82 (d, J=16 Hz, 1H), 3.50-3.57 (m, 1H), 3.16-3.22 (m, 1H), 2.49-2.57 (m, 1H), 2.24-2.30 (m, 1H), 1.22 (d, J=7 Hz, 3H), 1.17 (d, J=6.5 Hz, 3H).

Example 7-2

(2R,6R)-1-Benzyl-2,6-dimethyl-4-(4,4,5,5-tetramethyl-1,3,2-dioxaborolan-2-yl)-1,2,3,6-tetrahydropyridine Potassium acetate (1.8 g, 18 mmol) was dried under Ar at 180° C. for 30 min and then cooled to room temperature. To the solid was added rac-(2S,6R)-1-benzyl-2,6-dimethyl-1,2,3,6-tetrahydropyridin-4-yl trifluoromethanesulfonate (1.5 g, 4.3 mmol, prepared according to Example 36), Pd(dppf)Cl$_2$ (146 mg, 0.175 mmol), dppf (110 mg, 0.19 mmol), bis(pinacolato)diboron (1.2 g, 4.7 mmol), and 1,4-dioxane (14.5 mL). The mixture was heated at 80° C. for 15 h. The reaction mixture was then diluted in EtOAc and filtered through Celite. The filtrate was concentrated under vacuum. The residue was dissolved in EtOAc and washed with 800 mL of dilute aqueous NaHCO$_3$ and brine. The organic layer was dried over MgSO$_4$, filtered, and concentrated under vacuum. The residue was dissolved in ether and filtered through Celite to remove brown insoluble impurities. The filtrate was concentrated to afford (2S,6R)-1-benzyl-2,6-dimethyl-4-(4,4,5,5-tetramethyl-1,3,2-dioxaborolan-2-yl)-1,2,3,6-tetrahydropyridine (1.43 g, 80% pure, 81% yield) as a crude black oil.

$^1$H NMR (acetone-d$_4$) δ: 7.40-7.45 (m, 2H), 7.25-7.32 (m, 2H), 7.16-7.21 (m, 1H), 6.31 (s, 1H), 3.80 (m, 2H), 3.20-3.28 (m, 1H), 2.73-2.79 (m, 1H), 2.12-2.19 (m, 1H), 1.90-1.98 (m, 1H), 1.35 (s, 12H), 1.22 (d, J=5.5 Hz, 3H), 1.00 (d, J=6.5 Hz, 3H).

Example 7-3

(2R,6R)-1-Benzyl-2,6-dimethyl-4-(4,4,5,5-tetramethyl-1,3,2-dioxaborolan-2-yl)-1,2,3,6-tetrahydropyridine was prepared from rac-(2R,6R)-1-benzyl-2,6-dimethyl-1,2,3,6-tetrahydropyridin-4-yl trifluoromethanesulfonate according to Example 7-2

$^1$H NMR (acetone-d$_4$) δ: 7.40-7.45 (m, 2H), 7.25-7.32 (m, 2H), 7.16-7.21 (m, 1H), 6.38 (s, 1H), 3.62 (m, 2H), 3.12-3.21 (br s, 1H), 3.00-3.08 (m, 1H), 2.12-2.21 (m, 1H), 1.90-1.98 (m, 1H), 1.27 (s, 12H), 1.22 (m, 6H).

Example 7-4

(2R,6R)-1-Benzyl-2,6-dimethyl-4-(4,4,5,5-tetramethyl-1,3,2-dioxaborolan-2-yl)-1,2,3,6-tetrahydropyridine was prepared by substituting the appropriate acetaldehyde in Step A of Example 7-1

$^1$H NMR (acetone-d$_4$) δ: 7.40-7.45 (m, 2H), 7.25-7.32 (m, 2H), 7.16-7.21 (m, 1H), 6.38 (s, 1H), 3.62 (m, 2H), 3.12-3.21 (br s, 1H), 3.00-3.08 (m, 1H), 2.12-2.21 (m, 1H), 1.90-1.98 (m, 1H), 1.27 (s, 12H), 1.22 (m, 6H).

Example 8

Preparation of Compound 34

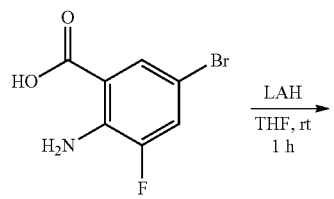

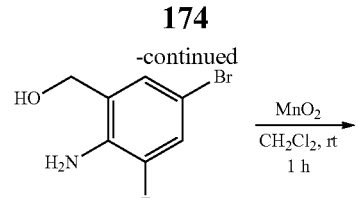

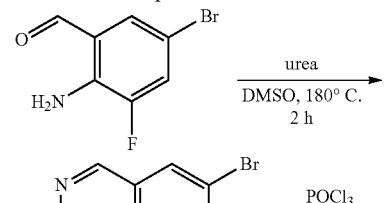

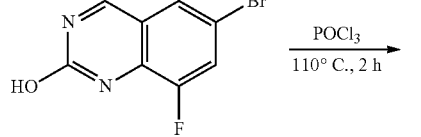

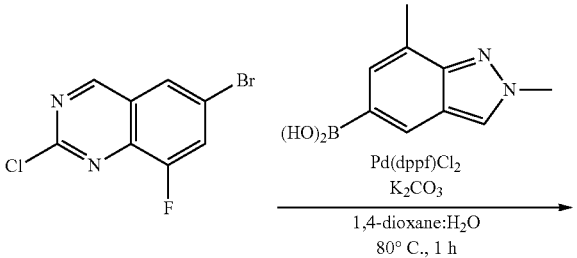

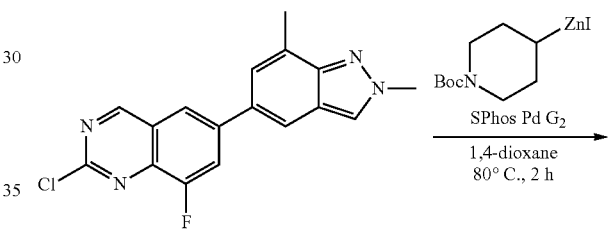

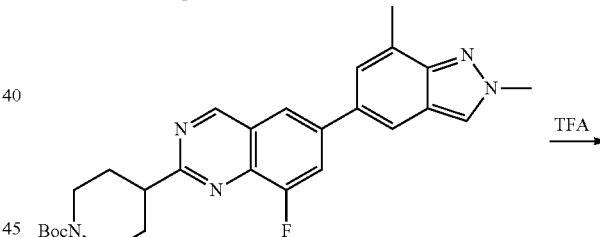

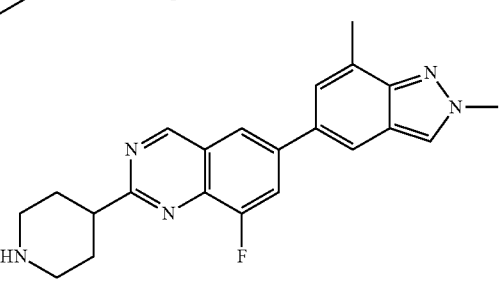

Step A: 2-Amino-5-bromo-3-fluoro-benzoic acid (1.0 g, 4.27 mmol) was dissolved in THF (20 mL). To the solution was added LAH (8.5 mL, 8.5 mmol, 1.0 M in THF) at 0° C. The mixture was warmed to room temperature. After 1 h, the mixture was quenched with aqueous 2 N NaOH at 0° C. After vigorous stirring for 30 min, the mixture was filtered over Celite. The filter cake was washed with THF and MeOH. The combined filtrate was concentrated to yield (2-amino-5-bromo-3-fluoro-phenyl)methanol (900 mg, 96%). MS m/z 220.2, 222.2 [M+H]$^+$.

Step B: (2-Amino-5-bromo-3-fluoro-phenyl)methanol (900 mg, 4.09 mmol) was combined with $MnO_2$ (6.9 g, 79 mmol) in $CH_2Cl_2$ (20 mL). The mixture was stirred at room temperature for 1 h. The mixture was filtered over Celite. The filtrate was concentrated to yield 2-amino-5-bromo-3-fluoro-benzaldehyde (650 mg, 73%). MS m/z 218.1, 220.1 [M+H]$^+$.

Step C: 2-Amino-5-bromo-3-fluoro-benzaldehyde (650 mg, 3.0 mmol) was combined with urea (3.6 g, 60 mmol) and DMSO (3 mL). The mixture was stirred at 180° C. for 2 h. The mixture was cooled to room temperature, upon which $H_2O$ (10 mL) was added. The precipitate was collected, washed with $H_2O$ and dried to yield 6-bromo-8-fluoro-quinazolin-2-ol (615 mg, 85%). MS m/z 243.1, 245.1 [M+H]$^+$.

Step D: 6-Bromo-8-fluoro-quinazolin-2-ol (615 mg, 2.53 mmol) was combined with $POCl_3$ (5 mL, 53 mmol). The mixture was stirred at 110° C. for 2 h. The mixture was cooled to room temperature and poured over ice. After vigorously stirring for 15 min, the solid was collected, dried and chromatographed on silica gel, eluting with 0-20% EtOAc in $CH_2Cl_2$ to yield 6-bromo-2-chloro-8-fluoroquinazoline (345 mg, 52%). MS m/z 261.1, 263.1, 265.1 [M+H]$^+$.

Steps E-G: Following a procedure similar to that found in Example 5 (Steps A-C), 6-bromo-2-chloro-8-fluoroquinazoline was converted to 6-(2,7-dimethyl-2H-indazol-5-yl)-8-fluoro-2-(piperidin-4-yl)quinazoline hydrochloride.

MS m/z 376.3 [M+H]$^+$; $^1$H NMR (DMSO-d$_6$) δ: 9.70 (s, 1H), 8.86-8.93 (br, 1H), 8.54-8.63 (br, 1H), 8.46 (s, 1H), 8.34 (d, J=1.9 Hz, 1H), 8.32 (dd, J=12.10, 1.9 Hz, 1H), 8.07 (s, 1H), 7.57 (s, 1H), 4.22 (s, 3H), 3.36-3.44 (m, 3H), 3.08-3.16 (m, 2H), 2.61 (s, 3H), 2.22-2.28 (m, 2H), 2.08-2.15 (m, 2H).

Using the procedure described for Example 8, above, additional compounds described herein were prepared by substituting the appropriate boronic acid in Step E, suitable reagents and reaction conditions, obtaining compounds such as those selected from:

| Cpd | Data |
|---|---|
| 35 | MS m/z 387.3 [M + H]$^+$; $^1$H NMR (DMSO-d$_6$) δ: 9.69 (d, J = 1.6 Hz, 1H), 8.79-8.85 (br, 1H), 8.78 (s, 1H), 8.67 (d, J = 1.9 Hz, 1H), 8.49-8.55 (br, 1H), 8.48 (d, J = 1.7 Hz, 1H), 8.47 (d, J = 1.8 Hz, 1H), 8.43 (dd, J = 12.2, 1.8 Hz, 1H), 4.30 (s, 3H), 3.37-3.46 (m, 3H), 3.07-3.17 (m, 2H), 2.22-2.28 (m, 2H), 2.07-2.16 (m, 2H). |
| 36 | MS m/z 380.3 [M + H]$^+$; $^1$H NMR (DMSO-d$_6$) δ: 9.69 (s, 1H), 8.73-8.79 (br, 1H), 8.63 (d, J = 1.9 Hz, 1H), 8.43-8.52 (br, 1H), 8.40 (d, J = 1.8 Hz, 1H), 8.37 (dd, J = 12.3, 1.8 Hz, 1H), 8.13 (d, J = 1.8 Hz, 1H), 7.65 (dd, J = 12.2, 1.9 Hz, 1H), 4.25 (s, 3H), 3.37-3.46 (m, 3H), 3.08-3.18 (m, 2H), 2.22-2.28 (m, 2H), 2.05-2.14 (m, 2H). |
| 37 | MS m/z 377.3 [M + H]$^+$; $^1$H NMR (DMSO-d$_6$) δ: 9.83 (s, 1H), 8.85-8.91 (br, 1H), 8.83 (d, J = 1.9 Hz, 1H), 8.59-8.64 (br, 1H), 8.56 (dd, J = 12.3, 1.8 Hz, 1H), 8.42 (s, 1H), 8.31 (s, 1H), 3.58 (s, 3H), 3.39-3.47 (m, 3H), 3.08-3.18 (m, 2H), 2.74 (s, 3H), 2.23-2.30 (m, 2H), 2.07-2.15 (m, 2H). |

Using the procedure described for Example 8, above, additional compounds described herein were prepared by substituting the indicated starting material, suitable reagents and reaction conditions, obtaining compounds such as those selected from:

| Cpd | Starting Material and Data |
|---|---|
| 38 | Starting material: 6-amino-3-bromo-2-fluorobenzoic acid<br>MS m/z 376.4 [M + H]$^+$; $^1$H NMR (methanol-d$_4$) δ: 8.70 (s, 1H), 7.94 (s, 1H), 7.81-7.86 (m, 1H), 7.58-7.61 (m, 1H), 7.47 (d, J = 8.5 Hz, 1H), 6.37 (s, 1H), 4.40 (s, 3H), 3.63-3.70 (m, 3H), 3.21-3.29 (m, 2H), 2.69 (s, 3H), 2.29-2.40 (m, 4H) NH proton not observed. |
| 39 | Starting material: 2-amino-5-bromo-4-fluorobenzoic acid<br>MS m/z 376.3 [M + H]+; $^1$H NMR (DMSO-d$_6$) δ: 8.77 (s, 1H), 7.98 (s, 1H), 7.81 (d, J = 7.6 Hz, 1H), 7.63-7.68 (m, 1H), 7.43 (d, J = 10.4 Hz, 1H), 6.27 (s, 1H), 4.42 (s, 3H), 3.63-3.70 (m, 3H), 3.24-3.31 (m, 2H), 2.69 (s, 3H), 2.28-2.45 (m, 4H), NH proton not observed. |

Example 9

Preparation of Compound 17

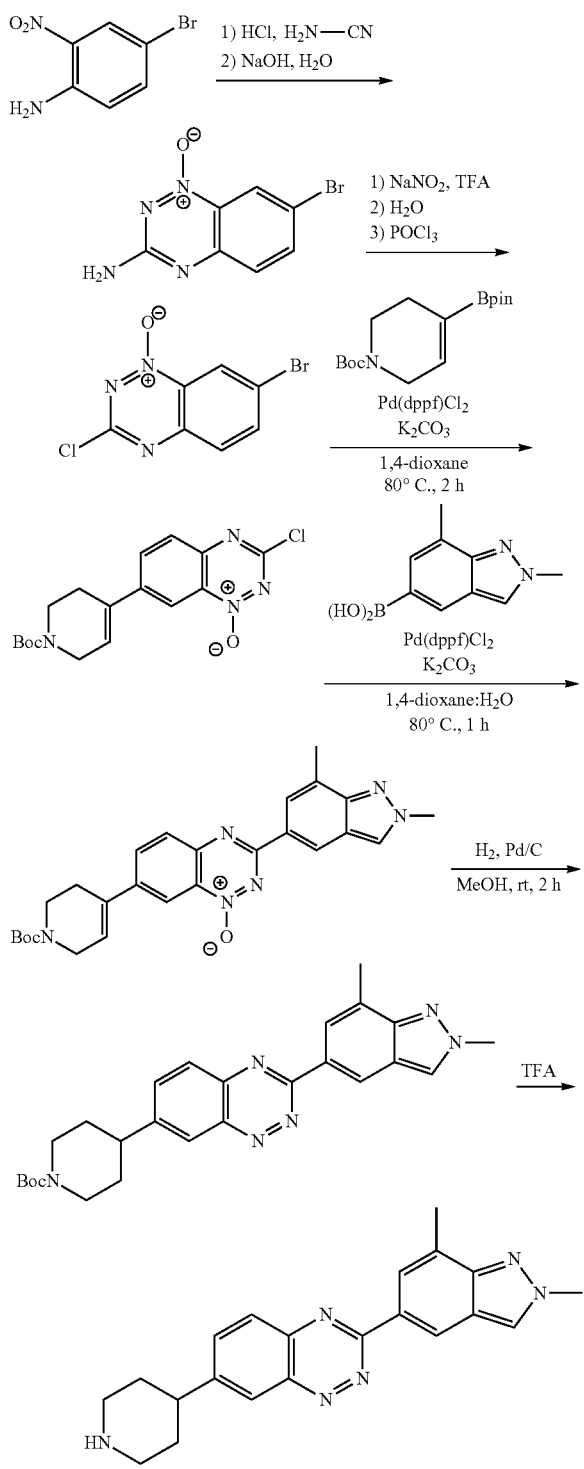

Step A: 4-Bromo-2-nitroaniline (3.7 g, 17 mmol), cyanamide (5.72 g, 135 mmol) and Et$_2$O (3 mL) were combined in a 75 mL tube. The mixture was stirred at 100° C. for 30 min. The mixture was cooled to 50° C. To the mixture was slowly added aqueous concentrated HCl (7.2 mL). The resulting mixture was stirred for 1 h at 110° C. The reaction mixture was again cooled to 50° C., before adding aqueous 7.5 M NaOH (16 mL). The mixture was again heated to 110° C. for 1 h. After cooling to room temperature, 20 mL of H$_2$O was added to the mixture. The solid material was collected, washed with H$_2$O and dried to yield 7-bromo-1-oxido-1,2,4-benzotriazin-1-ium-3-amine (3.2 g, 79%). MS m/z 240.8, 242.8 [M+H]$^+$.

Step B: To a solution of 7-bromo-1-oxido-1,2,4-benzotriazin-1-ium-3-amine (3.2 g, 13 mmol) and TFA (25 mL) was added NaNO$_2$ (2.76 g, 40.0 mmol) in small portions at room temperature. The mixture stirred at room temperature for 30 min. To the mixture was added H$_2$O (75 mL) to form a white precipitate. The solid was collected, washed with H$_2$O and dried. The solid was combined with POCl$_3$ (30 mL, 318.6 mmol). The mixture was stirred at 110° C. for 2 h. After cooling to room temperature, the mixture was poured onto ice with vigorous stirring. After stirring for 10 min, CH$_2$Cl$_2$ (400 mL) was added. The organic phase was collected and dried over Na$_2$SO$_4$, filtered and concentrated. The residue was chromatographed on silica gel, eluting with 0-10% EtOAc in CH$_2$Cl$_2$ to yield 7-bromo-3-chloro-1-oxido-1,2,4-benzotriazin-1-ium (2.37 g, 54%). MS m/z 259.9, 261.9, 264.0 [M+H]$^+$.

Step C: 7-Bromo-3-chloro-1-oxido-1,2,4-benzotriazin-1-ium (520 mg, 2.0 mmol) was combined with N-Boc-1,2,5,6-tetrahydropyridine-4-boronic acid pinacol ester (773 mg, 2.45 mmol), 1,1'-bis(diphenylphosphino)ferrocene-palladium(II)dichloride dichloromethane complex (80 mg, 0.10 mmol), 1,4-dioxane (10 mL), and aqueous 1 M K$_2$CO$_3$ (5 mL, 5.0 mmol). The mixture was stirred at 80° C. for 1 h. The mixture was partitioned between EtOAc and H$_2$O. The organic layer was washed with brine, dried over Na$_2$SO$_4$, filtered and concentrated. The residue was chromatographed on silica gel, eluting with 10-100% EtOAc in hexanes to yield tert-butyl 4-(3-chloro-1-oxido-1,2,4-benzotriazin-1-ium-7-yl)-3,6-dihydro-2H-pyridine-1-carboxylate (540 mg, 75%). MS m/z 307.1, 309.1 [M+H-tBu]$^+$ (molecule ionizes as M+H minus tBu).

Step D: tert-Butyl 4-(3-chloro-1-oxido-1,2,4-benzotriazin-1-ium-7-yl)-3,6-dihydro-2H-pyridine-1-carboxylate (72 mg, 0.20 mmol) was combined with 2,7-dimethyl-5-(4,4,5,5-tetramethyl-1,3,2-dioxaborolan-2-yl)indazole (80 mg, 0.30 mmol), 1,1'-bis(diphenylphosphino)ferrocene-palladium(II)dichloride dichloromethane complex (8 mg, 0.01 mmol), 1,4-dioxane (1 mL), and aqueous 1 M K$_2$CO$_3$ (0.5 mL, 0.5 mmol). The mixture was stirred at 80° C. for 1 h. The mixture was partitioned between EtOAc and H$_2$O. The organic layer was washed with brine, dried over Na$_2$SO$_4$, filtered and concentrated. The residue was chromatographed on silica gel, eluting with 5% MeOH in EtOAc to yield tert-butyl 4-[3-(2,7-dimethylindazol-5-yl)-1-oxido-1,2,4-benzotriazin-1-ium-7-yl]-3,6-dihydro-2H-pyridine-1-carboxylate (72 mg, 77%). MS m/z 473.4 [M+H]$^+$.

Step E: tert-Butyl 4-[3-(2,7-dimethylindazol-5-yl)-1-oxido-1,2,4-benzotriazin-1-ium-7-yl]-3,6-dihydro-2H-pyridine-1-carboxylate (60 mg, 0.13 mmol) was combined with 10% Pd/C (10 mg) and MeOH (3 mL). The mixture was stirred under H$_2$ (1 atm) for 2 h at 30° C. The mixture was filtered through a 0.2 μm syringe filter to yield tert-butyl 4-[3-(2,7-dimethylindazol-5-yl)-1,2,4-benzotriazin-7-yl]piperidine-1-carboxylate (58 mg, 99%). MS m/z 459.4 [M+H]$^+$.

Step F: tert-Butyl 4-[3-(2,7-dimethylindazol-5-yl)-1,2,4-benzotriazin-7-yl]piperidine-1-carboxylate (58 mg, 0.13 mmol) was dissolved in TFA (1 mL). After 20 min, the volatiles were removed from the mixture. The residue was partitioned between EtOAc and aqueous 1 M K$_2$CO$_3$. The organic layer was washed with brine, dried over Na$_2$SO$_4$, filtered and concentrated. The residue was chromatographed on silica gel, eluting with 0-10% MeOH (2 N NH$_3$) in CH$_2$Cl$_2$ to yield 3-(2,7-dimethyl-2H-indazol-5-yl)-7-(piperidin-4-yl)benzo[e][1,2,4]triazine (20 mg, 44%).

MS m/z 359.3 [M+H]$^+$; $^1$H NMR (DMSO-d$_6$) δ: 9.01 (s, 1H), 8.59 (s, 1H), 8.31 (s, 1H), 8.26 (s, 1H), 8.06-8.12 (m, 2H), 4.24 (s, 3H), 3.11-3.19 (m, 2H), 2.94-3.01 (m, 1H), 2.68-2.76 (m, 2H), 2.64 (s, 3H), 1.88-1.94 (m, 2H), 1.66-1.76 (m, 2H), NH proton not observed.

Using the procedure described for Example 9, above, additional compounds described herein were prepared by substituting the appropriate boronic acid in Steps B and/or C, suitable reagents and reaction conditions, obtaining compounds such as those selected from:

| Cpd | Data |
| --- | --- |
| 25 | MS m/z 363.3 [M + H]$^+$; $^1$H NMR (DMSO-d$_6$) δ: 9.03 (s, 1H), 8.76 (d, J = 2.7 Hz, 1H), 8.31 (s, 1H), 8.16 (dd, J = 13.0, 1.2 Hz, 1H), 8.10-8.14 (m, 2H), 4.24 (s, 3H), 3.14-3.20 (m, 2H), 2.97-3.05 (m, 1H), 2.71-2.79 (m, 2H), 1.90-1.97 (m, 2H), 1.69-1.79 (m, 2H), NH proton not observed. |
| 26 | MS m/z 370.3 [M + H]$^+$; $^1$H NMR (methanol-d$_4$) δ: 9.48 (d, J = 1.6 Hz, 1H), 9.05 (d, J = 1.6 Hz, 1H), 8.68 (s, 1H), 8.36 (s, 1H), 8.09-8.17 (m, 2H), 4.36 (s, 3H), 3.35-3.42 (m, 2H), 3.11-3.20 (m, 1H), 2.97-3.05 (m, 2H), 2.11-2.19 (m, 2H), 1.89-1.99 (m, 2H), NH proton not observed. |
| 27 | MS m/z 359.3 [M + H]$^+$; $^1$H NMR (methanol-d$_4$) δ: 9.52 (s, 1H), 8.29 (s, 1H), 8.18 (s, 1H), 8.01-8.07 (m, 2H), 7.73 (s, 1H), 3.27-3.32 (m, 2H), 3.03-3.10 (m, 1H), 2.88-2.94 (m, 2H), 2.63 (s, 3H), 2.45 (s, 3H), 2.04-2.09 (m, 2H), 1.81-1.91 (m, 2H), NH proton not observed. |
| 43 | MS m/z 363.3 [M + H]$^+$; $^1$H NMR (DMSO-d$_6$) δ: 9.78 (s, 1H), 8.36 (s, 1H), 8.10-8.17 (m, 3H), 8.04 (dd, J = 12.2, 1.3 Hz, 1H), 3.09-3.15 (m, 2H), 2.94-3.01 (m, 1H), 2.66-2.72 (m, 2H), 2.42 (s, 3H), 1.87-1.93 (m, 2H), 1.64-1.74 (m, 2H), NH proton not observed. |
| 52 | MS m/z 375.4 [M + H]$^+$; $^1$H NMR (DMSO-d$_6$) δ: 8.78 (s, 1H), 8.57 (s, 1H), 8.31 (s, 1H), 8.07-8.12 (m, 2H), 7.82 (s, 1H), 4.21 (s, 3H), 4.07 (s, 3H), 3.10-3.17 (m, 2H), 2.93-2.99 (m, 1H), 2.66-2.73 (m, 2H), 1.87-1.93 (m, 2H), 1.65-1.75 (m, 2H), NH proton not observed. |
| 56 | MS m/z 389.2 [M + H]$^+$; $^1$H NMR (methanol-d$_4$) δ: 10.01 (s, 1H), 8.88-8.92 (m, 1H), 8.75 (s, 1H), 8.36 (dd, J = 9.0, 2.2 Hz, 1H), 8.30-8.33 (m, 1H), 8.24-8.27 (m, 1H), 4.18-4.28 (m, 2H), 3.61-3.69 (m, 1H), 2.58-2.74 (m, 5H), 2.20-2.33 (m, 4H), 2.08-2.13 (m, 2H), NH proton not observed. |

Example 10

Preparation of Compound 28

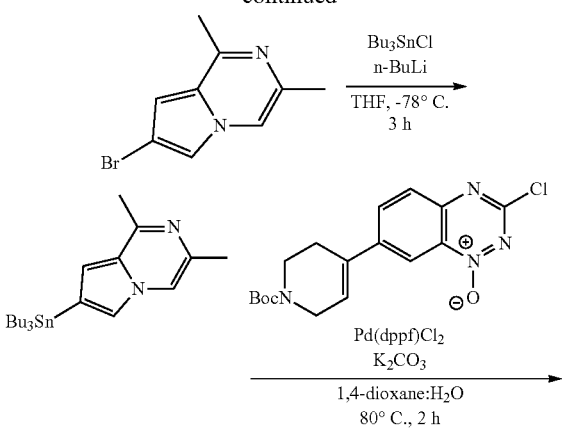

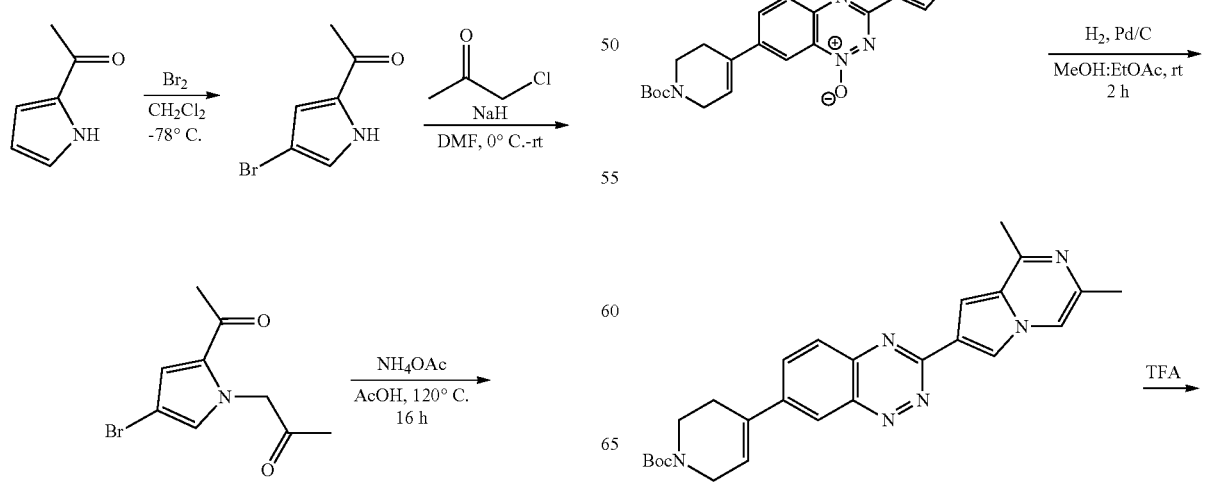

-continued

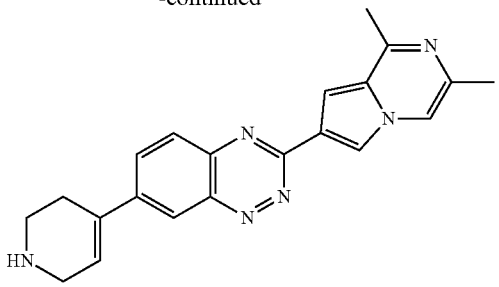

Step A: 1-(1H-Pyrrol-2-yl)ethanone (1.09 g, 10.0 mmol) was dissolved in 50 mL CH$_2$Cl$_2$ and cooled to −78° C. A solution of Br$_2$ (620 μL, 12.1 mmol) in 12 mL of CH$_2$Cl$_2$ was added dropwise to the solution. The reaction mixture was poured onto ice. The organic layer was washed with aqueous 1M NaOH, dried over MgSO$_4$, filtered and concentrated to yield 1-(4-bromo-1H-pyrrol-2-yl)ethanone (1.42 g, 76%).

$^1$H NMR (acetone-d$_6$) δ: 11.08 (br s, 1H), 7.19 (m, 1H), 7.02 (m, 1H), 2.34 (s, 3H).

Step B: 1-(4-Bromo-1H-pyrrol-2-yl)ethanone (1.36 g, 7.2 mmol) was dissolved in DMF (15 mL) and cooled to 0° C. To the solution was added NaH (60 mass % in mineral oil) (316 mg, 7.9 mmol). The mixture was warmed to room temperature for 30 min. Chloroacetone (0.6 mL, 7 mmol) was added dropwise. The mixture was stirred at room temperature for 16 h. The mixture was partitioned between H$_2$O and EtOAc. The organic layer was dried over MgSO$_4$, filtered and concentrated. The residue was chromatographed on silica gel, eluting with 30% EtOAc in hexanes to yield 1-(2-acetyl-4-bromo-pyrrol-1-yl)propan-2-one (1.2 g, 68%) as a white solid.

$^1$H NMR (acetone-d$_6$) δ: 7.13 (d, J=2 Hz, 1H), 7.10 (d, J=2 Hz, 1H), 5.17 (s, 2H), 2.36 (s, 3H), 2.18 (s, 3H).

Step C: 1-(2-Acetyl-4-bromo-pyrrol-1-yl)propan-2-one (1.15 g, 4.7 mmol), acetic acid (40 mL) and ammonium acetate (7.2 g, 93 mmol) were heated at 120° C. for 16 h. The volatiles were removed under reduced pressure. The residue was partitioned between aqueous 1 M NaOH and EtOAc. The organic layer was dried over MgSO$_4$, filtered and concentrated. The residue was chromatographed on silica gel, eluting with 10-50% EtOAc in CH$_2$Cl$_2$ to yield 7-bromo-1,3-dimethyl-pyrrolo[1,2-a]pyrazine (975 mg, 92%).

$^1$H NMR (acetone-d$_6$) δ: 7.86 (s, 1H), 7.63 (s, 1H), 6.84 (s, 1H), 2.56 (s, 3H), 2.31 (s, 3H).

Step D: 7-Bromo-1,3-dimethylpyrrolo[1,2-a]pyrazine (2.0 g, 8.9 mmol) was dissolved in THF (90 mL). The solution was cooled to −78° C., upon which n-butyllithium was added (6.7 mL, 13.3 mmol, 2 M solution in cyclohexane). The mixture was stirred at −78° C. for 30 min. To the mixture was added tributylchlorostannane. The mixture was allowed to slowly warm to 0° C. The excess reagent was quenched with saturated aqueous NH$_4$Cl. The mixture was partitioned between EtOAc and H$_2$O. The organic layer was dried over Na$_2$SO$_4$, filtered and concentrated. The residue was chromatographed on silica gel, eluting with 0-100% EtOAc in hexanes to yield tributyl-(1,3-dimethylpyrrolo[1,2-a]pyrazin-7-yl)stannane (1.3 g, 30%).

$^1$H NMR (chloroform-d) δ: 7.53 (s, 1H), 7.20 (s, 1H), 6.72 (s, 1H), 2.65 (s, 3H), 2.37 (s, 3H), 1.52-1.58 (m, 6H), 1.30-1.38 (m, 6H), 1.04-1.08 (m, 6H), 0.88-0.94 (m, 9H).

Step E: tert-Butyl 4-(3-chloro-1-oxido-1,2,4-benzotriazin-4-ium-7-yl)-3,6-dihydro-2H-pyridine-1-carboxylate (72 mg, 0.20 mmol, prepared according to the procedure in Example 9, Step C) was combined with tributyl-(1,3-dimethylpyrrolo[1,2-a]pyrazin-7-yl)stannane (140 mg, 0.32 mmol), 1,1′-bis(diphenylphosphino)ferrocene-palladium(II) dichloride dichloromethane complex (12 mg, 0.015 mmol), 1,4-dioxane (1.5 mL) and aqueous 1 M K$_2$CO$_3$ (0.75 mL, 0.75 mmol). The mixture was stirred at 80° C. for 2 h. The mixture was partitioned between EtOAc and H$_2$O. The organic layer was washed with brine, dried over Na$_2$SO$_4$, filtered and concentrated. The residue was chromatographed on silica gel, eluting with 50-100% EtOAc in CH$_2$Cl$_2$, then EtOAc containing 5% MeOH to yield tert-butyl 4-[3-(1,3-dimethylpyrrolo[1,2-a]pyrazin-7-yl)-1-oxido-1,2,4-benzotriazin-1-ium-7-yl]-3,6-dihydro-2H-pyridine-1-carboxylate (50 mg, 53%). MS m/z 473.5 [M+M]$^+$.

Step F: tert-Butyl 4-[3-(1,3-dimethylpyrrolo[1,2-a]pyrazin-7-yl)-1-oxido-1,2,4-benzotriazin-1-ium-7-yl]-3,6-dihydro-2H-pyridine-1-carboxylate (30 mg, 0.06 mmol) was combined with 10% Pd/C (10 mg) in EtOAc:MeOH (1:1, 2 mL). The mixture was stirred under H$_2$ (1 atm) for 2 h at 40° C. The mixture was filtered through a 2 μm syringe filter. The filtrate was concentrated to yield tert-butyl 4-(3-(1,3-dimethylpyrrolo[1,2-a]pyrazin-7-yl)benzo[e][1,2,4]triazin-7-yl)-3,6-dihydropyridine-1(2H)-carboxylate (25 mg, 86%). MS m/z 457.5 [M+H]$^+$.

Step G: tert-Butyl 4-[3-(1,3-dimethylpyrrolo[1,2-a]pyrazin-7-yl)-1,2,4-benzotriazin-7-yl]piperidine-1-carboxylate (25 mg, 0.05 mmol) was dissolved in TFA (1 mL). After 15 min, the volatiles were removed. The residue was partitioned between CH$_2$Cl$_2$ and aqueous 1 M K$_2$CO$_3$. The organic layer was loaded on silica gel, eluting with 0-10% MeOH (2 N NH$_3$) in CH$_2$Cl$_2$ to yield 3-(1,3-dimethylpyrrolo[1,2-a]pyrazin-7-yl)-7-(1,2,3,6-tetrahydropyridin-4-yl)benzo[e][1,2,4]triazine (8 mg, 43%).

$^1$H NMR (DMSO-d$_6$) δ: 8.34 (s, 1H), 8.25 (s, 1H), 8.23 (dd, T=9.0, 2.0 Hz, 1H), 7.90 (d, T=8.8 Hz, 1H), 7.86 (s, 1H), 7.57 (s, 1H), 6.62 (s, 1H), 3.58-3.62 (m, 2H), 3.15-3.19 (m, 2H), 2.64-2.70 (m, 5H), 2.35 (s, 3H), NH proton not observed.

Example 11

Preparation of Compound 44

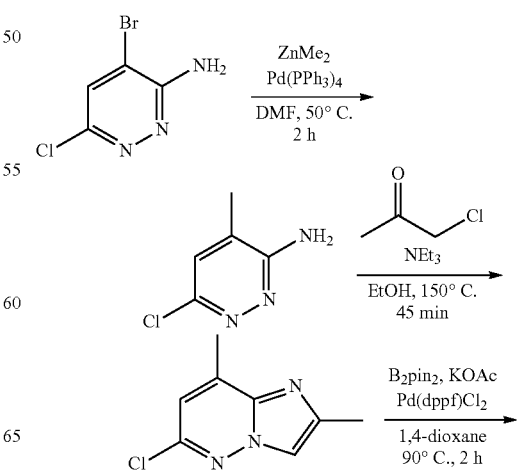

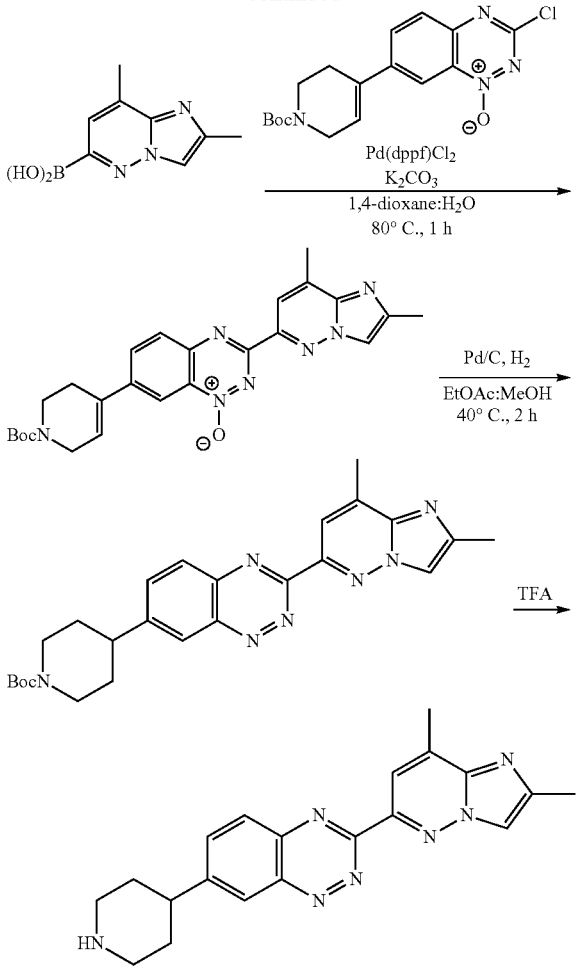

Step A: 4-Bromo-6-chloro-pyridazin-3-amine (5.2 g, 25 mmol) was combined with tetrakis(triphenylphosphine)palladium(0) (700 mg, 0.61 mmol) and DMF (50 mL). To the mixture was added dimethylzinc in heptane (50 mL, 50 mmol, 1.0 M) at room temperature. The mixture was heated at 50° C. for 2 h then 70° C. for 1 h. The mixture was cooled to 0° C. and excess reagent was quenched by the addition of $H_2O$. The mixture was filtered over Celite and concentrated. The residue was chromatographed on silica gel, eluting with 0-10% MeOH in $CH_2Cl_2$. MS m/z 144.2, 146.2 [M+H]$^+$.

Step B: 6-Chloro-4-methyl-pyridazin-3-amine (3.5 g, 24 mmol) was combined with ethanol (40 mL), triethylamine (8.7 mL, 62 mmol) and chloroacetone (4 mL, 49 mmol) in a 100 mL high pressure flask. The flask was sealed and heated behind a blast shield at 150° C. for 45 min. The mixture was concentrated and chromatographed on silica gel, eluting with 30-80% EtOAc in $CH_2Cl_2$ to yield 6-chloro-2,8-dimethylimidazo[1,2-b]pyridazine (2.2 g, 49%). MS m/z 182.3, 184.3 [M+H]$^+$.

Step C: 6-Chloro-2,8-dimethyl-imidazo[1,2-b]pyridazine (54 mg, 0.30 mmol) was combined with potassium acetate (87 mg, 0.89 mmol), 1,1'-bis(diphenylphosphino)ferrocene-palladium(II)dichloride dichloromethane complex (12 mg, 0.015 mmol), and bis(pinacolato)diboron (94 mg, 0.37 mmol) in 1,4-dioxane (1 mL). The mixture was stirred under $N_2$ at 95° C. for 2 h to yield (2,8-dimethylimidazo[1,2-b]pyridazin-6-yl)boronic acid. MS m/z 192.4 [M+H]$^+$. The crude mixture was used directly in the next step.

Step D: To the crude mixture from Step C was added aqueous 1 M $K_2CO_3$ (0.75 mL, 0.75 mmol), tert-butyl 4-(3-chloro-1-oxido-1,2,4-benzotriazin-1-ium-7-yl)-3,6-dihydro-2H-pyridine-1-carboxylate (72 mg, 0.20 mmol, prepared according to the procedure in Example 9, Step C), and 1,1'-bis(diphenylphosphino)ferrocene-palladium(II)dichloride dichloromethane complex (8 mg, 0.01 mmol). The mixture was stirred at 80° C. for 1 h. The mixture was partitioned between EtOAc and $H_2O$. The organic layer was washed with brine, dried over $Na_2SO_4$, filtered and concentrated. The residue was chromatographed on silica gel, eluting with 0-80% EtOAc in $CH_2Cl_2$ to yield tert-butyl 4-[3-(2,8-dimethylimidazo[1,2-b]pyridazin-6-yl)-1-oxido-1,2,4-benzotriazin-1-ium-7-yl]-3,6-dihydro-2H-pyridine-1-carboxylate (69 mg, 73%). MS m/z 474.4 [M+H]$^+$.

Step E: tert-Butyl 4-[3-(2,8-dimethylimidazo[1,2-b]pyridazin-6-yl)-1-oxido-1,2,4-benzotriazin-1-ium-7-yl]-3,6-dihydro-2H-pyridine-1-carboxylate (69 mg, 0.15 mmol) was combined with 10% Pd/C (20 mg) in MeOH (2 mL). The mixture was stirred under $H_2$ (1 atm) for 2 h at 40° C. The mixture was filtered. The filtrate was concentrated and chromatographed on silica gel, eluting with 20-100% EtOAc in hexanes to yield tert-butyl 4-[3-(2,8-dimethylimidazo[1,2-b]pyridazin-6-yl)-1-oxido-1,2,4-benzotriazin-1-ium-7-yl]-3,6-dihydro-2H-pyridine-1-carboxylate (69 mg, 97%). MS m/z 460.4 [M+H]$^+$.

Step F: tert-Butyl 4-[3-(2,8-dimethylimidazo[1,2-b]pyridazin-6-yl)-1-oxido-1,2,4-benzotriazin-1-ium-7-yl]-3,6-dihydro-2H-pyridine-1-carboxylate (69 mg, 0.15 mmol) was suspended in 4 N HCl in 1,4-dioxane (1 mL, 4 mmol). The volatiles were removed after 30 min. The residue was partitioned between $CH_2Cl_2$ and aqueous 1 M $K_2CO_3$. The organic layer was concentrated. The residue was chromatographed on silica gel, eluting with 0-10% MeOH (2 N $NH_3$) in $CH_2Cl_2$ to yield 3-(2,8-dimethylimidazo[1,2-b]pyridazin-6-yl)-7-(piperidin-4-yl)benzo[e][1,2,4]triazine.

MS m/z 360.4 [M+H]$^+$; $^1$H NMR (DMSO-d$_6$) δ: 8.47 (s, 1H), 8.32 (s, 1H), 8.18-8.25 (m, 2H), 8.10 (s, 1H), 3.35-3.40 (m, 2H), 3.15-3.22 (m, 1H), 2.96-3.04 (m, 2H), 2.78 (s, 3H), 2.56 (s, 3H), 2.12-2.18 (m, 2H), 1.89-1.99 (m, 2H), NH proton not observed.

Example 12

Preparation of Compound 16

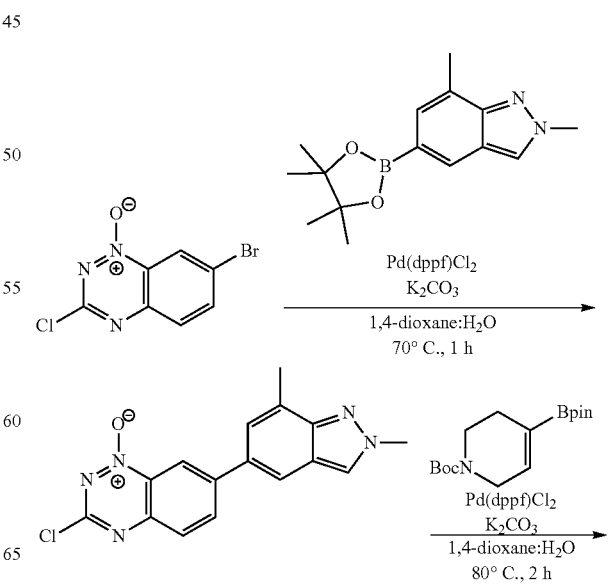

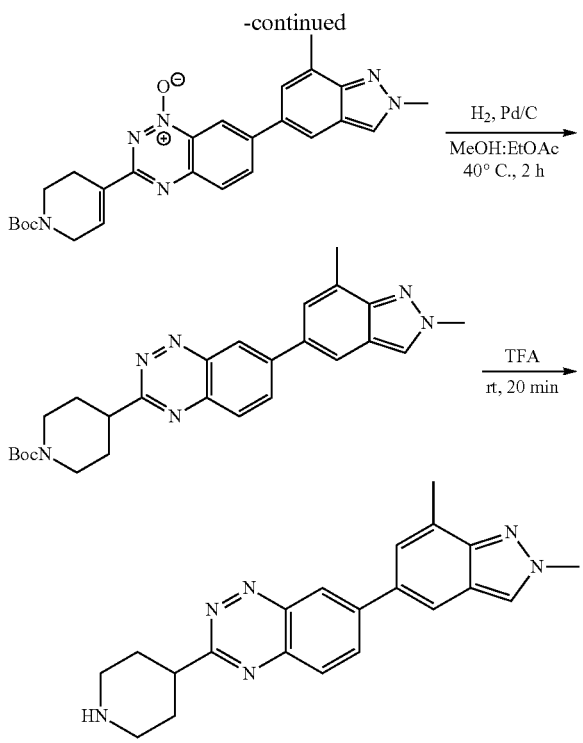

Step A: 7-Bromo-3-chloro-1-oxido-1,2,4-benzotriazin-1-ium (260 mg, 1.0 mmol, prepared in Example 9 Step B) was combined with 2,7-dimethyl-5-(4,4,5,5-tetramethyl-1,3,2-dioxaborolan-2-yl)-2H-indazole (360 mg, 1.06 mmol), 1,1'-bis(diphenylphosphino)ferrocene-palladium(II)dichloride dichloromethane complex (45 mg, 0.05 mmol), 1,4-dioxane (5 mL) and aqueous 1 M K₂CO₃ (2.5 mL). The mixture was stirred at 70° C. for 1 h. The mixture was partitioned between EtOAc and H₂O. The organic layer was washed with brine, dried over Na₂SO₄, filtered and concentrated. The residue was chromatographed on silica gel, eluting with 10-90% EtOAc in hexanes to yield 3-chloro-7-(2,7-dimethyl-2H-indazol-5-yl)benzo[e][1,2,4]triazine-1-oxide (200 mg, 54%). MS m/z 326.0, 328.0 [M+H]⁺.

Step B: 3-Chloro-7-(2,7-dimethyl-2H-indazol-5-yl)benzo[e][1,2,4]triazine-1-oxide (200 mg, 0.54 mmol) was combined with N-Boc-1,2,5,6-tetrahydropyridine-4-boronic acid pinacol ester (250 mg, 0.80 mmol), 1,1'-bis(diphenylphosphino)ferrocene-palladium(II)dichloride dichloromethane complex (40 mg, 0.05 mmol), 1,4-dioxane (3 mL) and aqueous 1 M K₂CO₃ (1.5 mL, 1.5 mmol). The mixture was stirred at 80° C. for 2 h. The mixture was partitioned between EtOAc and H₂O. The organic layer was washed with brine, dried over Na₂SO₄, filtered and concentrated. The residue was chromatographed on silica gel, eluting with 10-100% EtOAc in hexanes to yield tert-butyl 4-[7-(2,7-dimethylindazol-5-yl)-1-oxido-1,2,4-benzotriazin-1-ium-3-yl]-3,6-dihydro-2H-pyridine-1-carboxylate (200 mg, 78%). MS m/z 473.1 [M+H]⁺.

Step C: tert-Butyl 4-[7-(2,7-dimethylindazol-5-yl)-1-oxido-1,2,4-benzotriazin-1-ium-3-yl]-3,6-dihydro-2H-pyridine-1-carboxylate (200 mg, 0.085 mmol) was combined with 10% Pd/C (40 mg) in MeOH (5 mL). The mixture was stirred under H₂ (1 atm) for 2 h at 40° C. The mixture was filtered through a 2 μm syringe filter. The filtrate was concentrated and chromatographed on silica gel, eluting with 10-100% EtOAc in CH₂Cl₂ to yield tert-butyl 4-[7-(2,7-dimethylindazol-5-yl)-1,2,4-benzotriazin-3-yl]piperidine-1-carboxylate (100 mg, 50%). MS m/z 459.1 [M+H]⁺.

Step D: tert-Butyl 4-[7-(2,7-dimethylindazol-5-yl)-1,2,4-benzotriazin-3-yl]piperidine-1-carboxylate (50 mg, 0.11 mmol) was dissolved in TFA (1 mL). After 20 min, the volatiles were removed from the reaction mixture. The residue was partitioned between CH₂Cl₂ and aqueous 1 M K₂CO₃. The organic layer was loaded directly to silica gel, eluting with 0-10% MeOH (2 N NH₃) in CH₂Cl₂ to yield 7-(2,7-dimethyl-2H-indazol-5-yl)-3-(piperidin-4-yl)benzo[e][1,2,4]triazine (30 mg, 77%).

MS m/z 359.1 [M+H]⁺; ¹H NMR (DMSO-d₆) δ: 8.77 (d, J=2.5 Hz, 1H), 8.56 (dd, J=9.0, 1.9 Hz, 1H), 8.47 (s, 1H), 8.12-8.18 (m, 2H), 7.66 (s, 1H), 4.23 (s, 3H), 3.40-3.47 (m, 1H), 3.08-3.15 (m, 2H), 2.69-2.76 (m, 2H), 2.63 (s, 3H), 2.00-2.07 (m, 2H), 1.83-1.92 (m, 2H), NH proton not observed.

Example 13

Preparation of Compound 46

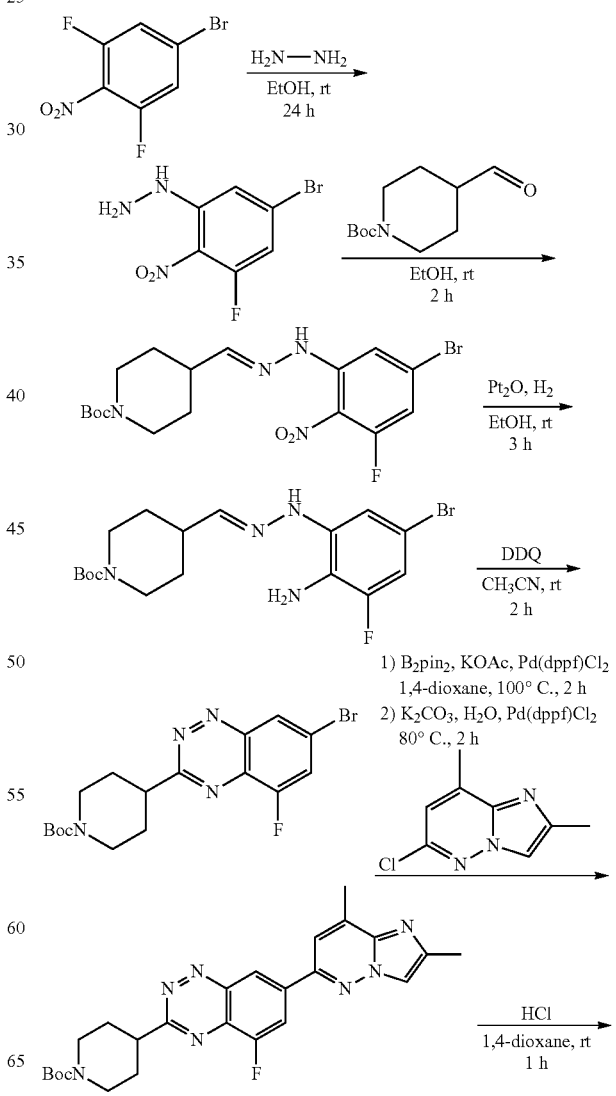

-continued

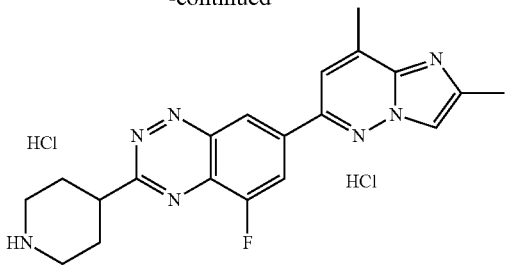

Step A: 5-Bromo-1,3-difluoro-2-nitro-benzene (9.52 g, 40.0 mmol) was dissolved in EtOH (50 mL). To the solution was added hydrazine monohydrate (16.6 mL, 160 mmol). The solution was stirred at room temperature for 24 h. The mixture was concentrated under reduced pressure. The residue was partitioned between EtOAc and H₂O. The organic layer was washed with brine, dried over Na₂SO₄, filtered and concentrated. The residue was chromatographed on silica gel, eluting with 0-30% EtOAc in hexanes to yield (5-bromo-3-fluoro-2-nitrophenyl)hydrazine (8.5 g, 85%). MS m/z 250.2, 252.2 [M+H]⁺.

Step B: (5-Bromo-3-fluoro-2-nitrophenyl)hydrazine (1.25 g, 5.0 mmol) and tert-butyl 4-formylpiperidine-1-carboxylate (3.2 g, 15 mmol) were combined in EtOH (25 mL). The mixture was stirred at room temperature for 2 h. The mixture was concentrated under reduced pressure. The residue was chromatographed on silica gel, eluting with 0-20% EtOAc in CH₂Cl₂ to yield tert-butyl (E)-4-((2-(5-bromo-3-fluoro-2-nitrophenyl)hydrazono)methyl)piperidine-1-carboxylate (2.2 g, 99%) MS m/z 443.1, 445.4 [M–H]⁻.

Step C: tert-Butyl (E)-4-((2-(5-bromo-3-fluoro-2-nitrophenyl)hydrazono)methyl)piperidine-1-carboxylate (2.2 g, 4.9 mmol) was suspended in EtOH (50 mL) with PtO₂ (100 mg, 0.4402 mmol). The mixture was stirred under H₂ (1 atm, balloon) at room temperature for 3 h. The reaction mixture was filtered over Celite. The filtrate was concentrated under reduced pressure to yield tert-butyl (E)-4-((2-(2-amino-5-bromo-3-fluorophenyl)hydrazono)methyl)piperidine-1-carboxylate (2.03 g, 98%). MS m/z 413.3, 415.3 [M–H]⁻.

Step D: tert-Butyl 4-(7-bromo-5-fluoro-1,2,3,4-tetrahydro-1,2,4-benzotriazin-3-yl)piperidine-1-carboxylate (2.03 g, 4.9 mmol) was dissolved in CH₃CN (40 mL, 765 mmol). To the mixture was added 2,3-dichloro-5,6-dicyano-1,4-benzoquinone (3.41 g, 15.0 mmol). The mixture was stirred at room temperature for 2 h. The mixture was concentrated under reduced pressure. The residue was suspended in CH₂Cl₂ and filtered. The filtrate was concentrated and chromatographed on silica gel, eluting with 0-30% EtOAc in hexanes to yield tert-butyl 4-(7-bromo-5-fluorobenzo[e][1,2,4]triazin-3-yl)piperidine-1-carboxylate (805 mg, 39%). MS m/z 411.2, 413.2 [M+H]⁺.

Step E: tert-Butyl 4-(7-bromo-5-fluorobenzo[e][1,2,4]triazin-3-yl)piperidine-1-carboxylate (500 mg, 1.22 mmol) was combined with KOAc (358 mg, 3.65 mmol), [1,1'-bis(diphenylphosphino)ferrocene]dichloropalladium(II), complex with dichloromethane (100 mg, 0.12 mmol), bis(pinacolato)diboron (386 mg, 1.52 mmol) and 1,4-dioxane (3 mL). The mixture was stirred at 100° C. for 2 h. After cooling the mixture to room temperature, aqueous 1 M K₂CO₃ (1.5 mL, 1.5 mmol), 6-chloro-2,8-dimethylimidazo[1,2-b]pyridazine (270 mg, 1.22 mmol, prepared according the procedure in Example 11), and [1,1'-bis(diphenylphosphino)ferrocene]dichloropalladium(II), complex with dichloromethane (100 mg, 0.12 mmol) were added. The mixture was stirred at 80° C. for 2 h. The mixture was partitioned between EtOAc and H₂O. The organic layer was washed with brine, dried over Na₂SO₄, filtered and concentrated. The residue was chromatographed on silica gel, eluting with 20-80% EtOAc in hexanes to yield tert-butyl 4-(7-(2,8-dimethylimidazo[1,2-b]pyridazin-6-yl)-5-fluorobenzo[e][1,2,4]triazin-3-yl)piperidine-1-carboxylate (550 mg, 94%). MS m/z 478.6 [M+H]⁺.

Step F: tert-Butyl 4-(7-(2,8-dimethylimidazo[1,2-b]pyridazin-6-yl)-5-fluorobenzo[e][1,2,4]triazin-3-yl)piperidine-1-carboxylate (67 mg, 0.14 mmol) was suspended in 4 N HCl in 1,4-dioxane (2 mL, 8 mmol). The mixture was stirred vigorously for 1 h. The solid was collected, washed with CH₃CN, and dried to afford 7-(2,8-dimethylimidazo[1,2-b]pyridazin-6-yl)-5-fluoro-3-(piperidin-4-yl)benzo[c][1,2,4]triazine hydrochloride (46 mg, 73%).

MS m/z 378.3 [M+H]⁺; ¹H NMR (methanol-d₄) δ: 9.24 (s, 1H), 8.68 (d, J=10.6 Hz, 1H), 8.60 (s, 1H), 8.44 (s, 1H), 3.91 (m, 1H), 3.59-3.67 (m, 2H), 3.34-3.42 (m, 2H), 2.87 (s, 3H), 2.70 (s, 3H), 2.53-2.61 (m, 2H), 2.32-2.43 (m, 2H), NH proton not observed.

Using the procedure described for Example 13, above, additional compounds described herein were prepared by substituting the appropriate aryl halide in Step E, suitable reagents and reaction conditions, obtaining compounds such as those selected from:

| Cpd | Data |
| --- | --- |
| 32 | MS m/z. 381.1 [M + H]⁺; ¹H NMR (methanol-d₄) δ: 8.67-8.69 (m, 1H), 8.49 (d, J = 2.8 Hz, 1H), 8.34 (dd, J = 11.0, 1.9 Hz, 1H), 8.12 (d, J = 1.6 Hz, 1H), 7.63 (dd, J = 12.6, 1.6 Hz, 1H), 4.31 (s, 3H), 3.83-3.90 (m, 1H), 3.60-3.67 (m, 2H), 3.32-3.38 (m, 2H), 2.52-2.59 (m, 2H), 2.32-2.42 (m, 2H), NH proton not observed. |
| 33 | MS m/z 377.3 [M + H]⁺; ¹H NMR (DMSO-d₆) δ: 8.69 (d, J = 1.9 Hz, 1H), 8.47-8.52 (m, 2H), 8.20-8.23 (m, 1H), 7.69-7.71 (m, 1H), 4.23 (s, 3H), 3.44-3.51 (m, 1H), 3.10-3.15 (m, 2H), 2.69-2.77 (m, 2H), 2.62 (s, 3H), 2.03-2.08 (m, 2H), 1.83-1.92 (m, 2H), NH proton not observed. |
| 58 | MS m/z 381.3 [M + H]⁺; ¹H NMR (DMSO-d₆) δ: 9.42 (s, 1H), 9.02-9.09 (br, 1H), 8.95 (s, 1H), 8.74-8.82 (br, 1H), 8.58 (dd, J = 13.0, 1.2 Hz, 1H), 8.30-8.37 (m, 1H), 8.07 (s, 1H), 3.77-3.84 (m, 1H), 3.43-3.49 (m, 2H), 3.14-3.24 (m, 2H), 2.51 (s, 3H), 2.33-2.39 (m, 2H), 2.17-2.27 (m, 2H). |
| 59 | MS m/z 408.2 [M + H]⁺; ¹H NMR (DMSO-d₆) δ: 9.35 (s, 1H), 8.94-9.01 (br, 1H), 8.65-8.75 (m, 2H), 8.26 (s, 1H), 7.82 (s, 1H), 4.64 (q, J = 7.3 Hz, 2H), 3.78-3.86 (m, 1H), 3.43-3.50 (m, 2H), 3.15-3.25 (m, 2H), 2.46 (s, 3H), 2.34-2.41 (m, 2H), 2.18-2.27 (m, 2H), 1.54 (t, J = 6.9 Hz, 3H). |
| 60 | MS m/z 377.4 [M + H]⁺; ¹H NMR (methanol-d₄) δ: 9.23 (s, 1H), 8.86 (d, J = 1.7 Hz, 1H), 8.37 (dd, J = 10.5, 1.5 Hz, 1H), 8.31 (s, 1H), 8.08 (s, 1H), 3.88-3.93 (m, 1H), 3.68-3.61 (m, 2H), 3.32-3.39 (m, 2H), 2.78 (s, 3H), 2.65 (s, 3H), 2.54-2.60 (m, 2H), 2.34-2.43 (m, 2H), NH proton not observed. |

| Cpd | Data |
|---|---|
| 61 | MS m/z 431.3 [M + H]+; 1H NMR (DMSO-d6) δ: 9.61 (s, 1H), 9.02 (br, 1H), 8.98 (s, 1H), 8.72 (br, 1H), 8.63 (dd, J = 11.8, 2.0 Hz, 1H), 8.40 (s, 1H), 8.00 (s, 1H), 3.77-3.83 (m, 1H), 3.42-3.49 (m, 2H), 3.15-3.24 (m, 2H), 2.47 (s, 3H), 2.33-2.39 (m, 2H), 2.16-2.27 (m, 2H). |
| 62 | MS m/z 378.4 [M + H]+; 1H NMR (DMSO-d6) δ: 8.84 (s, 1H), 8.56 (dd, J = 11.6, 1.9 Hz, 1H), 8.20 (s, 1H), 7.89 (s, 1H), 3.75-3.82 (m, 1H), 3.44-3.49 (m, 2H), 3.16-3.23 (m, 2H), 2.68 (s, 3H), 2.62 (s, 3H), 2.32-2.38 (m, 2H), 2.15-2.25 (m, 2H), NH proton not observed. |
| 63 | MS m/z 377.4 [M + H]+; 1H NMR (DMSO-d6) δ: 14.98 (br, 1H), 9.05 (br, 1H), 8.87 (s, 1H), 8.77 (br, 1H), 8.60 (dd, J = 11.5, 1.9 Hz, 1H), 8.17 (s, 1H), 8.02 (s, 1H), 3.77-3.83 (m, 1H), 3.44-3.49 (m, 2H), 3.16-3.23 (m, 2H), 2.85 (s, 3H), 2.70 (s, 3H), 2.32-2.38 (m, 2H), 2.15-2.25 (m, 2H). |
| 64 | MS m/z 377.4 [M + H]+; 1H NMR (methanol-d4) δ: 8.89-8.92 (m, 1H), 8.86 (d, J = 1.6 Hz, 1H), 8.46 (dd, J = 10.7, 1.9 Hz, 1H), 8.37-8.42 (m, 2H), 3.85-3.91 (m, 1H), 3.61-3.67 (m, 2H), 3.35-3.39 (m, 2H), 3.05 (s, 3H), 2.53-2.60 (m, 5H), 2.33-2.44 (m, 2H), NH proton not observed. |
| 65 | MS m/z 377.3 [M + H]+; 1H NMR (DMSO-d6) δ: 8.95 (br, 1H), 8.90 (s, 1H), 8.59-8.66 (m, 2H), 8.26 (s, 1H), 7.53 (s, 1H), 6.60 (s, 1H), 3.77-3.83 (m, 1H), 3.44-3.49 (m, 2H), 3.16-3.23 (m, 2H), 2.77 (s, 3H), 2.48 (s, 3H), 2.32-2.38 (m, 2H), 2.15-2.25 (m, 2H). |
| 66 | MS m/z 378.3 [M + H]+; 1H NMR (DMSO-d6) δ: 9.17 (s, 1H), 9.08 (br, 1H), 8.82 (dd, J = 11.5, 1.9 Hz, 1H), 8.78 (s, 1H), 8.76 (br, 1H), 8.21 (s, 1H), 4.28 (s, 3H), 3.75-3.83 (m, 1H), 3.43-3.49 (m, 2H), 3.15-3.23 (m, 2H), 2.69 (s, 3H), 2.32-2.38 (m, 2H), 2.15-2.25 (m, 2H). |
| 67 | MS m/z 378.1 [M + H]+; 1H NMR (DMSO-d6) δ: 9.17 (s, 1H), 8.79-8.86 (m, 2H), 8.64 (s, 1H), 8.58 (s, 1H), 8.52 (br, 1H), 4.31 (s, 3H), 3.77-3.83 (m, 1H), 3.44-3.51 (m, 2H), 3.15-3.23 (m, 2H), 2.89 (s, 3H), 2.32-2.38 (m, 2H), 2.15-2.25 (m, 2H). |
| 68 | MS m/z 382.0 [M + H]+; 1H NMR (methanol-d4) δ: 8.68 (s, 1H), 8.27 (d, J = 13.0, 1H), 8.01 (s, 1H), 7.72 (d, J = 13.0, 1H), 3.58-3.67 (m, 1H), 3.26-3.30 (m, 2H), 2.87-2.96 (m, 2H), 2.72 (s, 3H), 2.20-2.28 (m, 2H), 2.05-2.16 (m, 2H), NH proton not observed. |

Example 14

Preparation of Compound 57

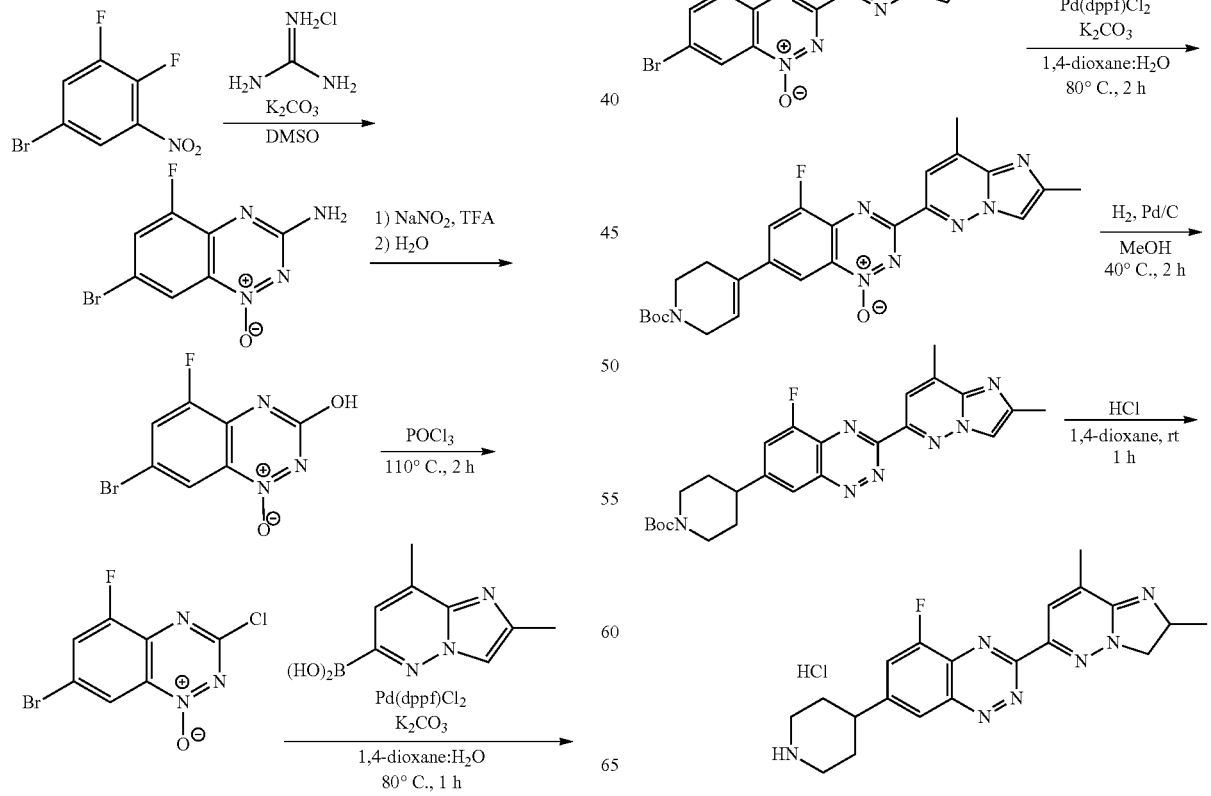

Step A: 5-Bromo-1,2-difluoro-3-nitro-benzene (11.7 g, 49 mmol, prepared according to the procedure in Example 7, Step A) was combined with guanidine hydrochloride (23.5 g, 246 mmol), $K_2CO_3$ (34 g, 246 mmol) and DMSO (75 mL). The mixture was vigorously stirred at 120° C. for 30 min. The mixture was cooled to room temperature. To the mixture was added aqueous 7.5 N NaOH (100 mL). The mixture was stirred at 60° C. for 30 min. To the mixture was added AcOH (75 mL) and $H_2O$ (400 mL). The mixture was filtered. The collected solid was dried to yield 7-bromo-5-fluoro-1-oxido-1,2,4-benzotriazin-1-ium-3-amine (9.6 g, 76%). MS m/z 259.1, 261.1 $[M+H]^+$.

Step B: 7-Bromo-5-fluoro-1-oxido-1,2,4-benzotriazin-1-ium-3-amine (9.6 g, 37 mmol) was dissolved in TFA (66 mL). To the mixture was added $NaNO_2$ (13.1 g, 190 mmol) in small portions at 0° C. The mixture was stirred at room temperature for 20 min, and then cooled to 0° C. Ice water was slowly added to the mixture (20 mL). A solid formed and was collected, washed with $H_2O$ and dried. The solid was suspended in $CH_3CN$, collected by filtration and dried to yield 7-bromo-5-fluoro-1-oxido-1,2,4-benzotriazin-1-ium-3-ol (5.3 g, 55%). MS m/z 260.1, 262.1 $[M+H]^+$.

Step C: 7-Bromo-5-fluoro-1-oxido-1,2,4-benzotriazin-1-ium-3-ol (2.9 g, 11 mmol) was combined with $POCl_3$ (30 mL, 320 mmol). The mixture was stirred at 110° C. for 2 h. The mixture was cooled to room temperature and then added to ice. The mixture was partitioned in $CH_2Cl_2$ and $H_2O$. The organic layer was collected and loaded onto silica gel, eluting with 0-10% EtOAc in $CH_2Cl_2$ to yield 7-(2,7-dimethyl-2H-indazol-5-yl)-5-fluoro-N-methyl-N-(piperidin-4-yl)benzo[e][1,2,4]triazin-3-amine (490 mg, 16%). MS m/z 277.9, 279.9, 281.9 $[M+H]^+$.

Step D: 7-Bromo-3-chloro-5-fluoro-1-oxido-1,2,4-benzotriazin-1-ium (78 mg, 0.28 mmol) was combined with (2,8-dimethylimidazo[1,2-b]pyridazin-6-yl)boronic acid (53 mg, 0.28 mmol, prepared according to the procedure in Example 11), 1,1'-bis(diphenylphosphino)ferrocene-palladium(II)dichloride dichloromethane complex (11 mg, 0.014 mmol), 1,4-dioxane (1.5 mL) and aqueous 1 M $K_2CO_3$ (0.75 mL). The mixture was stirred at 80° C. for 1 h. The mixture was partitioned between EtOAc and $H_2O$. The organic layer was washed with brine, dried over $Na_2SO_4$, filtered and concentrated. The residue was chromatographed on silica gel, eluting with 0-100% EtOAc in $CH_2Cl_2$ to yield 7-bromo-3-(2,8-dimethylimidazo[1,2-b]pyridazin-6-yl)-5-fluoro-1-(λ1-oxidanyl)-1λ4-benzo[e][1,2,4]triazine (69 mg, 63%). MS m/z 389.0, 391.0 $[M+H]^+$.

Step E: 7-Bromo-3-(2,8-dimethylimidazo[1,2-b]pyridazin-6-yl)-5-fluoro-1-(λ1-oxidanyl)-1λ4-benzo[e][1,2,4]triazine (20 mg, 0.051 mmol) was combined with N-Boc-1,2,5,6-tetrahydropyridine-4-boronic acid pinacol ester (19 mg, 0.062 mmol), 1,1'-bis(diphenylphosphino)ferrocene-palladium(II)dichloride dichloromethane complex (4 mg, 0.005 mmol), 1,4-dioxane (1 mL) and aqueous 1 M $K_2CO_3$ (0.5 mL). The mixture was heated at 80° C. for 2 h. The mixture was partitioned between EtOAc and $H_2O$. The organic layer was concentrated. The residue was chromatographed on silica gel, eluting with 10-100% EtOAc in $CH_2Cl_2$ to yield tert-butyl 4-(3-(2,8-dimethylimidazo[1,2-b]pyridazin-6-yl)-5-fluoro-1-(λ1-oxidanyl)-1λ4-benzo[e][1,2,4]triazin-7-yl)-3,6-dihydropyridine-1(2H)-carboxylate (20 mg, 79%). MS m/z 492.3 $[M+H]^+$.

Step F: tert-Butyl 4-(3-(2,8-dimethylimidazo[1,2-b]pyridazin-6-yl)-5-fluoro-1-(λ1-oxidanyl)-1λ4-benzo[e][1,2,4]triazin-7-yl)-3,6-dihydropyridine-1(2H)-carboxylate (20 mg, 0.04 mmol) was combined with 10% Pd/C (5 mg) in MeOH (2 mL). The mixture was stirred under $H_2$ (1 atm) for 2 h at 40° C. The mixture was filtered over Celite. The filtrate was concentrated and chromatographed on a reversed phase C18 column, eluting with 40-100% $CH_3CN$ in $H_2O$ to yield tert-butyl 4-(3-(2,8-dimethylimidazo[1,2-b]pyridazin-6-yl)-5-fluorobenzo[e][1,2,4]triazin-7-yl)piperidine-1-carboxylate (17 mg, 87%). MS m/z 478.5 $[M+H]^+$.

Step G: tert-Butyl 4-(3-(2,8-dimethylimidazo[1,2-b]pyridazin-6-yl)-5-fluorobenzo[e][1,2,4]triazin-7-yl)piperidine-1-carboxylate (17 mg, 0.036 mmol) was suspended in 4 N HCl in 1,4-dioxane (1 mL, 4 mmol HCl). The volatiles were removed from the mixture after 30 min. The residue was suspended in $CH_3CN$. The solid was collected and dried to yield 3-(2,8-dimethylimidazo[1,2-b]pyridazin-6-yl)-5-fluoro-7-(piperidin-4-yl)benzo[e][1,2,4]triazine hydrochloride (8 mg, 54%).

$^1H$ NMR (methanol-$d_4$) δ: 8.89 (d, J=1.6 Hz, 1H), 8.48 (d, J=1.9 Hz, 1H), 8.51 (d, J=1.3 Hz, 1H), 8.08 (dd, J=10.6, 1.7 Hz, 1H), 3.61-3.67 (m, 2H), 3.35-3.43 (m, 1H), 3.25-3.33 (m, 2H), 2.92 (s, 3H), 2.73 (s, 3H), 2.32-2.38 (m, 2H), 2.09-2.19 (m, 2H), NH protons not observed.

Using the procedure described for Example 14, above, additional compounds described herein were prepared by substituting the appropriate aryl boronic acid in Step D, suitable reagents and reaction conditions, obtaining compounds such as those selected from:

| Cpd | Data |
| --- | --- |
| 40 | MS m/z 377.4 $[M + H]^+$; $^1H$ NMR (methanol-$d_4$) δ: 8.84-8.86 (m, 1H), 8.64-8.67 (m, 1H), 8.25 (dd, J = 11.0, 1.9 Hz, 1H), 7.71 (s, 1H), 7.64 (s, 1H), 3.63-3.70 (m, 1H), 3.32-3.38 (m, 2H), 2.94-3.02 (m, 2H), 2.66 (s, 3H), 2.48 (s, 3H), 2.25-2.32 (m, 2H), 2.10-2.19 (m, 2H), NH proton not observed. |
| 41 | Starting material: 2-amino-5-bromo-4-fluorobenzoic acid<br>MS m/z 381.4 $[M + H]^+$; $^1H$ NMR (DMSO-$d_6$) δ: 8.89 (d, J = 1.6 Hz, 1H), 8.65-8.68 (m, 1H), 8.25 (dd, J = 10.8, 1.9 Hz, 1H), 7.83 (dd, J = 2.8, 0.6 Hz, 1H), 7.70 (dd, J = 12.0, 1.6 Hz, 1H), 3.60-3.68 (m, 1H), 3.27-3.32 (m, 2H), 2.89-2.97 (m, 2H), 2.48 (s, 3H), 2.21-2.29 (m, 2H), 2.06-2.16 (m, 2H), NH proton not observed. |

Example 15

Preparation of Compound 4

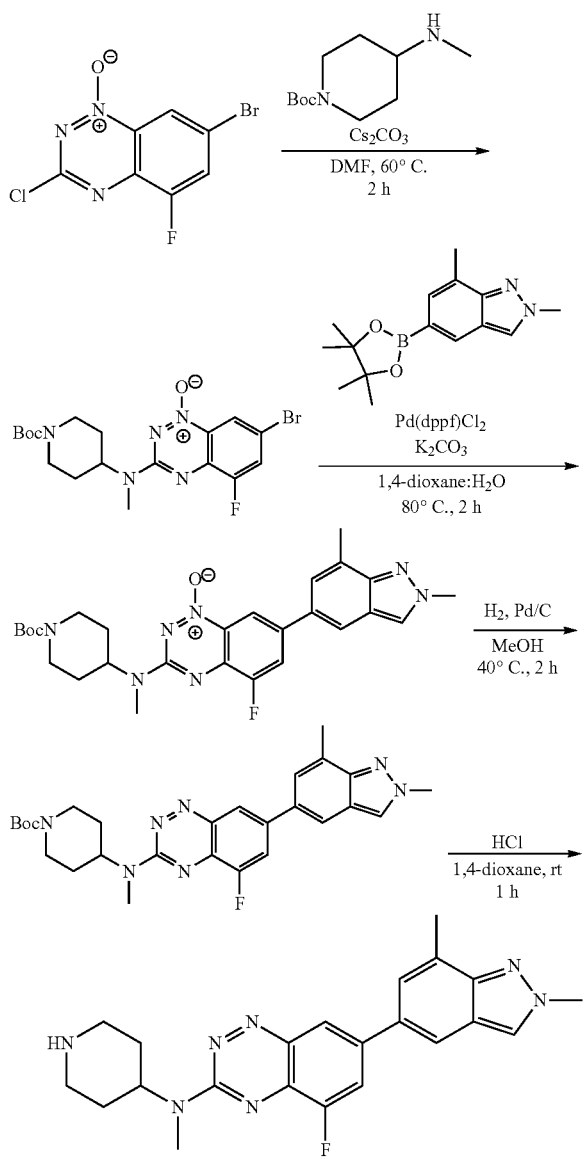

Step A: 7-Bromo-3-chloro-5-fluoro-1-oxido-1,2,4-benzotriazin-1-ium (60 mg, 0.22 mmol, prepared according to the procedure in Example 14, Step C) was combined with Cs$_2$CO$_3$ (104 mg, 0.32 mmol) and 1-Boc-4-methylaminopiperidine (56 mg, 0.26 mmol) in DMF (2 mL). The mixture was stirred at 60° C. for 2 h. The mixture was partitioned between EtOAc and H$_2$O. The organic layer was washed with brine, dried over Na$_2$SO$_4$, filtered and concentrated. The residue was chromatographed on silica gel, eluting with 10-80% EtOAc in CH$_2$Cl$_2$ to 7-bromo-3-((1-(tert-butoxycarbonyl)piperidin-4-yl)(methyl)amino)-5-fluorobenzo[e][1,2,4]triazine 1-oxide (64 mg, 65%). MS m/z 356.2, 358.2 [M-FH-Boc]$^+$.

Step B: 7-bromo-34(1-(tert-butoxycarbonyepiperidin-4-yl)(methyl)amino)-5-fluorobenzo[e][1,2,4]triazine 1-oxide (64 mg, 0.14 mmol) and 2,7-dimethyl-5-(4,4,5,5-tetramethyl-1,3,2-dioxaborolan-2-yl)indazole (46 mg, 0.17 mmol) were combined with 1,1'-bis(diphenylphosphino)ferrocene-palladium(II)dichloride dichloromethane complex (0.05 equiv., 0.007 mmol) and 1,4-dioxane (1 mL). To the mixture was added aqueous 1 M K$_2$CO$_3$ (0.5 mL).

The mixture was stirred at 80° C. for 2 h. The mixture was partitioned between EtOAc and H$_2$O. The organic layer was concentrated. The residue was chromatographed on silica gel, eluting with 10-90% EtOAc in CH$_2$Cl$_2$ to yield 3-((1-(tert-butoxycarbonyl)piperidin-4-yl)(methyl)amino)-7-(2,7-dimethyl-2H-indazol-5-yl)-5-fluorobenzo[e][1,2,4]triazine 1-oxide (74 mg, 100%). MS m/z 522.4 [M+H]$^+$.

Step C: 3-((1-(tert-butoxycarbonyl)piperidin-4-yl)(methyl)amino)-7-(2,7-dimethyl-2H-indazol-5-yl)-5-fluorobenzo[e][1,2,4]triazine 1-oxide (74 mg, 0.14 mmol) was combined with 10% Pd/C (20 mg) in MeOH (2 mL). The mixture was stirred under H$_2$ (1 atm) at rt for 1 h. The mixture was filtered over Celite. The filtrate was concentrated to yield tert-butyl 4-[[7-(2,7-dimethylindazol-5-yl)-5-fluoro-1,2,4-benzotriazin-3-yl]-methyl-amino]piperidine-1-carboxylate (70 mg, 97%). MS m/z 506.3 [M+H]$^+$.

Step D: tert-Butyl 4-[[7-(2,7-dimethylindazol-5-yl)-5-fluoro-1,2,4-benzotriazin-3-yl]-methyl-amino]piperidine-1-carboxylate (70 mg, 0.14 mmol) was suspended in 4 N HCl in 1,4-dioxane (1 mL, 4 mmol HCl). The mixture was stirred at room temperature for 1 h. The volatiles were removed from the reaction mixture with a stream of N$_2$. The residue was partitioned in CH$_2$Cl$_2$ and aqueous 1 M K$_2$CO$_3$. The organic layer was concentrated. The residue was chromatographed on silica gel, eluting with 0-10% MeOH (2 N NH$_3$) in CH$_2$Cl$_2$ to yield 7-(2,7-dimethyl-2H-indazol-5-yl)-5-fluoro-N-methyl-N-(piperidin-4-yl)benzo[e][1,2,4]triazin-3-amine (43 mg, 77%).

MS m/z 406.4 [M+H]$^+$; $^1$H NMR (DMSO-d$_6$) δ: 8.42 (s, 1H), 8.37 (s, 1H), 8.15-8.19 (m, 1H), 8.04-8.07 (m, 1H), 7.60 (s, 1H), 4.24-4.30 (m, 1H), 4.21 (s, 3H), 3.22 (br s, 3H), 3.06-3.11 (m, 2H), 2.61-2.66 (m, 2H), 2.60 (s, 3H), 1.72-1.81 (m, 2H), 1.64-1.70 (m, 2H), NH proton not observed.

Example 17

Preparation of Compound 50

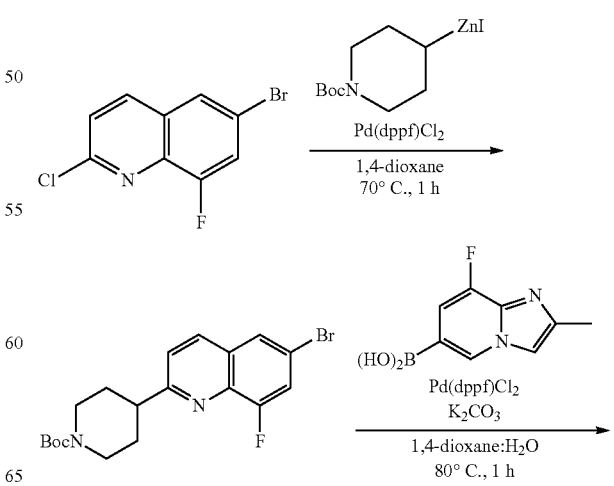

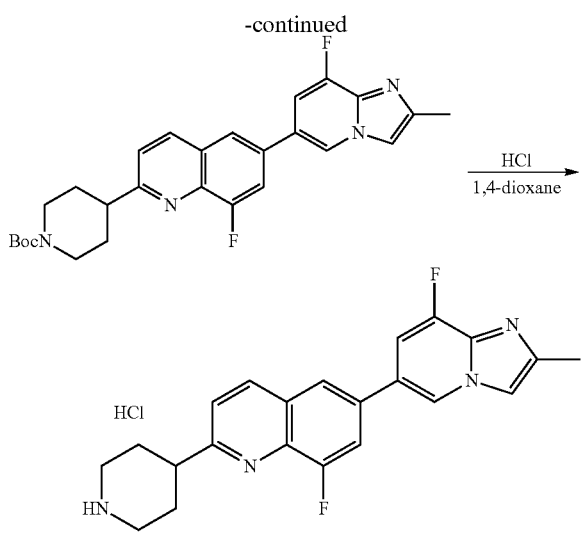

Step A: 6-Bromo-2-chloro-8-fluoro-quinoline (260 mg, 1.0 mmol) was combined with 1,1'-bis(diphenylphosphino)ferrocene-palladium(II)dichloride dichloromethane complex (80 mg, 0.10 mmol) and 1,4-dioxane (4 mL). To the mixture was added a solution of 1-tert-butoxycarbonylpiperidin-4-ylzinc iodide in N,N-dimethylacetamide (2 mL, 2 mmol, prepared according to the procedure in Example 5, Step B) at room temperature. The mixture was stirred at 70° C. for 1 h. The volatiles were removed from the mixture with a stream of $N_2$. The residue was chromatographed on silica gel, eluting with 0-30% EtOAc in hexanes to yield tert-butyl 4-(6-bromo-8-fluoro-2-quinolyl)piperidine-1-carboxylate (235 mg, 58%).

$^1$H NMR (DMSO-$d_6$) δ: 8.36 (dd, J=8.8, 1.6 Hz, 1H), 8.10-8.14 (m, 1H), 7.85 (dd, J=10.3, 2.2 Hz, 1H), 7.67 (d, J=8.5 Hz, 1H), 4.04-4.16 (m, 2H), 3.07-3.14 (m, 1H), 2.89 (br s, 2H), 1.88-1.96 (m, 2H), 1.64-1.74 (m, 2H), 1.44 (s, 9H).

Step B: tert-Butyl 4-(6-bromo-8-fluoro-2-quinolyl)piperidine-1-carboxylate (40 mg, 0.10 mmol) was combined with (8-fluoro-2-methyl-imidazo[1,2-a]pyridin-6-yl)boronic acid (40 mg, 0.21 mmol), 1,1'-bis(diphenylphosphino)ferrocene-palladium(II)dichloride dichloromethane complex (4 mg, 0.005 mmol), 1,4-dioxane (1.5 mL) and aqueous 1 M $K_2CO_3$ (0.75 mL). The mixture was stirred at 80° C. for 1 h. The mixture was partitioned between EtOAc and $H_2O$. The organic layer was washed with brine, dried over $Na_2SO_4$, filtered and concentrated. The residue was chromatographed on silica gel, eluting with 0-80% EtOAc in $CH_2Cl_2$ to yield tert-butyl 4-[8-fluoro-6-(8-fluoro-2-methyl-imidazo[1,2-a]pyridin-6-yl)-2-quinolyl]piperidine-1-carboxylate (45 mg, 96%). MS m/z 479.4 [M+H]$^+$.

Step C: tert-Butyl 4-[8-fluoro-6-(8-fluoro-2-methyl-imidazo[1,2-a]pyridin-6-yl)-2-quinolyl]piperidine-1-carboxylate (45 mg, 0.09 mmol) was suspended in 4 N HCl in 1,4-dioxane (1 mL, 4 mmol HCl). The volatiles were removed from the reaction mixture after 30 min. The residue was partitioned between $CH_2Cl_2$ and aqueous 1 M $K_2CO_3$. The organic layer was concentrated and chromatographed on silica gel, eluting with 0-10% MeOH (2 N $NH_3$) in $CH_2Cl_2$. The collected material was dissolved in 1.25 M HCl in MeOH. The volatiles were removed to yield 8-fluoro-6-(8-fluoro-2-methylimidazo[1,2-a]pyridin-6-yl)-2-(piperidin-4-yl)quinoline hydrochloride (35 mg, 90%).

MS m/z 379.3 [M+H]$^+$; $^1$H NMR (DMSO-$d_6$) δ: 9.36-9.39 (m, 1H), 9.16 (br, 1H), 8.88 (br, 1H), 8.46-8.50 (m, 1H), 8.41 (d, J=11.8 Hz, 1H), 8.34 (d, J=2.2 Hz, 1H), 8.17 (s, 1H), 8.13 (dd, J=12.1, 1.9 Hz, 1H), 7.69 (d, J=8.5 Hz, 1H), 3.39-3.46 (m, 2H), 3.27-3.35 (m, 1H), 3.03-3.12 (m, 2H), 2.54 (s, 3H), 2.04-2.18 (m, 4H).

Using the procedure described for Example 17, above, additional compounds described herein were prepared by substituting the indicated starting material in Step A, the appropriate boronic acid Step B, suitable reagents and reaction conditions, obtaining compounds such as those selected from:

| Cpd | Starting Material and Data |
|---|---|
| 29 | Starting material: 7-bromo-3-chloroquinoline |
|  | MS m/z 357.4 [M + H]$^+$; $^1$H NMR (DMSO-d6) δ: 9.26 (d, J = 2.5 Hz, 1H), 8.59 (d, J = 2.5 Hz, 1H), 8.43 (s, 1H), 8.01-8.03 (m, 1H), 7.98 (d, J = 8.5 Hz, 1H), 7.81-7.83 (m, 1H), 7.53-7.58 (m, 2H), 4.22 (s, 3H), 3.06-3.11 (m, 2H), 2.79-2.86 (m, 1H), 2.63-2.69 (m, 2H), 2.61 (s, 3H), 1.80-1.86 (m, 2H), 1.59-1.69 (m, 2H), NH proton not observed. |
| 45 | Starting material: 6-bromo-2-chloro-8-fluoro-quinoline |
|  | MS m/z 376.1 [M + H]$^+$; $^1$H NMR (methanol-$d_4$) δ: 8.63-8.68 (m, 2H), 8.48 (s, 1H), 8.38 (s, 1H), 8.35 (d, J = 11.5 Hz, 1H), 7.80 (d, J = 8.0 Hz, 1H), 3.60-3.65 (m, 2H), 3.46-3.50 (m, 1H), 3.25-3.33 (m, 2H), 2.86 (s, 3H), 2.70 (s, 3H), 2.27-2.33 (m, 4H), NH proton not observed. |
| 49 | Starting material: 6-bromo-2-chloro-8-fluoro-quinoline |
|  | MS m/z 391.4 [M + H]$^+$; $^1$H NMR (DMSO-$d_6$) δ: 9.11 (br, 1H), 8.77 (br, 1H), 8.46 (d, J = 8.5 Hz, 1H), 8.41 (s, 1H), 8.17-8.20 (m, 1H), 8.05 (dd, J = 12.7, 2.1, 1H), 7.73 (d, J = 1.3 Hz, 1H), 7.61 (d, J = 8.5 Hz, 1H), 7.06-7.08 (m, 1H), 4.18 (s, 3H), 4.05 (s, 3H), 3.39-3.45 (m, 2H), 3.24-3.31 (m, 1H), 3.02-3.12 (m, 2H), 2.04-2.18 (m, 4H). |

Example 18

Preparation of Compound 51

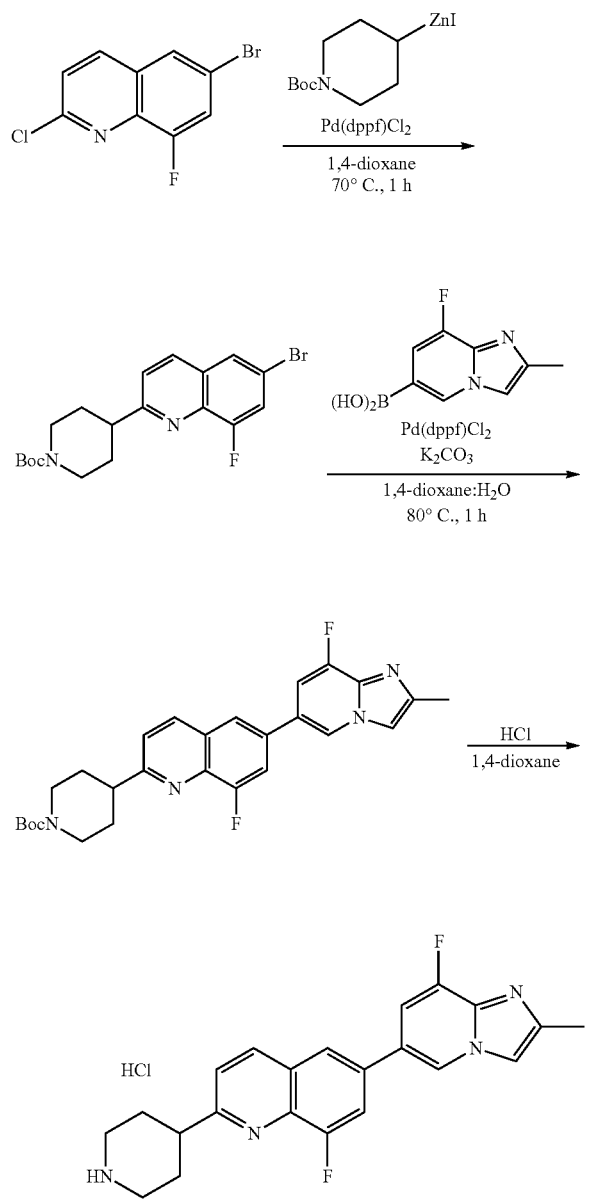

Step A: 8-Bromo-6-chloro-2-methyl-imidazo[1,2-b]pyridazine (250 mg, 1.01 mmol) was combined with $Cs_2CO_3$ (700 mg, 2.15 mmol) in $CH_3CN$ (5 mL). To the mixture was added MeOH (0.2 mL). The mixture was stirred at room temperature for 4 h. The volatiles were removed from the reaction mixture. The residue was partitioned between EtOAc and $H_2O$. The organic layer was collected, concentrated and chromatographed on silica gel, eluting with 20-100% EtOAc in hexanes to yield 6-chloro-8-methoxy-2-methyl-imidazo[1,2-b]pyridazine (180 mg, 90%). MS m/z 198.2, 202.2 $[M+H]^+$.

Step B: 6-Chloro-8-methoxy-2-methyl-imidazo[1,2-b]pyridazine (39 mg, 0.20 mmol) was combined with KOAc (59 mg, 0.60 mmol), 1,1'-bis(diphenylphosphino)ferrocene-palladium(II)dichloride dichloromethane complex (8 mg, 0.01 mmol), and bis(pinacolato)diboron (63 mg, 0.25 mmol) in 1,4-dioxane (1 mL). The mixture was stirred under $N_2$ at 95° C. for 1 h. To the mixture was added aqueous 1 M $K_2CO_3$ (0.75 mL), tert-butyl 4-(6-bromo-8-fluoro-2-quinolyl)piperidine-1-carboxylate (40 mg, 0.10 mmol, obtained in Example 17, Step A) and 1,1'-bis(diphenylphosphino)ferrocene-palladium(II)dichloride dichloromethane complex (4 mg, 0.005 mmol). The mixture was stirred at 80° C. for 1 h. The mixture was partitioned between EtOAc and $H_2O$. The organic layer was washed with brine, dried over $Na_2SO_4$, filtered and concentrated. The residue was chromatographed on silica gel, eluting with 0-80% EtOAc in $CH_2Cl_2$ to yield tert-butyl 4-[8-fluoro-6-(8-methoxy-2-methyl-imidazo[1,2-b]pyridazin-6-yl)-2-quinolyl]piperidine-1-carboxylate (38 mg, 79%). MS m/z 492.4 $[M+H]^+$.

Step C: tert-Butyl 4-[8-fluoro-6-(8-methoxy-2-methyl-imidazo[1,2-b]pyridazin-6-yl)-2-quinolyl]piperidine-1-carboxylate (38 mg, 0.08 mmol) was suspended in 4 N HCl in 1,4-dioxane (1 mL, 4 mmol HCl). The volatiles were removed from the reaction mixture with a stream of $N_2$ after 30 min. The residue was suspended in $CH_3CN$, collected by filtration and dried to yield 8-fluoro-6-(8-methoxy-2-methylimidazo[1,2-b]pyridazin-6-yl)-2-(piperidin-4-yl)quinoline hydrochloride (26 mg, 79%).

MS m/z 392.4 $[M+H]^+$; $^1H$ NMR (DMSO-$d_6$) δ: 9.22 (br, 1H), 8.95 (br, 1H), 8.77-8.80 (m, 1H), 8.60 (d, J=8.6 Hz, 1H), 8.47 (s, 1H), 8.37 (dd, J=12.0, 2.0 Hz, 1H), 7.99 (s, 1H), 7.73 (d, J=8.5 Hz, 1H), 4.35 (s, 3H), 3.39-3.45 (m, 2H), 3.29-3.37 (m, 1H), 3.02-3.12 (m, 2H), 2.53 (s, 3H), 2.06-2.20 (m, 4H).

Using the procedure described for Example 18, above, additional compounds described herein were prepared by substituting the appropriate reagent in Step A, suitable reagents and reaction conditions, obtaining compounds such as those selected from:

| Cpd | Data |
|---|---|
| 53 | MS m/z 436.3 $[M + H]^+$; $^1H$ NMR (DMSO-$d_6$) δ: 8.97 (br, 1H), 8.71 (br, 1H), 8.68 (s, 1H), 8.57 (d, J = 8.6 Hz, 1H), 8.28-8.35 (m, 2H), 7.76 (br s, 1H), 7.71 (d, J = 8.5 Hz, 1H), 4.70-4.74 (m, 2H), 3.84-3.88 (m, 2H), 3.42-3.47 (m, 2H), 3.39 (s, 3H), 3.29-3.37 (m, 1H), 3.05-3.14 (m, 2H), 2.48 (s, 3H), 2.06-2.20 (m, 4H). |
| 54 | MS m/z 435.3 $[M + H]^+$; $^1H$ NMR (methanol-$d_4$) δ: 8.59-8.64 (m, 2H), 8.30 (dd, J = 12.0, 1.7 Hz, 1H), 8.18 (d, J = 1.3 Hz, 1H), 7.76 (d, J = 8.5 Hz, 1H), 7.41 (s, 1H), 3.78-3.84 (m, 4H), 3.60-3.65 (m, 2H), 3.49 (s, 3H), 3.43-3.49 (m, 1H), 3.24-3.31 (m, 2H), 2.64 (s, 3H), 2.24-2.36 (m, 4H), NH protons not observed. |

Example 19

Preparation of Compound 70

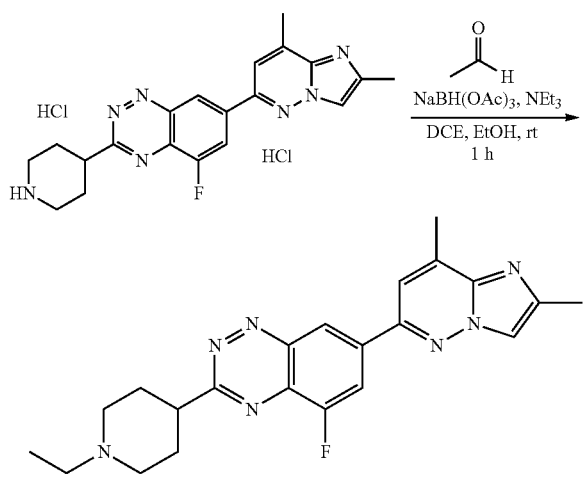

7-(2,8-Dimethylimidazo[1,2-b]pyridazin-6-yl)-5-fluoro-3-(4-piperidyl)-1,2,4-benzotriazine dihydrochloride (36 mg, 0.08 mmol, prepared according to the procedure in Example 13) was combined with 1,2-dichloroethane (1 mL), EtOH (0.2 mL) and triethylamine (22 uL, 0.16 mmol). To the mixture was added acetaldehyde (18 μL, 0.32 mmol). The mixture became homogeneous. The mixture was stirred for 5 min. To the mixture was added sodium triacetoxyborohydride (36 mg, 0.16 mmol). After 20 min of stirring at room temperature, the mixture was loaded directly to silica gel and chromatographed, eluting with 0-10% MeOH (2 N NH$_3$) in CH$_2$Cl$_2$ to afford 7-(2,8-dimethylimidazo[1,2-b]pyridazin-6-yl)-3-(1-ethylpiperidin-4-yl)-5-fluorobenzo[e][1,2,4]triazine (32 mg, 84%) as a yellow powder.

MS m/z 406.3 [M+H]$^+$; $^1$H NMR (methanol-d$_4$) δ: 9.06 (s, 1H), 8.62 (dd, J=10.9 Hz, 1H), 8.04 (s, 1H), 7.94 (s, 1H), 3.69-3.77 (m, 1H), 3.48-3.56 (m, 2H), 2.98 (q, J=7.2 Hz, 2H), 2.84-2.92 (m, 2H), 2.75 (s, 3H), 2.54 (s, 3H), 2.45-2.52 (in, 2H), 2.32-2.42 (m, 2H), 1.34 (t, J=7.3 Hz, 3H).

Using the reductive amination procedure described for Example 19, above, additional compounds described herein were prepared by substituting the indicated starting materials, aldehyde, suitable reagents and reaction conditions, obtaining compounds such as those selected from:

| Cpd | Starting Material and Data |
|---|---|
| 2 | Starting material: 2-(2-methyl-2H-indazol-5-yl)-6-(piperidin-4-yl)quinoline (prepared according to the procedure in Example 6) and acetaldehyde<br>MS m/z 371.1 [M + H]$^+$; 1H NMR (methanol-d4) δ: 8.99 (br s, 1H), 8.66 (s, 1H), 8.57 (s, 1H), 8.34-8.40 (m, 2H), 8.15-8.20 (m, 1H), 8.04-8.10 (m, 2H), 7.19 (d, J = 9.5 Hz, 1H), 4.33 (s, 3H), 3.76-3.82 (m, 2H), 3.49-3.56 (m, 1H), 3.26 (q, J = 7.5 Hz, 2H), 3.19-3.24 (m, 2H), 2.31-2.36 (m, 2H), 2.18-2.23 (m, 2H), 1.44 (t, J = 7.5 Hz, 3H). |
| 6 | Starting material: 6-(2,8-dimethylimidazo[1,2-b]pyridazin-6-yl)-8-fluoro-2-(piperidin-4-yl)quinoline (prepared according to the procedure in Example 17) and formaldehyde<br>MS m/z 357.2 [M + H]$^+$; $^1$H NMR (DMSO-d$_6$) δ: 8.95 (br s, 1H), 8.57 (s, 1H), 8.51 (s, 1H), 8.44-8.50 (m, 2H), 8.24 (s, 1H), 7.86 (d, J = 8.5 Hz, 1H), 7.76-7.78 (m, 2H), 4.22 (s, 3H), 4.00-4.07 (m, 2H), 3.22-3.28 (m, 1H), 3.14-3.20 (m, 2H), 2.81 (s, 3H), 2.27-2.33 (m, 4H). |
| 9 | Starting material: 6-(2-methyl-2H-indazol-5-yl)-2-(piperidin-4-yl)quinoline (prepared according to the procedure in Example 2) and acetaldehyde<br>MS m/z 371.2 [M + H]$^+$; $^1$H NMR (DMSO-d$_6$) δ: 9.11 (d, J = 8.5 Hz, 1H), 8.58-8.64 (m, 2H), 8.48-8.54 (m, 2H), 8.23 (s, 1H), 7.96 (d, J = 8.5 Hz, 1H), 7.74-7.78 (m, 2H), 4.23 (s, 3H), 3.75-3.80 (m, 1H), 3.63-3.67 (m, 2H), 3.08-3.18 (m, 4H), 2.32-2.46 (m, 4H), 1.32 (t, J = 7.5 Hz, 3H). |
| 47 | Starting material: 6-(2,8-dimethylimidazo[1,2-b]pyridazin-6-yl)-8-fluoro-2-(piperidin-4-yl)quinoline (prepared according to the procedure in Example 17) and formaldehyde<br>MS m/z 390.2 [M + H]$^+$; $^1$H NMR (DMSO-d$_6$) δ: 8.67 (s, 1H), 8.57 (d, J = 8.0 Hz, 1H), 8.47 (s, 1H), 8.42 (s, 1H), 8.27 (d, J = 12.0 Hz, 1H), 7.73 (d, J = 8.0 Hz, 1H), 3.54-3.57 (m, 1H), 3.14-3.25 (m, 4H), 2.80 (s, 3H), 2.76 (s, 3H), 2.58 (s, 3H), 2.20-2.25 (m, 4H). |
| 48 | Starting material: 6-(2,8-dimethylimidazo[1,2-b]pyridazin-6-yl)-8-fluoro-2-(piperidin-4-yl)quinoline (prepared according to the procedure in Example 17) and acetaldehyde<br>MS m/z 404.2 [M + H]$^+$; $^1$H NMR (DMSO-d$_6$) δ: 8.67 (s, 1H), 8.57 (d, J = 8.0 Hz, 1H), 8.47 (s, 1H), 8.42 (s, 1H), 8.27 (d, J = 12.0 Hz, 1H), 7.73 (d, J = 8.0 Hz, 1H), 3.60-3.64 (m, 1H), 3.27-3.32 (m, 2H), 3.07-3.16 (m, 4H), 2.77 (s, 3H), 2.59 (s, 3H), 2.22-2.26 (m, 4H), 1.30 (t, J = 7.5 Hz, 3H). |
| 69 | Starting material: 7-(2,8-Dimethylimidazo[1,2-b]pyridazin-6-yl)-5-fluoro-3-(4-piperidyl)-1,2,4-benzotriazine (prepared according to the procedure in Example 13) and formaldehyde<br>MS m/z 392.2 [M + H]$^+$; $^1$H NMR (DMSO-d$_6$) δ: 9.27 (s, 1H), 8.70 (dd, J = 11.0, 1.7 Hz, 1H), 8.54 (s, 1H), 8.45 (s, 1H), 3.70-3.77 (m, 1H), 3.59-3.65 (m, 2H), 3.21-3.30 (m, 2H), 2.84 (d, J = 4.7 Hz, 3H), 2.76 (s, 3H), 2.56 (s, 3H), 2.41-2.47 (m, 2H), 2.25-2.35 (m, 2H). |
| 75 | Starting material: 7-(2,8-dimethylimidazo[1,2-b]pyridazin-6-yl)-5-fluoro-3-(piperidin-4-yl)cinnoline (prepared according to the procedure in Example 7) and 1,4-dioxane-2,5-diol<br>MS m/z 421.5 [M + H]$^+$; 1H NMR (methanol-d4) δ:: 9.17 (s, 1H), 8.61 (d, J = 1.0 Hz, 1H), 8.42-8.47 (m, 2H), 8.35 (s, 1H), 3.98-4.01 (m, 2H), 3.88-3.94 (m, 2H), 3.63-3.70 (m, 1H), 3.35-3.42 (m, 4H), 2.88 (s, 3H), 2.71 (s, 3H), 2.44-2.52 (m, 4H), OH proton not observed. |

| Cpd | Starting Material and Data |
|---|---|
| 76 | Starting material: 7-(2,8-dimethylimidazo[1,2-b]pyridazin-6-yl)-5-fluoro-3-(piperidin-4-yl)cinnoline and acetaldehyde (prepared according to the procedure in Example 7)<br>MS m/z 405.4 [M + H]$^+$; $^1$H NMR (methanol-d$_4$) δ: 9.17 (s, 1H), 8.60 (d, J = 1.0 Hz, 1H), 8.42-8.47 (m, 2H), 8.35 (s, 1H), 3.81-3.87 (m, 2H), 3.63-3.70 (m, 1H), 3.25-3.38 (m, 4H), 2.88 (s, 3H), 2.71 (s, 3H), 2.38-2.52 (m, 4H), 1.47 (t, J = 7.4 Hz, 3H). |
| 77 | Starting material: 7-(2,8-dimethylimidazo[1,2-b]pyridazin-6-yl)-5-fluoro-3-(piperidin-4-yl)cinnoline dihydrochloride (prepared according to the procedure in Example 7)<br>MS m/z 419.5 [M + H]$^+$; $^1$H NMR (DMSO-d$_6$) δ: 9.02 (s, 1H), 8.32 (dd, J = 11.0, 1.3 Hz, 1H), 8.15 (s, 1H), 8.14 (d, J = 0.6 Hz, 1H), 8.05 (d, J = 0.9 Hz, 1H), 3.10-3.22 (m, 3H), 2.94-3.07 (m, 2H), 2.65 (d, J = 0.9 Hz, 3H), 2.43 (d, J = 0.6 Hz, 3H), 2.02-2.14 (m, 4H), 1.52-1.61 (m, 2H), 1.12-1.18 (m, 2H), 0.92 (t, J = 7.4 Hz, 3H), HCl protons not observed. |
| 79 | Starting material: 7-(2,8-dimethylimidazo[1,2-b]pyridazin-6-yl)-5-fluoro-3-(piperidin-4-yl)cinnoline dihydrochloride (prepared according to the procedure in Example 7)<br>MS m/z 391.4 [M + H]$^+$; $^1$H NMR (DMSO-d$_6$) δ: 9.05 (s, 1H), 8.36 (dd, J = 10.9, 1.4 Hz, 1H), 8.19 (s, 1H), 8.15 (d, J = 0.6 Hz, 1H), 8.07 (d, J = 0.9 Hz, 1H), 3.36-3.48 (m, 3H), 2.80-2.94 (m, 2H), 2.67 (s, 3H), 2.65 (s, 3H), 2.44 (d, J = 0.6 Hz, 3H), 2.18-2.28 (m, 4H), HCl protons not observed. |
| 85 | Starting material: 7-(2,8-dimethylimidazo[1,2-b]pyridazin-6-yl)-3-(piperidin-4-yl)cinnoline (prepared according to the procedure in Example 7)<br>MS m/z 387.3 [M + H]$^+$; $^1$H NMR (methanol-d$_4$) δ: 9.01 (s, 1H), 8.57 (dd, J = 9, 1.5 Hz, 1H), 8.13 (m, 2H), 8.00 (s, 1H), 7.85 (s, 1H), 3.26-3.33 (m, 3H), 2.74 (s, 3H), 2.65 (q, J = 7.5 Hz, 2H), 2.52 (s, 3H), 2.35-2.41 (m, 2H), 2.20-2.24 (m, 2H), 2.06-2.18 (m, 2H), 1.23 (t, J = 7.5 Hz, 3H). |
| 100 | Starting material: 5-fluoro-7-(2-methylimidazo[1,2-b]pyridazin-6-yl)-3-(piperidin-4-yl)cinnoline dihydrochloride (prepared according to the procedure in Example 29)<br>MS m/z 391.5 [M + H]$^+$; $^1$H NMR (methanol-d$_4$) δ: 9.14 (s, 1H), 8.58 (d, J = 9.5 Hz, 1H), 8.43-8.48 (m, 2H), 8.40 (s, 1H), 8.32 (s, 1H), 3.82-3.86 (m, 2H), 3.61-3.68 (m, 1H), 3.24-3.33 (m, 4H), 2.67 (s, 3H), 2.38-2.52 (m, 4H), 1.46 (t, J = 7.6 Hz, 3H), HCl protons not observed. |
| 102 | Starting material: 5-fluoro-7-(8-fluoro-2-methylimidazo[1,2-a]pyridin-6-yl)-3-(piperidin-4-yl)cinnoline hydrochloride (prepared according to the procedure in Example 29)<br>MS m/z 408.5 [M + H]$^+$; $^1$H NMR (methanol-d$_4$) δ: 9.28 (d, J = 1.2 Hz, 1H), 8.78 (s, 1H), 8.47 (dd, J = 11.0, 1.2 Hz, 1H), 8.33 (s, 1H), 8.21 (d, J = 1.2 Hz, 1H), 8.12(dd, J = 10.5, 1.7 Hz, 1H), 3.84 (br d, J = 12.5 Hz, 2H), 3.61-3.69 (m, 1H), 3.24-3.35 (m, 4H), 2.66 (d, J = 0.9 Hz, 3H), 2.38-2.51 (m, 4H), 1.46 (t, J = 7.3 Hz, 3H), HCl protons not observed. |
| 110 | Starting material: 6-(2,8-dimethylimidazo[1,2-a]pyridin-6-yl)-8-fluoro-2-(piperidin-4-yl)quinoxaline hydrochloride (prepared according to the procedure in Example 38)<br>MS m/z 405.5 [M + H]$^+$; $^1$H NMR (methanol-d$_4$) δ: 8.88 (s, 1H), 8.26 (d, J = 0.9 Hz, 1H), 8.03 (dd, J = 11.3, 1.8 Hz, 1H), 7.81 (s, 1H), 7.57 (d, J = 1.2 Hz, 1H), 3.17 (d, J = 11.3 Hz, 2H), 3.06 (spt, J = 4.9 Hz, 1H), 2.59-2.61 (m, 1H), 2.60 (s, 2H), 2.54 (q, J = 7.3 Hz, 2H), 2.60 (s, 3H), 2.21 (td, J = 11.3, 3.7 Hz, 2H), 2.03-2.12 (m, 4H), 1.18 (t, J = 7.3 Hz, 3H). |
| 111 | Starting material: 5-fluoro-7-(8-methoxy-2-methylimidazo[1,2-b]pyridazin-6-yl)-3-(piperidin-4-yl)cinnoline dihydrochloride (prepared according to the procedure in Example 29)<br>MS m/z 421.0 [M + H]$^+$; $^1$H NMR (chloroform-d) δ: 8.80 (s, 1H), 8.21 (d, J = 12 Hz, 1H), 7.94 (s, 1H), 7.75 (s, 1H), 7.00 (s, 1H), 4.23 (s, 3H), 3.37-3.42 (m, 1H), 3.21 (d, J = 11.3 Hz, 2H), 2.52-2.55 (m, 5H), 2.19-2.25 (m, 4H), 2.01-2.09 (m, 2H), 1.17 (t, J = 7.2 Hz, 3H). |
| 113 | Starting material: (6-(5-fluoro-3-(piperidin-4-yl)cinnolin-7-yl)-2-methylimidazo[1,2-b]pyridazin-8-yl)methanol dihydrochloride (prepared according to the procedure in Example 29)<br>MS m/z 421.5 [M + H]$^+$; $^1$H NMR (methanol-d$_4$) δ: 9.13 (s, 1H), 8.61 (s, 1H), 8.46 (d, J = 0.9 Hz, 1H), 8.43 (dd, J = 10.6, 1.3 Hz, 1H), 8.33 (s, 1H), 5.17 (d, J = 1.1 Hz, 2H), 3.82 (br d, J = 12.2 Hz, 2H), 3.61-3.70 (m, 1H), 3.23-3.30 (m, 4H), 2.69 (s, 3H), 2.39-2.50 (m, 4H), 1.45 (t, J = 7.3 Hz, 3H), HCl and OH protons not observed. |
| 114 | Starting material: 6-(5-fluoro-3-(piperidin-4-yl)cinnolin-7-yl)-2-methylimidazo[1,2-b]pyridazine-8-carbonitrile dihydrochloride (prepared according to the procedure in Example 29)<br>MS m/z 416.0 [M + H]$^+$; $^1$H NMR (chloroform-d) δ: 8.53 (s, 1H), 8.23 (dd, J = 10.8, 1.5 Hz, 1H), 8.02 (s, 1H), 7.99 (d, J = 0.4 Hz, 1H), 7.95 (s, 1H), 3.36-3.43 (m, 1H), 3.19 (br d, J = 11 Hz, 2H), 2.64 (s, 3H), 2.52-2.54 (m, 2H), 2.21-2.23 (m, 4H), 1.98-2.08 (m, 2H), 1.17 (t, J = 7.2 Hz, 3H). |
| 115 | Starting material: 7-(8-cyclopropyl-2-methylimidazo[1,2-b]pyridazin-6-yl)-5-fluoro-3-(piperidin-4-yl)cinnoline (prepared according to the procedure in Example 29)<br>MS m/z 431.1 [M + H]$^+$; $^1$H NMR (chloroform-d) δ: 8.78 (s, 1H), 8.19 (d, J = 12 Hz, 1H), 7.94 (s, 1H), 7.81 (s, 1H), 7.10 (s, 1H), 3.28-3.42 (m, 1H), 3.29 (br d, J = 12 Hz, 2H), 2.60-2.72 (m, 3H), 2.56 (s, 3H), 2.24-2.27 (m, 2H), 2.09-2.13 (m, 4H), 1.33-1.37 (m, 2H), 1.19-1.25 (m, 5H). |
| 119 | Starting material: 7-(6,8-dimethylimidazo[1,2-a]pyrazin-2-yl)-5-fluoro-3-(piperidin-4-yl)cinnoline (prepared according to the procedure in Example 41)<br>MS m/z 405.1 [M + H]$^+$; $^1$H NMR (chloroform-d) δ: 8.86 (s, 1H), 8.56 (s, 1H), 8.21 (m, 3H), 4.59 (s, 1H), 3.28 (s, 2H), 2.90 (s, 3H), 2.65 (dd, J = 14.4, 7.1 Hz, 2H), 2.48 (s, 3H), 2.39 (t, J = 11.8 Hz, 2H), 2.27-2.06 (m, 4H), 1.23 (t, J = 7.2 Hz, 3H). |

| Cpd | Starting Material and Data |
|---|---|
| 120 | Starting material: 6-(5-fluoro-3-(piperidin-4-yl)cinnolin-7-yl)-2,4-dimethylbenzo[d]thiazole (prepared according to the procedure in Example 29)<br>MS m/z 421.1 [M + H]$^+$; $^1$H NMR (chloroform-d) δ: 8.58 (s, 1H), 8.03 (d, J = 1.6 Hz, 1H), 7.90 (s, 1H), 7.71 (dd, J = 10.6, 1.2 Hz, 1H), 7.63 (d, J = 0.8 Hz, 1H), 3.34-3.40 (m, 1H), 3.20 (d, J = 11.2 Hz, 2H), 2.89 (s, 3H), 2.83 (s, 3H), 2.51-2.56 (m, 2H), 2.08-2.24 (m, 4H), 2.01-2.05 (m, 2H), 1.23 (t, J = 7.2 Hz, 3H). |
| 121 | Starting material: 7-(8-ethyl-2-methylimidazo[1,2-b]pyridazin-6-yl)-5-fluoro-3-(piperidin-4-yl)cinnoline dihydrochloride (prepared according to the procedure in Example 29)<br>MS m/z 419.5 [M + H]$^+$; $^1$H NMR (methanol-d$_4$) δ: 9.18 (s, 1H), 8.54 (s, 1H), 8.40-8.50 (m, 2H), 8.33 (s, 1H), 3.84 (br d, J = 12.5 Hz, 2H), 3.61-3.70 (m, 1H), 3.16-3.31 (m, 6H), 2.71 (s, 3H), 2.38-2.52 (m, 4H), 1.58 (t, J = 7.6 Hz, 3H), 1.46 (t, J = 7.6 Hz, 3H), HCl protons not observed. |
| 122 | Starting material: 7-(8-ethyl-2-methylimidazo[1,2-b]pyridazin-6-yl)-5-fluoro-3-(piperidin-4-yl)cinnoline dihydrochloride (prepared according to the procedure in Example 29)<br>MS m/z 405.5 [M + H]$^+$; 1H NMR (methanol-d$_4$) δ: 9.16 (s, 1H), 8.47 (s, 1H), 8.45 (d, J = 10.4 Hz, 1H), 8.40 (s, 1H), 8.33 (s, 1H), 3.75-3.80 (m, 2H), 3.59-3.69 (m, 1H), 3.32-3.38 (m, 2H), 3.23 (q, J = 7.5 Hz, 2H), 3.02 (s, 3H), 2.69 (s, 3H), 2.37-2.49 (m, 4H), 1.57 (t, J = 7.5 Hz, 3H) HCl protons not observed. |
| 123 | Starting material: 7-(8-ethyl-2-methylimidazo[1,2-b]pyridazin-6-yl)-5-fluoro-3-(piperidin-4-yl)cinnoline dihydrochloride (prepared according to the procedure in Example 29)<br>MS m/z 435.5 [M + H]$^+$; $^1$H NMR (methanol-d$_4$) δ: 9.17 (s, 1H), 8.50 (s, 1H), 8.45 (d, J = 10.7 Hz, 1H), 8.42 (s, 1H), 8.33 (s, 1H), 3.98-4.02 (m, 2H), 3.88-3.94 (m, 2H), 3.62-3.68 (m, 1H), 3.35-3.42 (m, 4H), 3.23 (q, J = 7.5 Hz, 2H), 2.70 (s, 3H), 2.44-2.51 (m, 4H), 1.58 (t, J = 7.5 Hz, 3H), HCl and OH protons not observed. |
| 124 | Starting material: rac-7-(2,8-dimethylimidazo[1,2-b]pyridazin-6-yl)-3-((2R,6R)-2,6-dimethylpiperidin-4-yl)-5-fluorocinnoline dihydrochloride (prepared according to the procedure in Example 7)<br>MS m/z 419.5 [M + H]$^+$; $^1$H NMR (methanol-d$_4$) δ: 8.92 (s, 1H), 8.32 (d, J = 10 Hz, 1H), 8.19 (s, 1H), 8.00 (s, 1H), 7.88 (s, 1H), 3.76 (tt, J = 12.5, 3.5 Hz, 1H), 3.43 (m, 1H), 3.00 (m, 1H), 2.73 (s, 3H), 2.52 (s, 3H), 2.47 (s, 3H), 2.30-2.36 (dd, J = 13, 5 Hz, 1H), 2.05-2.15 (m, 2H), 1.8 (q, J = 12.5 Hz, 1H), 1.32 (d, J = 7 Hz, 3H), 1.23 (d, J = 6 Hz, 3H). |
| 125 | Starting material: rac-7-(2,8-dimethylimidazo[1,2-b]pyridazin-6-yl)-3-((2R,6R)-2,6-dimethylpiperidin-4-yl)-5-fluorocinnoline hydrochloride (prepared according to the procedure in Example 7)<br>MS m/z 433.5 [M + H]$^+$; $^1$H NMR (methanol-d$_4$) δ: 8.91 (s, 1H), 8.31 (d, J = 11 Hz, 1H), 8.19 (s, 1H), 8.00 (s, 1H), 7.87 (s, 1H), 3.65-3.80 (m, 2H), 3.13-3.27 (m, 2H), 2.73 (s, 3H), 2.64 (m, 1H), 2.51 (s, 3H), 2.31 (m, 1H), 2.13 (t, J = 13.5 Hz, 2H), 1.90 (q, J = 12.5 Hz, 1H), 1.34 (d, J = 6.5 Hz, 3H), 1.21-1.30 (m, 6H). |
| 131 | Starting material: rac-3-((2R,6R)-2,6-diethylpiperidin-4-yl)-7-(2,8-dimethylimidazo[1,2-b]pyridazin-6-yl)-5-fluorocinnoline (prepared according to the procedure in Example 7)<br>MS m/z 447.6 [M + H]$^+$; $^1$H NMR (methanol-d$_4$) δ: 8.94 (s, 1H), 8.33 (d, J = 11 Hz, 1H), 8.23 (s, 1H), 8.00 (s, 1H), 7.89 (s, 1H), 3.71 (m, 1H), 3.32 (m, 1H), 3.18 (br s, 1H), 2.73 (s, 3H), 2.66 (s, 3H), 2.52 (s, 3H), 2.28-2.35 (m, 1H), 2.16-2.23 (m, 2H), 1.80-2.00 (m, 4H), 1.51 (m, 1H), 1.08 (t, J = 7.5 Hz, 3H), 1.02 (t, J = 7.5 Hz, 3H). |
| 132 | Starting material: 7-(2,7-dimethyl-3H-imidazo[4,5-b]pyridin-5-yl)-5-fluoro-3-(piperidin-4-yl)cinnoline dihydrochloride (prepared according to the procedure in Example 29)<br>MS m/z 405.2 [M + H]$^+$; $^1$H NMR (chloroform-d) δ: 9.30 (s, 1H), 8.50 (d, J = 12 Hz, 1H), 7.99 (s, 1H), 7.37 (s, 1H), 3.37 (t, J = 13.2, 1H), 3.20 (d, J = 11.2, 2H), 2.93 (s, 3H), 2.69 (s, 3H), 2.56-2.51 (m, 2H), 2.22-2.04 (m, 6H), 1.17 (t, J = 8 Hz, 3H), NH proton not observed. |
| 135 | Starting material: 5-(5-fluoro-3-(piperidin-4-yl)cinnolin-7-yl)-2,7-dimethylthiazolo[5,4-b]pyridine dihydrochloride (prepared according to the procedure in Example 29)<br>MS m/z 422.3 [M + H]$^+$; $^1$H NMR (chloroform-d) δ: 8.90 (s, 1H), 8.34 (dd, J = 11, 1.2 Hz, 1H), 7.93 (s, 2H), 3.42 (m, 1H), 3.33 (d, J = 12.4 Hz, 2H), 2.90 (s, 3H), 2.84 (s, 3H), 2.65-2.71 (m, 2H), 2.37-2.39 (m, 2H), 2.24-2.29 (m, 2H), 2.13-2.20 (m, 2H), 1.23 (t, J = 7.4 Hz, 3H). |
| 136 | Starting material: 2-(5-fluoro-3-(piperidin-4-yl)cinnolin-7-yl)-4,6-dimethyloxazolo[4,5-c]pyridine dihydrochloride (prepared according to the procedure in Example 29)<br>MS m/z 406.2 [M + H]$^+$; $^1$H NMR (methanol-d$_4$) δ: 9.11 (s, 1H), 8.35 (dd, J = 9.9, 1.2 Hz, 1H), 8.25 (s, 1H), 7.57 (s, 1H), 3.41-3.56 (m, 1H), 3.28-3.25 (m, 2H), 2.86 (s, 3H), 2.69 (s, 3H), 2.61 (q, J = 7.2 Hz, 2H), 2.34 (td, J = 11.6, 2.1 Hz, 2H), 2.24-2.10 (m, 4H), 1.22 (t, J = 7.3 Hz, 3H). |
| 147 | Starting material: 2-(5-fluoro-3-(piperidin-4-yl)cinnolin-7-yl)-4,6-dimethylthiazolo[4,5-c]pyridine dihydrochloride (prepared according to the procedure in Example 29)<br>MS m/z 422.3 [M + H]$^+$; $^1$H NMR (chloroform-d) δ: 8.89 (s, 1H), 8.32 (dd, J = 10,1.2 Hz, 1H), 7.94 (s, 1H), 7.59 (s, 1H), 3.40 (m, 1H), 3.22 (d, J = 12.4 Hz, 2H), 3.04 (s, 3H), 2.68 (s, 3H), 2.54-2.57 (m, 2H), 2.21-2.25 (br s, 4H), 2.04-2.11 (m, 2H), 1.18 (t, J = 14.4 Hz, 3H). |

| Cpd | Starting Material and Data |
|---|---|
| 152 | Starting material: 5-(5-fluoro-3-(piperidin-4-yl)cinnolin-7-yl)-2,7-dimethyloxazolo[5,4-b]pyridine dihydrochloride (prepared according to the procedure in Example 29)<br>MS m/z 406.2 [M + H]$^+$; $^1$H NMR (chloroform-d) δ: 8.89 (s, 1H), 8.29 (dd, J = 10.6, 1.6 Hz, 1H), 7.92 (s, 1H), 7.86 (s, 1H), 3.35-3.39 (m, 1H), 3.21 (d, J = 10.4 Hz, 2H), 2.70 (s, 6H), 2.55 (d, J = 6.8 Hz, 2H), 2.18-2.21 (m, 4H), 2.03-2.07 (m, 2H), 1.18 (t, J = 7.2 Hz, 3H). |
| 155 | Starting material: rac-7-(2,8-dimethylimidazo[1,2-b]pyridazin-6-yl)-3-((2R,6R)-2,6-dimethylpiperidin-4-yl)-5-fluorocinnoline hydrochloride (prepared according to the procedure in Example 7)<br>MS m/z 449.5 [M + H]$^+$; $^1$H NMR (DMSO-d$_6$) δ: 8.96 (s, 1H), 8.26 (d, J = 11.5 Hz, 1H), 8.06 (m, 2H), 7.88 (s, 1H), 3.68 (m, 1H), 3.52 (t, J = 6.5 Hz, 2H), 3.43 (m, 1H), 3.09 (br s, 1H), 2.83 (m, 1H), 2.60-2.70 (m, 4H), 2.47 (s, 3H), 2.22 (td, J = 12.5, 5.5 Hz, 1H), 1.98 (d, J = 12 Hz, 1H), 1.90 (d, J = 11.5 Hz, 1H), 1.70 (q, J = 12.5 Hz, 1H), 1.26 (d, J = 6.5 Hz, 3H), 1.13 (d, J = 6.5 Hz, 3H), OH proton not observed. |
| 161 | Starting material: 7-(2,8-dimethylimidazo[1,2-b]pyridazin-6-yl)-3-((2S,4r,6R)-2,6-dimethylpiperidin-4-yl)-5-fluorocinnoline dihydrochloride (prepared according to the procedure in Example 7)<br>MS m/z 419.5 [M + H]$^+$; $^1$H NMR (methanol-d$_4$) δ: 8.92 (s, 1H), 8.32 (d, J = 11 Hz, 1H), 8.18 (s, 1H), 8.00 (s, 1H), 7.88 (s, 1H), 3.51 (m, 1H), 2.8 (br s, 2H), 2.73 (s, 3H), 2.56 (s, 3H), 2.52 (s, 3H), 2.20 (d, J = 11.5 Hz, 2H), 1.96 (q, J = 12.5 Hz, 2H), 1.37 (d, J = 6.5 Hz, 6H). |
| 164 | Starting material: 7-(2,7-dimethyl-2H-pyrazolo[4,3-b]pyridin-5-yl)-5-fluoro-3-(piperidin-4-yl)cinnoline dihydrochloride (prepared according to the procedure in Example 29)<br>MS m/z 405.2 [M + H]$^+$; $^1$H NMR (chloroform-d) δ: 8.88 (s, 1H), 8.38 (dd, J = 10.8, 1.2 Hz, 1H), 8.24 (s, 1H), 7.95 (s, 1H), 7.78 (d, J = 0.8 Hz, 1H), 4.32 (s, 3H), 3.32-3.44 (m, 3H), 2.86 (s, 3H), 2.66-2.71 (m, 2H), 2.25-2.29 (m, 4H), 2.20 (s, 3H), 1.25-1.29 (m, 2H). |
| 173 | Starting material: 5-fluoro-7-(7-methoxy-2-methyl-2H-pyrazolo[4,3-b]pyridin-5-yl)-3-(piperidin-4-yl)cinnoline dihydrochloride (prepared according to the procedure in Example 29)<br>MS m/z 421.1 [M + H]$^+$; $^1$H NMR (chloroform-d) δ: 8.84 (s, 1H), 8.37 (dd, J = 10.8, 1.2 Hz, 1H), 8.20 (s, 1H), 7.93 (s, 1H), 7.29 (s, 1H), 4.29 (s, 3H), 4.22 (s, 3H), 3.34-3.41 (m, 1H), 3.20 (br d, J = 12 Hz, 2H), 2.50-2.55 (m, 2H), 2.17-2.23 (m, 4H), 1.98-2.08 (m, 2H) 1.21 (t, J = 6.4 Hz, 3H). |
| 174 | Starting material: 7-(7-ethyl-2-methyl-2H-pyrazolo[4,3-b]pyridin-5-yl)-5-fluoro-3-(piperidin-4-yl)cinnoline (prepared according to the procedure in Example 29)<br>MS m/z 419.1 [M + H]$^+$; $^1$H NMR (chloroform-d) δ: 8.89 (s, 1H), 8.38 (dd, J = 10.9, 1.3 Hz, 1H), 8.24 (s, 1H), 7.93 (s, 1H), 7.79 (s, 1H), 4.31 (s, 3H), 3.39 (t, J = 11.9 Hz, 1H), 3.27-3.13 (m, 4H), 2.56 (dd, J = 14.0, 7.5 Hz, 2H), 2.24 (d, J = 10.5 Hz, 4H), 2.07 (dd, J = 24.6, 12.5 Hz, 2H), 1.52 (t, J = 7.6 Hz, 3H), 1.19 (t, J = 7.2 Hz, 3H). |
| 176 | Starting material: 6-(5-fluoro-3-(piperidin-4-yl)cinnolin-7-yl)-2-methylimidazo[1,2-b]pyridazine-8-carbonitrile dihydrochloride (prepared according to the procedure in Example 29)<br>MS m/z 402.4 [M + H]$^+$; $^1$H NMR (methanol-d$_4$) δ: 9.22 (s, 1H), 9.17 (s, 1H), 8.58 (s, 1H), 8.43 (dd, J = 10.8, 0.9 Hz, 1H), 8.37 (s, 1H), 3.76 (br d, J = 12.5 Hz, 2H), 3.64 (tt, J = 10.6, 6.2 Hz, 1H), 3.35 (dd, J = 12.0, 4.4 Hz, 2H), 3.00 (s, 3H), 2.71 (s, 3H), 2.49-2.34 (m, 4H), HCl protons not observed. |
| 178 | Starting material: 6-(5-fluoro-3-(piperidin-4-yl)cinnolin-7-yl)-2-methylimidazo[1,2-b]pyridazine-8-carbonitrile dihydrochloride (prepared according to the procedure in Example 29)<br>MS m/z 432.5 [M + H]$^+$; $^1$H NMR (methanol-d$_4$) δ: 9.16 (s, 2H), 8.55 (s, 1H), 8.43 (br d, J = 10.22 Hz, 1H), 8.34 (s, 1H), 3.96-4.02 (m, 2H), 3.89 (br d, J = 12.51 Hz, 2H), 3.58-3.71 (m, 2H), 3.35-3.40 (m, 3H), 2.69 (s, 3H), 2.41-2.51 (m, 4H), OH and HCl protons not observed. |
| 179 | Starting material: 6-(5-fluoro-3-(piperidin-4-yl)cinnolin-7-yl)-2-methylimidazo[1,2-b]pyridazine-8-carbonitrile (prepared according to the procedure in Example 29)<br>MS m/z 434.5 [M + H]$^+$; $^1$H NMR (methanol-d$_4$) δ: 9.16 (s, 1H), 9.14 (s, 1H), 8.54 (s, 1H), 8.42 (d, J = 10.0 Hz, 1H), 8.35 (s, 1H), 4.98-5.02 (m, 1H), 4.89-4.93 (m, 1H), 3.90 (br d, J = 12.5 Hz, 2H), 3.62-3.71 (m, 3H), 3.39-3.50 (m, 2H), 2.69 (s, 3H), 2.44-2.52 (m, 4H), HCl protons not observed. |
| 180 | Starting material: (6-(5-fluoro-3-(piperidin-4-yl)cinnolin-7-yl)-2-methylimidazo[1,2-b]pyridazin-8-yl)methanol (prepared according to the procedure in Example 29)<br>MS m/z 407.5 [M + H]$^+$; $^1$H NMR (methanol-d$_4$) δ: 8.94 (s, 1H), 8.33-8.39 (m, 1H), 8.25 (s, 1H), 8.04 (d, J = 1.98 Hz, 2H), 5.10 (s, 2H), 3.48-3.63 (m, 3H), 3.11 (br s, 2H), 2.87 (s, 3H), 2.50 (s, 3H), 2.31-2.40 (m, 4H), OH proton not observed. |
| 181 | Starting material: (6-(5-fluoro-3-(piperidin-4-yl)cinnolin-7-yl)-2-methylimidazo[1,2-b]pyridazin-8-yl)methanol dihydrochloride (prepared according to the procedure in Example 29)<br>MS m/z 437.5 [M + H]$^+$; $^1$H NMR (methanol-d$_4$) δ: 9.14 (s, 1 H), 8.62 (s, 1 H), 8.46 (s, 1 H), 8.44 (d, J = 10.1 Hz, 1 H), 8.36 (s, 1 H), 5.17 (s, 2 H), 3.96-4.01 (m, 2 H), 3.89 (br d, J = 12.7 Hz, 2 H), 3.35-3.40 (m, 3 H), 3.20-3.27 (m, 2 H), 2.69 (s, 3 H), 2.43-2.50 (m, 4 H), OH and HCl protons not observed. |
| 182 | Starting material: (6-(5-fluoro-3-(piperidin-4-yl)cinnolin-7-yl)-2-methylimidazo[1,2-b]pyridazin-8-yl)methanol dihydrochloride<br>MS m/z 439.5 [M + H]$^+$; $^1$H NMR (methanol-d$_4$) δ: 9.14 (s, 1H), 8.62 (s, 1H), 8.45- |

-continued

| Cpd | Starting Material and Data |
|---|---|
| | 8.49 (m, 1H), 8.43 (d, J = 10 Hz, 1H), 8.33-8.37 (m, 1H), 5.17 (s, 2H), 4.91-5.06 (m, 2H), 3.90 (br d, J = 12.21 Hz, 2H), 3.61-3.72 (m, 3H), 3.37-3.47 (m, 2H), 2.69 (s, 3H), 2.43-2.54 (m, 4H), OH and HCl protons not observed. |
| 188 | Starting material: 3-(azepan-4-yl)-7-(2,8-dimethylimidazo[1,2-b]pyridazin-6-yl)-5-fluorocinnoline dihydrochloride (prepared according to the procedure in Example 7)<br>MS m/z 405.3 [M + H]$^+$; $^1$H NMR (methanol-d$_4$) δ: 8.92 (s, 1H), 8.32 (d, J = 11.5 Hz, 1H), 8.18 (s, 1H), 8.01 (s, 1H), 7.89 (s, 1H), 3.62 (septet, J = 5 Hz, 1H), 3.03-3.09 (m, 1H), 2.85-2.92 (m, 3H), 2.73 (s, 3H), 2.52 (s, 3H), 2.51 (s, 3H), 2.28-2.40 (m, 1H), 2.20-2.28 (m, 2H), 2.03-2.20 (m, 2H), 1.90-1.99 (m, 1H). |
| 189 | Starting material: rac-3-(azepan-4-yl)-7-(2,8-dimethylimidazo[1,2-b]pyridazin-6-yl)-5-fluorocinnoline (prepared according to the procedure in Example 7)<br>MS m/z 419.3 [M + H]$^+$; $^1$H NMR (methanol-d$_4$) δ: 8.87 (s, 1H), 8.27 (d, J = 11 Hz, 1H), 8.15 (s, 1H), 7.98 (s, 1H), 7.85 (s, 1H), 3.60 (septet, J = 5 Hz, 1H), 3.09-3.15 (m, 1H), 2.83-3.00 (m, 3H), 2.75 (q, J = 7 Hz, 2H), 2.71 (s, 3H), 2.51 (s, 3H), 2.20-2.35 (m, 3H), 2.00-2.20 (m, 2H), 1.90-1.98 (m, 1H), 1.20 (t, J = 7 Hz, 3H). |
| 190 | Starting material: rac-3-(azepan-4-yl)-7-(2,8-dimethylimidazo[1,2-b]pyridazin-6-yl)-5-fluorocinnoline (prepared according to the procedure in Example 7)<br>MS m/z 435.3 [M + H]$^+$; $^1$H NMR (methanol-d$_4$) δ: 8.91 (s, 1H), 8.31 (d, J = 11 Hz, 1H), 8.18 (s, 1H), 8.00 (s, 1H), 7.87 (s, 1H), 3.76 (t, J = 6 Hz, 2H), 3.60 (m, 1H), 3.17-3.21 (m, 1H), 2.99-3.07 (m, 3H), 2.88 (t, J = 6 Hz, 2H), 2.73 (s, 3H), 2.51 (s, 3H), 2.00-2.34 (m, 5 H), 1.91-1.98 (m, 1H), OH proton not observed. |
| 197 | Starting material: 2-(5-fluoro-3-(piperidin-4-yl)cinnolin-7-yl)-4,6-dimethylthiazolo[5,4-c]pyridine (prepared according to the procedure in Example 29)<br>MS m/z 422.1 [M + H]$^+$; $^1$H NMR (chloroform-d) δ: 8.93 (s, 1H), 8.21 (dd, J = 9.9, 1.4 Hz, 1H), 7.88 (s, 1H), 7.62 (s, 1H), 3.38-3.29 (m, 1H), 3.16 (d, J = 11.2 Hz, 2H), 2.79 (s, 3H), 2.64 (s, 3H), 2.49 (q, J = 7.2 Hz, 2H), 2.25-2.09 (m, 4H), 2.06-1.93 (m, 2H), 1.12 (t, J = 7.2 Hz, 3H). |
| 200 | Starting material: 5-fluoro-7-(2-methyl-8-phenoxyimidazo[1,2-b]pyridazin-6-yl)-3-(piperidin-4-yl)cinnoline (prepared according to the procedure in Example 29)<br>MS m/z 483.3 [M + H]$^+$; $^1$H NMR (methanol-d$_4$) δ: 8.59 (s, 1H), 8.25 (dd, J = 10.8, 1.2 Hz, 1H), 8.21 (s, 1H), 8.09 (s, 1H), 7.61-7.65 (m, 2H), 7.42-7.49 (m, 3H), 6.95 (s, 1H), 3.33-3.34 (m, 1H), 3.23-3.32 (m, 2H), 2.54-2.62 (m, 2H), 2.54 (s, 3H), 2.28-2.34 (m, 2H), 2.07-2.19 (m, 4H), 1.20 (t, J = 7.2 Hz, 3H). |
| 205 | Starting material: 2-(6-(5-fluoro-3-(piperidin-4-yl)cinnolin-7-yl)-2-methylimidazo[1,2-b]pyridazin-8-yl)acetonitrile dihydrochloride (prepared according to the procedure in Example 29)<br>MS m/z 430.2 [M + H]$^+$; $^1$H NMR (methanol-d$_4$) δ: 9.00 (s, 1H), 8.39 (dd, J = 11, 1.6 Hz, 1H), 8.26 (s, 1H), 8.15 (s, 1H), 8.09 (s, 1H), 3.49-3.52 (m, 3H), 2.91-2.94 (m, 2H), 2.70-2.79 (br s, 2H), 2.56 (s, 3H), 2.22-2.35 (m, 6H), 1.32 (t, J = 7.2 Hz, 3H). |
| 206 | Starting material: 2-(6-(5-fluoro-3-(piperidin-4-yl)cinnolin-7-yl)-2-methylimidazo[1,2-b]pyridazin-8-yl)ethan-1-ol dihydrochloride (prepared according to the procedure in Example 29)<br>MS m/z 435.2 [M + H]$^+$; $^1$H NMR (methanol-d$_4$) δ: 8.96 (s, 1H), 8.36 (dd, J = 11.6, 1.2 Hz, 1H), 8.22 (s, 1H), 8.04 (s, 1H), 7.93 (s, 1H), 4.09 (t, J = 6.2 Hz, 2H), 3.34-3.37 (br s, 3H), 3.25-3.28 (m, 2H), 2.61-2.63 (m, 2H), 2.53 (s, 3H), 2.34 (m, 2H), 2.14-2.20 (m, 4H), 1.22 (t, J = 7.2 Hz, 3H), OH proton not observed. |
| 212 | Starting material: 5-fluoro-7-(2-methyl-8-propylimidazo[1,2-b]pyridazin-6-yl)-3-(piperidin-4-yl)cinnoline dihydrochloride (prepared according to the procedure in Example 29)<br>MS m/z 433.1 [M + H]$^+$; $^1$H NMR (chloroform-d) δ: 8.84 (s, 1H), 8.22 (dd, J = 10.4 Hz, 1.2 Hz, 1H), 7.95 (s, 1H), 7.81 (s, 1H), 7.51 (s, 1H), 3.43 (t, J = 12 Hz, 1H), 3.26 (d, J = 10.8 Hz, 2H), 3.12 (t, J = 7.6 Hz, 2H), 2.60 (d, J = 7.2 Hz, 2H), 2.56 (s, 3H), 2.27-1.91 (m, 8H), 1.21 (t, J = 7.2 Hz, 3H), 1.11 (t, J = 7.2 Hz, 3H). |
| 213 | Starting material: 2-(5-fluoro-3-(piperidin-4-yl)cinnolin-7-yl)-4,6-dimethyloxazolo[4,5-c]pyridine dihydrochloride (prepared according to the procedure in Example 29)<br>MS m/z 422.1[M + H]$^+$; $^1$H NMR (chloroform-d) δ: 9.11 (s, 1H), 8.22 (dd, J = 9.6, 1.2 Hz, 1H), 7.90 (s, 1H), 7.25 (s, 1H), 3.80-3.66 (m, 2H), 3.46-3.27 (m, 3H), 2.87-2.70 (m, 5H), 2.64-2.50 (m, 5H), 2.30-2.18 (m, 4H), OH proton not observed. |
| 214 | Starting material: 2-(5-fluoro-3-(piperidin-4-yl)cinnolin-7-yl)-4,6-dimethyloxazolo[4,5-c]pyridine (prepared according to the procedure in Example 29)<br>MS m/z 392.1 [M + H]$^+$; $^1$H NMR (chloroform-d) δ: 9.17 (s, 1H), 8.26 (dd, J = 9.7, 1.3 Hz, 1H), 7.93 (s, 1H), 7.32 (s, 1H), 3.40-3.29 (m, 1H), 3.10 (d, J = 11.7 Hz, 2H), 2.89 (s, 3H), 2.71 (s, 3H), 2.39 (s, 3H), 2.30-2.15 (m, 4H), 2.11-1.98 (m, 2H). |
| 222 | Starting material: 5-fluoro-7-(8-isopropyl-2-methylimidazo[1,2-b]pyridazin-6-yl)-3-(piperidin-4-yl)cinnoline (prepared according to the procedure in Example 29)<br>MS m/z 433.2 [M + H]$^+$; $^1$H NMR (methanol-d$_4$) δ: 8.97 (s, 1H), 8.36 (dd, J = 10.9, 1.3 Hz, 1H), 8.22 (s, 1H), 8.04 (s, 1H), 7.84 (s, 1H), 3.76-3.69 (m, 1H), 3.39 (d, J = 11.7 Hz, 2H), 3.28 (s, 1H), 2.65 (dd, J = 14.4, 7.2 Hz, 2H), 2.54 (s, 3H), 2.38 (t, J = 11.0 Hz, 2H), 2.27-2.10 (m, 4H), 1.54 (d, J = 6.9 Hz, 6H), 1.23 (t, J = 7.3 Hz, 3H). |

Example 20

Preparation of Compound 18

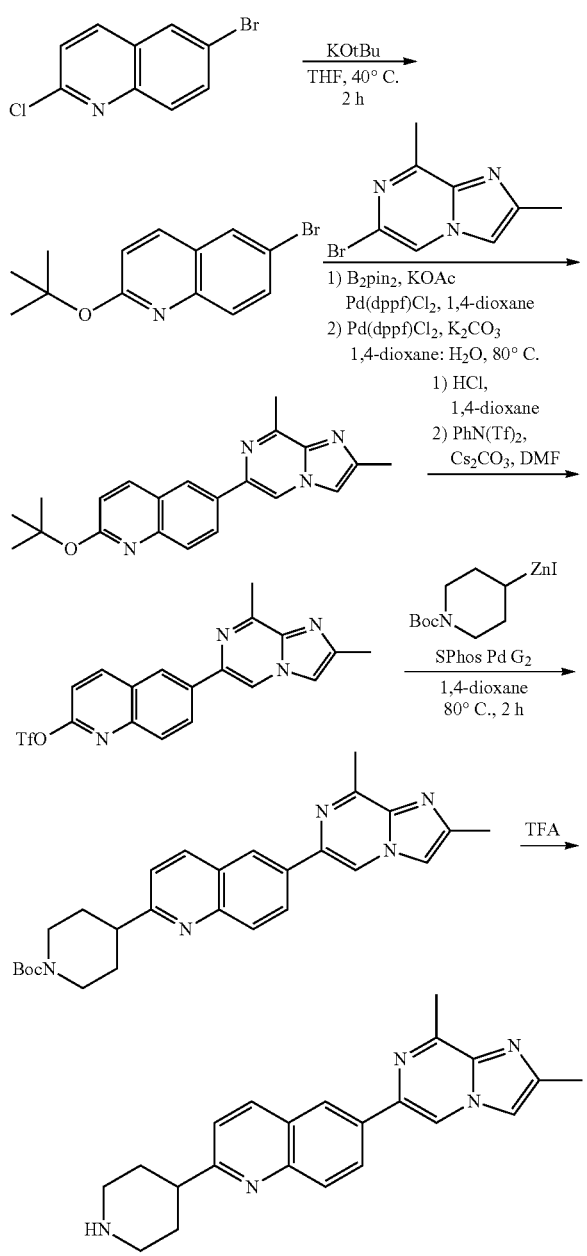

Step A: 6-Bromo-2-chloro-quinoline (300 mg, 1.2 mmol) was dissolved in THF (7.5 mL). To the solution was added a solution of KOtBu in THF (2.5 mL, 2.5 mmol, 1.0 M). The mixture was heated at 40° C. for 2 h. The mixture was partitioned between EtOAc and H₂O. The organic layer was washed with brine, dried over Na₂SO₄, filtered and concentrated. The residue was chromatographed on silica gel, eluting with 0-20% EtOAc in hexanes to yield 6-bromo-2-tert-butoxy-quinoline (310 mg, 89%). MS m/z 224.2, 226.2 [M+H-tBu]⁺.

Step B: 6-Bromo-2-tert-butoxy-quinoline (310 mg, 1.11 mmol) was combined with bis(pinacolato)diboron (375 mg, 1.46 mmol), 1,1'-bis(diphenylphosphino)ferrocene-palladium(II)dichloride dichloromethane complex (40 mg, 0.048 mmol), KOAc (300 mg, 3.03 mmol) and 1,4-dioxane (4 mL). The mixture was stirred at 90° C. for 2 h to yield 2-tert-butoxy-6-(4,4,5,5-tetramethyl-1,3,2-dioxaborolan-2-yl)quinoline as a crude mixture that was used without purification. MS m/z 272.3 [M-FH-tBu]⁺.

6-Bromo-2,8-dimethyl-imidazo[1,2-a]pyrazine (100 mg, 0.44 mmol) and 2-tert-butoxy-6-(4,4,5,5-tetramethyl-1,3,2-dioxaborolan-2-yl)quinoline (164 mg, 0.50 mmol, prepared above) were combined with 1,1'-bis(diphenylphosphino)ferrocene-palladium(II)dichloride dichloromethane complex (20 mg, 0.024 mmol), 1,4-dioxane (2.5 mL) and aqueous 1 M K₂CO₃ (1.5 mL). The mixture was heated at 80° C. for 2 h. The mixture was partitioned between EtOAc and H₂O. The organic layer was washed with brine, dried over Na₂SO₄, filtered and concentrated. The residue was chromatographed on silica gel, eluting with 0-20% EtOAc in hexanes to yield 2-tert-butoxy-6-(2,8-dimethylimidazo[1,2-a]pyrazin-6-yl)quinoline (140 mg, 73%). MS m/z 347.3 [M+H]⁺.

Step C: 2-tert-Butoxy-6-(2,8-dimethylimidazo[1,2-a]pyrazin-6-yl)quinoline (130 mg, 0.38 mmol) was suspended in 4 N HCl in 1,4-dioxane (1 mL, 4 mmol). The mixture was stirred at room temperature for 1 h. The volatiles were removed. The residue was suspended in DMF (1 mL) with Cs₂CO₃ (325 mg, 1.0 mmol). To the mixture was added N,N-bis(trifluoromethylsulfonyl)aniline (107 mg, 0.30 mmol). The mixture was stirred at room temperature for 2 h. The mixture was partitioned between EtOAc and H₂O. The organic layer was washed with brine, dried over Na₂SO₄, filtered and concentrated. The residue was chromatographed on silica gel, eluting with 10-100% EtOAc in hexanes to yield [6-(2,8-dimethylimidazo[1,2-a]pyrazin-6-yl)-2-quinolyl]trifluoromethanesulfonate (90 mg, 56%). MS m/z 423.3 [M+H]⁺.

Step D: [6-(2,8-Dimethylimidazo[1,2-a]pyrazin-6-yl)-2-quinolyl]trifluoromethanesulfonate (90 mg, 0.21 mmol) was combined with 1-tert-butoxycarbonylpiperidin-4-ylzinc iodide (0.25 mL, 0.25 mmol, prepared according to the procedure in Example 5, Step B), 1,1'-bis(diphenylphosphino)ferrocene-palladium(II)dichloride dichloromethane complex (8 mg, 0.01 mmol), 1,4-dioxane (2 mL). The mixture was heated at 80° C. for 20 min. The mixture was partitioned between EtOAc and H₂O. The organic layer was washed with brine, dried over Na₂SO₄, filtered and concentrated. The residue was chromatographed on silica gel, eluting with 10-100% EtOAc in hexanes, followed by 5% MeOH in EtOAc to yield tert-butyl 4-[6-(2,8-dimethylimidazo[1,2-a]pyrazin-6-yl)-2-quinolyl]piperidine-1-carboxylate (60 mg, 62%). MS m/z 458.4 [M+H]⁺.

Step E: tert-Butyl 4-[6-(2,8-dimethylimidazo[1,2-a]pyrazin-6-yl)-2-quinolyl]piperidine-1-carboxylate (60 mg, 0.1311 mmol) was dissolved in TFA (1 mL). After 20 min, the volatiles were removed. The residue was partitioned between CH₂Cl₂ and aqueous 1 M K₂CO₃. The organic layer was loaded directly onto silica gel, eluting with 0-20% MeOH (2 M NH₃) in CH₂Cl₂ to yield 6-(2,8-dimethylimidazo[1,2-a]pyrazin-6-yl)-2-(piperidin-4-yl)quinoline as white powder (15 mg, 32%).

MS m/z 358.4 [M+H]⁺. ¹H NMR (DMSO-d₆) δ: 9.17 (s, 1H), 8.61 (d, J=2.2 Hz, 1H), 8.39 (d, J=8.5 Hz, 1H), 8.36 (dd, J=8.8, 2.2 Hz, 1H), 8.04 (d, J=8.8 Hz, 1H), 7.88 (s, 1H), 7.51 (d, J=8.5 Hz, 1H), 3.11-3.17 (m, 2H), 2.98-3.05 (m, 1H), 2.83 (s, 3H), 2.69-2.77 (m, 2H), 2.44 (s, 3H), 1.87-1.95 (m, 2H), 1.75-1.85 (m, 2H).

Using the procedure described for Example 20, above, additional compounds described herein were prepared by substituting the appropriate aryl boronic acid in Step B, suitable reagents and reaction conditions, obtaining compounds such as those selected from:

| Cpd | Data |
|---|---|
| 19 | MS m/z 358.4 [M + H]⁺; $^1$H NMR (DMSO-$d_6$) δ: 8.67 (d, J = 2.2 Hz, 1H), 8.45 (d, J = 8.5 Hz, 1H), 8.42 (dd, J = 8.8, 2.0 Hz, 1H), 8.11 (s, 1H), 8.08 (d, J = 8.8 Hz, 1H), 7.82 (d, J = 1.3 Hz, 1H), 7.57 (d, J = 8.5 Hz, 1H), 3.24-3.30 (m, 2H), 3.09-3.15 (m, 1H), 2.84-2.91 (m, 2H), 2.65 (s, 3H), 2.43 (s, 3H), 1.87-1.95 (m, 2H), 1.75-1.85 (m, 2H). |

Example 21

Preparation of Compound 55

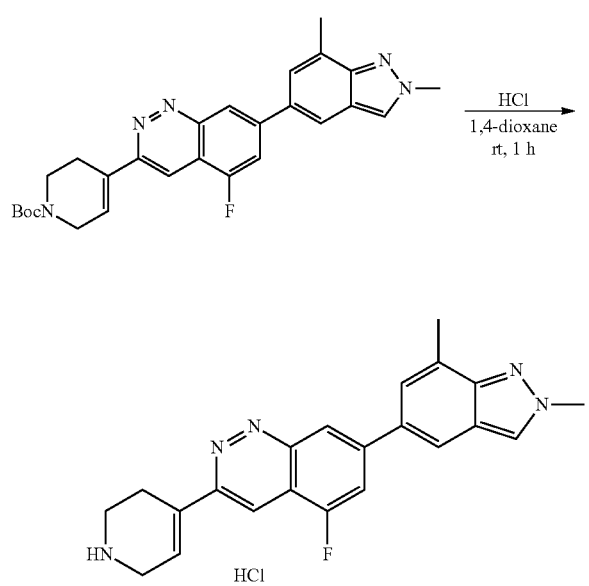

tert-Butyl 4-(7-(2,7-dimethyl-2H-indazol-5-yl)-5-fluoro-cinnolin-3-yl)-3,6-dihydropyridine-1(2H)-carboxylate (25 mg, 0.053 mmol, prepared according to Example 7, Step I) was stirred in the presence of HCl in dioxane (4M, 1 mL, 4 mmol) for 1 h. The reaction mixture was filtered, and the solids were washed with ether, then 9:1 CH$_2$Cl$_2$:MeOH to yield 7-(2,7-dimethyl-2H-indazol-5-yl)-5-fluoro-3-(1,2,3,6-tetrahydropyridin-4-yl)cinnoline hydrochloride (19 mg, 88%).

MS m/z 374.4 [M+H]⁺; $^1$H NMR (DMSO-$d_6$) δ: 9.30-9.40 (br s, 2H), 8.66 (s, 1H), 8.48 (s, 1H), 8.32 (s, 1H), 8.24 (dd, J=11.5, 1 Hz, 1H), 8.20 (s, 1H), 7.69 (s, 1H), 7.21 (br s, 1H), 4.23 (s, 3H), 3.94 (br s, 2H), 3.40-3.50 (m, 2H), 3.05 (br s, 2H), 2.64 (s, 3H).

Using the procedure described for Example 2, above, additional compounds described herein were prepared by substituting the appropriate starting material, suitable reagents and reaction conditions, obtaining compounds such as those selected from:

| Cpd | Data |
|---|---|
| 225 | MS m/z 375.3 [M + H]⁺; $^1$H NMR (chloroform-d) δ: 8.70 (s, 1H), 8.08 (dd, J = 10.7, 1.0 Hz, 1H), 7.86 (s, 1H), 7.73-7.67 (m, 1H), 7.40 (s, 1H), 7.11 (br s, 1H), 4.23 (dd, J = 6.8, 2.2 Hz, 2H), 3.73 (dd, J = 5.2 Hz, 2H), 2.79 (br s, 2H), 2.69 (s, 3H), 2.48 (s, 3H), NH and HCl protons not observed. |
| 208 | MS m/z 431.5 [M + H]⁺; $^1$H NMR (chloroform-d) δ: 8.81-8.89 (m, 1H), 8.21 (d, J = 10.1 Hz, 1H), 8.00 (s, 1H), 7.82 (s, 1H), 7.54 (d, J = 0.9 Hz, 1H), 7.13 (br s, 1H), 2.78 (s, 3H), 2.59-2.73 (br m, 2H), 2.53-2.57 (m, 3H), 1.43 (br s, 12H). |

Example 22

Preparation of Compound 4

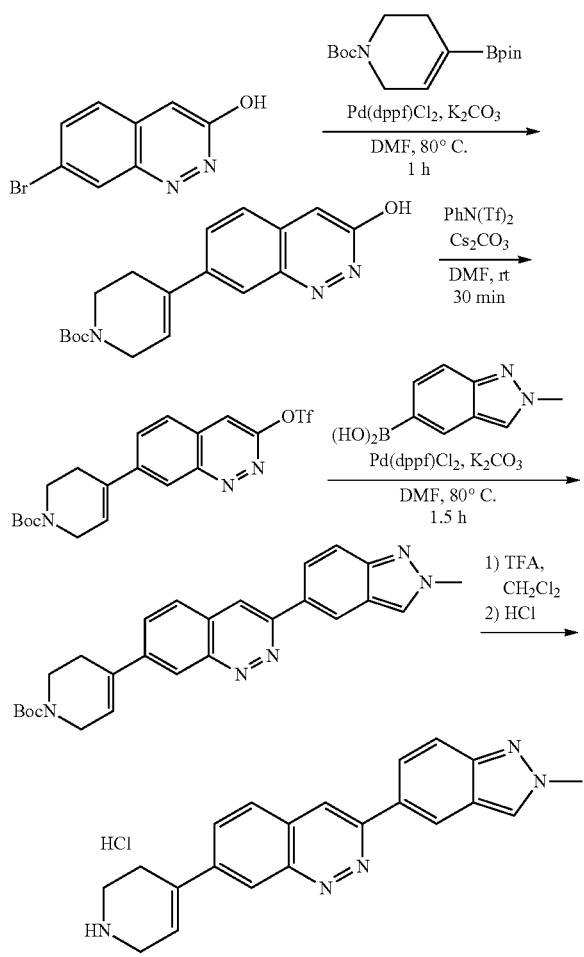

Step A: 7-Bromocinnolin-3-ol (100 mg, 0.44 mmol, prepared according to the procedure used for 7-Bromo-5-fluoro-cinnolin-3-ol in Example 7), tert-butyl 4-(4,4,5,5-tetramethyl-1,3,2-dioxaborolan-2-yl)-3,6-dihydropyridine-1(2H)-carboxylate (200 mg, 0.65 mmol), Pd(dppf)Cl$_2$—CH$_2$Cl$_2$ (50 mg, 0.061 mmol), DMF (2.5 mL), and aqueous K$_2$CO$_3$ (2M, 0.825 mL, 1.65 mmol) were heated at 80° C. for 1 hour. The mixture was then partitioned between H$_2$O and EtOAc. The organic layer was washed with H$_2$O and then brine. The organic layer was dried over MgSO$_4$, filtered, and concentrated under vacuum. Purification by silica gel chromatography (5% MeOH in CH$_2$Cl$_2$), followed by ether trituration, yielded tert-butyl 4-(3-hydroxycinnolin-7-yl)-3,6-dihydropyridine-1(2H)-carboxylate (110 mg) as a yellow solid. MS m/z 328.0 [M+H]$^+$.

Step B: tert-Butyl 4-(3-hydroxycinnolin-7-yl)-3,6-dihydropyridine-1(2H)-carboxylate (108 mg, 0.33 mmol), 1,1,1-trifluoro-N-phenyl-N-((trifluoromethyl)sulfonyl)methanesulfonamide (143 mg, 0.4 mmol), Cs$_2$CO$_3$ (175 mg, 0.54 mmol) and DMF (1 mL) were stirred at room temperature for 30 min. The mixture was partitioned between H$_2$O and EtOAc. The organic layer was washed with H$_2$O and brine. The organic layer was dried over MgSO$_4$, filtered, and concentrated under vacuum. Purification by silica gel chromatography (0-5% EtOAc in CH$_2$Cl$_2$) yielded tert-butyl 4-(3-(((trifluoromethyl)sulfonyl)oxy)cinnolin-7-yl)-3,6-dihydropyridine-1(2H)-carboxylate (109 mg, 54% over two steps) as a white solid.

$^1$H NMR (acetone-d$_6$) δ: 8.53 (s, 1H), 8.43 (s, 1H), 8.28 (dd, J=9 Hz, 2 Hz, 1H), 8.23 (d, J=9 Hz, 1H), 6.69 (br s, 1H), 4.22 (s, 2H), 3.75 (in, 2H), 2.79 (m, 2H), 1.51 (s, 9H).

Step C: A mixture of tert-butyl 4-(3-(((trifluoromethyl)sulfonyl)oxy)cinnolin-7-yl)-3,6-dihydropyridine-1(2H)-carboxylate (85 mg, 0.18 mmol), (2-methyl-2H-indazol-5-yl)boronic acid (51 mg, 0.29 mmol), Pd(dppf)Cl$_2$—CH$_2$Cl$_2$ (40 mg, 0.05 mmol), dioxane (1.05 mL), and aqueous K$_2$CO$_3$ (2M, 220 µL, 0.44 mmol) were heated at 80° C. for 90 min. The mixture was partitioned between H$_2$O and CH$_2$Cl$_2$. The organic layer was dried over MgSO$_4$, filtered and concentrated under vacuum. The residue was purified by silica gel chromatography (20% acetone in CH$_2$Cl$_2$, followed by 5% MeOH in CH$_2$Cl$_2$). The material obtained was triturated with 2:1 hexanes:CH$_2$Cl$_2$. The solid material was collected and dried yielding tert-butyl 4-(3-(2-methyl-2H-indazol-5-yl)cinnolin-7-yl)-3,6-dihydropyridine-1(2H)-carboxylate (51 mg, 64%) as a yellow solid.

$^1$H NMR (DMSO-d$_6$) δ: 8.72 (s, 1H), 8.71 (s, 1H), 8.55 (s, 1H), 8.39 (s, 1H), 8.21 (dd, J=9 Hz, 2 Hz, 1H), 8.11 (dd, J=9 Hz, 2 Hz, 1H), 8.06 (d, J=9 Hz, 1H), 7.80 (d, J=9 Hz, 1H), 6.61 (br s, 1H), 4.23 (s, 3H), 4.13 (s, 2H), 3.64 (t, J=5.5 Hz, 2H), 2.72 (s, 2H), 1.46 (s, 9H).

Step D: A solution of tert-butyl 4-(3-(2-methyl-2H-indazol-5-yl)cinnolin-7-yl)-3,6-dihydropyridine-1(2H)-carboxylate (51 mg, 0.12 mmol) in CH$_2$Cl$_2$ (1 mL) and TFA (0.3 mL) was stirred at room temperature for 1 h. The volatiles were removed by a N$_2$ stream. The solid material was triturated with 1 N HCl in ether for 1 h and the volatiles were removed by a N$_2$ stream. The residue was washed with 4:1 CH$_2$Cl$_2$:MeOH and dried to yield 3-(2-methyl-2H-indazol-5-yl)-7-(1,2,3,6-tetrahydropyridin-4-yl)cinnoline hydrochloride (42 mg, 100%) as a light tan solid.

MS m/z 342.0 [M+H]$^+$; $^1$H NMR (DMSO-d$_6$) δ: 9.25 (br s, 1H), 8.75 (s, 1H), 8.73 (s, 1H), 8.56 (s, 1H), 8.47 (s, 1H), 8.22 (dd, J=9 Hz, 1.5 Hz, 1H), 8.14 (dd, J=9 Hz, 2 Hz, 1H), 8.10 (d, J=9 Hz, 1H), 7.81 (d, J=9 Hz, 1H), 6.65 (br s, 1H), 4.24 (s, 3H), 3.88 (s, 2H), 3.41 (m, 2H), 2.95 (s, 2H).

Example 23

Preparation of Compound 24

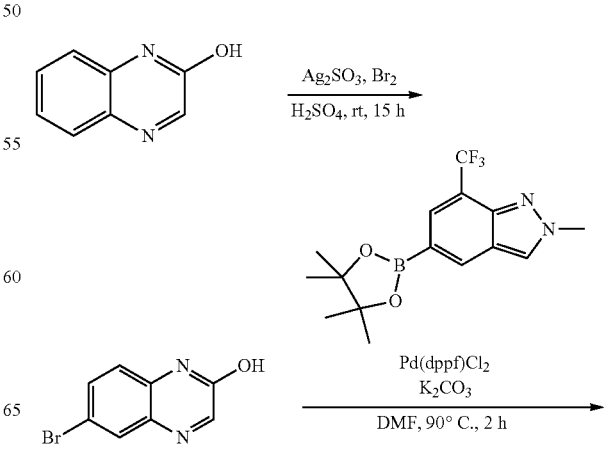

-continued

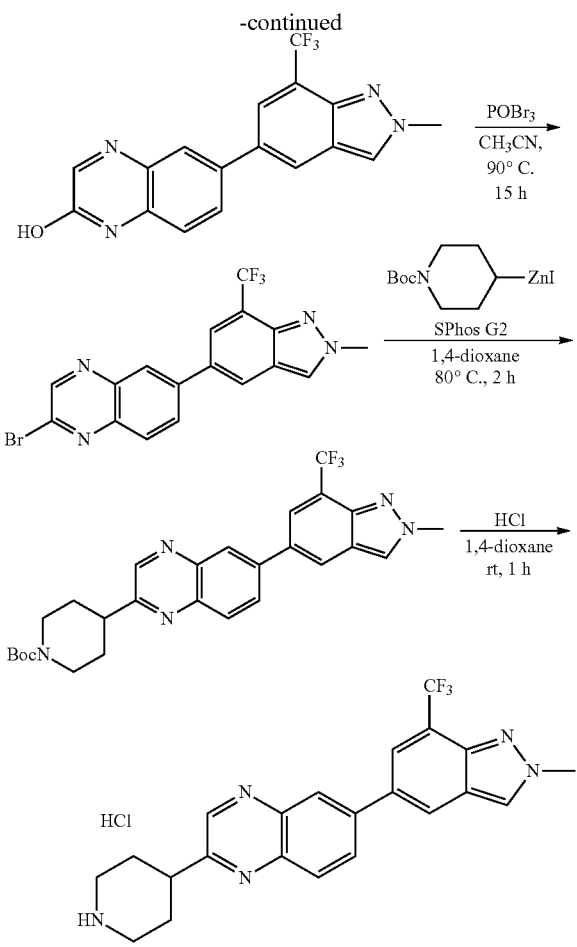

Step A: Quinoxalin-2-ol (2.0 g, 13.7 mmol), concentrated H$_2$SO$_4$ (14 mL), Ag$_2$SO$_4$ (2.12 g, 6.8 mmol), and Br$_2$ (0.7 mL, 13.6 mmol) were stirred at room temperature for 15 h. The mixture was filtered to remove AgBr. The solid was washed with sulfuric acid. The combined filtrate was poured onto ice. A white solid was collected by filtration, washed with H$_2$O, EtOH, and ether, and then dried to yield 6-bromoquinoxalin-2-ol (2.7 g, 87%) as a light tan solid containing 10% unreacted starting material.

$^1$H NMR (DMSO-d$_6$) δ: 12.54 (br s, 1H), 8.21 (s, 1H), 7.99 (d, J=2 Hz, 1H), 7.73 (dd, J=9 Hz, 2 Hz, 1H), 7.27 (d, J=9 Hz, 1H).

Step B: 6-Bromoquinoxalin-2-ol (200 mg, 0.88 mmol), 2-methyl-5-(4,4,5,5-tetramethyl-1,3,2-dioxaborolan-2-yl)-7-(trifluoromethyl)-2H-indazole (300 mg, 1.09 mmol), Pd(dppf)Cl$_2$—CH$_2$Cl$_2$ (50 mg, 0.061 mmol), DMF (5 mL), and aqueous K$_2$CO$_3$ (2M, 1.65 mL, 3.3 mmol) were heated at 90° C. for 2 h. To the mixture was added dilute aqueous HCl. The solid material was collected by filtration, washed with H$_2$O, EtOH and ether, and then dried to yield crude 6-(2-methyl-7-(trifluoromethyl)-2H-indazol-5-yl)quinoxalin-2-ol (231 mg). MS m/z 345.2 [M+H]$^+$.

Step C: 6-(2-Methyl-7-(trifluoromethyl)-2H-indazol-5-yl)quinoxalin-2-ol (231 mg, 0.67 mmol), CH$_3$CN (3 mL) and POBr$_3$ (1.2 g, 4.18 mmol) were heated at 90° C. for 15 h. The mixture was diluted in ether and filtered. The solid material was washed with CH$_2$Cl$_2$. The mixture was dissolved in CH$_2$Cl$_2$:MeOH and was filtered through a silica plug to remove baseline impurities. The filtrate was concentrated under vacuum. The residue was purified by silica gel chromatography (30% EtOAc in CH$_2$Cl$_2$). The product was triturated with CH$_2$Cl$_2$. The solid was collected and dried to yield 2-bromo-6-(2-methyl-7-(trifluoromethyl)-2H-indazol-5-yl)quinoxaline (117 mg, 32% over two steps) as an off-white solid.

$^1$H NMR (acetone-d$_6$) δ: 9.02 (s, 1H), 8.61 (s, 1H), 8.55 (s, 1H), 8.46 (d, J=2 Hz, 1H), 8.37 (dd, J=8.5 Hz, 2 Hz, 1H), 8.14-8.17 (m, 2H), 4.36 (s, 3H).

Step D: 2-Bromo-6-(2-methyl-7-(trifluoromethyl)-2H-indazol-5-yl)quinoxaline (85 mg, 0.21 mmol), chloro(2-dicyclohexylphosphino-2',6'-dimethoxy-1,1'-biphenyl)[2-(2'-amino-1,1'-biphenyl)]palladium(II) (10 mg, 0.013 mmol), 1,4-dioxane (0.5 mL), and (1-(tert-butoxycarbonyl)piperidin-4-yl)zinc(II) iodide (1M in DMA, 0.5 mL, 0.5 mmol, prepared according to Example 5) were heated at 80° C. for 2 h. The mixture was partitioned between EtOAc and aqueous saturated NH$_4$Cl. The organic layer was dried over MgSO$_4$, filtered and concentrated under vacuum. The residue was purified by silica gel chromatography (1:1 CH$_2$Cl$_2$:EtOAc, followed by 20% acetone in CH$_2$Cl$_2$). The collected material was triturated with 1:1 hexanes:ether. The solid material was collected by vacuum filtration and dried to yield tert-butyl 4-(6-(2-methyl-7-(trifluoromethyl)-2H-indazol-5-yl)quinoxalin-2-yl)piperidine-1-carboxylate (41 mg, 38%) as a pink solid.

$^1$H NMR (acetone-d$_6$) δ: 8.97 (s, 1H), 8.59 (s, 1H), 8.51 (s, 1H), 8.39 (d, J=2 Hz, 1H), 8.26 (dd, J=8.5 Hz, 2 Hz, 1H), 8.14-8.17 (m, 2H), 4.36 (s, 3H), 4.25-4.34 (m, 2H), 3.42 (m, 1H), 2.90-3.15 (br s, 2H), 2.05-2.10 (m, 2H), 1.91 (qd, J=12.5 Hz, 4 Hz, 2H), 1.50 (s, 9H).

Step E: tert-Butyl 4-(6-(2-methyl-7-(trifluoromethyl)-2H-indazol-5-yl)quinoxalin-2-yl)piperidine1-carboxylate (25 mg, 0.049 mmol) and 4 N HCl in dioxane (1 mL, 4 mmol) were heated at 80° C. for 1 h. The mixture was diluted in ether. The solid material was collected by vacuum filtration and dried to yield 6-(2-methyl-7-(trifluoromethyl)-2H-indazol-5-yl)-2-(piperidin-4-yl)quinoxaline hydrochloride as a yellow solid (20 mg, 91%).

MS m/z 412.1 [M+H]$^+$; $^1$H NMR (methanol-d$_4$) δ: 8.97 (s, 1H), 8.55 (s, 1H), 8.47 (s, 1H), 8.37 (d, J=2 Hz, 1H), 8.27 (dd, J=9 Hz, 2 Hz, 1H), 8.21 (d, J=8.5 Hz, 1H), 8.12 (s, 1H), 4.34 (s, 3H), 3.59-3.66 (m, 2H), 3.45-3.54 (m, 1H), 3.24-3.33 (m, 2H), 2.33-2.40 (m, 2H), 2.22-2.33 (m, 2H), NH proton not observed.

Using the procedure described for Example 23, above, additional compounds described herein were prepared by substituting the appropriate boronic acid in Step B, suitable reagents and reaction conditions, obtaining compounds such as those selected from:

| Cpd | Data |
|---|---|
| 31 | MS m/z 358.2 [M + H]$^+$; $^1$H NMR (methanol-d$_4$) δ: 8.98 (s, 1H), 8.86 (s, 1H), 8.39 (d, J = 2 Hz, 1H), 8.27 (dd, J = 9 Hz, 2 Hz, 1H), 8.23 (s, 1H), 8.21 (d, J = 8.5 Hz, 1H), 8.00 (s, 1H), 4.46 (s, 3H), 3.60-3.69 (m, 2H), 3.46-3.54 (m, 1H), 3.24-3.33 (m, 2H), 2.75 (s, 3H), 2.33-2.40 (m, 2H), 2.21-2.31 (m, 2H), NH proton not observed. |

Example 24

Preparation of Compound 5

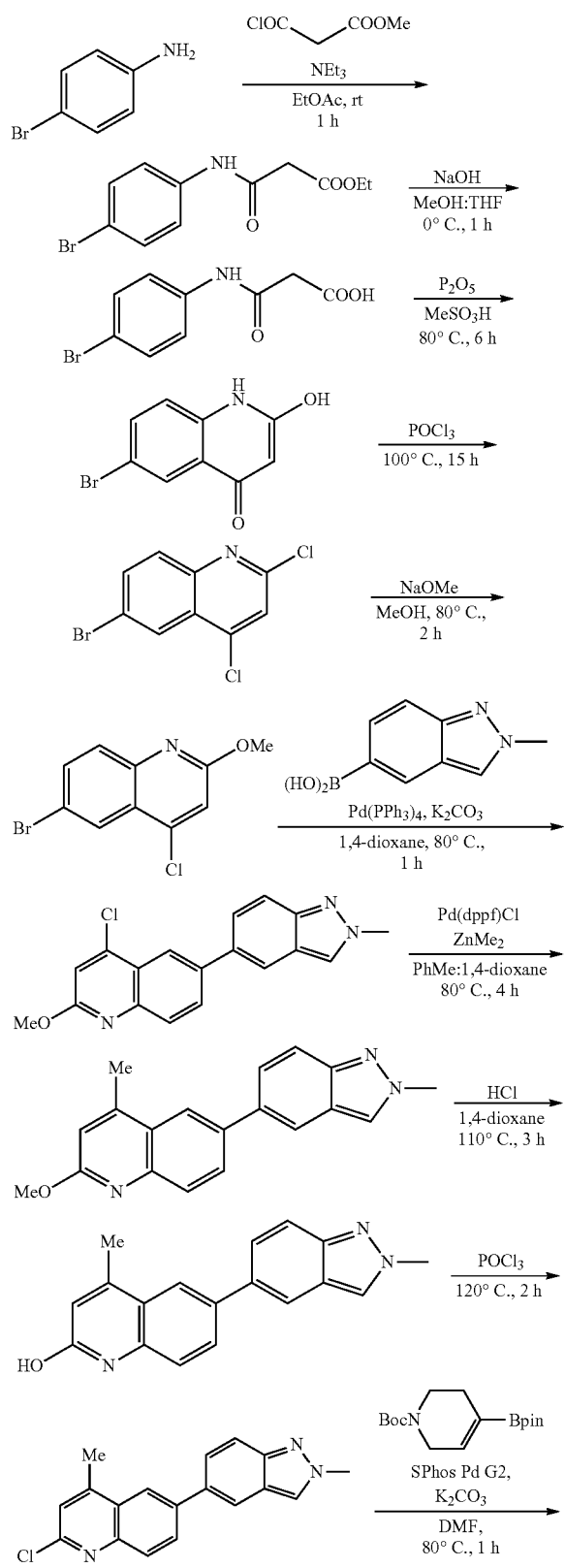

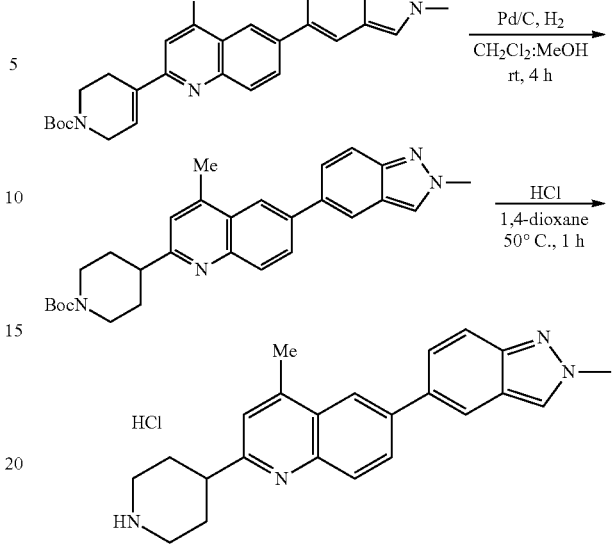

Step A: 4-Bromoaniline (5.0 g, 29.1 mmol) was dissolved in EtOAc (60 mL) and Et₃N (5.25 mL, 37.5 mmol) at 0° C. Methyl 3-chloro-3-oxopropanoate (3.95 mL, 31.5 mmol) was added dropwise to the solution. The reaction mixture was stirred at room temperature for 1 h. The reaction mixture was partitioned between EtOAc and dilute aqueous HCl. The organic layer was washed with aqueous NaHCO₃ and brine. The organic layer was dried over MgSO₄, filtered and concentrated under vacuum. The residue was triturated with 2:1 hexane:ether. The solid material was collected by vacuum filtration and dried to yield ethyl 3-((4-bromophenyl)amino)-3-oxopropanoate (6.23 g, 75%) as a white solid.

$^1$H NMR (acetone-$d_6$) δ: 9.50 (br s, 1H), 7.64 (m, 2H), 7.49 (m, 2H), 4.19 (q, J=7 Hz, 2H), 3.48 (s, 2H), 1.26 (t, J=7 Hz, 3H).

Step B: Ethyl 3-((4-bromophenyl)amino)-3-oxopropanoate (6.23 g, 22.1 mmol) was dissolved in THF (60 mL) and MeOH (15 mL) at 0° C. Aqueous 2 N NaOH (15 mL, 30 mmol) was added dropwise to the mixture. The mixture was stirred at 0° C. for 1 h, upon which excess reagent was quenched with aqueous 6 N HCl (7.5 mL). The mixture was concentrated under vacuum. The residue was suspended in H₂O. The solid material was collected by vacuum filtration and dried to yield 3-((4-bromophenyl)amino)-3-oxopropanoic acid (5.7 g, 100%) as a white solid.

$^1$H NMR (acetone-$d_6$) δ: 9.63 (br s, 1H), 7.64 (m, 2H), 7.49 (m, 2H), 3.50 (s, 2H), CO₂H proton not observed.

Step C: Methanesulfonic acid (28 mL), 3-((4-bromophenyl)amino)-3-oxopropanoic acid (5.7 g, 22.1 mmol), and P₂O₅ (9 g, 63.4 mmol) were combined and heated at 80° C. for 6 h. The mixture was poured onto ice, and the resulting solid material was collected by vacuum filtration. The solid material was washed with EtOH and ether, and dried to yield 6-bromo-2-hydroxyquinolin-4(1H)-one (3.48 g, 65%) as a tan solid. MS m/z 240.0, 242.0 [M-al]⁺.

Step D: 6-Bromo-2-hydroxyquinolin-4(1H)-one (3.48 g, 14.5 mmol) and POCl₃ (25 mL) were heated at 100° C. for 15 h. The mixture was poured into ice-water. The resulting mixture was extracted with CH₂Cl₂. The organic layer was dried over MgSO₄, filtered and concentrated under vacuum. The residue was purified by silica gel chromatography (30% hexanes in CH$_2$Cl$_2$) to yield 6-bromo-2,4-dichloroquinoline (2.9 g, 72%) as a white solid.

$^1$H NMR (acetone-d$_6$) δ: 8.42 (d, J=2 Hz, 1H), 8.06 (dd, J=9 Hz, 2 Hz, 1H), 7.98 (d, J=9 Hz, 1H), 7.85 (s, 1H).

Step E: 6-Bromo-2,4-dichloroquinoline (2.82 g, 10.2 mmol) and 0.5 M NaOMe in MeOH (21.2 mL, 10.6 mmol) were combined and heated at reflux for 2 h. The mixture was partitioned between H$_2$O and CH$_2$Cl$_2$. The organic layer was dried over MgSO$_4$, filtered and concentrated under vacuum. The residue was purified by silica gel chromatography (50-70% CH$_2$Cl$_2$ in hexanes) to yield 6-bromo-4-chloro-2-methoxyquinoline (1.02 g, 37%).

$^1$H NMR (acetone-d$_6$) δ: 8.25 (d, J=2 Hz, 1H), 7.88 (dd, J=9, 2 Hz, 1H), 7.80 (d, J=9 Hz, 1H), 7.22 (s, 1H), 4.06 (s, 3H).

Step F: 6-Bromo-4-chloro-2-methoxyquinoline (210 mg, 0.77 mmol), (2-methyl-2H-indazol-5-yl)boronic acid (161 mg, 0.91 mmol), Pd(PPh$_3$)$_4$ (90 mg, 0.078 mmol), 2 M aqueous K$_2$CO$_3$ (1.4 mL, 2.8 mmol) and 1,4-dioxane (4.2 mL) were combined and heated at 80° C. for 1 h. The reaction mixture was partitioned between CH$_2$Cl$_2$ and H$_2$O. The organic layer was dried over MgSO$_4$, filtered and concentrated under vacuum. The residue was purified by silica gel chromatography (30% EtOAc in CH$_2$Cl$_2$). The collected product was triturated in ether. The solid material was collected by vacuum filtration and dried to yield 4-chloro-2-methoxy-6-(2-methyl-2H-indazol-5-yl)quinoline (182 mg, 73%) as a while solid.

$^1$H NMR (acetone-d$_6$) δ: 8.37 (d, J=2 Hz, 1H), 8.32 (s, 1H), 8.14 (dd, J=9 Hz, 2 Hz, 1H), 8.11 (m, 1H), 7.96 (d, J=8.5 Hz, 1H), 7.76-7.80 (m, 1H), 7.72 (dd, J=8.5 Hz, 1.5 Hz, 1H), 7.20 (s, 1H), 4.27 (s, 3H), 4.08 (s, 3H).

Step G: 4-Chloro-2-methoxy-6-(2-methyl-2H-indazol-5-yl)quinoline (120 mg, 0.37 mmol) was combined with Pd(dppf)Cl$_2$—CH$_2$Cl$_2$ (35 mg, 0.043 mmol) in 1,4-dioxane (0.5 mL). To the mixture was added dimethylzinc (1.2 M in toluene, 1 mL, 1.2 mmol). The mixture was heated at 80° C. for 4 h. The reaction mixture was cooled to room temperature, upon which excess reagent was carefully quenched with MeOH. The mixture was partitioned between NH$_4$OH and CH$_2$Cl$_2$. The organic layer was dried over MgSO$_4$, filtered and concentrated under vacuum. Purification by silica gel chromatography (30% EtOAc in CH$_2$Cl$_2$), followed by ether trituration, yielded 2-methoxy-4-methyl-6-(2-methyl-2H-indazol-5-yl)quinoline (102 mg, 91%) as a white solid.

$^1$H NMR (acetone-d$_6$) δ: 8.31 (s, 1H), 8.23 (d, J=2 Hz, 1H), 8.08 (t, J=1.5 Hz, 1H), 8.02 (dd, J=8.5 Hz, 2.5 Hz, 1H), 7.89 (d, J=9 Hz, 1H), 7.74 (m, 2H), 6.88 (s, 1H), 4.27 (s, 3H), 4.03 (s, 3H), 2.76 (s, 3H).

Step H: 2-Methoxy-4-methyl-6-(2-methyl-2H-indazol-5-yl)quinoline (100 mg, 0.33 mmol) and 4 N HCl in 1,4-dioxane (1.5 mL, 6 mmol) were heated at 110° C. for 3 h. The mixture was diluted in ether and was filtered. The solid was dried, yielding 4-methyl-6-(2-methyl-2H-indazol-5-yl)quinolin-2-ol (82 mg, 84%) as a light tan solid. MS m/z 289.9 [M+H]$^+$.

Step I: 4-Methyl-6-(2-methyl-2H-indazol-5-yl)quinolin-2-ol (82 mg, 0.28 mmol) and POCl$_3$ (1.5 mL) were heated at 120° C. for 2 h. The mixture was poured onto ice. Aqueous saturated NaHCO$_3$ was added to the ice to neutralize the mixture. The aqueous mixture was washed with CH$_2$Cl$_2$. The organic layer was dried over MgSO$_4$, filtered and concentrated under vacuum. The residue was purified by silica gel chromatography (5% MeOH in CH$_2$Cl$_2$). The collected product was triturated with 1:1 acetone:CH$_2$Cl$_2$. The solid was collected and dried to yield 2-chloro-4-methyl-6-(2-methyl-2H-indazol-5-yl)quinoline (84 mg, 100%) as an orange solid.

$^1$H NMR (DMSO-d$_6$) δ: 8.46 (s, 1H), 8.32 (d, J=2 Hz, 1H), 8.17-8.23 (m, 2H), 8.01 (d, J=9 Hz, 1H), 7.79 (dd, J=9 Hz, 1.5 Hz, 1H), 7.75 (d, J=9 Hz, 1H), 7.52 (s, 1H), 4.22 (s, 3H), 2.80 (s, 3H).

Step J: 2-Chloro-4-methyl-6-(2-methyl-2H-indazol-5-yl)quinoline (75 mg, 0.24 mmol), tert-butyl 4-(4,4,5,5-tetramethyl-1,3,2-dioxaborolan-2-yl)-3,6-dihydropyridine-1(2H)-carboxylate (93 mg, 0.3 mmol), chloro(2-dicyclohexylphosphino-2',6'-dimethoxy-1,1'-biphenyl)[2-(2'-amino-1,1'-biphenyl)]palladium(II) (10 mg, 0.014 mmol), aqueous 2 M K$_2$CO$_3$ (0.45 mL, 0.9 mmol) and DMF (1.35 mL) were combined and heated at 80° C. for 1 h. The mixture was partitioned between EtOAc and H$_2$O. The organic layer was dried over MgSO$_4$, filtered and concentrated under vacuum. The residue was purified by silica gel chromatography (30-50% EtOAc in CH$_2$Cl$_2$). The collected product was triturated with ether. The solid was collected and dried to yield tert-butyl 4-(4-methyl-6-(2-methyl-2H-indazol-5-yl)quinolin-2-yl)-3,6-dihydropyridine-1(2H)-carboxylate (73 mg, 67%) as a white solid.

$^1$H NMR (acetone-d$_6$) δ: 8.32 (s, 1H), 8.31 (s, 1H), 8.14 (t, J=1.5 Hz, 1H), 8.06-8.12 (m, 2H), 7.75-7.80 (m, 2H), 7.73 (s, 1H), 6.86 (br s, 1H), 4.27 (s, 3H), 4.20 (s, 2H), 3.69 (t, J=5.5 Hz, 2H), 2.88 (m, 2H), 2.83 (s, 3H), 1.51 (s, 9H).

Step K: tert-Butyl 4-(4-methyl-6-(2-methyl-2H-indazol-5-yl)quinolin-2-yl)-3,6-dihydropyridine-1(2H)-carboxylate (70 mg, 0.15 mmol) was combined with 4:1 CH$_2$Cl$_2$:MeOH (1.5 mL) and 10% Pd/C (35 mg). The mixture was stirred at room temperature under H$_2$ (1 atm) for 4 h. The mixture was filtered through Celite. The filtrate was concentrated under vacuum. The residue was purified by silica gel chromatography (1:1 CH$_2$Cl$_2$:EtOAc, followed by 20% acetone in CH$_2$Cl$_2$). The collected material was triturated in ether. The solid was collected and dried to yield tert-butyl 4-(4-methyl-6-(2-methyl-2H-indazol-5-yl)quinolin-2-yl)piperidine-1-carboxylate (55 mg, 79%) as a white solid.

$^1$H NMR (acetone-d$_6$) δ: 8.32 (s, 1H), 8.30 (s, 1H), 8.12 (t, J=1.5 Hz, 1H), 8.04-8.11 (m, 2H), 7.73-7.78 (m, 2H), 7.37 (s, 1H), 4.27 (m, 5H), 3.03-3.14 (m, 1H), 2.85-3.01 (m, 2H), 2.82 (s, 3H), 1.95-2.03 (m, 2H), 1.82-1.92 (m, 2H), 1.49 (s, 9H).

Step L: tert-Butyl 4-(4-methyl-6-(2-methyl-2H-indazol-5-yl)quinolin-2-yl)piperidine-1-carboxylate (53 mg, 0.12 mmol) and 4 N HCl in 1,4-dioxane (1 mL, 4 mmol) were combined and heated at 50° C. for 1 h. The mixture was diluted with ether. The solid material was collected by vacuum filtration, washed with 9:1 CH$_2$Cl$_2$:MeOH and dried to yield 4-methyl-6-(2-methyl-2H-indazol-5-yl)-2-(piperidin-4-yl)quinoline hydrochloride (46 mg, 100%) as a yellow solid.

MS m/z 357.0 [M+H]$^+$; $^1$H NMR (DMSO-d$_6$) δ: 9.11-9.23 (br s, 1H), 8.95-9.10 (br s, 1H), 8.38-8.53 (m, 4H), 8.28 (s, 1H), 7.83 (dd, J=9 Hz, 1.5 Hz, 1H), 7.72-7.80 (m, 2H), 4.23 (s, 3H), 3.50-3.60 (m, 1H), 3.41-3.49 (m, 2H), 3.09 (m, 2H), 3.00 (s, 3H), 2.20-2.38 (m, 4H).

Example 25

Preparation of Compound 7

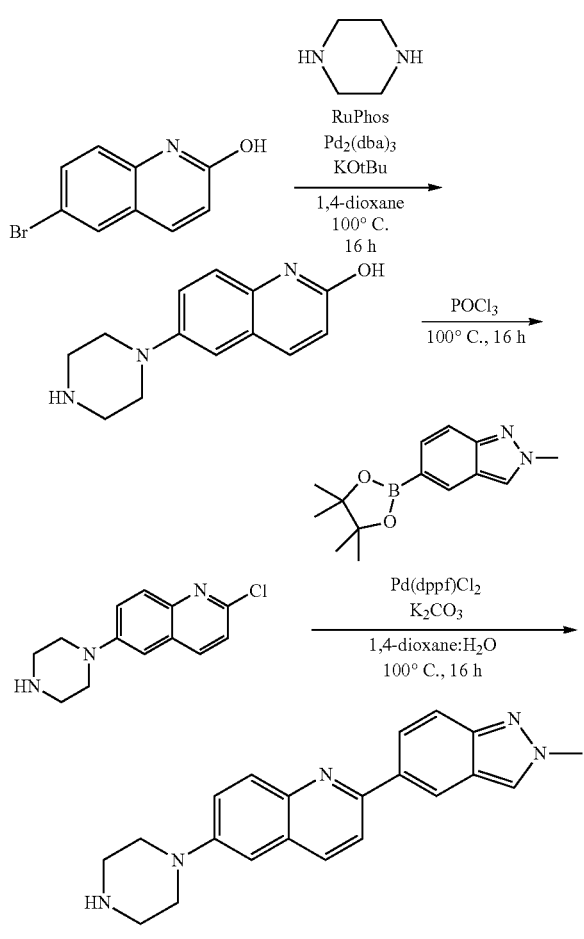

Step A: 6-Bromoquinolin-2-ol (670 mg, 3.0 mmol) was combined with piperazine (504 mg, 6.0 mmol), potassium tert-butoxide (840 mg, 7.5 mmol), 2-dicyclohexylphosphino-2',6'-diisopropoxybiphenyl (280 mg, 0.6 mmol) and tris(dibenzylideneacetone)dipalladium(0) (275 mg, 0.3 mmol) in 1,4-dioxane (10 mL). The mixture was heated at 100° C. for 16 h. The mixture was partitioned between EtOAc and H$_2$O. The organic layer was washed with brine, dried over Na$_2$SO$_4$, filtered and concentrated. The residue was chromatographed on silica gel, eluting with 0-20% MeOH in CH$_2$Cl$_2$ to yield 6-(piperazin-1-yl)quinolin-2-ol (575 mg, 84%). MS m/z 230.1 [M+H]$^+$.

Step B: 6-(Piperazin-1-yl)quinolin-2-ol (575 mg, 2.5 mmol) was suspended in POCl$_3$ (4.6 mL, 50 mmol). The mixture was heated at 100° C. for 16 h. The mixture was slowly added to a vigorously stirred mixture of CH$_2$Cl$_2$ (100 mL), H$_2$O (100 mL), and 10 g of (NaHCO$_3$). The organic layer was collected and concentrated. The residue was chromatographed on silica gel, eluting with 0-15% MeOH in CH$_2$Cl$_2$ to yield 2-chloro-6-(piperazin-1-yl)quinoline (280 mg, 45%). MS m/z 248.1, 250.1 [M+H]$^+$.

Step C: 2-Chloro-6-(piperazin-1-yl)quinoline (280 mg, 1.1 mmol) was combined with 2-methylindazole-5-boronic acid (387 mg, 1.5 mmol), 1,1'-bis(diphenylphosphino) ferrocene-palladium(II)dichloride dichloromethane complex (80 mg, 0.10 mmol), 1,4-dioxane (10 mL), and aqueous 1 M K$_2$CO$_3$ (5 mL, 5 mmol). The mixture was stirred at 100° C. for 16 h. The mixture was partitioned between EtOAc and H$_2$O. The organic layer was washed with brine, dried over Na$_2$SO$_4$, filtered and concentrated. The residue was chromatographed on silica gel, eluting with 0-15% MeOH in CH$_2$Cl$_2$ to yield 2-(2-methyl-2H-indazol-5-yl)-6-(piperazin-1-yl)quinoline (51 mg, 20%).

MS m/z 344.1 [M+H]$^+$; $^1$H NMR (DMSO-d$_6$) δ: 8.52 (s, 1H), 8.46 (s, 1H), 8.18-8.22 (m, 2H), 8.05 (d, J=8.5 Hz), 7.88 (d, J=9.0 Hz), 7.69 (d, J=9.0 Hz), 7.60 (d, J=8.5 Hz), 7.18 (s, 1H), 4.20 (s, 3H), 3.19-3.22 (m, 4H), 2.88-2.91 (m, 4H), NH proton not observed.

Example 26

Preparation of Compound 117

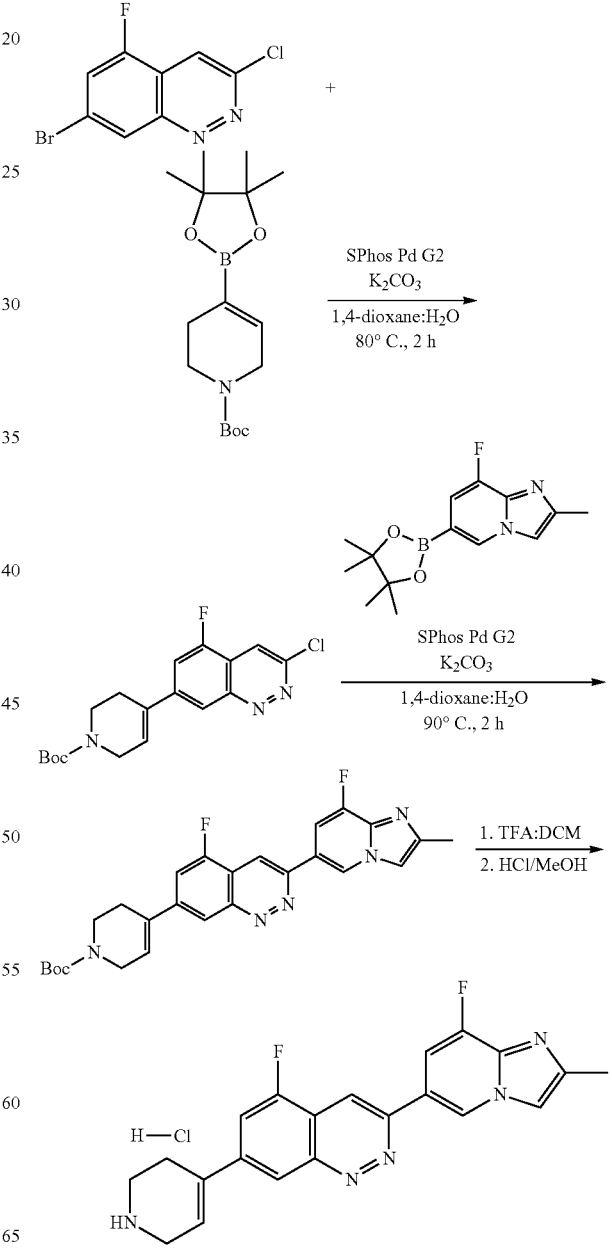

Step A: A mixture of 7-bromo-3-chloro-5-fluorocinnoline (120 mg, 0.46 mmol, prepared according to Example 7), tert-butyl 4-(4,4,5,5-tetramethyl-1,3,2-dioxaborolan-2-yl)-3,6-dihydropyridine-1(2H)-carboxylate (153 mg, 0.49 mmol), and chloro(2-dicyclohexylphosphino-2',6'-dimethoxy-1,1'-biphenyl)(2'-amino-1,1'-biphenyl-2-yl) palladium(II) (25 mg, 0.034 mmol) in 1,4-dioxane (3.5 mL) and aqueous 2 M $K_2CO_3$ (0.7 mL, 1.4 mmol) was heated to 80° C. for 2 h.

The crude reaction mixture was cooled to room temperature, filtered over celite, and concentrated. The residue was chromatographed on silica gel, eluting with 10-50% EtOAc in hexanes to yield tert-butyl 4-(3-chloro-5-fluorocinnolin-7-yl)-3,6-dihydropyridine-1(2H)-carboxylate (120 mg, 72%) as a tan solid. MS m/z 364.4, 366.4 [M+H]$^+$.

Step B: A mixture of 8-fluoro-2-methyl-6-(4,4,5,5-tetramethyl-1,3,2-dioxaborolan-2-yl)imidazo[1,2-a]pyridine (69 mg, 0.25 mmol), tert-butyl 4-(3-chloro-5-fluorocinnolin-7-yl)-3,6-dihydropyridine-1(2H)-carboxylate (60 mg, 0.16 mmol), and chloro(2-dicyclohexylphosphino-2',6'-dimethoxy-1,1'-biphenyl)(2'-amino-1,1'-biphenyl-2-yl) palladium(II) (12 mg, 0.016 mmol) in 1,4-dioxane (1.5 mL) and aqueous 2 M $K_2CO_3$ (0.25 mL, 0.5 mmol) was heated to 90° C. for 2 h. The mixture was cooled to room temperature, filtered over celite, and concentrated. The residue was chromatographed on silica gel, eluting with 5-10% MeOH in $CH_2Cl_2$ to yield tert-butyl 4-(5-fluoro-3-(8-fluoro-2-methylimidazo[1,2-a]pyridin-6-yl)cinnolin-7-yl)-3,6-dihydropyridine-1(2H)-carboxylate (54 mg, 69%) as a brown solid. MS m/z 478.5 [M+H]$^+$.

Step C: To a solution of tert-butyl 4-(5-fluoro-3-(8-fluoro-2-methylimidazo[1,2-a]pyridin-6-yl)cinnolin-7-yl)-3,6-dihydropyridine-1(2H)-carboxylate (54 mg, 0.11 mmol) in $CH_2Cl_2$ (1.5 mL) was added trifluoroacetic acid (1.5 mL). The reaction was stirred at room temperature for 15 minutes, then concentrated. The residue was dissolved in HCl in MeOH (1.25 M) and concentrated. This procedure was repeated once more to afford 5-fluoro-3-(8-fluoro-2-methylimidazo[1,2-a]pyridin-6-yl)-7-(1,2,3,6-tetrahydropyridin-4-yl)cinnoline hydrochloride (26 mg, 56%) as a yellow solid.

MS m/z 378.4 [M+H]$^+$; $^1$H NMR (DMSO-$d_6$) δ: 9.82 (s, 1H), 9.35-9.42 (br s, 2H), 8.92 (s, 1H), 8.64 (d, J=11.9 Hz, 1H), 8.43 (s, 1H), 8.21-8.25 (br s, 1H), 8.13 (d, J=11.6 Hz, 1H), 6.74-6.77 (br s, 1H), 3.87-3.92 (br s, 2H), 3.39-3.44 (m, 2H), 2.92-2.97 (m, 2H), 2.53 (s, 3H).

Using the procedure described for Example 26, above, additional compounds described herein were prepared by substituting the appropriate boronic acid in Step B, suitable reagents and reaction conditions, obtaining compounds such as those selected from:

| Cpd | Data |
| --- | --- |
| 134 | MS m/z 378.4 [M + H]$^+$; $^1$H NMR (DMSO-$d_6$) δ: 9.21-9.26 (br s, 2H), 8.77 (s, 1H), 8.65-8.74 (m, 2H), 8.38 (s, 1H), 8.12 (d, J = 13.4 Hz, 1H), 8.06 (d, J = 11.9 Hz, 1H), 6.70-6.74 (br s, 1H), 4.27 (s, 3H), 3.85-3.90 (m, 2H), 3.35-3.44 (m, 2H), 2.90-2.95 (m, 2H). |
| 156 | MS m/z 374.4 [M + H]$^+$; $^1$H NMR (methanol-$d_4$) δ: 9.65 (s, 1H), 8.89 (d, J = 1.0 Hz, 1H), 8.69 (t, J = 1.2 Hz, 1H), 8.46 (s, 1H), 8.14 (d, J = 0.9 Hz, 1H), 8.00 (dd, J = 11.1, 1.4 Hz, 1H), 6.67 (dt, J = 3.4, 1.8 Hz, 1H), 4.02 (d, J = 3.1 Hz, 2H), 3.61 (t, J = 6.1 Hz, 2H), 3.01-3.11 (m, 2H), 2.81 (s, 3H), 2.65 (s, 3H), NH and HCl protons not observed. |
| 157 | MS m/z 374.4 [M + H]$^+$; $^1$H NMR (methanol-$d_4$) δ: 8.82 (s, 1H), 8.58-8.61 (m, 2H), 8.38 (s, 1H), 8.14 (s, 1H), 7.97 (d, J = 10.4 Hz, 1H), 6.64-6.67 (m, 1H), 4.36 (s, 3H), 4.01-4.03 (m, 2H), 3.60 (t, J = 6.1 Hz, 2H), 3.04-3.08 (m, 2H), 2.75 (s, 3H), NH and HCl protons not observed. |
| 165 | MS m/z 378.4 [M + H]$^+$; $^1$H NMR (methanol-$d_4$) δ: 8.73 (d, J = 2.4 Hz, 1H), 8.37 (s, 1H), 7.66-7.72 (m, 1H), 7.62 (s, 1H), 7.50 (d, J = 11.4 Hz, 1H), 6.37-6.43 (m, 1H), 6.24-6.28 (m, 1H), 4.34-4.39 (s, 3H), 3.92-3.97 (m, 2H), 3.51-3.55 (m, 2H), 2.84-2.93 (m, 2H), NH and HCl protons not observed. |
| 166 | MS m/z 377.4 [M + H]$^+$; $^1$H NMR (methanol-$d_4$) δ: 8.70 (d, J = 9.8 Hz, 1H), 8.57 (dd, J = 2.4, 1.4 Hz, 1H), 8.44 (s, 1H), 8.31 (d, J = 8.9 Hz, 1H), 7.99 (s, 1H), 7.94 (m, 2H), 6.52 (br s, 1H), 4.29-4.36 (m, 3H), 3.98 (d, J = 2.1 Hz, 2H), 3.58 (dd, J = 7.8, 6.1 Hz, 2H), 2.96-3.04 (m, 2H), NH and HCl protons not observed. |
| 167 | MS m/z 375.4 [M + H]$^+$; $^1$H NMR (methanol-$d_4$) δ: 9.08 (s, 1H), 8.86 (s, 1H), 8.39 (s, 1H), 8.32 (s, 1H), 7.91 (d, J = 11.0 Hz, 1H), 6.57-6.59 (br s, 1H), 3.87-3.95 (m, 2H), 3.49 (t, J = 6.1 Hz, 2H), 2.94-2.98 (m, 2H), 2.78 (s, 3H), 2.59 (s, 3H), NH protons not observed. |
| 171 | MS m/z 379.4 [M + H]$^+$; $^1$H NMR (DMSO-$d_6$) δ: 9.20-9.25 (br s, 2H), 8.96 (s, 1H), 8.88 (s, 1H), 8.41 (s, 1H), 8.36 (d, J = 12.5 Hz, 1H), 8.11 (d, J = 11.6 Hz, 1H), 6.73-6.76 (br s, 1H), 4.62 (s, 3H), 3.87-3.91 (m, 2H), 3.39-3.44 (m, 2H), 2.92-2.97 (m, 2H). |
| 175 | MS m/z 385.4 [M + H]$^+$; $^1$H NMR (DMSO-$d_6$) δ: 9.25 (s, 1H), 9.05-9.10 (br s, 2H), 8.90 (s, 1H), 8.94 (s, 1H), 8.84 (s, 1H), 8.41 (s, 1H), 8.09 (d, J = 11.0 Hz, 1H), 6.72-6.75 (m, 1H), 4.32 (s, 3H), 3.88-3.92 (m, 2H), 3.40-3.45 (m, 2H), 2.91-2.96 (m, 2H). |
| 198 | MS m/z 388.3 [M + H]$^+$. $^1$H NMR (DMSO-$d_6$) δ: 8.67 (s, 1H), 8.65 (s, 1H), 8.52 (s, 1H), 8.37 (s, 1H), 8.08 (s, 1H), 7.86-7.88 (d, J = 11 Hz, 1H), 6.45 (t, J = 6.5 Hz, 1H), 4.34 (s, 3H), 3.97 (m, 2H), 3.00 (m, 2H), 2.65 (s, 3H), 2.37 (m, 2H), 2.02, (m, 2H). NH proton not observed. |

Example 27

Preparation of Compound 128

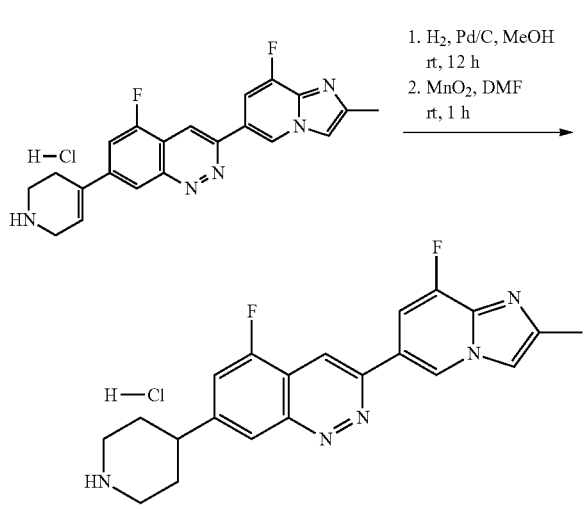

A suspension of 5-fluoro-3-(8-fluoro-2-methylimidazo[1,2-a]pyridin-6-yl)-7-(1,2,3,6-tetrahydropyridin-4-yl)cinnoline hydrochloride (22 mg, 0.05 mmol) and Pd/C (20 mg) in MeOH (2 mL) was stirred under $H_2$ (1 atm) at room temperature for 12 h. The mixture was filtered over celite and concentrated. The residue was dissolved in DMF (1 mL). To the solution was added $MnO_2$ (45 mg, 0.5 mmol). The reaction was stirred at room temperature for 1h, then filtered over celite. The filtrate was concentrated. The residue was dissolved in 1.25 M HCl in MeOH. Concentration afforded 5-fluoro-3-(8-fluoro-2-methylimidazo[1,2-a]pyridin-6-yl)-7-(piperidin-4-yl)cinnoline hydrochloride (15 mg, 62%) as a yellow solid.

MS m/z 380.4 [M+H]$^+$; $^1$H NMR (methanol-$d_4$) δ: 9.69 (s, 1H), 8.93 (s, 1H), 8.79 (d, J=11.0 Hz, 1H), 8.33 (s, 1H), 8.25 (s, 1H), 7.74 (d, J=10.7 Hz, 1H), 3.61 (d, J=12.5 Hz, 2H), 3.21-3.35 (m, 3H), 2.65 (s, 3H), 2.31 (d, J=14.0 Hz, 2H), 2.00-2.18 (m, 2H), NH and HCl protons not observed.

Using the procedure described for Example 27, above, additional compounds described herein were prepared by substituting suitable reagents and reaction conditions, obtaining compounds such as those selected from:

Example 28

Preparation of Compound 144

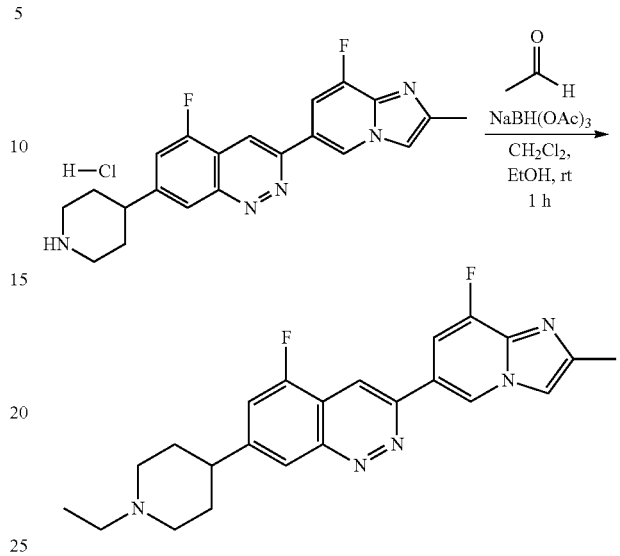

To a suspension of 5-fluoro-3-(8-fluoro-2-methylimidazo[1,2-a]pyridin-6-yl)-7-(piperidin-4-yl)cinnoline hydrochloride (175 mg, 0.42 mmol) and sodium triacetoxyborohydride (900 mg, 4.2 mmol) in $CH_2Cl_2$ (4 mL) and EtOH (1 mL) was added a solution of acetaldehyde (0.25 mL, 4.4 mmol) in EtOH (1 mL). The reaction was stirred at room temperature for 1 h, then quenched with saturated aqueous $K_2CO_3$. The mixture was partitioned between $CH_2Cl_2$ and $H_2O$. The aqueous layer was extracted once with $CH_2Cl_2$. The combined organics were dried over $Na_2SO_4$ filtered and concentrated. The residue was chromatographed on silica gel, eluting with 0-20% 1.4 N $NH_3$/MeOH in $CH_2Cl_2$ to yield 7-(1-ethylpiperidin-4-yl)-5-fluoro-3-(8-fluoro-2-methylimidazo[1,2-a]pyridin-6-yl)cinnoline (120 mg, 70%) as a light orange solid.

MS m/z 408.5 [M+H]$^+$; $^1$H NMR (methanol-$d_4$) δ: 9.29 (d, J=1.2 Hz, 1H), 8.70 (s, 1H), 8.22 (s, 1H), 8.01 (dd, J=12.2, 1.2 Hz, 1H), 7.88 (d, J=2.1 Hz, 1H), 7.65 (d, J=10.7 Hz, 1H), 3.36-3.39 (m, 2H), 2.98-3.09 (m, 1H), 2.76 (q, J=7.2 Hz, 2H), 2.44-2.55 (m, 5H), 2.16 (d, J=13.1 Hz, 2H), 1.95-2.03 (m, 2H), 1.27 (t, J=7.2 Hz, 3H).

| Cpd | Data |
|---|---|
| 151 | MS m/z 380.4 [M + H]$^+$; $^1$H NMR (methanol-$d_4$) δ: 8.71 (s, 1H), 8.47-8.57 (m, 2H), 8.23 (s, 1H), 8.02 (d, J = 12.2 Hz, 1H), 7.64 (d, J = 10.1 Hz, 1H), 4.31 (s, 3H), 3.62 (d, J = 11.6 Hz, 2H), 3.21-3.29 (m, 3H), 2.32 (d, J = 13.4 Hz, 2H), 1.97-2.15 (m, 2H), NH and HCl protons not observed. |
| 177 | MS m/z 376.4 [M + H]$^+$; $^1$H NMR (DMSO-$d_6$) δ: 9.00-9.07 (br s, 1H), 8.87-8.95 (br s, 1H), 8.60-8.66 (m, 2H), 8.51 (s, 1H), 8.17 (s, 1H), 8.06 (s, 1H), 7.68 (d, J = 10.5 Hz, 1H), 4.23 (s, 3H), 3.46-3.55 (m, 1H), 3.15-3.22 (m, 2H), 3.01-3.10 (br s, 2H), 2.64 (s, 3H), 2.12-2.19 (m, 2H), 1.98-2.07 (m, 2H). |
| 185 | MS m/z 377.3 [M + H]$^+$; $^1$H NMR (methanol-$d_4$) δ: 9.21 (s, 1H), 9.01 (s, 1H), 8.45 (s, 1H), 8.38 (s, 1H), 7.78 (d, J = 9.5 Hz, 1H), 3.63 (d, J = 12.5 Hz, 2H), 3.23-3.40 (m, 3H), 2.90 (s, 3H), 2.71 (s, 3H), 2.34 (d, J = 14.0 Hz, 2H), 2.06-2.17 (m, 2H), NH and HCl protons not observed. |
| 192 | MS m/z 379.4 [M + H]$^+$; $^1$H NMR (methanol-$d_4$) δ: 8.46 (d, J = 2.4 Hz, 1H), 8.35-8.40 (m, 2H), 8.16 (d, J = 8.9 Hz, 1H), 8.03 (dd, J = 13.2, 1.1 Hz, 1H), 7.61 (s, 1H), 7.48 (dd, J = 11.9, 1.5 Hz, 1H), 4.29 (s, 3H), 3.30 (br s, 2H), 2.88-3.01 (m, 3H), 2.04 (d, J = 12.5 Hz, 2H), 1.80-1.90 (m, 2H), NH proton not observed. |

Using the procedure described for Example 28 above, additional compounds described herein were prepared by substituting suitable reagents and reaction conditions, obtaining compounds such as those selected from:

| Cpd | Data |
|---|---|
| 153 | MS m/z 406.5 [M + H]+; 1H NMR (methanol-$d_4$) δ: 8.83 (s, 1H), 8.55 (d, J = 1.5 Hz, 2H), 8.38 (s, 1H), 8.01 (dd, J = 12.8, 1.2 Hz, 1H), 7.97 (dd, J = 11.3, 1.2 Hz, 1H), 6.63-6.67 (br s, 1H), 4.32 (s, 3H), 4.25 (d, J = 13.1 Hz, 1H), 3.88-4.01 (m, 2H), 3.38-3.50 (m, 3H), 3.10-3.18 (m, 2H), 1.49 (t, J = 7.3 Hz, 3H), HCl proton not observed. |
| 154 | MS m/z 408.5 [M + H]+; 1H NMR (methanol-$d_4$) δ: 8.66-8.71 (m, 1H), 8.48-8.54 (m, 2H), 8.21 (s, 1H), 8.01 (dd, J = 12.8, 1.2 Hz, 1H), 7.63 (d, J = 10.7 Hz, 1H), 4.31 (s, 3H), 3.42-3.55 (m, 2H), 3.12 (t, J = 12.4 Hz, 1H), 2.91-2.97 (m, 2H), 2.70-2.78 (m, 2H), 2.23 (d, J = 13.1 Hz, 2H), 1.98-2.14 (m, 2H), 1.33 (t, J = 7.3 Hz, 3H). |
| 183 | MS m/z 404.4 [M + H]+; 1H NMR (DMSO-$d_6$) δ: 8.63 (d, J = 6.4 Hz, 2H), 8.51 (s, 1H), 8.18 (s, 1H), 8.06 (s, 1H), 7.74 (d, J = 10.4 Hz, 1H), 4.23 (s, 3H), 3.12-3.25 (m, 3H), 2.86-2.96 (m, 2H), 2.64 (s, 3H), 2.45-2.55 (m, 2H), 1.97-2.05 (m, 2H), 1.84-1.91 (m, 2H), 1.06-1.17 (m, 3H). |
| 184 | MS m/z 405.5 [M + H]+; 1H NMR (methanol-$d_4$) δ: 8.83 (d, J = 9.5 Hz, 1H), 8.61 (d, J = 2.3 Hz, 1H), 8.45 (s, 1H), 8.35 (d, J = 8.5 Hz, 1H), 8.07 (s, 1H), 8.02 (d, J = 11.7 Hz, 1H), 7.91 (d, J = 12.4 Hz, 1H), 6.54 (br s, 1H), 4.33 (s, 3H), 4.22 (d, J = 15.4 Hz, 1H), 3.81-3.99 (m, 2H), 3.37-3.49 (m, 3H), 3.04-3.15 (m, 2H), 1.48 (t, J = 7.2 Hz, 3H). |
| 186 | MS m/z 405.3 [M + H]+; 1H NMR (methanol-$d_4$) δ: 9.04 (d, J = 0.9 Hz, 1H), 8.39 (d, J = 1.2 Hz, 1H), 8.27 (s, 1H), 8.05 (d, J = 0.9 Hz, 1H), 7.66-7.73 (m, 1H), 3.47 (d, J = 11.9 Hz, 2H), 3.07-3.17 (m, 1H), 2.90 (q, J = 7.2 Hz, 2H), 2.76 (d, J = 0.9 Hz, 3H), 2.69 (t, J = 11.6 Hz, 2H), 2.54 (s, 3H), 2.23 (d, J = 13.7 Hz, 2H), 2.04 (qd, J = 12.9, 3.5 Hz, 2H), 1.32 (t, J = 7.3 Hz, 3H). |
| 193 | MS m/z 407.5 [M + H]+; 1H NMR (methanol-$d_4$) δ: 8.47 (d, J = 2.4 Hz, 1H), 8.37-8.41 (m, 2H), 8.18 (d, J = 8.7 Hz, 1H), 8.04 (d, J = 13.3 Hz, 1H), 7.63 (s, 1H), 7.49 (d, J = 12.2 Hz, 1H), 4.30 (s, 3H), 3.42-3.52 (m, 2H), 2.87-3.01 (m, 3H), 2.59-2.76 (m, 2H), 2.15 (d, J = 16.6 Hz, 2H), 2.00 (m, 2H), 1.32 (t, J = 7.3 Hz, 3H). |
| 201 | MS m/z 406.3 [M + H]+; 1H NMR (methanol-$d_4$) δ: 9.58 (s, 1H), 8.89 (s, 1H), 8.50 (d, J = 2.6 Hz, 1H), 8.24 (d, J = 14.3 Hz, 1H), 7.97 (d, J = 11.6 Hz, 1H), 7.91 (s, 1H), 6.50 (br s, 1H), 4.29 (s, 3H), 2.92 (t, J = 6.7 Hz, 2H), 2.77-2.83 (m, 2H), 2.70 (d, J = 7.3 Hz, 2H), 1.31 (br s, 2H), 1.25 (t, J = 7.2 Hz, 3H). |
| 202 | MS m/z 408.3 [M + H]+; 1H NMR (methanol-$d_4$) δ: 9.59 (br s, 1H), 8.91 (br s, 1H), 8.51 (br s, 1H), 8.25 (d, J = 13.1 Hz, 1H), 7.82 (br s, 1H), 7.74 (d, J = 12.4 Hz, 1H), 4.30 (br s, 3H), 3.68 (d, J = 9.3 Hz, 2H), 3.20 (br s, 3H), 3.08 (br s, 2H), 2.28 (d, J = 14.8 Hz, 2H), 1.99-2.12 (m, 2H), 1.35-1.44 (t, J = 7.2 Hz, 3H). |

Example 29

Preparation of Compound 108

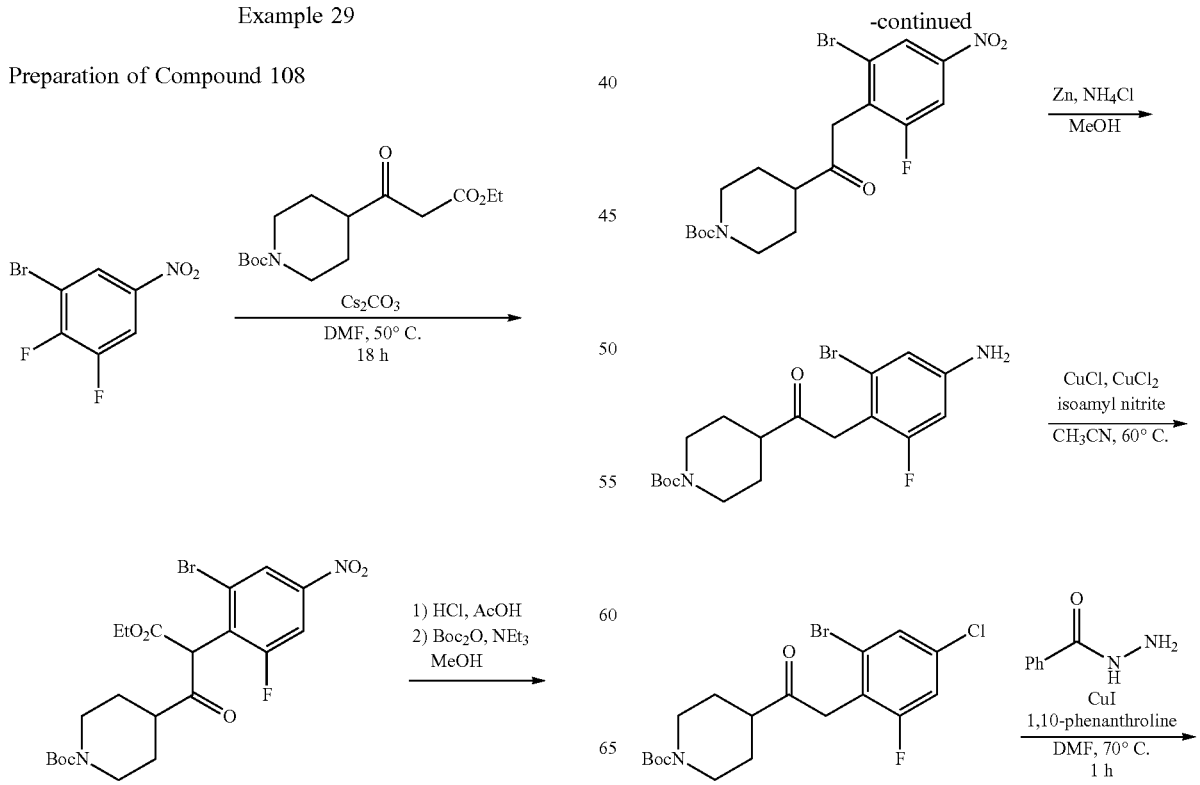

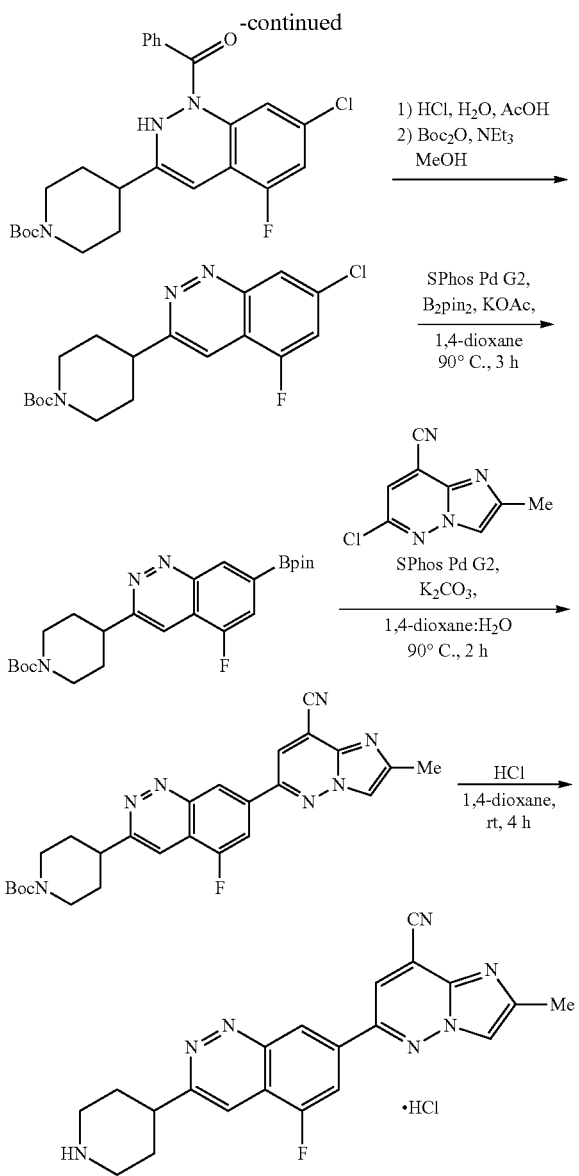

Step A: 1-Bromo-2,3-difluoro-5-nitrobenzene (10.0 g, 42.0 mmol, prepared in Example 7, Step A) was combined with tert-butyl 4-(3-ethoxy-3-oxo-propanoyl)piperidine-1-carboxylate (13.8 g, 46.2 mmol) in DMF (100 mL). To the solution was added $Cs_2CO_3$ (27.4 g, 84.0 mmol). The mixture turned dark red upon addition. The mixture was stirred at 60° C. for 4 h. The mixture was partitioned between EtOAc and aqueous 0.5 M HCl. The organic layer was washed with brine, dried over $Na_2SO_4$, filtered and concentrated to yield tert-butyl 4-[2-(2-bromo-6-fluoro-4-nitro-phenyl)-3-ethoxy-3-oxo-propanoyl]piperidine-1-carboxylate (21.5 g) as a crude oil. MS m/z 515.5, 517.5 [M–H]⁻.

Step B: The crude material from Step A was suspended in AcOH (40 mL) and conc. aqueous HCl (37 mass %, 40 mL). The mixture was heated at 120° C. for 4 h, then 100° C. for 16 h. Volatiles were removed under reduced pressure. The residue was dissolved in MeOH (100 mL) and triethylamine (23.4 mL, 168.0 mmol). To the mixture was added di-tert-butyl dicarbonate (13.7 g, 63.0 mmol). The mixture was stirred at room temperature for 30 min. The volatile material was removed from the mixture under reduced pressure. The residue was chromatographed on silica gel, eluting with 0-20% EtOAc in $CH_2Cl_2$ to yield tert-butyl 4-[2-(2-bromo-6-fluoro-4-nitro-phenyl)acetyl]piperidine-1-carboxylate (10.2 g, 55%). MS m/z 443.5, 445.5 [M–H]⁻.

Step C: tert-Butyl 4-[2-(2-bromo-6-fluoro-4-nitro-phenyl)acetyl]piperidine-1-carboxylate (10 g, 22.5 mmol) was combined with Zn (73.2, 112 mmol), $NH_4Cl$ (24.1 g, 450 mmol) and MeOH (100 mL). The mixture was stirred at 40° C. for 3 h. The mixture was diluted with EtOAc and filtered through celite. The filtrate was concentrated to yield tert-butyl 4-[2-(4-amino-2-bromo-6-fluoro-phenyl)acetyl]piperidine-1-carboxylate (9.5 g, 100%). MS m/z 315.2, 317.2 [M-Boc+H]⁺.

Step D: tert-Butyl 4-[2-(4-amino-2-bromo-6-fluoro-phenyl)acetyl]piperidine-1-carboxylate (9.5 g, 23 mmol) was combined with CuCl (4.6 g, 46 mmol), $CuCl_2$ (9.3 g, 69 mmol) and $CH_3CN$ (100 mL). To the mixture was added isoamyl nitrite (9.3 mL, 69 mmol) dropwise at 0° C. The mixture was stirred at 60° C. for 2 h. The mixture was partitioned between EtOAc and $H_2O$. The organic layer was washed with brine, dried over $Na_2SO_4$, filtered and concentrated. The residue was chromatographed on silica gel, eluting with 0-40% EtOAc in hexanes to yield tert-butyl 4-[2-(2-bromo-4-chloro-6-fluoro-phenyl)acetyl]piperidine-1-carboxylate (7.5 g, 75% Yield). ¹H NMR (acetone-d₆) H: 7.56 (t, J=1.7 Hz, 1H), 7.34 (dd, J=9.1, 1.9 Hz, 1H), 4.15 (d, J=1.9 Hz, 2H), 4.11 (br d, J=12.0 Hz, 2H), 2.78-2.96 (m, 3H), 1.98 (br d, J=12.3 Hz, 2H), 1.48-1.58 (m, 2H), 1.46 (s, 9H).

Step E: tert-Butyl 4-[2-(2-bromo-4-chloro-6-fluoro-phenyl)acetyl]piperidine-1-carboxylate (7.5 g, 17 mmol) was combined benzoyl hydrazide (3.6 g, 26 mmol), CuI (0.32 g, 1.7 mmol), 1,10-phenanthroline (0.31 g, 1.7 mmol) and sodium tert-butoxide (3.36 g, 35 mmol) in DMF (50 mL). The mixture was stirred under $N_2$ at 70° C. for 1 h. The mixture was partitioned between EtOAc and 0.25 M HCl (aq). The organic layer was washed with brine, dried over $Na_2SO_4$, filtered and concentrated. The residue was chromatographed on silica gel, eluting with 0-40% EtOAc in hexanes to yield tert-butyl 4-(1-benzoyl-7-chloro-5-fluoro-2H-cinnolin-3-yl)piperidine-1-carboxylate (6.4 g, 79%). MS m/z 470.6, 472.6 [M–H]⁻.

Step F: tert-Butyl 4-(1-benzoyl-7-chloro-5-fluoro-2H-cinnolin-3-yl)piperidine-1-carboxylate (6.2 g, 13 mmol) was suspended in conc. aqueous HCl (37 mass %, 30 mL) and EtOH (20 mL). The mixture was heated at 100° C. for 24 h. The mixture was cooled to 60° C. Air was bubbled through the mixture for 5 h. The volatile material was removed with a stream of $N_2$. To the crude residue was added MeOH (50 mL), triethylamine (7.4 mL, 53 mmol) and then di-tert-butyl dicarbonate (5.7 g, 26 mmol). The mixture was stirred at room temperature for 30 min. The volatiles were removed under reduced pressure. The residue was chromatographed on silica gel, eluting with 0-60% EtOAc in hexanes to yield tert-butyl 4-(7-chloro-5-fluoro-cinnolin-3-yl)piperidine-1-carboxylate (3.0 g, 62%).

MS m/z 310.2, 312.2 [M-tBu+H]⁺. ¹H NMR (acetone-d₆) δ: 8.38 (s, 1H), 8.09 (s, 1H), 7.71 (dd, J=9.5, 1.9 Hz, 1H), 4.26-4.38 (m, 2H), 3.49 (tt, J=12.0, 3.7 Hz, 1H), 3.00 (br s, 2H), 2.10-2.15 (m, 2H) 1.95 (qd, J=12.6, 4.4 Hz, 2H), 1.49 (s, 9H).

Step G: Powdered tert-butyl 4-(7-chloro-5-fluoro-cinnolin-3-yl)piperidine-1-carboxylate (1.00 g, 2.73 mmol) was weighed into a 50-mL screw-cap tube, followed by anhydrous 1,4-dioxane (27 mL), followed by (Bpin)₂ (0.76 g, 3.0 mmol), SPhos Pd G2 pre-catalyst (0.20 g, 0.27 mmol), and powdered potassium acetate (1.02 g, 10.4 mmol) last. The yellow mixture was then sparged for 2 minutes with argon, the headspace was purged, and the vial was capped and sealed tightly. The vial was placed in an aluminum heating block and stirred vigorously at 90° C. for 3 h. After this time, the reaction mixture was cooled to room temperature. The dark-brown reaction mixture was filtered through Celite. The Celite was washed with EtOAc (60 mL). The brown filtrate was then washed with water (60 mL), 50% aq. NaHCO$_3$ (2×60 mL), and brine (60 mL), then dried over anhydrous Na$_2$SO$_4$, filtered, and concentrated under reduced pressure to afford tert-butyl 4-[5-fluoro-7-(4,4,5,5-tetramethyl-1,3,2-dioxaborolan-2-yl)cinnolin-3-yl]piperidine-1-carboxylate as a crude, dark brown powder without further purification.

MS m/z 490.5 [M+MeOH+H]$^+$; $^1$H NMR (chloroform-d) δ: ppm 8.84 (s, 1H), 7.87 (s, 1H), 7.72 (d, J=9.5 Hz, 1H), 4.37 (br s, 2H), 3.45 (It, 1H), 2.98 (br s, 2H), 2.16 (br d, J=13.6 Hz, 2H), 1.93 (qd, J=12.6, 4.0, 2H), 1.52 (s, 12H), 1.42 (s, 9H).

Step H: A screw-top vial was charged with solid 6-chloro-2-methyl-imidazo[1,2-b]pyridazine-8-carbonitrile (0.14 g, 0.72 mmol) and anhydrous 1,4-dioxane (6.56 mL), followed by tert-butyl 4-[5-fluoro-7-(4,4,5,5-tetramethyl-1,3,2-dioxaborolan-2-yl)cinnolin-3-yl]piperidine-1-carboxylate (0.30 g, 0.66 mmol), SPhos Pd G2 pre-catalyst (0.047 g, 0.065 mmol), granular K$_2$CO$_3$ (0.27 g, 1.96 mmol), and water (0.33 mL). The brown mixture was sparged with argon for 5 minutes, then sealed with a screw cap. The reaction mixture was stirred vigorously at 90° C. for 3 h. The reaction mixture was cooled to room temperature, diluted with EtOAc (100 mL), washed with water (2×100 mL) and brine (100 mL), then dried over anhydrous Na$_2$SO$_4$, filtered, and concentrated under reduced pressure. The dark-brown, crude material was purified by silica gel column chromatography (hexanes/EtOAc gradient elution) to afford tert-butyl 4-[7-(8-cyano-2-methyl-imidazo[1,2-b]pyridazin-6-yl)-5-fluoro-cinnolin-3-yl]piperidine-1-carboxylate (0.182 g, 57%) as a yellow powder.

MS m/z 488.5 [M+H]$^+$; $^1$H NMR (chloroform-d) δ: 8.87 (s, 1H), 8.18 (d, J=10.2 Hz, 1H), 8.03 (s, 1H), 8.00 (s, 1H), 7.91 (s, 1H), 4.37 (br d, J=5.6 Hz, 2H), 3.49 (tt, J=12.0, 3.4 Hz, 1H), 2.98 (br t, J=12.2 Hz, 2H), 2.63 (s, 3H), 2.16 (br d, J=12.5 Hz, 2H), 1.93 (qd, J=12.6, 4.0 Hz, 2H), 1.50 (s, 9H).

Step I: tert-Butyl 4-[7-(8-cyano-2-methyl-imidazo[1,2-b]pyridazin-6-yl)-5-fluoro-cinnolin-3-yl]piperidine-1-carboxylate (0.060 g, 0.12 mmol) was dissolved in anhydrous 1,4-dioxane (4 mL), and a 4.0 M solution of HCl in 1,4-dioxane (0.15 mL, 0.60 mmol) was added. The reaction mixture was stirred at room temperature for 4 h, after which time the reaction mixture was concentrated on a rotovap. The crude product was triturated in Et$_2$O (5 mL), then dried under high vacuum to afford 6-[5-fluoro-3-(4-piperidyl)cinnolin-7-yl]-2-methyl-imidazo[1,2-b]pyridazine-8-carbonitrile hydrochloride (0.060 g, 100%) as a tan solid.

MS m/z 388.4 [M+H]$^+$; $^1$H NMR (methanol-d$_4$) δ: 9.11 (s, 1H), 8.81 (s, 1H), 8.42 (d, J=11.3 Hz, 1H), 8.37 (s, 1H), 8.30 (s, 1H), 3.58-3.77 (m, 5H), 2.63 (s, 3H), 2.21-2.47 (m, 4H).

Using the procedure described for Example 29, above, additional compounds described herein were prepared by substituting the appropriate aryl halide in Step H, suitable reagents and reaction conditions, obtaining compounds such as those selected from:

| Cpd | Data |
|---|---|
| 91 | MS m/z 363.4 [M + H]$^+$; $^1$H NMR (methanol-d$_4$) δ: 9.77 (d, J = 2.4 Hz, 1H), 9.54 (d, J = 2.1 Hz, 1H), 8.84 (s, 1H), 8.35 (s, 1H), 8.16 (d, J = 9.2 Hz, 1H), 8.08 (s, 1H), 3.61-3.70 (m, 3H), 3.28-3.37 (m, 2H), 2.67 (s, 3H), 2.31-2.44 (m, 4H), NH and HCl protons not observed. |
| 92 | MS m/z 380.4 [M + H]$^+$; $^1$H NMR (methanol-d$_4$) δ: 9.27 (d, J = 1.2 Hz, 1H), 8.78 (s, 1H), 8.46 (dd, J = 11.0, 1.2 Hz, 1H), 8.31 (s, 1H), 8.21 (s, 1H), 8.12 (dd, J = 10.4, 1.5 Hz, 1H), 3.59-3.69 (m, 3H), 3.27-3.37 (m, 2H), 2.66 (d, J = 0.9 Hz, 3H), 2.32-2.45 (m, 4H), NH and HCl protons not observed. |
| 93 | MS m/z 387.5 [M + H]$^+$; $^1$H NMR (methanol-d$_4$) δ: 9.61 (d, J = 1.5 Hz, 1H), 9.01 (d, J = 1.5 Hz, 1H), 8.80 (s, 1H), 8.31 (s, 1H), 8.21 (d, J = 1.2 Hz, 1H), 8.13 (dd, J = 10.5, 1.7 Hz, 1H), 3.60-3.70 (m, 3H), 3.28-3.36 (m, 2H), 2.66 (d, J = 0.9 Hz, 3H), 2.31-2.45 (m, 4H), NH and HCl protons not observed. |
| 94 | MS m/z 363.4 [M + H]$^+$; $^1$H NMR (methanol-d$_4$) δ: 9.47 (s, 1H), 8.75 (s, 1H), 8.44 (br d, J = 9.5 Hz, 1H), 8.29 (s, 1H), 8.15 (dd, J = 10.7, 1.5 Hz, 1H), 7.99 (d, J = 9.5 Hz, 1H), 3.60-3.69 (m, 3H), 3.25-3.37 (m, 2H), 2.69 (s, 3H), 2.30-2.44 (m, 4H), NH and HCl protons not observed. |
| 95 | MS m/z 362.4 [M + H]$^+$; $^1$H NMR (methanol-d$_4$) δ: 8.61 (s, 2H), 8.47 (s, 1H), 8.40 (s, 1H), 8.19 (dd, J = 10.7, 1.2 Hz, 1H), 8.03 (dd, J = 9.0, 1.7 Hz, 1H), 7.87 (d, J = 9.2 Hz, 1H), 4.36 (s, 3H), 3.62-3.70 (m, 3H), 2.39-2.46 (m, 2H), 2.28-2.39 (m, 2H), NH and HCl protons not observed; CH$_2$ obscured by solvent peak. |
| 96 | MS m/z 380.4 [M + H]$^+$; $^1$H NMR (methanol-d$_4$) δ: 8.99 (s, 1H), 8.51 (d, J = 17.4 Hz, 2H), 8.32 (d, J = 10.7 Hz, 1H), 8.18 (s, 1H), 7.59 (d, J = 12.2 Hz, 1H), 4.25 (s, 3H), 3.72 (t, J = 10.1 Hz, 1H), 3.61 (d, J = 12.2 Hz, 2H), 3.28-3.32 (m, 2H), 2.22-2.47 (m, 4H), NH and HCl protons not observed. |
| 97 | MS m/z 380.4 [M + H]$^+$; $^1$H NMR (methanol-d$_4$) δ: 9.06 (s, 1H), 8.84 (s, 1H), 8.60 (s, 1H), 8.41 (br d, J = 7.0 Hz, 1H), 8.22 (br d, J = 10.1 Hz, 1H), 7.66 (d, J = 11.3 Hz, 1H), 4.40 (s, 3H), 3.82 (t, J = 10.4 Hz, 1H), 3.68 (d, J = 12.5 Hz, 2H), 3.35-3.42 (m, 2H), 2.47 (d, J = 11.9 Hz, 2H), 2.33-2.44 (m, 2H), NH and HCl protons not observed. |
| 99 | MS m/z 363.4 [M + H]$^+$; $^1$H NMR (methanol-d$_4$) δ: 9.14 (s, 1H), 8.59 (d, J = 9.8 Hz, 1H), 8.47 (d, J = 10.1 Hz, 1H), 8.44 (dd, J = 10.7, 1.5 Hz, 1H), 8.41 (s, 1H), 8.31 (s, 1H), 3.60-3.70 (m, 3H), 3.30-3.35 (m, 2H), 2.67 (d, J = 0.9 Hz, 3H), 2.31-2.43 (m, 4H), NH and HCl protons not observed. |
| 101 | MS m/z 376.5 [M + H]$^+$; $^1$H NMR (methanol-d$_4$) δ: 8.84 (d, J = 1.2 Hz, 1H), 8.81 (s, 1H), 8.39 (s, 2H), 8.29 (s, 1H), 8.21 (dd, J = 10.4, 1.2 Hz, 1H), 3.62-3.67 (m, 3H), 3.28-3.33 (m, 2H), 3.04 (s, 3H), 2.55 (s, 3H), 2.30-2.43 (m, 4H), NH and HCl protons not observed. |

| Cpd | Data |
|---|---|
| 103 | MS m/z 376.5 [M + H]$^+$; $^1$H NMR (methanol-d$_4$) δ: 9.21 (s, 1H), 8.75 (s, 1H), 8.27-8.39 (m, 2H), 8.12 (d, J = 10.6 Hz, 1H), 8.08 (s, 1H), 3.62-3.69 (m, 3H), 3.29-3.36 (m, 2H), 2.78 (s, 3H), 2.65 (s, 3H), 2.30-2.45 (m, 4H), NH and HCl protons not observed. |
| 104 | MS m/z 387.4 [M + H]$^+$; $^1$H NMR (methanol-d$_4$) δ: 8.67 (d, J = 1.5 Hz, 1H), 8.64 (s, 1H), 8.64 (br s, 1H), 8.63 (br s, 1H), 8.42 (d, J = 1.5 Hz, 1H), 8.25 (br d, J = 10.1 Hz, 1H), 4.36 (s, 3H), 3.69-3.75 (m, 1H), 3.66 (d, J = 12.8 Hz, 2H), 2.42 (d, J = 12.5 Hz, 2H), 2.35 (qd, J = 12.8, 3.4 Hz, 2H), NH and HCl protons not observed, CH$_2$ obscured by solvent peak. |
| 105 | MS m/z 391.2 [M + H]$^+$; $^1$H NMR (chloroform-d) δ: 8.86 (s, 1H), 8.23 (dd, J = 10.8, 1.5 Hz, 1H), 7.92 (s, 1H), 7.81 (d, J = 0.7 Hz, 1H), 7.53 (s, 1H), 3.42-3.52 (m, 1H), 3.33 (br d, J = 12.2 Hz, 2H), 3.20 (q, J = 7.6 Hz, 2H), 2.87-2.96 (m, 2H), 2.56 (s, 3H), 2.14-2.22 (m, 2H), 1.92 (dq, J = 11.2, 4.2 Hz, 2H), 1.51 (t, J = 7.6 Hz, 3H), NH proton not observed. |
| 106 | MS m/z 393.1 [M + H]$^+$; $^1$H NMR (DMSO-d$_6$) δ: 9.18 (s, 1H), 8.39 (dd, J = 11, 1.5 Hz, 1H), 8.16 (s, 1H), 8.09 (d, J = 0.7 Hz, 1H), 7.56 (s, 1H), 4.22 (s, 3H), 3.47-3.56 (m, 3H), 3.01-3.09 (m, 2H), 2.39 (s, 3H), 2.07-2.24 (m, 4H), NH proton not observed. |
| 107 | MS m/z 393.1 [M + H]$^+$; $^1$H NMR (DMSO-d$_6$) δ: 8.93 (s, 1H), 8.32 (d, J = 11 Hz, 1H), 8.19 (s, 1H), 8.13 (s, 1H), 7.99 (s, 1H), 5.77 (br s, 1H), 4.99 (s, 2H), 3.12-3.20 (m, 3H), 2.71-2.80 (m, 2H), 2.43 (s, 3H), 1.96-2.03 (m, 2H), 1.82-1.96 (m, 2H), NH proton not observed. |
| 109 | MS m/z 380.4 [M + H]$^+$; $^1$H NMR (methanol-d$_4$) δ: 9.22 (s, 1H), 8.75 (s, 1H), 8.60 (s, 1H), 8.31 (d, J = 10.4 Hz, 1H), 7.82 (t, J = 8.2 Hz, 1H), 7.68 (d, J = 8.9 Hz, 1H), 4.37 (s, 3H), 3.85 (t, J = 11.3 Hz, 1H), 3.68 (d, J = 12.2 Hz, 2H), 3.34-3.42 (m, 2H), 2.48 (d, J = 12.8 Hz, 2H), 2.39 (q, J = 11.8 Hz, 2H), NH and HCl protons not observed. |
| 112 | MS m/z 403.1 [M + H]$^+$; $^1$H NMR (chloroform-d) δ: 8.78 (s, 1H), 8.22 (d, J = 12 Hz, 1H), 7.90 (s, 1H), 7.80 (s, 1H), 7.10 (s, 1H), 3.33-3.49 (m, 1H), 3.31 (d, J = 12.4 Hz, 2H), 2.90 (t, J = 12.2 Hz, 2H), 2.70-2.74 (m, 1H), 2.56 (s, 3H), 2.17 (d, J = 12.4 Hz, 2H), 1.85-1.92 (m, 2H), 1.25-1.38 (m, 2H), 1.22-1.25 (m, 2H), NH proton not observed. |
| 118 | MS m/z 393.1 [M + H]$^+$; $^1$H NMR (chloroform-d) δ: 8.59 (s, 1H), 8.03 (d, J = 1.2 Hz, 1H), 7.91 (s, 1H), 7.74 (dd, J = 10.4, 1.2 Hz, 1H), 7.63 (s, 1H), 3.43-3.50 (m, 3H), 3.01 (t, J = 12 Hz, 2H), 2.90 (s, 3H), 2.83 (s, 3H), 2.25 (d, J = 13.2 Hz, 2H), 2.03-2.06 (m, 2H), NH proton not observed. |
| 126 | MS m/z 377.2 [M + H]$^+$; $^1$H NMR (DMSO-d$_6$) δ: 9.13 (s, 1H), 8.41 (d, J = 10.5 Hz, 1H), 8.11 (s, 1H), 7.33 (s, 1H), 3.43 (s, 2H), 3.24 (s, 1H), 3.16 (d, J = 12.0 Hz, 2H), 2.78 (s, 3H), 2.55 (s, 3H), 2.05-1.82 (m, 4H), NH protons not observed. |
| 133 | MS m/z 394.1 [M + H]$^+$; $^1$H NMR (melhanol-d$_4$) δ: 9.03 (s, 1H), 8.47 (dd, J = 11.2, 1.6 Hz, 1H), 8.24 (s, 1H), 8.22 (s, 1H), 3.59-3.63 (m, 3H), 3.24-3.28 (m, 2H), 2.92 (s, 3H), 2.85 (s, 3H), 2.29-2.37 (m, 4H), NH proton observed. |
| 137 | MS m/z 378.0 [M + H]$^+$; $^1$H NMR (DMSO-d$_6$) δ: 9.00 (s, 1H), 8.29 (d, J = 9.8 Hz, 1H), 8.16 (s, 1H), 7.63 (s, 1H), 3.22-3.31 (m, 1H), 3.14 (d, J = 11.9 Hz, 2H), 2.76 (s, 3H), 2.71 (d, J = 11.0 Hz, 2H), 2.60 (s, 3H), 1.97-2.00 (m, 2H), 1.82-1.93 (m, 2H). |
| 148 | MS m/z 378.1 [M + H]$^+$; $^1$H NMR (chloroform-d) δ: 8.91 (s, 1H), 8.54 (dd, J = 11, 1.6 Hz, 1H), 7.89 (s, 2H), 3.42-3.48 (m, 1H), 3.33 (br d, J = 12 Hz, 2H), 2.89-2.95 (m, 2H), 2.73 (s, 6H), 2.16-2.19 (m, 2H), 1.92-1.96 (m, 2H), NH proton not observed. |
| 148 | MS m/z 394.1 [M + H]$^+$; $^1$H NMR (chloroform-d) δ: 8.89 (s, 1H), 8.33 (dd, J = 10, 1.2 Hz, 1H), 7.91 (s, 1H), 7.59 (s, 1H), 3.44-3.50 (m, 1H), 3.33 (d, J = 12.4 Hz, 2H), 3.04 (s, 3H), 2.89-2.95 (m, 2H), 2.68 (s, 3H), 2.18 (d, J = 12.4 Hz, 2H), 1.90-1.94 (m, 2H), NH proton not observed. |
| 162 | MS m/z 377.1 [M + H]$^+$; $^1$H NMR (chloroform-d) δ: 8.89 (s, 1H), 8.38 (dd, J = 9.6, 1.2 Hz, 1H), 8.24 (s, 1H), 7.91 (s, 1H), 7.79 (s, 1H), 4.32 (s, 3H), 3.38-3.51 (m, 3H), 2.94-3.00 (m, 2H), 2.78 (s, 3H), 2.21-2.24 (m, 2H), 1.97-2.07 (m, 2H), NH proton not observed. |
| 163 | MS m/z 393.1 [M + H]$^+$; $^1$H NMR (chloroform-d) δ: 8.88 (s, 1H), 8.42 (dd, J = 10.8, 1.2 Hz, 1H), 8.20 (s, 1H), 7.97 (s, 1H), 7.31 (s, 1H), 4.29 (s, 3H), 4.23 (s, 3H), 3.57-3.62 (m, 3H), 3.05-3.15 (m, 4H), 2.31-2.36 (m, 2H), NH proton not observed. |
| 172 | MS m/z 391.2 [M + H]$^+$; $^1$H NMR (DMSO-d$_6$) δ: 9.06 (s, 1H), 8.74 (s, 1H), 8.44-8.57 (m, 1H), 8.08 (d, J = 12.9 Hz, 2H), 4.26 (s, 3H), 3.03-3.20 (m, 4H), 2.95 (d, J = 7.9 Hz, 1H), 2.71 (t, J = 11.6 Hz, 2H), 1.97 (d, J = 11.9 Hz, 2H), 1.85 (qd, J = 12.3, 3.9 Hz, 2H), 1.44 (t, J = 7.6 Hz, 3H). |
| 187 | MS m/z 402.2 [M + H]$^+$; $^1$H NMR (chloroform-d) δ: 8.94 (s, 1H), 8.62 (br s, 1H); 8.23 (dd, J = 10.4, 1.2 Hz, 1H), 7.99 (s, 1H), 7.90 (s, 1H), 7.86 (s, 1H), 4.32 (s, 2H), 3.56-3.60 (m, 3H), 3.11 (br s, 2H), 2.56 (s, 3H), 2.26-2.35 (m, 4H). |
| 194 | MS m/z 429.1 [M + H]$^+$; $^1$H NMR (methanol-d$_4$) δ: 9.29 (s, 1H), 9.15 (s, 1H) 8.55 (br s, 2H), 8.27-8.28 (m, 2H), 8.19 (s, 1H), 7.33 (s, 1H), 3.60-3.64 (m, 3H), 3.25-3.29 (m, 2H), 2.58 (s, 3H), 2.30-2.41 (m, 4H), NH proton not observed. |
| 195 | MS m/z 455.2 [M + H]$^+$; $^1$H NMR (methanol-d$_4$) δ: 8.59 (s, 1H), 8.25 (dd, J = 10.8, 1.2 Hz, 1H), 8.21 (s, 1H), 8.09 (s, 1H), 7.61-7.65 (m, 2H), 7.42-7.49 (m, 3H), 6.96 (s, 1H), 3.59-3.63 (m, 3H), 3.25-3.28 (m, 2H), 2.55 (s, 3H), 2.27-2.38 (m, 4H), NH proton not observed. |
| 196 | MS m/z 394.0 [M + H]$^+$; $^1$H NMR (DMSO-d$_6$) δ: 9.00 (s, 1H), 8.30-8.48 (m, 2H), 8.17 (s, 1H), 7.80 (s, 1H), 3.44-3.51 (m, 1H), 3.33 (d, J = 10.2 Hz, 2H), 2.89-3.00 (m, 2H), 2.75 (s, 3H), 2.60 (s, 3H), 2.00-2.17 (m, 4H). |

-continued

| Cpd | Data |
|---|---|
| 204 | MS m/z 405.2 [M + H]+; 1H NMR (methanol-d4) δ: 8.93 (s, 1H), 8.33 (dd, J = 10.9, 1.3 Hz, 1H), 8.20 (s, 1H), 8.01 (d, J = 0.6 Hz, 1H), 7.86 (s, 1H), 3.43-3.50 (m, 2H), 3.26-3.31 (m, 1H), 3.09 (t, J = 8 Hz, 2H), 2.91-2.98 (m, 2H), 2.53 (s, 3H), 2.17 (d, J = 12.2 Hz, 2H), 1.90-2.08 (m, 4H), 1.12 (t, J = 7.4 Hz, 3H), NH proton not observed. |
| 207 | MS m/z 407.2 [M + H]+; 1H NMR (methanol-d4) δ: 9.05 (s, 1H), 8.42 (dd, J = 10.8, 1.2 Hz, 1H), 8.28 (s, 1H), 8.15 (s, 1H), 8.10 (s, 1H), 4.10 (t, J = 6 Hz, 2H), 3.63-3.66 (br s, 3H), 3.35-3.36 (m, 2H), 3.28-3.32 (m, 2H), 2.58 (s, 3H), 2.32-2.42 (m, 4H), NH and OH protons not observed. |
| 211 | MS m/z 405.2 [M + H]+; 1H NMR (methanol-d4) δ: 8.94 (s, 1H), 8.33 (dd, J = 10.9, 1.3 Hz, 1H), 8.19 (s, 1H), 8.01 (d, J = 0.7 Hz, 1H), 7.82 (s, 1H), 3.74-3.67 (m, 1H), 3.48-3.44 (m, 1H), 3.36 (s, 2H), 2.97 (td, J = 12.5, 2.6 Hz, 2H), 2.53 (s, 3H), 2.19 (d, J = 12.7 Hz, 2H), 3.01-2.94 (m, 2H), 1.53 (d, J = 6.9 Hz, 6H). NH proton not observed. |

Halides for use in Step H were prepared according to the following procedures:

Example 29-1

8-(((tert-Butyldimethylsilyl)oxy)methyl)-6-chloro-2-methylimidazo[1,2-b]pyridazine Step A: To ethyl 3-amino-6-chloropyridazine-4-carboxylate (4.0 g, 19.9 mmol) in dry THF (1 mL) was slowly added LiAlH4 (2.42 g, 64 mmol) at 0° C. The mixture was stirred at 0° C. for 30 min. Excess reagent was quenched carefully with water (1 mL), then 15% aqueous NaOH (1 mL) was added. The mixture was partitioned between EtOAc and H2O. The organic layer was washed with brine, dried over Na2SO4, filtered and concentrated. The residue was chromatographed on silica gel, eluting with 0-35% EtOAc in petroleum ether to yield (3-amino-6-chloropyridazin-4-yl)methanol (1.0 g, 32%). MS m/z 160.1, 162.1 [M+H]+.

Step B: (3-Amino-6-chloropyridazin-4-yl)methanol (1.0 g, 6.3 mmol) was combined with DIEA (2.44 g, 18.8 mmol) and 1-bromopropan-2-one (860 mg, 6.3 mmol) in isopropyl alcohol (10 mL). The reaction vessel was degassed and then charged with nitrogen three times. The mixture was stirred at 80° C. for 16 h. The mixture was partitioned between EtOAc and H2O. The organic layer was washed with brine, dried over Na2SO4, filtered and concentrated. The residue was chromatographed on silica gel, eluting with 0-50% EtOAc in petroleum ether to yield (6-chloro-2-methylimidazo[1,2-b]pyridazin-8-yl)methanol (0.9 g, 73%). MS m/z 198.2, 200.2 [M+H]+.

Step C: (6-chloro-2-methylimidazo[1,2-b]pyridazin-8-yl)methanol (900 mg, 4.5 mmol) was combined with TBS-Cl (1.72 g, 9.1 mmol) and imidazole (1.24 g, 14.6 mmol) in CH2Cl2 (15 mL). The mixture was stirred at room temperature for 16 h. The mixture was partitioned between EtOAc and H2O. The organic layer was washed with brine, dried over Na2SO4, filtered and concentrated. The residue was chromatographed on silica gel, eluting with 0-20% EtOAc in petroleum ether to yield 8-(((tert-butyldimethylsilyl)oxy)methyl)-6-chloro-2-methylimidazo[1,2-b]pyridazine (500 mg, 35.2% yield). MS m/z 312.1, 314.1 [M+H]+.

Example 29-2

6-Chloro-8-ethyl-2-methylimidazo[1,2-b]pyridazine

Step A: 6-Chloropyridazin-3-amine (50 g, 388 mmol) and NaHCO3 (65 g, 775 mmol) were combined in MeOH (500 mL). To the mixture was added Br2 (30 mL, 580 mmol) dropwise at 0° C. The mixture was stirred at room temperature for 16 h. One half of the volume of solvent was removed under reduced pressure. The remaining was poured into ice water. The solid formed was collected and dried to yield 4-bromo-6-chloropyridazin-3-amine (80 g, 99%). MS m/z 207.9 [M+H]+.

Step B: 4-Bromo-6-chloropyridazin-3-amine (20 g, 97 mmol), Na2CO3 (10.2 g, 97 mmol) and 1-bromopropan-2-one (9.7 mL, 116 mmol) were added into isopropyl alcohol (200 mL). The reaction vessel was degassed and then charged with nitrogen three times. The mixture was stirred at 90° C. for 16 h. The mixture was partitioned between EtOAc and H2O. The organic layer was washed with brine, dried over Na2SO4, filtered and concentrated. The residue was chromatographed on silica gel, eluting with 0-20% EtOAc in petroleum ether to yield 8-bromo-6-chloro-2-methylimidazo[1,2-b]pyridazine (8.1 g, 34%). MS m/z 245.9, 247.9 [M+H]+.

Step C: 8-Bromo-6-chloro-2-methylimidazo[1,2-b]pyridazine (200 mg, 0.82 mmol) was combined with triethylborane (1M in THF, 2 mL, 2 mmol), K2CO3 (283 mg, 2.05 mmol) and Pd(PPh3)4 (92 mg, 0.08 mmol) in DMF (3 mL). The reaction vessel was degassed and then charged with nitrogen three times. The mixture was stirred at 100° C. for 5 h. The mixture was partitioned between EtOAc and H2O. The organic layer was washed with brine, dried over Na2SO4, filtered and concentrated. The residue was chromatographed on silica gel, eluting with 0-35% EtOAc in petroleum ether to yield 6-chloro-8-ethyl-2-methylimidazo[1,2-b]pyridazine (80 mg, 50%). MS m/z 196.0, 198.0 [M+H]+.

Example 29-3

6-Chloro-8-cyclopropyl-2-methylimidazo[1,2-b]pyridazine

A mixture of 8-bromo-6-chloro-2-methylimidazo[1,2-b]pyridazine (1.2 g, 4.9 mmol), cyclopropylboronic acid (843 mg, 9.8 mmol), Pd(dppf)Cl2 (359 mg, 0.49 mmol) and Na2CO3 (1.56 g, 14.7 mmol) in 1,4-dioxane (12 mL) and water (3 mL) was stirred at 90° C. under N2 for 48 h. The mixture was partitioned between EtOAc and H2O. The organic layer was washed with brine, dried over Na2SO4, filtered and concentrated. The residue was chromatographed on silica gel, eluting with 0-35% EtOAc in petroleum ether to yield 6-chloro-8-cyclopropyl-2-methylimidazo[1,2-b]pyridazine (405 mg, 40%). MS m/z 208.0, 210.0 [M+H]+.

Example 29-4

6-Chloro-2-methylimidazo[1,2-b]pyridazine-8-carbonitrile

8-Bromo-6-chloro-2-methylimidazo[1,2-b]pyridazine (1.2 g, 4.9 mmol) was combined with Zn(CN)2 (850 mg, 7.3 mmol) and Pd(PPh$_3$)$_4$ (570 mg, 0.49 mmol) in DMF (20 mL). The reaction vessel was degassed and then charged with nitrogen three times. The mixture was stirred at 100° C. for 1 h under μwave irradiation. The mixture was partitioned between EtOAc and H$_2$O. The organic layer was washed with brine, dried over Na$_2$SO$_4$, filtered and concentrated. The residue was chromatographed on silica gel, eluting with 0-35% EtOAc in petroleum ether to yield 6-chloro-2-methylimidazo[1,2-b]pyridazine-8-carbonitrile (0.5 g, 53%). MS m/z 193.0, 195.0 [M+H]$^+$.

Example 29-5

6-bromo-2,4-dimethylbenzo[d]thiazole

Step A: 2,4-Dibromo-6-methylaniline (3.8 g, 14.5 mmol) was combined with KOAc (1.56 g, 15.9 mmol) and acetic anhydride (5.5 mL, 58 mmol) in toluene (40 mL). The mixture was stirred at room temperature for 16 h. The solvent was removed in vacuo. The residue was chromatographed on silica gel, eluting with 0-35% EtOAc in petroleum ether to yield N-(2,4-dibromo-6-methylphenyl)acetamide (3.9 g, 82%). MS m/z 305.9, 308.0 [M+H]$^+$.

Step B: N-(2,4-Dibromo-6-methylphenyl)acetamide (4.0 g, 13 mmol) was combined with Lawesson's reagent (10.6 g, 26 mmol) in toluene (40 mL). The mixture was stirred at 110° C. for 16 h. The solvent was removed in vacuo. The residue was chromatographed on silica gel, eluting with 0-35% EtOAc in petroleum ether to yield N-(2,4-dibromo-6-methylphenyl)ethanethioamide (3.9 g, 93%). MS m/z, 322.9, 324.9 [M+H]$^+$.

Step C: N-(2,4-Dibromo-6-methylphenyl)ethanethioamide (3.8 g, 11.8 mmol) was dissolved in NMP (40 mL). To the solution was added NaH (94.7 mg, 2.4 mmol) in portions at room temperature. The reaction vessel was degassed and then charged with nitrogen three times. The mixture was stirred at 120° C. for 2 h. The mixture was partitioned between EtOAc and H$_2$O. The organic layer was washed with brine, dried over Na$_2$SO$_4$, filtered and concentrated. The residue was chromatographed on silica gel, eluting with 0-25% EtOAc in petroleum ether to yield 6-bromo-2,4-dimethylbenzo[d]thiazole (369 mg, 12%). MS m/z 241.9, 243.9 [M+H]$^+$.

Example 29-6

5-Chloro-2,7-dimethyl-3-((2-(trimethylsilyl)ethoxy)methyl)-3H-imidazo[4,5-b]pyridine Step A: 6-Chloro-4-methyl-3-nitropyridin-2-amine (187 mg, 1 mmol), iron powder (56 mg, 10 mmol) in AcOH (3 mL) was stirred at 100° C. for 16 h. The mixture was concentrated. To the residue was added aqueous NaOH (2 N) until pH>9. The mixture was filtered through Celite. The filtrate was extracted with EtOAc (50 mL×3). The organic layer was washed with brine, dried over Na$_2$SO$_4$ and concentrated to afford 5-chloro-2,7-dimethyl-3H-imidazo[4,5-b]pyridine, which was used without further purification (154 mg crude, 85% crude). MS m/z 182.0, 184.0 [M+H]$^+$.

Step B: 5-Chloro-2,7-dimethyl-3H-imidazo[4,5-b]pyridine (1.1 g, 6.07 mmol) was dissolved in THF (30 mL). To the mixture was added NaH (310 mg, 7.9 mmol) in portions at 0° C. After stirring the mixture at 0° C. for 10 min, 2-(trimethylsilyl)ethoxymethyl chloride (1.2 mL, 6.69 mmol) was added. The resulting mixture was stirred at room temperature for 2 h. MeOH (10 mL) was added to the solution, after which all volatile material was removed under reduced pressure. The residue was chromatographed on silica gel, eluting with 25% EtOAc in petroleum ether to afford a mixture of N-alkylated products, which was used without separation (900 mg, 76%). MS m/z 312.0, 314.0 [M+H]$^+$.

Example 29-7

5-Chloro-2,7-dimethyloxazolo[5,4-b]pyridine

Step A: A solution of 2,6-dichloro-4-methylnicotinonitrile (3 g, 16 mmol) in H$_2$SO$_4$ (15 mL) was stirred at 80° C. for 4 h. The mixture was cooled to room temperature, and then poured into ice water (100 mL). The suspension was filtered. The filter cake was washed with water to afford 2,6-dichloro-4-methylnicotinamide (3.2 g, 91%) as a yellow solid. MS m/z 204.9, 206.9 [M+H]$^+$.

Step B: To a solution of NaOH (3.7 g, 93 mmol) in H$_2$O (100 mL) was added Br$_2$ (4.7 g, 29.4 mmol) dropwise at 0° C. The mixture was stirred at 0° C. for 1 h before adding 2,6-dichloro-4-methylnicotinamide (5 g, 24.5 mmol). The mixture was allowed to warm to room temperature gradually over 1 h. The mixture was then heated to 75° C. for 1 h. The resulting suspension was cooled to room temperature with stirring overnight. The suspension was filtered. The collected solid material was washed with water to afford 2,6-dichloro-4-methylpyridin-3-amine (3.3 g, 76%). MS m/z 176.9, 178.9 [M+H]$^+$.

Step C: To a solution of 2,6-dichloro-4-methylpyridin-3-amine (3 g, 17 mmol) in toluene (50 mL) was added KOAc (2 g, 20.4 mmol) and Ac$_2$O (6.9 g, 68 mmol). The mixture was stirred at 70° C. for 48 h. The mixture was cooled to room temperature, and then poured into ice water (100 mL). The water was extracted with EtOAc (60 mL×3). The combined organic phases were concentrated under reduced pressure. The residue was chromatographed on silica gel eluting with 25% EtOAc in petroleum ether to afford N-(2,6-dichloro-4-methylpyridin-3-yl) acetamide (842 mg, 22%) as a yellow solid. MS m/z 219.0, 221.0 [M+H]$^+$.

Step D: To a solution of N-(2,6-dichloro-4-methylpyridin-3-yl)acetamide (700 mg, 3.2 mmol) in NMP (10 mL) was added NaH (128 mg, 3.2 mmol) in portions at room temperature. The reaction vessel was degassed and then charged with nitrogen three times. The mixture was stirred at 120° C. for 2 h. The mixture was partitioned between EtOAc and H$_2$O. The organic layer was washed with brine, dried over Na$_2$SO$_4$, filtered and concentrated. The residue was chromatographed on silica gel, eluting with 0-25% EtOAc in petroleum ether to yield 5-chloro-2,7-dimethyloxazolo[5,4-b]pyridine (400 mg, 68%). MS m/z 183.1, 185.1 [M+H]$^+$.

Example 29-8

5-Chloro-2,7-dimethylthiazolo[5,4-b]pyridine

N-(2,6-dichloro-4-methylpyridin-3-yl)acetamide (1.6 g, 7.3 mmol) was combined with Lawesson's reagent (5.93 g, 14.7 mmol) in toluene (20 mL). The mixture was stirred at 110° C. for 16 h. The solvent was removed under reduced pressure. The residue was chromatographed on silica gel, eluting with 0-35% EtOAc in petroleum ether to yield 5-chloro-2,7-dimethylthiazolo[5,4-b]pyridine (500 mg, 34.4% yield). MS m/z 199.0, 201.0 [M+H]$^+$.

Example 29-9

2-Bromo-4,6-dimethyloxazolo[4,5-c]pyridine

Step A: 2,6-Dimethylpyridin-4-ol (3 g, 24.3 mmol) was added in portions to conc. HNO$_3$ (11 mL). Conc. H$_2$SO$_4$ (16 mL) was then added slowly while keeping the temperature below 20° C. The mixture was stirred at room temperature for 3 h. The mixture was then slowly poured onto ice and neutralized with $K_2CO_3$. The mixture was extracted with $CH_2Cl_2$. The organic phases were concentrated under reduced pressure. The residue was chromatographed on silica gel, eluting with 10-20% MeOH in $CH_2Cl_2$ to afford 2,6-dimethyl-3-nitropyridin-4-ol as a white solid (3.69 g, 90%). MS m/z 169.1 $[M+H]^+$.

Step B: A mixture of 2,6-dimethyl-3-nitropyridin-4-ol (1.68 g, 10 mmol) and 10% Pd/C (106 mg, 0.1 mmol) in MeOH (16 mL) was stirred under $H_2$ for 16 h. The mixture was filtered over Celite to afford 3-amino-2,6-dimethylpyridin-4-ol as a white solid (1.3 g, 95%). MS m/z 139.0 $[M+H]^+$.

Step C: To a solution of 3-amino-2,6-dimethylpyridin-4-ol (1.38 g, 10 mmol) in EtOH (10 mL) was added cyanogen bromide (1.16 g, 11 mmol) at room temperature. The mixture was stirred at room temperature for 16 h. A precipitate was formed and collected by filtration. The solid material was dried to afford 4,6-dimethyloxazolo[4,5-c]pyridin-2-amine as a white solid (1.2 g, 75%). MS m/z 164.1 $[M+H]^+$.

Step D: To a mixture of 4,6-dimethyloxazolo[4,5-c]pyridin-2-amine (600 mg, 3.7 mmol) and $CuBr_2$ (2.5 g, 11.1 mmol) in $CH_3CN$ (6 mL) was added t-butylnitrite (1.3 mL, 11.1 mmol) at 0° C. The mixture was stirred at 0° C. for 10 min and then stirred at 55° C. for 2 h. The reaction mixture was made basic with sat. $NaHCO_3$ and then extracted with EtOAc (200 mL). The organic layer was washed with brine, dried over $Na_2SO_4$ and concentrated. The residue was chromatographed on silica gel, eluting 10-20% EtOAc in petroleum ether to afford 2-bromo-4,6-dimethyloxazolo[4,5-c]pyridine as a white solid (416 mg, 50% yield). MS m/z 227.0, 229.0 $[M+H]^+$.

Example 29-10

2-Bromo-4,6-dimethylthiazolo[4,5-c]pyridine

Step A: 4-Chloro-2,6-dimethyl-3-nitropyridine (4.7 g, 25 mmol) was combined with Fe powder (4.24 mg, 75 mmol) in AcOH (40 mL). The mixture was stirred at 70° C. for 2 h. The volatile material was removed under reduced pressure. The residue was partitioned between EtOAc and $H_2O$. The organic layer was washed with brine, dried over $Na_2SO_4$, filtered and concentrated. The residue was chromatographed on silica gel, eluting with 0-80% EtOAc in petroleum ether to yield 4-chloro-2,6-dimethylpyridin-3-amine (4.0 g, 99%). MS m/z 157.2, 159.2 $[M+H]^+$.

Step B: 4-Chloro-2,6-dimethylpyridin-3-amine (3.8 g, 24 mmol) was combined with benzoyl isothiocyanate (4.77 g, 29 mmol) in acetone (40 mL) and the mixture was stirred at 56° C. for 2 h. The solvent was removed under reduced pressure. The residue was chromatographed on silica gel, eluting with 0-50% EtOAc in petroleum ether to yield N-(4,6-dimethylthiazolo[4,5-c]pyridin-2-yl)benzamide (6.5 g, 95%). MS m/z 284.2 $[M+H]^+$.

Step C: N-(4,6-Dimethylthiazolo[4,5-c]pyridin-2-yl)benzamide (4.5 g,16 mmol) was combined with NaOH (1.27 g, 32 mmol) in $H_2O$ (10 mL) and MeOH (30 mL). The mixture was stirred at 100° C. for 1 h under µwave irradiation. The volatile material was removed under reduced pressure. The residue was chromatographed on silica gel, eluting with 0-60% EtOAc in petroleum ether to yield 4,6-dimethylthiazolo[4,5-c]pyridin-2-amine (2.7 g, 95%). MS m/z 180.0 $[M+H]^+$.

Step D: 4,6-Dimethylthiazolo[4,5-c]pyridin-2-amine (2.7 g, 15 mmol) was combined with isobutyl nitrite (4.67 g, 45 mmol) and $CuBr_2$ (16.8 g, 75 mmol) in $CH_3CN$ (30 mL). The mixture was stirred at 50° C. for 0.5 h. The volatile material was removed under reduced pressure. The residue was chromatographed on silica gel, eluting with 0-50% EtOAc in petroleum ether to yield 2-bromo-4,6-dimethylthiazolo[4,5-c]pyridine (1.0 g, 27%). MS m/z 242.9, 245 $[M+H]^+$.

Example 29-11

5-Chloro-2,7-dimethyl-2H-pyrazolo[4,3-b]pyridine

Step A: 6-Chloro-2-methylpyridin-3-amine (40 g, 282 mmol) was combined with AcOH (32 mL) in MeOH (400 mL). To the solution was added $Br_2$ (26 mL, 507 mmol) dropwise at 0° C. The mixture was stirred at room temperature for 16 h. The volatile material was removed under reduced pressure. The residual reagent was quenched by the addition of aqueous $NaHSO_3$. The aqueous solution was neutralized with aqueous sat'd $NaHCO_3$ and extracted with EtOAc. The organic layer was washed with brine, dried over $Na_2SO_4$, filtered and concentrated. The residue was chromatographed on silica gel, eluting with 0-20% EtOAc in petroleum ether to yield 4-bromo-6-chloro-2-methylpyridin-3-amine (60 g, 97%). MS m/z 220.9, 222.9 $[M+H]^+$.

Step B: 4-Bromo-6-chloro-2-methylpyridin-3-amine (13 g, 59 mmol) was combined with isobutyl nitrite (9.13 g, 89 mmol), KOAc (13.3 g, 136 mmol) and AcOH (34 ml, 590 mmol) in toluene (130 mL). The mixture was stirred at 60° C. for 10 h. The volatile material was removed under reduced pressure. The residue was treated with aqueous sat'd $NaHCO_3$. The mixture was diluted with $H_2O$ and extracted with EtOAc. The organic layer was washed with brine, dried over $Na_2SO_4$, filtered and concentrated. The residue was chromatographed on silica gel, eluting with 0-30% EtOAc in petroleum ether to yield 7-bromo-5-chloro-2H-pyrazolo[4,3-b]pyridine (3.7 g, 27%). MS m/z 232.0, 234.0 $[M+H]^+$.

Step C: 7-Bromo-5-chloro-2H-pyrazolo[4,3-b]pyridine (3.7 g, 16 mmol) was combined with $K_2CO_3$ (4.4 g, 32 mmol) and iodomethane (2.7 g, 19 mmol) in DMF (40 mL). The mixture was stirred at room temperature for 1 h. The mixture was partitioned between EtOAc and $H_2O$. The organic layer was washed with brine, dried over $Na_2SO_4$, filtered and concentrated. The residue was chromatographed on silica gel, eluting with 0-20% EtOAc in petroleum ether to yield 7-bromo-5-chloro-2-methyl-2H-pyrazolo[4,3-b]pyridine (1.5 g, 38%). MS m/z 245.9, 247.9 $[M+H]^+$.

Step D: 7-Bromo-5-chloro-2-methyl-2H-pyrazolo[4,3-b]pyridine (3.0 g, 12 mmol) was combined with 2,4,6-trimethyl-1,3,5,2,4,6-trioxatriborinane (5.2 mL, 18 mmol), $K_2CO_3$ (6.7 g, 49 mmol) and $Pd(PPh_3)_4$ (707 mg, 0.6 mmol) in DMF (30 mL). The reaction mixture was degassed and then charged with nitrogen three times. The mixture was stirred at 100° C. for 5 h. The mixture was partitioned between EtOAc and $H_2O$. The organic layer was washed with brine, dried over $Na_2SO_4$, filtered and concentrated. The residue was chromatographed on silica gel, eluting with 0-35% EtOAc in petroleum ether to yield 5-chloro-2,7-dimethyl-2H-pyrazolo[4,3-b]pyridine (1.2 g, 54%). MS m/z 182.0, 184.0 $[M+H]^+$.

Example 29-12

5-Chloro-7-methoxy-2-methyl-2H-pyrazolo[4,3-b]pyridine

7-Bromo-5-chloro-2-methyl-2H-pyrazolo[4,3-b]pyridine (250 mg, 1.0 mmol) was combined with MeOH (0.2 mL, 5 mmol) and K$_2$CO$_3$ (296.7 mg, 2.15 mmol) in CH$_3$CN (5 mL). The mixture was stirred at room temperature for 16 h. The mixture was partitioned between EtOAc and H$_2$O. The organic layer was washed with brine, dried over Na$_2$SO$_4$, filtered and concentrated. The residue was chromatographed on silica gel, eluting with 0-25% EtOAc in petroleum ether to yield (190 mg, 80%). MS m/z 198.0, 200.0 [M+H]$^+$.

Example 29-13

5-Chloro-7-ethyl-2-methyl-2H-pyrazolo[4,3-b]pyridine

7-Bromo-5-chloro-2-methyl-2H-pyrazolo[4,3-b]pyridine (200 mg, 0.8 mmol) was combined with triethylborane (1 M in THF, 1.95 mL, 1.95 mmol), K$_2$CO$_3$ (441.6 g, 3.2 mmol) and Pd(PPh$_3$)$_4$ (30 mg, 0.04 mmol) in DMF (3 mL). The reaction mixture was degassed and then charged with nitrogen three times. The mixture was stirred at 100° C. for 5 h. The mixture was partitioned between EtOAc and H$_2$O. The organic layer was washed with brine, dried over Na$_2$SO$_4$, filtered and concentrated. The residue was chromatographed on silica gel, eluting with 0-35% EtOAc in petroleum ether to yield 5-chloro-7-ethyl-2-methyl-2H-pyrazolo[4,3-b]pyridine (72 mg, 45%). MS m/z 196.0, 198.0 [M+H]$^+$.

Example 29-14

2-Bromo-4,6-dimethylthiazolo[5,4-c]pyridine

Step A: A mixture of 2,6-dimethylpyridin-4-amine (0.5 g, 4.07 mmol) and bromine (0.21 mL, 4.07 mmol) in acetic acid (1 mL) was stirred at room temperature for 2 h. The mixture was treated with aqueous 20% sodium hydroxide (10 mL) and extracted with 30 mL CH$_2$Cl$_2$. The combined organics were washed with brine, dried over Na$_2$SO$_4$ and concentrated. The residue was suspended in hot heptanes. The solid material was collected and dried to yield 3-bromo-2,6-dimethylpyridin-4-amine (0.43 g, 52%). MS m/z 201.1, 203.1 [M+H]$^+$.

Step B: A mixture of 3-bromo-2,6-dimethylpyridin-4-amine (400 mg, 2 mmol) and benzoyl isothiocyanate (296 μL, 2.2 mmol) in THF (4 mL) was stirred at 45° C. for 2 h. The mixture was concentrated and the residue was chromatographed on silica gel, eluting with 17% EtOAc in petroleum ether to afford N-((3-bromo-2,6-dimethylpyridin-4-yl)carbamothioyl)benzamide as a light-yellow solid (363 mg, 50%). MS m/z 364.0, 366.0 [M+H]$^+$.

Step C: A mixture of N-((3-bromo-2,6-dimethylpyridin-4-yl)carbamothioyl)benzamide (181 mg, 0.5 mmol), Pd(PPh$_3$)$_4$ (58 mg, 0.05 mmol) and Cs$_2$CO$_3$ (326 mg, 1 mmol) in DME (5 mL) was stirred at 100° C. under N$_2$ for 3 h. After completion, the reaction mixture was cooled to room temperature and partitioned between EtOAc (50 mL) and water (50 mL). The organic layer was washed with brine, dried over Na$_2$SO$_4$ and concentrated. The residue was chromatographed on silica gel, eluting 30-100% EtOAc in petroleum ether to afford N-(4,6-dimethylthiazolo[5,4-c]pyridin-2-yl)benzamide as a light-yellow solid (92 mg, 65%). MS m/z 284.1 [M+H]$^+$.

Step D: A mixture of N-(4,6-dimethylthiazolo[5,4-c]pyridin-2-yl)benzamide (2 g, 7.1 mmol) and NaOH (1.42 g, 36 mmol) in MeOH (45 mL) and water (15 mL) was stirred in a sealed tube at 85° C. for 24 h. The mixture was extracted with EtOAc (150 mL×2). The combined organic phases were washed with brine, dried over Na$_2$SO$_4$ and concentrated. The residue was chromatographed n silica gel, eluting 50-100% EtOAc in CH$_2$Cl$_2$ to afford 4,6-dimethylthiazolo[5,4-c]pyridin-2-amine as a light-yellow solid (0.88 g, 70%). MS m/z 180.1 [M+H]$^+$.

Step E: To a mixture of 4,6-dimethylthiazolo[5,4-c]pyridin-2-amine (880 mg, 4.9 mmol) and CuBr$_2$ (3.25 g, 14.7 mmol) in MeCN (10 mL) was added tert-butyl nitrite (1.74 mL, 14.7 mmol) at 0° C. The mixture was stirred at 0° C. for 2 h and then 55° C. for 1 h. To the reaction mixture was added aqueous sat'd NaHCO$_3$. The mixture was extracted with EtOAc (200 mL). The organic layer was washed with brine, dried over Na$_2$SO$_4$ and concentrated. The residue was chromatographed on silica gel, eluting 20% EtOAc in petroleum ether to afford 2-bromo-4,6-dimethylthiazolo[5,4-c]pyridine as a white solid (595 mg, 50%). MS m/z 242.9, 245.0 [M+H]$^+$.

Example 29-15

2-(6-Chloro-2-methylimidazo[1,2-b]pyridazin-8-yl)ethan-1-ol

Step A: A dry three-necked round-bottomed flask at −78° C. under inert atmosphere was charged with anhydrous THF (20 mL). A solution of n-butyllithium (2.5 M in hexane, 26.1 mL, 65.3 mmol) was added dropwise, followed by addition of anhydrous acetonitrile (4 mL, 65.3 mmol). The internal temperature was maintained below −70° C. during the entire addition process. After stirring 30 min at −78° C., a solution of 8-bromo-6-chloro-2-methylimidazo[1,2-b]pyridazine (2.0 g, 8.2 mmol, prepared according to Example 43) in anhydrous THF (20 mL) was added drop-wise. The mixture was stirred for 2 h at −78° C. The excess reagent was quenched carefully with sat'd aqueous NH$_4$Cl. The mixture was partitioned between EtOAc and H$_2$O. The organic layer was washed with brine, dried over Na$_2$SO$_4$, filtered and concentrated. The residue was chromatographed on silica gel, eluting with 0-35% EtOAc in petroleum ether to yield 2-(6-chloro-2-methylimidazo[1,2-b]pyridazin-8-yl)acetonitrile (1.2 g, 71%). MS m/z 207.1, 209.1 [M+H]$^+$.

Step B: 2-(6-Chloro-2-methylimidazo[1,2-b]pyridazin-8-yl)acetonitrile (500 mg, 2.4 mmol) was combined with MeOH (0.97 mL, 24 mmol) in conc. H$_2$SO$_4$ (2 mL). The mixture was stirred at 60° C. for 16 h. The mixture was partitioned between EtOAc and H$_2$O. The organic layer was washed with brine, dried over Na$_2$SO$_4$, filtered and concentrated. The residue was chromatographed on silica gel, eluting with 0-30% EtOAc in petroleum ether to yield methyl 2-(6-chloro-2-methylimidazo[1,2-b]pyridazin-8-yl)acetate (500 mg, 86%). MS m/z 240.1, 242.1 [M+H]$^+$.

Step C: To methyl 2-(6-chloro-2-methylimidazo[1,2-b]pyridazin-8-yl)acetate (500 mg, 2.1 mmol) in dry THF (5 mL) was added LiAlH$_4$ (183 mg, 5.2 mmol) in small portions at 0° C. The mixture was stirred at 0° C. for 20 min. The reaction was quenched carefully with water (1 mL), followed by aqueous 15% NaOH (1 mL). The mixture was partitioned between EtOAc and H$_2$O. The organic layer was washed with brine, dried over Na$_2$SO$_4$, filtered and concentrated. The residue was chromatographed on silica gel, eluting with 0-35% EtOAc in petroleum ether to yield 2-(6-chloro-2-methylimidazo[1,2-b]pyridazin-8-yl)ethan-1-ol (144 mg, 33%). MS m/z 212.1, 214.1 [M+H]$^+$.

Example 29-16

6-Chloro-8-(1H-imidazol-1-yl)-2-methylimidazo[1,2-b]pyridazine

8-Bromo-6-chloro-2-methylimidazo[1,2-b]pyridazine (500 mg, 2.0 mmol, prepared according to Example 43) was combined with K₂CO₃ (550 mg, 4.0 mmol) and 1H-imidazole (250 mg, 0.36 mmol) in NMP (5 mL). The mixture was stirred at 120° C. for 16 h. The mixture was partitioned between EtOAc and H₂O. The organic layer was washed with brine, dried over Na₂SO₄, filtered and concentrated. The residue was chromatographed on silica gel, eluting with 0-30% EtOAc in petroleum ether to yield 6-chloro-8-(1H-imidazol-1-yl)-2-methylimidazo[1,2-b]pyridazine (228 mg, 48%). MS m/z 234.0, 236.0 [M+H]⁺.

Example 29-17

6-Chloro-2-methyl-8-phenoxyimidazo[1,2-b]pyridazine

8-Bromo-6-chloro-2-methylimidazo[1,2-b]pyridazine (1.0 g, 4.0 mmol) was combined with K₂CO₃ (1.1 g, 8 mmol) and phenol (0.6 g, 6.0 mmol) in NMP (10 mL). The mixture was stirred at 60° C. for 16 h. The mixture was partitioned between EtOAc and H₂O. The organic layer was washed with brine, dried over Na₂SO₄, filtered and concentrated. The residue was chromatographed on silica gel, eluting with 0-30% EtOAc in petroleum ether to yield 6-chloro-2-methyl-8-phenoxyimidazo[1,2-b]pyridazine (560 mg, 53%). MS m/z 260.0, 262.0 [M+H]⁺.

Example 29-18

6-Chloro-8-isopropyl-2-methylimidazo[1,2-b]pyridazine

Step A: 8-Bromo-6-chloro-2-methylimidazo[1,2-b]pyridazine (500 mg, 2.05 mmol, prepared according to example 43) was combined with vinylboronic acid pinacol ester (0.43 mL, 2.3 mmol), Pd(dppf)Cl₂ (150 mg, 0.21 mmol) and K₂CO₃ (850 mg, 6.15 mmol) in 1,4-dioxane (10 mL) and H₂O (2 mL). The mixture was stirred at 90° C. for 2 h under N₂. The mixture was partitioned between EtOAc and H₂O. The organic layer was washed with brine, dried over Na₂SO₄, filtered and concentrated. The residue was chromatographed on silica gel, eluting with 10-20% EtOAc in petroleum ether to yield 6-chloro-2-methyl-8-(prop-1-en-2-yl)imidazo[1,2-b]pyridazine (300 mg, 77%). MS m/z 208.0, 210.0 [M+H]⁺.

Step B: 6-Chloro-2-methyl-8-(prop-1-en-2-yl)imidazo[1,2-b]pyridazine (250 mg, 1.21 mmol) was combined with PtO₂ (30 mg, 0.13 mmol) in EtOAc (10 mL). The mixture was stirred at room temperature for 3 h under an atmosphere of H₂. The mixture was filtered over Celite, and the filtrate was removed under reduce pressure. The residue was chromatographed on silica gel, eluting with 20-35% EtOAc in petroleum ether to yield 6-chloro-8-isopropyl-2-methylimidazo[1,2-b]pyridazine (200 mg, 80%). MS m/z 210.0, 212.0 [M+H]⁺.

Example 29-19

6-Chloro-2-methyl-8-propylimidazo[1,2-b]pyridazine

8-Bromo-6-chloro-2-methylimidazo[1,2-b]pyridazine (1 g, 4.1 mmol, prepared according to Example 43) was combined with propylmagnesiumbromide (660 mg, 4.5 mmol) and iron(III) 2,4-pentanedionate (140 mg, 0.4 mmol) in dry THF (30 mL). The mixture was stirred at 50° C. for 1 h under N₂. The mixture was partitioned between EtOAc and H₂O. The organic layer was washed with brine, dried over Na₂SO₄, filtered and concentrated. The residue was chromatographed on silica gel, eluting with 20-30% EtOAc in petroleum ether to yield 6-chloro-2-methyl-8-propylimidazo[1,2-b]pyridazine (230 mg, 27%). MS m/z 210.0, 212.0 [M+H]⁺.

Example 30

Preparation of Compound 78

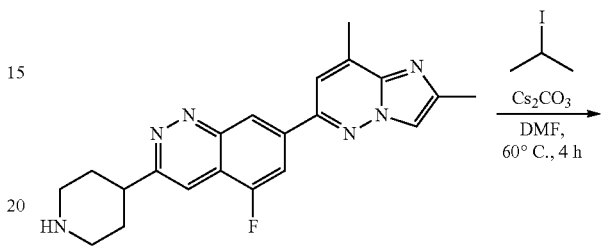

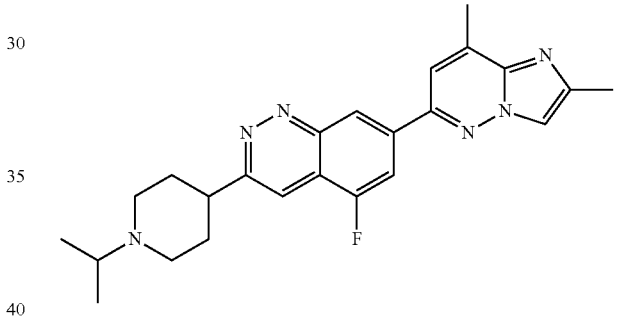

7-(2,8-Dimethylimidazo[1,2-b]pyridazin-6-yl)-5-fluoro-3-(4-piperidyl)cinnoline dihydrochloride (55 mg, 0.13 mmol, prepared in Example 7) was combined with Cs₂CO₃ (85 mg, 0.26 mmol), 2-iodopropane (26 μL, 0.26 mmol) and DMF (1 mL). The mixture was stirred at 60° C. for 4 h. The mixture was partitioned between EtOAc and H₂O. The organic layer was washed with brine, dried over Na₂SO₄, filtered and concentrated. The residue was chromatographed on silica gel, eluting with 0-10% MeOH (2 N NH₃) in CH₂Cl₂ to yield 7-(2,8-dimethylimidazo[1,2-b]pyridazin-6-yl)-5-fluoro-3-(1-isopropyl-4-piperidyl)cinnoline (6 mg, 11%).

MS m/z 419.4 [M+H]⁺; ¹H NMR (methanol-d₄) δ: 8.92 (s, 1H), 8.32 (dd, J=11.0, 1.5 Hz, 1H), 8.19 (s, 1H), 8.00 (s, 1H), 7.88 (s, 1H), 3.91-4.02 (m, 2H), 3.61-3.68 (m, 1H), 3.24-3.33 (m, 2H), 2.73 (s, 3H), 2.56-2.62 (m, 1H), 2.52 (s, 3H), 2.20-2.26 (m, 2H), 2.06-2.16 (m, 2H), 1.21 (d, J=7.2 Hz, 6H).

Using the procedure described for Example 30, above, additional compounds described herein were prepared by substituting the appropriate aryl halide, suitable reagents and reaction conditions, obtaining compounds such as those selected from:

| Cpd | Data |
|---|---|
| 83 | MS m/z 423.5 [M + H]+; 1H NMR (methanol-d4) δ: 9.17 (s, 1H), 8.60 (d, J = 1.3 Hz, 1H), 8.43-8.47 (m, 2H), 8.35 (s, 1H), 4.98 (ddd, J = 47, 5.1, 3.7 Hz, 2H), 3.89-3.95 (m, 2H), 3.63-3.73 (m, 3H), 3.40-3.48 (m, 2H), 2.88 (d, J = 0.9 Hz, 3H), 2.71 (d, J = 0.9 Hz, 3H), 2.46-2.53 (m, 4H), HCl protons not observed. |
| 98 | MS m/z 441.5 [M + H]+; 1H NMR (methanol-d4) δ: 9.15 (s, 1H), 8.54 (d, J = 1.2 Hz, 1H), 8.44 (dd, J = 10.7, 1.5 Hz, 1H), 8.41 (d, J = 0.9 Hz, 1H), 8.34 (s, 1H), 6.53 (tt, J = 53.7, 3.5 Hz, 1H), 3.82-3.96 (m, 4H), 3.64-3.71 (m, 1H), 3.49-3.59 (m, 2H), 2.87 (d, J = 1.2 Hz, 3H), 2.69 (d, J = 0.9 Hz, 3H), 2.46-2.57 (m, 4H), HCl protons not observed. |
| 168 | MS m/z 433.5 [M + H]+; 1H NMR (methanol-d4) δ: 8.92 (s, 1H), 8.32 (d, J = 11 Hz, 1H), 8.19 (s, 1H), 8.00 (s, 1H), 7.88 (s, 1H), 3.60 (m, 1H), 3.30 (br s, 4H), 2.73 (s, 3H), 2.52 (s, 3H), 2.26-2.32 (m, 2H), 2.01 (m, 2H), 1.41 (d, J = 6 Hz, 6H), 1.21 (m, 3H). |
| 170 | MS m/z 451.6 [M + H]+; 1H NMR (methanol-d4) δ: 8.90 (s, 1H), 8.30 (d, J = 10.5 Hz, 1H), 8.15 (s, 1H), 8.00 (s, 1H), 7.87 (s, 1H), 4.64 (dd, J = 50, 5.0 Hz, 2H), 3.51 (m, 1H), 3.15-3.32 (m, 2H), 3.07 (br s, 2H), 2.73 (s, 3H), 2.52 (s, 3H), 2.13 (d, J = 12.5 Hz, 2H), 1.85 (q, J = 12 Hz, 2H), 1.32 (d, J = 6 Hz, 6H). |
| 199 | MS m/z 437.3 [M + H]+; 1H NMR (methanol-d4) δ: 8.90 (s, 1H), 8.29 (d, J = 10 Hz, 1H), 8.16 (s, 1H), 7.99 (s, 1H), 7.87 (s, 1H), 4.64 (dd, J = 50, 5.0 Hz, 2H), 3.60 (m, 1H), 3.13-3.19 (m, 1H), 2.95-3.08 (m, 5H), 2.72 (s, 3H), 2.52 (s, 3H), 2.00-2.30 (m, 5H), 1.90-2.00 (m, 1H). |

Example 31

Preparation of Compound 158

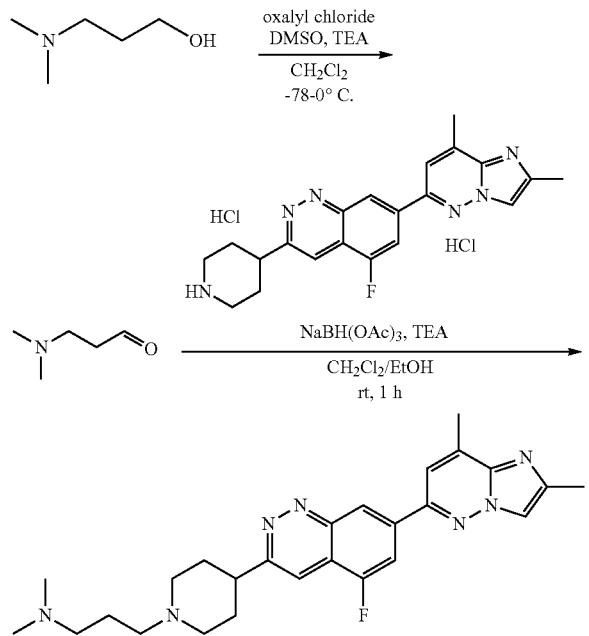

Step A: A solution of oxalyl chloride (105 μL, 1.2 mmol) in CH2Cl2 (1.4 mL) was cooled to −78° C. To the solution was added DMSO (150 μL, 2.1 mmol) in CH2Cl2 (0.5 mL). The solution was stirred at −78° C. for 30 min. To the solution was added 3-(dimethylamino)propan-1-ol (55 mg, 0.53 mmol) in CH2Cl2 (1 mL). The solution was stirred for 30 min at −78° C. Triethylamine (42 μL, 0.30 mmol) was added to the solution. The mixture was allowed to slowly warm to 0° C. over ~30 min. The excess reagent was quenched by the addition of aqueous saturated NaHCO3. The organic layer was removed and dried over Na2SO4, filtered and concentrated. The crude product was used directly in the next step without additional purification.

Step B: 7-(2,8-dimethylimidazo[1,2-b]pyridazin-6-yl)-5-fluoro-3-(4-piperidyl)cinnoline dihydrochloride (45 mg, 0.10 mmol, prepared in Example 7) was combined with CH2Cl2 (2 mL), triethylamine (42 μL, 0.30 mmol), and EtOH (0.2 mL). To the mixture was added 3-(dimethylamino)propanal (53 mg, 0.52 mmol, from Step A) in CH2Cl2 (0.5 mL). The mixture was stirred at room temperature until homogeneous, and then sodium triacetoxyborohydride (64, 0.30 mmol) was added. After stirring for 20 min at room temperature, the mixture was concentrated. The residue was dissolved in TFA and CH2Cl2 and was dried onto Celite. The dry material was chromatographed on a reverse phase C18 column, eluting with 5-60% CH3CN (0.1% TFA) in H2O (0.1% TFA). The collected fractions were concentrated. The residue was partitioned in CH2Cl2 and aqueous 1 M K2CO3. The organic layer was loaded onto silica gel, eluting with 0-10% MeOH (2 N NH3) in CH2Cl2 to afford 3-[4-[7-(2,8-dimethylimidazo[1,2-b]pyridazin-6-yl)-5-fluoro-cinnolin-3-yl]-1-piperidyl]-N,N-dimethyl-propan-1-amine (7 mg, 15%).

MS m/z 462.5 [M+H]+; 1H NMR (methanol-d4) δ: 8.96 (s, 1H), 8.36 (dd, J=11.0, 1.5 Hz, 1H), 8.25 (s, 1H), 8.02 (s, 1H), 7.90 (d, J=0.9 Hz, 1H), 3.54-3.60 (m, 2H), 3.46-3.53 (m, 1H), 3.20-3.26 (m, 2H), 2.99-3.08 (m, 2H), 2.92 (s, 6H), 2.81-2.90 (m, 2H), 2.74 (d, J=0.9 Hz, 3H), 2.53 (s, 3H), 2.26-2.37 (m, 4H), 2.14 (quin, J=7.2 Hz, 2H).

Using the procedure described for Example 31, above, additional compounds described herein were prepared by substituting the appropriate alcohol in Step A, suitable reagents and reaction conditions, obtaining compounds such as those selected from:

| Cpd | Data |
|---|---|
| 145 | MS m/z 535.5 [M + H]+; 1H NMR (methanol-d4) δ: 8.91 (s, 1H), 8.31 (dd, J = 10.8, 1.4 Hz, 1H), 8.25 (s, 1H), 8.15 (s, 1H), 8.00 (s, 1H), 7.87 (s, 1H), 7.71 (d, J = 7.9 Hz, 1H), 7.67 (d, J = 7.9 Hz, 1H), 7.37 (t, J = 7.6 Hz, 1H), 7.31 (t, J = 7.7 Hz, 1H), 4.45 (t, J = 6.6 Hz, 2H), 3.23-3.31 (m, 1H), 3.12 (br d, J = 11.3 Hz, 2H), 2.73 (s, 3H), 2.52 (s, 3H), 2.47 (t, J = 6.6 Hz, 2H), 2.16-2.28 (m, 4H), 2.01-2.15 (m, 4H), HCl protons not observed. |

-continued

| Cpd | Data |
|---|---|
| 159 | MS m/z 521.2 [M + H]⁺; $^1$H NMR (methanol-$d_4$) δ: 8.94 (s, 1H), 8.34 (dd, J = 10.7, 1.3 Hz, 1H), 8.29 (s, 1H), 8.17 (s, 1H), 8.02 (s, 1H), 7.90 (d, J = 0.9 Hz, 1H), 7.71 (d, J = 7.9 Hz, 1H), 7.66 (d, J = 8.2 Hz, 1H), 7.37 (d, J = 8.0 Hz, 1H), 7.31 (d, J = 8.2 Hz, 1H), 4.51 (t, J = 6.4 Hz, 2H), 3.24-3.31 (m, 1H), 3.18 (br d, J = 11.3 Hz, 2H), 2.94 (t, J = 6.4 Hz, 2H), 2.75 (s, 3H), 2.53 (s, 3H), 2.39-2.46 (m, 2H), 2.02-2.20 (m, 4H). |
| 160 | MS m/z 485.5 [M + H]⁺; $^1$H NMR (methanol-$d_4$) δ: 8.89 (s, 1H), 8.29 (dd, J = 11.0, 1.2 Hz, 1H), 8.16 (s, 1H), 7.98 (s, 1H), 7.85 (d, J = 1.2 Hz, 1H), 7.70 (d, J = 2.1 Hz, 1H), 7.53 (d, J = 1.8 Hz, 1H), 6.32 (t, J = 2.1 Hz, 1H), 4.29 (m, 2H), 3.26-3.31 (m, 1H), 3.20 (br d, J = 11.6 Hz, 2H), 2.72 (d, J = 0.9 Hz, 3H), 2.51 (s, 3H), 2.46-2.50 (m, 2H), 2.28-2.36 (m, 2H), 2.07-2.21 (m, 6H). |

Example 32

Preparation of Compound 127

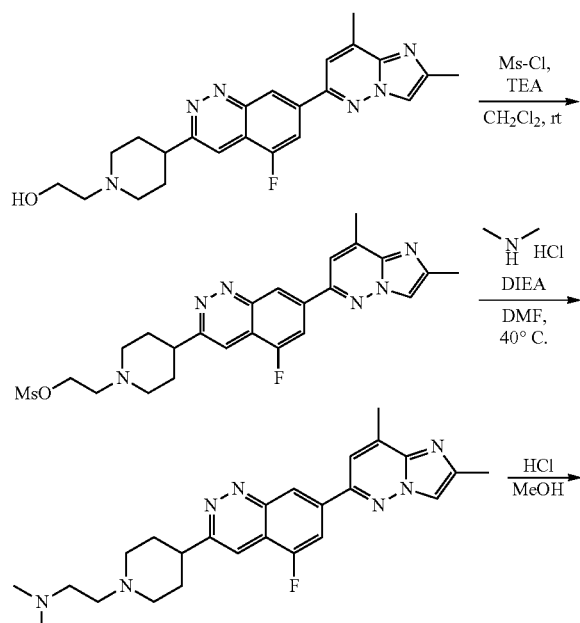

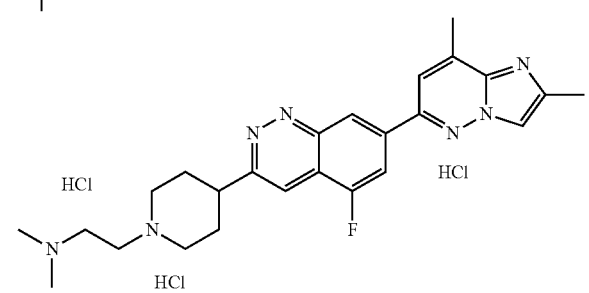

Step A: 2-[4-[7-(2,8-Dimethylimidazo[1,2-b]pyridazin-6-yl)-5-fluoro-cinnolin-3-yl]-1-piperidyl]ethanol dihydrochloride (200 mg, 0.41 mmol, prepared in Example 19) was combined with CH$_2$Cl$_2$ (4 mL) and triethylamine (0.22 mL, 1.6 mmol). To the mixture was added methanesulfonyl chloride (137 μL, 0.81 mmol) at room temperature. The mixture was stirred at room temperature for 30 min. The mixture was washed with aqueous 1 M K$_2$CO$_3$. The organic layer was Loaded onto silica gel, eluting with 0-10% MeOH (2 N NH$_3$) in CH$_2$Cl$_2$ to provide 2-[4-[7-(2,8-Dimethylimidazo[1,2-b]pyridazin-6-yl)-5-fluoro-cinnolin-3-yl]-1-piperidyl]ethyl methanesulfonate. MS m/z 499.4 [M+H]⁺.

Step B: 2-[4-[7-(2,8-Dimethylimidazo[1,2-b]pyridazin-6-yl)-5-fluoro-cinnolin-3-yl]-1-piperidyl]ethyl methanesulfonate (30 mg, 0.06 mmol) was combined with N,N-diisopropylethylamine (105 μL, 0.60 mmol), DMF (1 mL) and dimethylamine hydrochloride (55 mg, 0.60 mmol). The mixture was heated at 40° C. for 18 h. The volatile material was removed. The residue was dissolved in TFA and CH$_2$Cl$_2$ and was dried onto Celite. The dry material was chromatographed on a reverse phase C18 column, eluting with 5-65% CH$_3$CN (0.1% TFA) in H$_2$O (0.1% TFA). The collected material was concentrated. The residue was dissolved in 1.25 M HCl in MeOH. The volatiles were removed. The residue was suspended in CH$_3$CN, sonicated, collected by filtration and dried yielding 2-[4-[7-(2,8-dimethylimidazo[1,2-b]pyridazin-6-yl]-5-fluoro-cinnolin-3-yl]-1-piperidyl]-N,N-dimethyl-ethanamine trihydrochloride (13 mg, 39%). MS m/z 448.5 [M+H]⁺; $^1$H NMR (methanol-$d_4$) δ: 9.15 (s, 1H), 8.56 (m, 1H), 8.43 (d, J=9.5 Hz, 1H), 8.42 (s, 1H), 8.35 (s, 1H), 3.93 (br s, 2H), 3.68-3.83 (m, 5H), 3.46 (br d, J=10.4 Hz, 2H), 3.07 (s, 6H), 2.87 (s, 3H), 2.70 (s, 3H), 2.48-2.63 (m, 4H), HCl protons not observed.

Example 33

Preparation of Compound 141

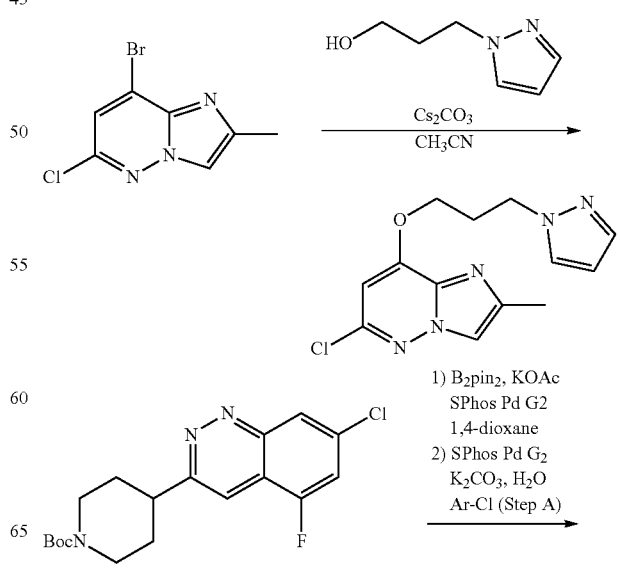

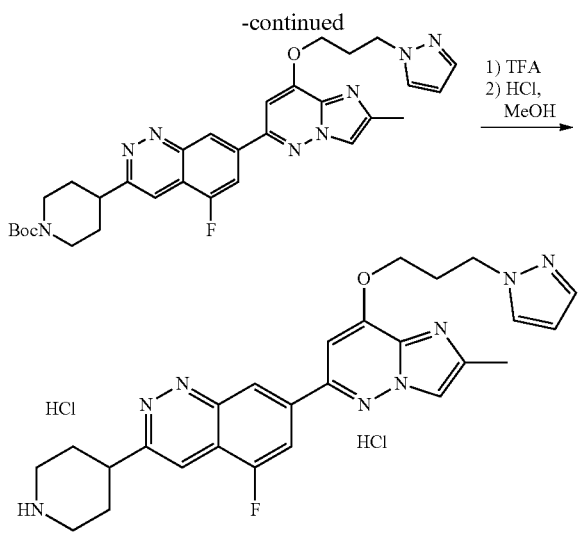

Step A: 8-Bromo-6-chloro-2-methyl-imidazo[1,2-b]pyridazine (124 mg, 0.50 mmol) was combined with 3-(1H-pyrazol-1-yl)propan-1-ol (252 mg, 2.0 mmol) and cesium carbonate (650 mg, 2.0 mmol) in $CH_3CN$ (4 mL). The mixture was stirred at 40° C. for 16 h. To the mixture was added EtOAc (10 mL). The mixture was filtered over Celite. The filtrate was concentrated. The residue was chromatographed on silica gel, eluting with 0-10% MeOH in EtOAc to yield 6-chloro-2-methyl-8-(3-pyrazol-1-ylpropoxy)imidazo[1,2-b]pyridazine (70 mg, 48%). MS m/z 292.3 [M+H]$^+$.

Step B: tert-Butyl 4-(7-chloro-5-fluoro-cinnolin-3-yl)piperidine-1-carboxylate (73 mg, 0.20 mmol, prepared in Example 29) was combined with bis(pinacolato)diboron (64 mg, 0.25 mmol), KOAc (59 mg, 0.60 mmol), chloro(2-dicyclohexylphosphino-2',6'-dimethoxy-1,1'-biphenyl)(2'-amino-1,1'-biphenyl-2-yl) palladium(II) (14 mg, 0.02 mmol) and 1,4-dioxane (3 mL). The mixture was stirred at 90° C. for 1 h. To the mixture was added aqueous 1 M $K_2CO_3$ (1 mL), followed by another portion of chloro(2-dicyclohexylphosphino-2',6'-dimethoxy-1,1'-biphenyl)(2'-amino-1,1'-biphenyl-2-yl) palladium(II) (14 mg, 0.02 mmol) and 6-chloro-2-methyl-8-(3-pyrazol-1-ylpropoxy)imidazo[1,2-b]pyridazine (70 mg, 0.24 mmol) (in 1 mL of 1,4-dioxane). The mixture was stirred at 80° C. for 1 h. The mixture was partitioned between EtOAc and $H_2O$. The organic layer was concentrated. The residue was chromatographed on silica gel, eluting with 0-10% MeOH in EtOAc to yield tert-butyl 4-[5-fluoro-7-[2-methyl-8-(3-pyrazol-1-ylpropoxy)imidazo[1,2-b]pyridazin-6-yl]cinnolin-3-yl]piperidine-1-carboxylate (110 mg, 94%). MS m/z 587.3 [M+H]$^+$.

Step C: tert-Butyl 4-[5-fluoro-7-[2-methyl-8-(3-pyrazol-1-ylpropoxy)imidazo[1,2-b]pyridazin-6-yl]cinnolin-3-yl]piperidine-1-carboxylate (110 mg, 0.18 mmol) was dissolved in trifluoroacetic acid (1 mL) and 1 mL $CH_2Cl_2$. The solution was dried onto Celite. The dry material was chromatographed on a reverse phase C18 column, eluting with 5-65% $CH_3CN$ (0.1% TFA) in $H_2O$ (0.1% TFA). The desired fractions were concentrated. The residue was dissolved in 1.25 M HCl in MeOH. The volatiles were removed. The residue was suspended in $CH_3CN$, sonicated, filtered and dried to yield 5-fluoro-7-[2-methyl-8-(3-pyrazol-1-ylpropoxy)imidazo[1,2-b]pyridazin-6-yl]-3-(4-piperidyl)cinnoline dihydrochloride (66 mg, 63%) as a pale yellow solid.

MS m/z 487.4 [M+H]$^+$; $^1$H NMR (methanol-$d_4$) δ: 9.18 (s, 1H), 8.44 (d, J=10.7 Hz, 1H), 8.40 (d, J=0.6 Hz, 1H), 8.33 (s, 1H), 8.08 (s, 1H), 7.84 (d, J=2.1 Hz, 1H), 7.66 (d, J=1.8 Hz, 1H), 6.41 (t, J=2.3 Hz, 1H), 4.67 (t, J=6.7 Hz, 2H), 4.58 (t, J=6.7 Hz, 2H), 3.63-3.70 (m, 3H), 3.29-3.35 (m, 2H), 2.70 (s, 3H), 2.59 (quin, J=6.3 Hz, 2H), 2.33-2.45 (m, 4H), NH and HCl protons not observed.

Using the procedure described for Example 33, above, additional compounds described herein were prepared by substituting the appropriate alcohol in Step A, suitable reagents and reaction conditions, obtaining compounds such as those selected from:

| Cpd | Data |
| --- | --- |
| 138 | MS m/z 450.5 [M + H]$^+$; $^1$H NMR (methanol-$d_4$) δ: 9.20 (s, 1H), 8.46 (dd, J = 10.7, 1.2 Hz, 1H), 8.38 (s, 1H), 8.32 (s, 1H), 8.14 (s, 1H), 5.06 (t, J = 5.0 Hz, 2H), 3.90 (t, J = 5.0 Hz, 2H), 3.63-3.71 (m, 3H), 3.29-3.37 (m, 2H), 3.12 (s, 6H), 2.69 (s, 3H), 2.32-2.46 (m, 4H), NH and HCl protons not observed. |
| 139 | MS m/z 464.5 [M + H]$^+$; $^1$H NMR (methanol-$d_4$) δ: 9.19 (s, 1H), 8.45 (dd, J = 10.5, 1.4 Hz, 1H), 8.39 (s, 1H), 8.32 (s, 1H), 8.10 (s, 1H), 4.82 (t, J = 6.1 Hz, 2H), 3.63-3.70 (m, 3H), 3.55-3.60 (m, 2H), 3.28-3.37 (m, 2H), 3.03 (s, 6H), 2.70 (s, 3H), 2.49-2.56 (m, 2H), 2.31-2.45 (m, 4H), NH and HCl protons not observed. |
| 140 | MS m/z 473.4 [M + H]$^+$; $^1$H NMR (methanol-$d_4$) δ: 9.16 (s, 1H), 8.42 (d, J = 10.4 Hz, 1H), 8.38 (s, 1H), 8.35 (s, 1H), 8.04 (s, 1H), 7.92 (d, J = 1.8 Hz, 1H), 7.63 (s, 1H), 6.40 (t, J = 2.1 Hz, 1H), 5.01-5.06 (m, 2H), 4.85-4.90 (m, 2H), 3.63-3.71 (m, 3H), 3.29-3.37 (m, 2H), 2.69 (s, 3H), 2.32-2.46 (m, 4H), NH and HCl protons not observed. |
| 142 | MS m/z 487.4 [M + H]$^+$; $^1$H NMR (methanol-$d_4$) δ: 9.19 (s, 2H), 8.45 (dd, J = 10.5, 1.4 Hz, 1H), 8.41 (d, J = 0.9 Hz, 1H), 8.33 (s, 1H), 8.11 (s, 1H), 7.84 (t, J = 1.7 Hz, 1H), 7.67 (t, J = 1.7 Hz, 1H), 4.77 (t, J = 5.8 Hz, 2H), 4.71 (t, J = 7.3 Hz, 2H), 3.62-3.71 (m, 3H), 3.29-3.37 (m, 2H), 2.71 (s, 3H), 2.65-2.70 (m, 2H), 2.32-2.45 (m, 4H), NH and HCl protons not observed. |
| 150 | MS m/z 537.4 [M + H]$^+$; $^1$H NMR (methanol-$d_4$) δ: 9.72 (s, 1H), 9.16 (s, 1H), 8.44 (d, J = 10.6 Hz, 1H), 8.40 (s, 1H), 8.32 (s, 1H), 8.11-8.16 (m, 1H), 8.08 (s, 1H), 7.89-7.95 (m, 1H), 7.68-7.77 (m, 2H), 5.00 (t, J = x Hz, 2H), 4.83 (t, J = x Hz, 2H), 3.63-3.70 (m, 3H), 3.28-3.37 (m, 2H), 2.80 (dt, J = 13.4, 6.4 Hz, 2H), 2.72 (d, J = 0.9 Hz, 3H), 2.31-2.45 (m, 4H), NH proton not observed. |

Example 34

Preparation of Compound 223

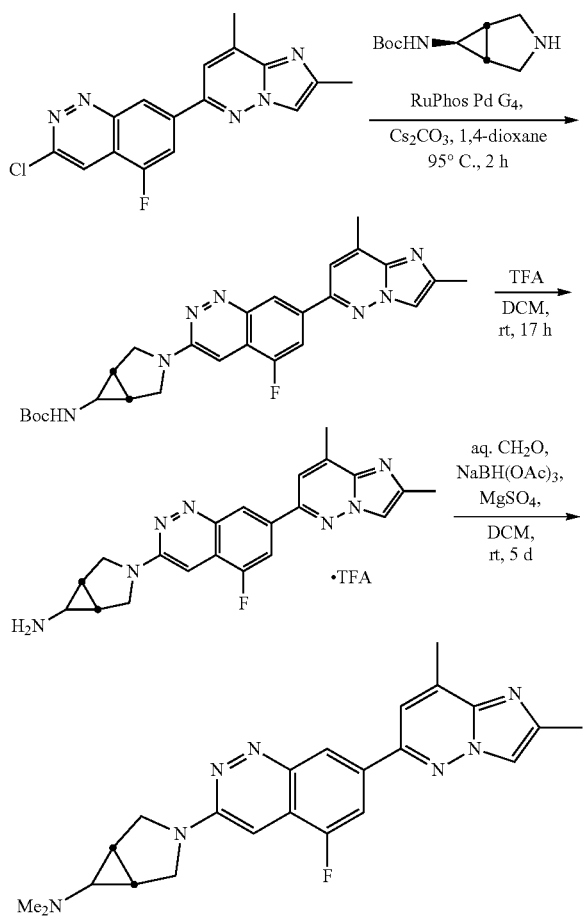

Step A: A screw-cap tube was charged with 3-chloro-7-(2,8-dimethylimidazo[1,2-b]pyridazin-6-yl)-5-fluoro-cinnoline (0.037 g, 0.11 mmol), tert-butyl N-[(1S*,5R*)-3-azabicyclo[3.1.0]hexan-6-yl]carbamate (0.034 g, 0.17 mmol), granular cesium carbonate (0.110 g, 0.338 mmol), and RuPhos Pd G4 pre-catalyst (0.0011 g, 0.0013 mmol). Anhydrous 1,4-dioxane (5 mL) was added last, and the mixture was sparged with argon for 10 minutes. The vial was tightly capped with a screw-cap, placed on a pre-heated aluminum block, and stirred vigorously at 100° C. for 2 h. After this time, the reaction mixture was cooled to room temperature. The brown, heterogeneous reaction mixture was diluted with sat. aq. Na$_2$CO$_3$ (20 mL) and extracted with CH$_2$Cl$_2$ (2×30 mL). The combined CH$_2$Cl$_2$ extracts were diluted with more CH$_2$Cl$_2$ (30 mL) and washed with brine (30 mL), dried over anhydrous Na$_2$SO$_4$, filtered, and concentrated under reduced pressure. The brown, crude product was purified by silica gel column chromatography (CH$_2$Cl$_2$/methanolic ammonia (1.0M) gradient elution) to afford the desired tert-butyl N-[(1S*,5R*)-3-[7-(2,8-dimethylimidazo[1,2-b]pyridazin-6-yl)-5-fluoro-cinnolin-3-yl]-3-azabicyclo[3.1.0]hexan-6-yl]carbamate (0.048 g, 87%) as a yellow solid.

MS m/z 490.3 [M+H]$^+$; $^1$H NMR (chloroform-d) δ: 8.54 (s, 1H), 7.97 (dd, J=11.3, 1.2 Hz, 1H), 7.97 (d, J=1.3 Hz, 1H), 7.47 (s, 1H), 6.76 (s, 1H), 4.83 (br s, 1H), 4.07 (br d, J=9.6 Hz, 2H), 3.72 (br d, J=9.9 Hz, 2H), 2.76 (s, 3H), 2.55 (s, 3H), 2.46 (br s, 1H), 2.00 (br s, 2H), 1.47 (m, 9H).

Step B: tert-Butyl N-[(1S*,5R*)-3-[7-(2,8-dimethylimidazo[1,2-b]pyridazin-6-yl)-5-fluoro-cinnolin-3-yl]-3-azabicyclo[3.1.0]hexan-6-yl]carbamate (0.048 g, 0.098 mmol) was dissolved in CH$_2$Cl$_2$ (5 mL), and trifluoroacetic acid (0.10 mL, 1.3 mmol) was added dropwise to the yellow solution, resulting in instantaneous color change to a wine red. The reaction mixture was capped and allowed to sit at room temperature for 17 h. After this time, the wine-red solution was concentrated on a rotovap. The red, crude oil was purified by C18 reverse-phase column chromatography (H$_2$O:MeCN (0.1% TFA) gradient elution) to afford (1S*,5R*)-3-[7-(2,8-dimethylimidazo[1,2-b]pyridazin-6-yl)-5-fluoro-cinnolin-3-yl]-3-azabicyclo[3.1.0]hexan-6-amine tetra(trifluoroacetic acid) (0.054 g, 65%) as a dark red oil. MS m/z 390.3 [M+H]$^+$.

Step C: (1S*,5R*)-3-[7-(2,8-dimethylimidazo[1,2-b]pyridazin-6-yl)-5-fluoro-cinnolin-3-yl]-3-azabicyclo[3.1.0]hexan-6-amine tetra(trifluoroacetic acid) (0.050 g, 0.059 mmol), was dissolved in CH$_2$Cl$_2$ (3 mL) in a screw-top vial. A 37% aqueous solution of formaldehyde (0.018 mL, 0.24 mmol) was added, followed by anhydrous MgSO$_4$ (0.021 g, 0.17 mmol), triethylamine (0.025 mL, 0.18 mmol), and NaBH(OAc)$_3$ (0.031 g, 0.15 mmol). The vial was sealed with a screw-cap, and the reaction mixture was stirred vigorously at room temperature for 5 days. After this time, the reaction mixture was diluted with CH$_2$Cl$_2$ (30 mL), washed with sat. aq. Rochelle's salt (20 mL) and brine (20 mL), then dried over anhydrous Na$_2$SO$_4$, decanted, and concentrated on a rotovap to afford a dark yellow solid/oil mixture. The crude product was purified by silica gel column chromatography (CH$_2$Cl$_2$/methanolic ammonia (1.0 M) gradient) to afford the desired (1S*,5R*)-3-[7-(2,8-dimethylimidazo[1,2-b]pyridazin-6-yl)-5-fluoro-cinnolin-3-yl]-N,N-dimethyl-3-azabicyclo[3.1.0]hexan-6-amine (0.021 g, 85%) as a yellow solid.

MS m/z 418.3 [M+H]$^+$; $^1$H NMR (chloroform-d) δ: 8.54 (s, 1H), 7.98 (dd, J=11.3, 1.3 Hz, 1H), 7.76 (s, 1H), 7.45 (s, 1H), 6.76 (s, 1H), 3.83 (ABq, J=126.7, 9.6 Hz, 4H), 2.74 (s, 3H), 2.54 (s, 3H), 2.40 (s, 6H), 1.93 (s, 2H), 1.57 (s, 1H).

Using the procedure described for Example 34, above, additional compounds described herein were prepared by substituting the appropriate amine in Step A, suitable reagents and reaction conditions, obtaining compounds such as those selected from:

| Cpd | Data |
| --- | --- |
| 80 | MS m/z 378.4 [M + H]$^+$; $^1$H NMR (DMSO-d$_6$) δ: 9.29 (br s, 2H), 8.94 (s, 1H), 8.44 (br s, 1H), 8.39 (br s, 1H), 8.19 (dd, J = 11.3, 1.3 Hz, 1H), 7.60 (s, 1H), 4.06-4.20 (m, 4H), 3.26-3.35 (m, 4H), 2.73 (s, 3H), 2.54 (s, 3H). |
| 81 | MS m/z 406.4 [M + H]$^+$; $^1$H NMR (DMSO-d$_6$) δ: 9.53 (br s, 1H), 9.11 (br s, 1H), 8.93 (s, 1H), 8.45 (br s, 1H), 8.39 (br s, 1H), 8.19 (d, J = 11.3 Hz, 1H), 7.67 (s, 1H), 4.87 (br d, J = 12.0 Hz, 2H), 3.45 (br s, 2H), 3.12 (dd, J = 14.2, 11.7 Hz, 2H), 2.73 (s, 3H), 2.54 (m, 3H), 1.39 (d, J = 6.3 Hz, 6H). |

-continued

| Cpd | Data |
|---|---|
| 86 | MS m/z 406.3 [M + H]+; 1H NMR (methanol-d4) δ: 8.44 (s, 1H), 7.84-7.94 (m, 2H), 7.66 (s, 1H), 6.90 (s, 1H), 3.92-4.00 (m, 1H), 3.83-3.90 (m, 1H), 3.54-3.62 (m, 1H), 3.35-3.46 (m, 2H), 2.99-3.08 (m, 1H), 2.66 (s, 3H), 2.47 (s, 3H), 2.42 (s, 6H), 1.99-2.09 (m, 1H). |
| 88 | MS m/z 420.3 [M + H]+; 1H NMR (methanol-d4) δ: 8.50 (s, 1H), 7.96 (dd, J = 11.4, 1.4 Hz, 1H), 7.88 (s, 1H), 7.69 (s, 1H), 7.29 (s, 1H), 4.64-4.73 (m, 2H), 3.02-3.13 (m, 2H), 2.67 (s, 3H), 2.57 (tt, J = 11.3, 3.8 Hz, 1H), 2.48 (s, 3H), 2.37 (s, 6H), 2.10 (br d, J = 12.2 Hz, 2H), 1.60 (qd, J = 12.2, 4.0 Hz, 2H). |
| 89 | MS m/z 406.3 [M + H]+; 1H NMR (methanol-d4) δ: 8.49 (s, 1H), 7.95 (dd, J = 11.6, 1.5 Hz, 1H), 7.89 (d, J = 0.6 Hz, 1H), 7.70 (d, J = 0.9 Hz, 1H), 6.94 (s, 1H), 3.95-4.02 (m, 1H), 3.85-3.92 (m, 1H), 3.60 (td, J = 10.1, 7.0 Hz, 1H), 3.40-3.47 (m, 1H), 2.99-3.07 (m, 1H), 2.68 (d, J = 0.9 Hz, 3H), 2.48 (s, 3H), 2.38-2.45 (m, 7H), 1.99-2.08 (m, 1H). |
| 209 | MS m/z 404.3 [M + H]+; 1H NMR (chloroform-d) δ: 8.55 (s, 1H), 7.99 (dd, J = 11.3, 1.4 Hz, 1H), 7.77 (s, 1H), 7.46 (s, 1H), 6.81 (s, 1H), 5.13 (bs, 1H), 3.74 (d, J = 9.3 Hz, 1H), 3.69 (s, 1H), 3.57 (dd, J = 9.7, 1.7 Hz, 1H), 3.09 (dd, J = 9.9, 1.4 Hz, 1H), 2.80 (d, J = 8.0 Hz, 1H), 2.75 (s, 3H), 2.54 (s, 3H), 2.48 (s, 3H), 2.15 (d, J = 9.6 Hz, 1H), 1.99 (d, J = 9.7 Hz, 1H). |
| 215 | MS m/z 404.3 [M + H]+; 1H NMR (chloroform-d) δ: 8.55 (s, 1H), 7.99 (dd, J = 11.3, 1.3 Hz, 1H), 7.77 (s, 1H), 7.46 (s, 1H), 6.81 (s, 1H), 5.13 (bs, 1H), 3.73 (bs, 1H), 3.68 (bs, 1H), 3.57 (d, J = 9.0 Hz, 1H), 3.09 (d, J = 9.3 Hz, 1H), 2.80 (bs, 1H), 2.75 (s, 3H), 2.54 (s, 3H), 2.48 (s, 3H), 2.15 (d, J = 9.5 Hz, 1H), 2.00 (d, J = 9.5 Hz, 1H). |
| 217 | MS m/z 404.3 [M + H]+; 1H NMR (methanol-d4) δ: 8.77 (s, 1H), 8.50 (s, 1H), 8.39 (s, 1H), 8.22 (d, J = 10.7 Hz, 1H), 7.58 (s, 1H), 4.48 (ABq, J = 36.1, 9.0 Hz, 4H), 3.68 (s, 2H), 3.47 (dd, J = 7.4 Hz, 2H), 2.84 (s, 3H), 2.68 (s, 3H), 2.50 (dd, J = 7.3 Hz, 2H), NH and HCl protons not observed. |
| 218 | MS m/z 418.3 [M + H]+; 1H NMR (methanol-d4) δ: 8.82 (s, 1H), 8.49 (s, 1H), 8.37 (s, 1H), 8.18 (d, J = 10.8 Hz, 1H), 7.28 (s, 1H), 4.21 (ABq, J = 59.7, 8.7 Hz, 4H), 3.53 (s, 2H), 3.23-3.18 (m, 2H), 2.83 (s, 3H), 2.68 (s, 3H), 2.14-2.06 (m, 2H), 1.97-1.90 (m, 2H), NH and HCl protons not observed. |
| 219 | MS m/z 418.3 [M + H]+; 1H NMR (methanol-d4) δ: 8.43 (s, 1H), 7.90 (dd, J = 11.5, 1.3 Hz, 1H), 7.83 (s, 1H), 7.63 (s, 1H), 7.25 (s, 1H), 3.98 (s, 4H), 3.81 (ddd, J = 7.5, 3.7, 1.9 Hz, 4H), 2.61 (s, 3H), 2.45 (s, 3H), 2.04 (ddd, J = 7.4, 3.7, 1.9 Hz, 4H), NH and TFA protons not observed. |
| 220 | MS m/z 404.3 [M + H]+; 1H NMR (chloroform-d) δ: 8.63 (s, 1H), 8.21 (s, 1H), 8.18 (s, 1H), 8.00 (dd, J = 11.2, 1.0 Hz, 1H), 6.99 (s, 1H), 4.23 (ABq, J = 51.2, 11.5 Hz, 4H), 4.00 (s, 2H), 3.74 (dd, J = 6.9 Hz, 2H), 2.74 (s, 3H), 2.59 (s, 3H), 2.51 (dd, J = 7.0 Hz, 2H), NH and TFA protons not observed. |
| 221 | MS m/z 418.3 [M + H]+; 1H NMR (methanol-d4) δ: 8.73 (s, 1H), 8.29 (s, 1H), 8.24 (s, 1H), 8.08 (d, J = 11.2 Hz, 1H), 7.04 (s, 1H), 4.13 (s, 4H), 3.28 (dd, J = 7.3, 5.7 Hz, 4H), 2.77 (s, 3H), 2.62 (s, 3H), 2.18 (dd, J = 7.3, 5.6 Hz, 4H), NH and TFA protons not observed. |
| 224 | MS m/z 434.3 [M + H]+; 1H NMR (chloroform-d) δ: 8.56 (s, 1H), 7.98 (dd, J = 11.3, 1.3 Hz, 1H), 7.77 (s, 1H), 7.46 (s, 1H), 7.09 (s, 1H), 3.92-3.79 (m, 4H), 2.74 (s, 3H), 2.54 (s, 3H), 2.29 (s, 6H), 2.00 (dd, J = 13.7, 5.9 Hz, 2H), 1.67 (dt, J = 12.9, 5.9 Hz, 2H), 1.03 (s, 3H). |

Example 35

Preparation of Compound 203

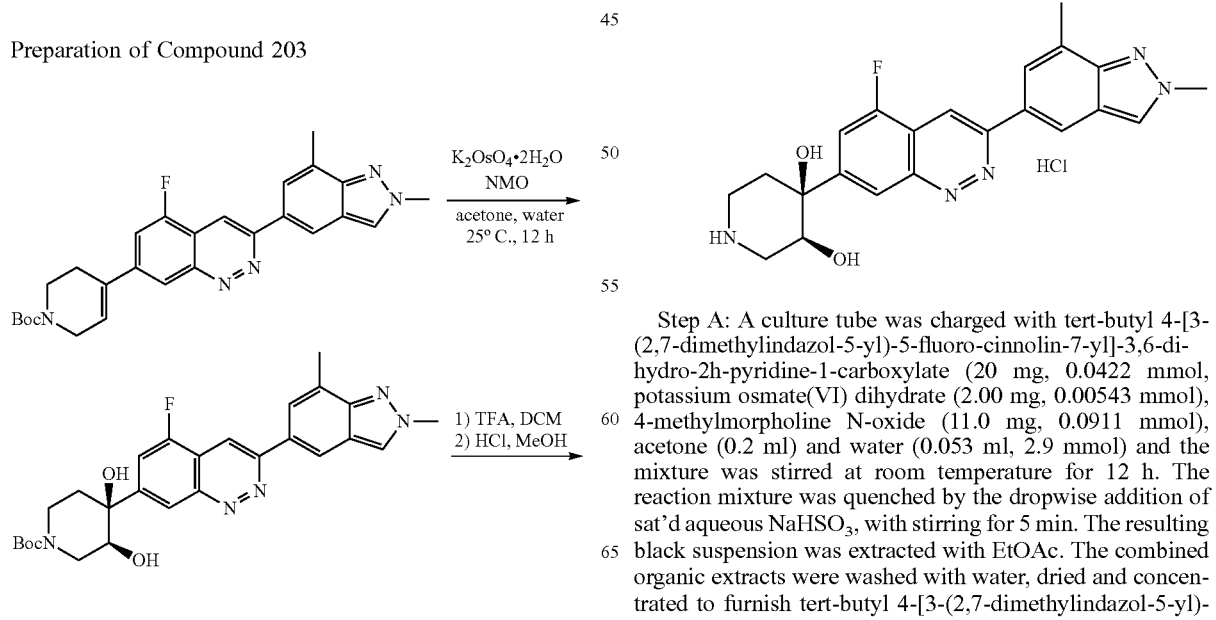

Step A: A culture tube was charged with tert-butyl 4-[3-(2,7-dimethylindazol-5-yl)-5-fluoro-cinnolin-7-yl]-3,6-dihydro-2h-pyridine-1-carboxylate (20 mg, 0.0422 mmol, potassium osmate(VI) dihydrate (2.00 mg, 0.00543 mmol), 4-methylmorpholine N-oxide (11.0 mg, 0.0911 mmol), acetone (0.2 ml) and water (0.053 ml, 2.9 mmol) and the mixture was stirred at room temperature for 12 h. The reaction mixture was quenched by the dropwise addition of sat'd aqueous NaHSO3, with stirring for 5 min. The resulting black suspension was extracted with EtOAc. The combined organic extracts were washed with water, dried and concentrated to furnish tert-butyl 4-[3-(2,7-dimethylindazol-5-yl)-

5-fluoro-cinnolin-7-yl]-3,4-dihydroxy-piperidine-1-carboxylate (cis-diol, racemate) (14.0 mg, 0.0276 mmol, 65.3% yield) as a yellow solid. MS m/z 508.2 [M+H]⁺.

Step B: A vial was charged with tert-butyl 4-[3-(2,7-dimethylindazol-5-yl)-5-fluoro-cinnolin-7-yl]-3,4-dihydroxy-piperidine-1-carboxylate (7.00 mg, 0.0138 mmol), trifluoroacetic acid (0.22 ml, 2.9 mmol) and dichloromethane (0.5 ml). The mixture was stirred at room temperature for 1 h. The mixture was concentrated. To the mixture was added 1.25 N HCl in methanol (1 mL). The mixture concentrated (this step was repeated three times). The solid was washed with ethyl acetate, ether and hexanes in a fritted funnel and then freeze dried to give 4-(3-(2,7-dimethyl-2H-indazol-5-yl)-5-fluorocinnolin-7-yl)piperidine-3,4-diol hydrogen chloride (cis-diol, racemate) (7.3 mg, 0.018 mmol, 100% yield).

MS m/z 408.3 [M+H]⁺; ¹H NMR (methanol-d₄) δ: 8.69 (s, 1H), 8.53 (s, 1H), 8.50 (s, 1H), 8.42 (s, 1H), 8.03 (s, 1H), 7.85 (d, J=11 Hz, 1H), 4.35 (dd, J=5, 1.5 Hz, 1H), 4.30 (s, 3H), 3.40 (m, 6H), 2.70 (s, 3H). NH and OH protons not observed.

Example 36

Preparation of Compound 146

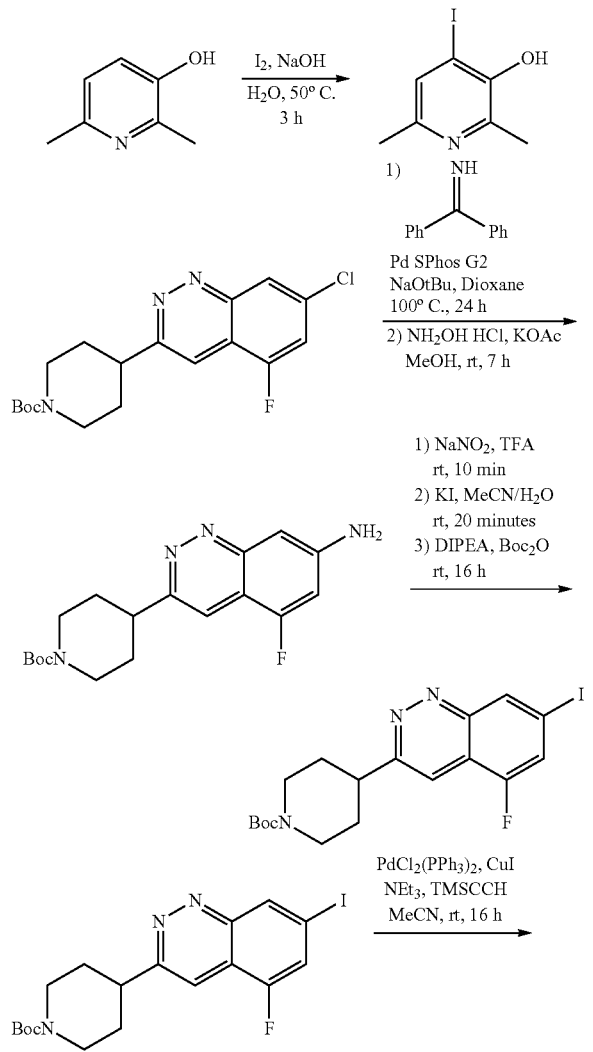

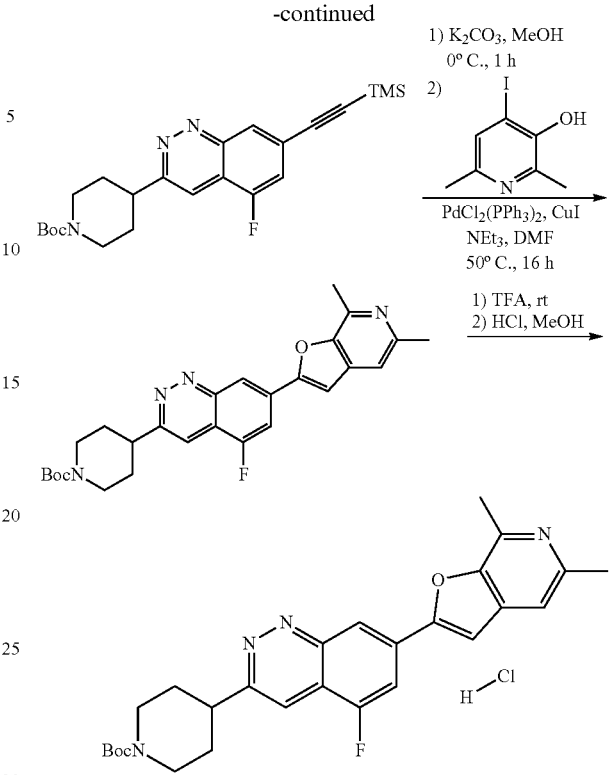

Step A: 2,6-Dimethylpyridin-3-ol (996 mg, 8.1 mmol) was dissolved in aqueous sodium hydroxide (2.0 M, 4.1 mL) while stirring at room temperature. To this stirred solution was added iodine (2.65 g, 10.4 mmol). The mixture was warmed to 50° C. and stirred for 3 h. The mixture was neutralized with aqueous hydrochloric acid (6 M), then quenched with saturated aqueous sodium thiosulfate solution. MeOH (5 mL) was added to the mixture, and then the reaction mixture was concentrated. CH₂Cl₂ (90 mL) and MeOH (10 mL) were added, the reaction was stirred for 10 min, then filtered. The filtrate was concentrated. The residue was chromatographed on silica gel, eluting with 0-100% EtOAc in hexanes to yield 4-iodo-2,6-dimethyl-pyridin-3-ol (564.6 mg, 28%).

MS m/z 250.1 [M+H]⁺; ¹H NMR (methanol-d₄) δ: 7.61 (s, 1H), 2.47 (s, 3H), 2.39 (s, 3H), OH proton not observed.

Step B: tert-Butyl 4-(7-chloro-5-fluoro-cinnolin-3-yl)piperidine-1-carboxylate (500 mg, 1.37 mmol), sodium tert-butoxide (198 mg, 2.06 mmol), and chloro(2-dicyclohexylphosphino-2',6'-dimethoxy-1,1'-biphenyl)[2-2'-amino-1,1'-biphenyl)]palladium(II) (103 mg, 0.14 mmol), 1,4-dioxane (10 mL), and diphenylmethanimine (260 uL, 1.55 mmol) were combined, argon degassed, and heated to 100° C. for 16 h. After cooling the reaction mixture to room temperature, hydroxylamine hydrochloride (445 mg, 6.4 mmol), potassium acetate (815 mg, 8.3 mmol) and methanol (30 mL) were added. The reaction mixture was stirred at room temperature for 7 h. The mixture was concentrated, and the residue was partitioned between EtOAc and H₂O. The layers were separated and the aqueous layer was extracted twice with EtOAc. The combined organic layers were dried over Na₂SO₄, filtered and concentrated. The residue was chromatographed on silica gel, eluting with 0-10% MeOH in CH₂Cl₂ to yield tert-butyl 4-(7-amino-5-fluoro-cinnolin-3-yl)piperidine-1-carboxylate (337 mg, 71%).

MS m/z 347.3 [M+H]⁺; ¹H NMR (methanol-d₄) δ: 7.87 (s, 1H), 7.14 (s, 1H), 7.06 (dd, J=11.6, 1.8 Hz, 1H), 4.30 (d, J=13.7 Hz, 2H), 3.29 (tt, J=12.2, 3.7 Hz, 1H), 2.92-3.11 (m, 2H), 2.04 (d, J=12.2 Hz, 2H), 1.87 (qd, J=12.6, 4.3 Hz, 2H), 1.51 (s, 9H), NH₂ protons not observed.

Step C: tert-Butyl 4-(7-amino-5-fluoro-cinnolin-3-yl)piperidine-1-carboxylate (187 mg, 0.54 mmol) was dissolved in trifluoroacetic acid (4.0 mL) and stirred at room temperature for 5 min. Sodium nitrite (43 mg, 0.63 mmol) was added to the mixture, which was stirred at room temperature for 10 min. The mixture was concentrated under reduced pressure. The residue was dissolved in acetonitrile (4.0 mL) and water (1.0 mL). To this stirred solution at room temperature was added potassium iodide (394 mg, 2.37 mmol) portion wise. The mixture was stirred for 20 min at room temperature. Diisopropylethylamine (1.4 mL, 8.0 mmol) and di-tert-butyl dicarbonate (800 uL, 3.35 mmol) were added to the mixture. The mixture was stirred at room temperature for 18 h. The mixture was concentrated, and the residue was chromatographed on silica gel, eluting with 0-100% EtOAc in hexanes to yield tert-butyl 4-(5-fluoro-7-iodocinnolin-3-yl)piperidine-1-carboxylate (119 mg, 48%).

MS m/z 402.3 [M+H-tBu]⁺; ¹H NMR (CDCl₃) δ: 8.82 (s, 1H), 7.84 (s, 1H), 7.69 (d, J=8.2 Hz, 1H), 4.36 (br s, 2H), 3.45 (tt, J=12.2, 3.7 Hz, 1H), 2.97 (t, J=11.0 Hz, 2H), 2.15 (br d, J=13.1 Hz, 2H), 1.91 (qd, J=12.5, 4.3 Hz, 2H), 1.50-1.54 (m, 9H).

Step D: tert-butyl 4-(5-fluoro-7-iodocinnolin-3-yl)piperidine-1-carboxylate, cuprous iodide (1.0 mg, 0.0053 mmol), and bis(triphenylphosphine)palladium(II) dichloride (6.2 mg, 0.0088 mmol) were combined under a nitrogen atmosphere, followed by the addition of CH₃CN (2.0 mL). The solution was argon degassed for 30 s, followed by the addition of trimethylamine (40 uL, 0.29 mmol). The solution was argon degassed for 3 min, followed by the addition of trimethylsilylacetylene (20 uL, 0.14 mmol). This mixture was stirred at room temperature under a nitrogen atmosphere for 16 h. The mixture was concentrated, and the residue was chromatographed on silica gel, eluting with 0-100% EtOAc in hexanes to yield tert-butyl 4-(5-fluoro-7-((trimethylsilyl)ethynyl)cinnolin-3-yl)piperidine-1-carboxylate (24.5 mg, 72%). MS m/z 372.5 [M+H-t-Bu]⁺.

Step E: tert-Butyl 4-(5-fluoro-7-((trimethylsilyl)ethynyl)cinnolin-3-yl)piperidine-1-carboxylate (25 mg, 0.057 mmol) was dissolved in MeOH (2.0 mL). The stirred solution was cooled to 0° C. Potassium carbonate (17.9 mg, 0.130 mmol) was added and the reaction mixture continued stirring at 0° C. for 1 h. The reaction was quenched with sat'd aqueous NH₄Cl (8.0 mL). The mixture was partitioned between CH₂Cl₂ and H₂O. The aqueous layer was extracted twice with CH₂Cl₂. The combined organic layers were dried over Na₂SO₄, filtered and concentrated to yield tert-butyl 4-(7-ethynyl-5-fluoro-cinnolin-3-yl)piperidine-1-carboxylate as a crude mixture that was used without purification. MS m/z 300.0 [M-FH-t-Bu]⁺. tert-Butyl 4-(7-ethynyl-5-fluoro-cinnolin-3-yl)piperidine-1-carboxylate (20 mg, 0.057 mmol), cuprous iodide (0.3 mg, 0.002 mmol), bis(triphenylphosphine)palladium(II) dichloride (4.4 mg, 0.0063 mmol), and 4-iodo-2,6-dimethyl-pyridin-3-ol (15.8 mg, 0.063 mmol) were combined under a nitrogen atmosphere, followed by the addition of N,N-dimethylformamide (1.0 mL). The solution was argon degassed for 30 s, followed by the addition of trimethylamine (50.0 uL, 0.36 mmol). This solution was argon degassed for 5 min, then stirred at 45° C. under an argon atmosphere for 20 h. The mixture was concentrated, and the residue was chromatographed on silica gel, eluting with 0-30% MeOH in CH₂Cl₂ to yield tert-butyl 4-[7-(5,7-dimethylfuro[2,3-c]pyridin-2-yl)-5-fluoro-cinnolin-3-yl]piperidine-1-carboxylate (10.3 mg, 38%). MS m/z 477.5 [M+H]⁺.

Step F: tert-Butyl 4-[7-(5,7-dimethylfuro[2,3-c]pyridin-2-yl)-5-fluoro-cinnolin-3-yl]piperidine-1-carboxylate (10.3 mg, 0.022 mmol) was dissolved in trifluoroacetic acid (2 mL). After 15 minutes, the volatile material was removed. The residue was chromatographed on a reversed phase C18 column, eluting with 0-100% CH₃CN in H₂O (0.1% v/v TFA additive). The collected fractions were concentrated. The residue was dissolved in 1.25 M HCl in MeOH. The volatile material was removed to yield 2-[5-fluoro-3-(4-piperidyl)cinnolin-7-yl]-5,7-dimethyl-furo[2,3-c]pyridine hydrochloride (8.3 mg, 93%).

MS m/z 377.5 [M+H]⁺; ¹H NMR (methanol-d₄) δ: 9.11 (s, 1H), 8.48 (s, 1H), 8.40 (br d, J=10.1 Hz, 1H), 8.04 (s, 1H), 7.99 (s, 1H), 3.69-3.77 (m, 1H), 3.66 (br d, J=12.8 Hz, 2H), 3.34-3.39 (m, 2H), 3.12 (s, 3H), 2.84 (s, 3H), 2.27-2.50 (m, 4H), NH and HCl protons not observed.

Example 37

Preparation of Compound 191

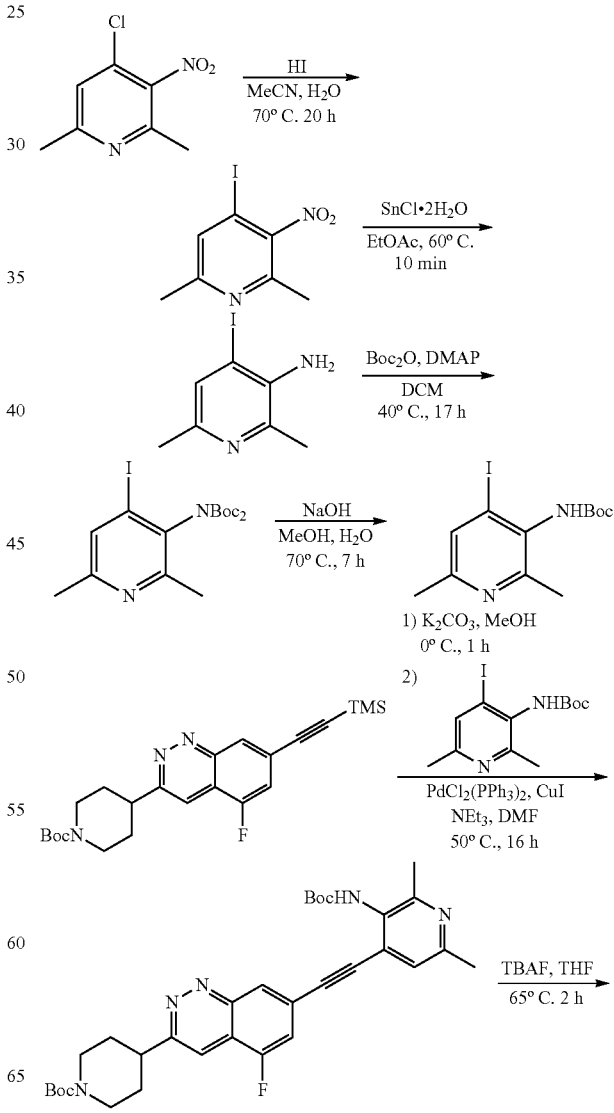

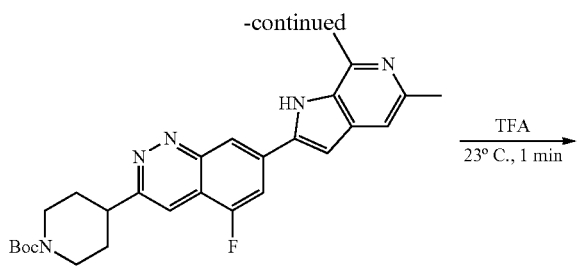

Step A: 4-Chloro-2,6-dimethyl-3-nitro-pyridine (1.1054 g, 5.9239 mmol), acetonitrile (4.0 mL), and aqueous hydroiodic acid (concentrated, 57%, 4.0 mL) were combined and heated to 70° C. for 20 h. The mixture was partitioned between $CH_2Cl_2$, aqueous sat'd $Na_2C_3$, and aqueous NaOH (1 M). The aqueous layer was extracted with $CH_2Cl_2$. The combined organic phases were dried over $Na_2SO_4$, filtered and concentrated. The residue was chromatographed on silica gel, eluting with 0-100% EtOAc in hexanes to yield 4-iodo-2,6-dimethyl-3-nitro-pyridine (1.48 g, 90%). MS m/z 279.1 $[M+H]^+$.

Step B: 4-Iodo-2,6-dimethyl-3-nitro-pyridine (1.004 g, 3.611 mmol), stannous chloride dihydrate (3.32 g, 14.7 mmol) and EtOAc (5.0 mL) were combined and heated to 60° C. for 10 min. The mixture was partitioned between EtOAc, aqueous sat'd $Na_2CO_3$ and aqueous NaOH (1 M). The aqueous layer was extracted with EtOAc. The combined organic phases were dried over $Na_2SO_4$, filtered and concentrated to yield 4-iodo-2,6-dimethyl-pyridin-3-amine (723.7 mg, 81%). MS m/z 249.1 $[M+H]^+$.

Step C: 4-Iodo-2,6-dimethyl-pyridin-3-amine (724 mg, 2.92 mmol), di-tert-butyl dicarbonate (2.2 mL, 9.2 mmol), 4-dimethylaminopyridine (42 mg, 0.34 mmol) and $CH_2Cl_2$ (5.0 mL) were combined and stirred at 40° C. for 17 h. The mixture was concentrated, and the residue was chromatographed on silica gel, eluting with 0-100% EtOAc in hexanes to yield tert-butyl N-tert-butoxycarbonyl-N-(4-iodo-2,6-dimethyl-3-pyridyl)carbamate (489 mg, 37%). MS m/z 449.4 $[M+H]^+$.

Step D: tert-Butyl N-tert-butoxycarbonyl-N-(4-iodo-2,6-dimethyl-3-pyridyl)carbamate (489 mg, 1.1 mmol), aqueous NaOH (1 M, 4.0 mL), and MeOH (4.0 mL) were combined and stirred at 70° C. for 7 h. The mixture was partitioned between $CH_2Cl_2$ and $H_2O$. The aqueous layer was extracted twice with $MeOH/CH_2Cl_2$ (1:9) and the combined organic phases were dried over $Na_2SO_4$, filtered and concentrated. The residue was chromatographed on silica gel, eluting with 0-100% EtOAc in hexanes to yield tert-butyl N-(4-iodo-2,6-dimethyl-3-pyridyl)carbamate (278 mg, 73%). MS m/z 349.1 $[M+H]^+$; $^1H$ NMR ($CDCl_3$) δ: 7.54 (s, 1H), 6.00 (br d, J=2.7 Hz, 1H), 2.57 (s, 3H), 2.48 (s, 3H), 1.53 (s, 9H).

Step E: tert-Butyl 4-(5-fluoro-7-((trimethylsilyl)ethynyl)cinnolin-3-yl)piperidine-1-carboxylate (from Example 38, 104 mg, 0.24 mmol) was dissolved in methanol (2.0 mL). The stirred solution was cooled to 0° C. Potassium carbonate (50.6 mg, 0.366 mmol) was added and the mixture was stirred at 0° C. for 1 h. The reaction mixture was quenched with sat'd aqueous $NH_4Cl$ (8.0 mL). The mixture was partitioned between $CH_2Cl_2$ and $H_2O$. The aqueous layer was extracted twice with $CH_2Cl_2$. The combined organic layers were dried over $Na_2SO_4$, filtered and concentrated to yield tert-butyl 4-(7-ethynyl-5-fluoro-cinnolin-3-yl)piperidine-1-carboxylate as a crude mixture that was used without purification. MS m/z 300.0 $[M+H-tBu]^+$. tert-Butyl 4-(7-ethynyl-5-fluoro-cinnolin-3-yl)piperidine-1-carboxylate (86 mg, 0.24 mmol) was dissolved in DMF (1.0 mL). The vessel was purged with argon. Triethylamine (135 uL, 0.97 mmol) was added. The vessel was again purged with argon. This solution was added to a mixture of cuprous iodide (1.4 mg, 0.0073 mmol), bis(triphenylphosphine) palladium(II) dichloride (10.2 mg, 0.0146 mmol), and tert-butyl N-(4-iodo-2,6-dimethyl-3-pyridyl)carbamate (93 mg, 0.27 mmol) under an argon atmosphere. The solution was stirred at 50° C. for 17 h. The mixture was concentrated, and the residue partitioned between $CH_2Cl_2$ and brine. The aqueous layer was extracted with $CH_2Cl_2$. The combined organic phases were dried over $Na_2SO_4$, filtered and concentrated to yield tert-butyl 4-[7-[2-[3-(tert-butoxycarbonylamino)-2,6-dimethyl-4-pyridyl]ethynyl]-5-fluoro-cinnolin-3-yl]piperidine-1-carboxylate as a crude mixture that was used without purification. MS m/z 576.5 $[M+H]^+$.

Step F: tert-Butyl 4-[7-[2-[3-(tert-butoxycarbonylamino)-2,6-dimethyl-4-pyridyl]ethynyl]-5-fluoro-cinnolin-3-yl]piperidine-1-carboxylate (140 mg, 0.24 mmol), tetrahydrofuran (4.0 mL), and tetrabutylammonium fluoride (1.0 M in THF, 730 uL, 0.73 mmol) were combined and stirred at 65° C. for 2 h. The reaction was concentrated and the residue was chromatographed on silica gel, eluting with 0-30% MeOH in $CH_2Cl_2$ to yield tert-butyl 4-[7-(5,7-dimethyl-1H-pyrrolo[2,3-c]pyridin-2-yl)-5-fluoro-cinnolin-3-yl]piperidine-1-carboxylate (34.2 mg, 30%). MS m/z 476.5 $[M+H]^+$.

Step G: tert-Butyl 4-[7-(5,7-dimethyl-1H-pyrrolo[2,3-c]pyridin-2-yl)-5-fluoro-cinnolin-3-yl]piperidine-1-carboxylate (34.2 mg, 0.0719 mmol) was dissolved in trifluoroacetic acid (1 mL). After 1 min, the volatile material was removed. The residue was chromatographed on a reversed phase C18 column, eluting with 0-100% $CH_3CN$ in $H_2O$ (0.1% v/v TFA additive), and subsequently chromatographed on silica gel, eluting with 0-100% MeOH (2.5% v/v $NH_4OH$ additive) in $CH_2Cl_2$, to yield 7-(5,7-dimethyl-1H-pyrrolo[2,3-c]pyridin-2-yl)-5-fluoro-3-(piperidin-4-yl)cinnoline hydrochloride.

MS m/z 376.3 $[M+H]^+$; $^1H$ NMR (methanol-$d_4$) δ: 8.95 (s, 1H), 8.23 (s, 1H), 8.22 (dd, J=10.7, 1.2 Hz, 1H), 7.67 (s, 1H), 7.41 (s, 1H), 3.50-3.61 (m, 3H), 3.17-3.26 (m, 2H), 2.99 (s, 3H), 2.64 (s, 3H), 2.18-2.34 (m, 4H), NH and HCl protons not observed.

Example 38

Preparation of Compound 82

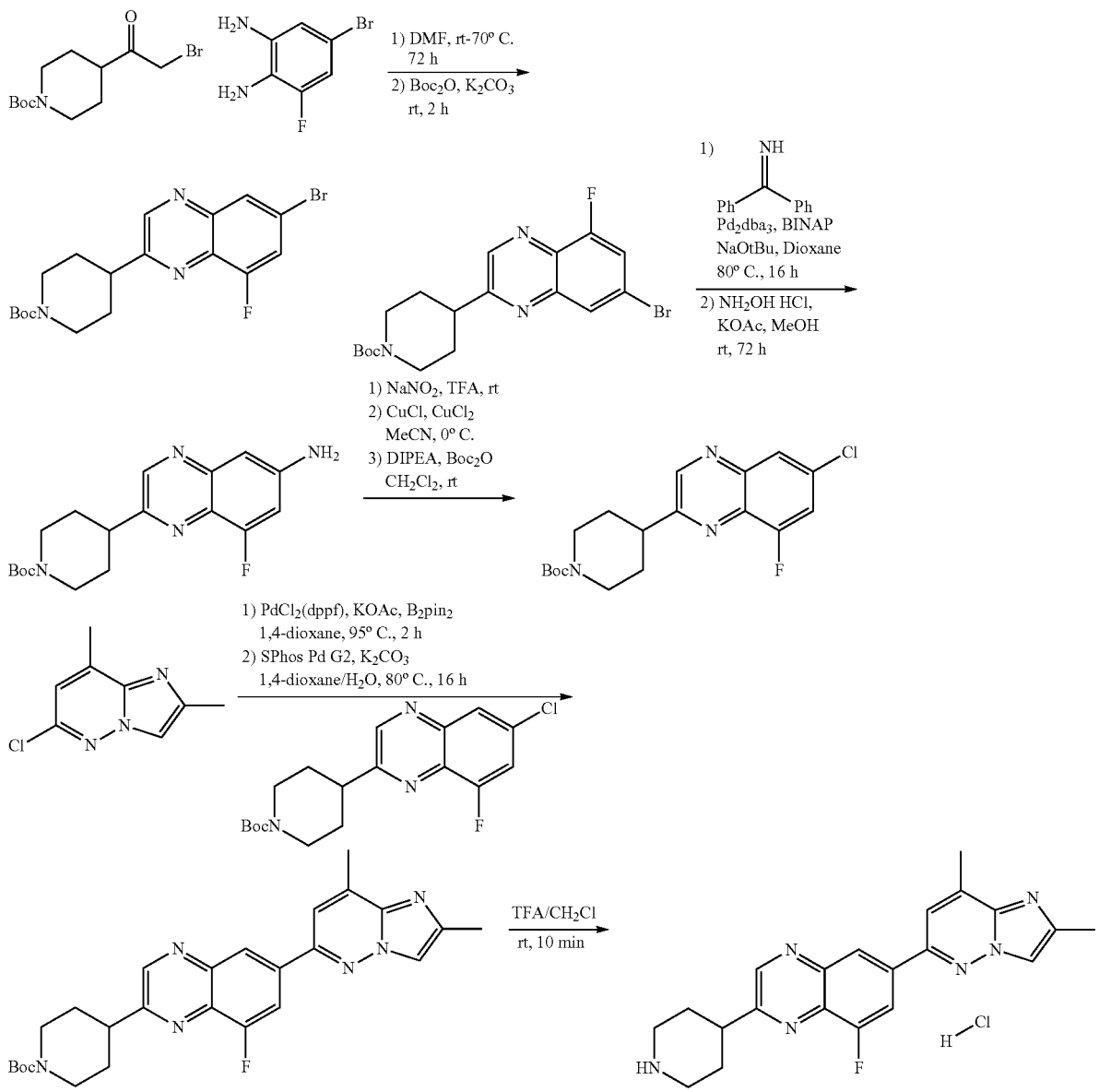

Step A: 5-Bromo-3-fluoro-benzene-1,2-diamine (1.07 g, 5.2 mmol), tert-butyl 4-(2-bromoacetyl)piperidine-1-carboxylate (1.60 g, 5.2 mmol), and DMF (80 mL) were combined and stirred at room temperature for 16 h, 50° C. for 24 h, and 70° C. for 24 h. After cooling to room temperature, potassium carbonate (1.08 g, 7.84 mmol) and di-tert-butyl dicarbonate (1.4 mL, 6.3 mmol) were added. The reaction mixture was stirred at room temperature for 2 h. The mixture was partitioned between EtOAc and brine. The organic layer was washed twice with brine, dried over $Na_2SO_4$, filtered and concentrated. The residue was chromatographed on silica gel, eluting with 0-100% EtOAc in hexanes to yield tert-butyl 4-(6-bromo-8-fluoro-quinoxalin-2-yl)piperidine-1-carboxylate and tert-butyl 4-(7-bromo-5-fluoroquinoxalin-2-yl)piperidine-1-carboxylate as an approximate 1:1 mixture (labeled distinguishable peaks as compounds A and B in $^1$H NMR; labeled overlapping peaks as apparent peaks "apt") (1.23 g, 58%).

MS m/z 310.2 [M+H—$CO_2$-t-Bu]$^+$; $^1$H NMR (CDCl$_3$) δ: 8.84 (s, 1H, A), 8.82 (s, 1H, B), 8.12 (t, J=1.7 Hz, 1H, A), 8.09 (t, J=1.7 Hz, 1H, B), 7.61 (dd, J=9.2, 2.1 Hz, 1H, A), 7.58 (dd, J=9.0, 2.0 Hz, 1H, B), 4.34 (apt d, J=12.2 Hz, 4H), 3.17 (apt qt, J=11.9, 3.7 Hz, 2H), 2.94 (apt br tt, J=13.1, 2.8 Hz, 4H), 1.99-2.06 (m, 4H), 1.93 (apt quint J=11.6, 4.0 Hz, 4H), 1.51 (apt d, J=1.8 Hz, 18H).

Step B: A 1:1 mixture of tert-butyl 4-(6-bromo-8-fluoro-quinoxalin-2-yl)piperidine-1-carboxylate and tert-butyl 4-(7-bromo-5-fluoroquinoxalin-2-yl)piperidine-1-carboxylate was combined with sodium tert-butoxide (760 mg, 7.9 mmol), tris(dibenzylideneacetone) dipalladium(0) (74 mg, 0.08 mmol), racemic 2,2'-bis(diphenylphosphino)-1,1'-binaphthyl (144 mg, 0.23 g), toluene (13.0 mL) and benzophenone imine (500 uL, 3.6 mmol) were combined under a nitrogen atmosphere. The vessel was argon purged for 6 min, then warmed to 80° C. for 20 h. Hydroxylamine hydrochloride (1.37 g, 19.6 mmol), potassium acetate (2.47 g, 25.2 mmol), and MeOH (65 mL) were added to the mixture. The mixture was stirred at room temperature for 24 h and then was concentrated. The residue was partitioned between sat'd aqueous $Na_2CO_3$, brine, and $CH_2Cl_2$. The aqueous layer was extracted twice with $CH_2Cl_2$. The combined organic layers were dried over $Na_2SO_4$, filtered and concentrated. The residue was chromatographed on silica gel, eluting with 0-100% EtOAc in hexanes to yield tert-butyl 4-(6-amino-8-fluoro-quinoxalin-2-yl)piperidine-1-carboxylate (340.0 mg, 38%).

MS m/z 291.3 [M-FH-t-Bu]$^+$; $^1$H NMR (DMSO-d$_6$) δ: 8.69 (s, 1H), 7.01 (dd, J=12.5, 2.1 Hz, 1H), 6.77 (d, J=2.1 Hz, 1H), 6.11 (s, 2H), 4.03-4.21 (m, 2H), 3.06 (tt, J=11.5, 3.4 Hz, 1H), 2.89 (br s, 2H), 1.86-1.93 (m, 2H), 1.66 (qd, J=12.6, 4.4 Hz, 2H), 1.43 (s, 9H).

Step C: Sodium nitrite (23.9 mg, 0.346 mmol) was added to a stirred solution of tert-butyl 4-(6-amino-8-fluoro-quinoxalin-2-yl)piperidine-1-carboxylate in trifluoroacetic acid (1.5 mL). The mixture was stirred at room temperature for 1 min. The mixture was concentrated and azeotroped twice with MeCN. The residue was dissolved in acetonitrile (1.4 mL) and cooled to 0° C. This solution was added dropwise to a solution of copper(I) chloride (47 mg, 0.47 mmol) and copper(II) chloride (95 mg, 0.71 mmol) in acetonitrile (1.2 mL) at 0° C. After stirring for 1 min at 0° C., the reaction mixture was partitioned between EtOAc, aqueous sat'd $Na_2CO_3$, and aqueous NaOH (1 M). The aqueous layer was extracted with EtOAc. The combined organic phases were dried over $Na_2SO_4$, filtered and concentrated to yield 6-chloro-8-fluoro-2-(4-piperidyl)quinoxaline (130.0 mg) as a crude mixture that was used without purification. MS m/z 266.3 [M+H]$^+$. 6-Chloro-8-fluoro-2-(4-piperidyl)quinoxaline (61 mg, 0.23 mmol), $CH_2Cl_2$ (3.0 mL), N,N-diisopropylethylamine (400 uL, 2.3 mmol), and di-tert-butyl dicarbonate (230 uL, 0.96 mmol) were combined and stirred at room temperature for 18 h. The mixture was partitioned between $CH_2Cl_2$ and $H_2O$. The aqueous layer was extracted twice with $CH_2Cl_2$. The combined organic phases were dried over $Na_2SO_4$, filtered and concentrated. The residue was chromatographed on silica gel, eluting with 0-40% EtOAc in hexanes to yield tert-butyl 4-(6-chloro-8-fluoro-quinoxalin-2-yl)piperidine-1-carboxylate (52.7 mg, 50%).

MS m/z 310.3 [M+H-t-Bu]$^+$; $^1$H NMR (CDCl$_3$) δ: 8.84 (s, 1H), 7.93 (t, J=1.8 Hz, 1H), 7.48 (dd, J=9.5, 2.1 Hz, 1H), 4.26-4.44 (m, 2H), 3.19 (tt, J=11.7, 3.8 Hz, 1H), 2.94 (br t, J=12.2 Hz, 2H), 2.04 (d, J=11.9 Hz, 2H), 1.94 (qd, J=12.2, 4.3 Hz, 2H), 1.52 (s, 9H).

Step D: 6-Chloro-2,8-dimethyl-imidazol[1,2-b]pyridazine (50.0 mg, 0.275 mmol), 1,1'-bis(diphenylphosphino)ferrocene palladium(II) dichloride (15 mg, 0.019 mmol), bis(pinacolato)diboron (96 mg, 0.37 mmol), and potassium acetate (dried at 250° C. under vacuum immediately prior to using, 89 mg, 0.89 mmol), and 1,4-dioxane (1.5 mL) were combined. The mixture stirred under argon at 95° C. for 2 h. tert-Butyl 4-(6-chloro-8-fluoro-quinoxalin-2-yl)piperidine-1-carboxylate (65.8 mg, 0.180 mmol), chloro(2-dicyclohexylphosphino-2'6'-dimethoxy-1,1'-biphenyl)(2'-amino-1,1'-biphenyl-2-yl) palladium(II) (6.6 mg, 0.0091 mmol), and aqueous $K_2CO_3$ (1 M, 750 uL) were added to the mixture. The mixture was argon flushed, and then was stirred at 80° C. for 16 h. The reaction was partitioned between EtOAc and $H_2O$. The aqueous layer was extracted with EtOAc. The combined organic layers were dried over $Na_2SO_4$, filtered and concentrated. The residue was chromatographed on silica gel, eluting with 0-100% EtOAc in hexanes to yield tert-butyl 4-[6-(2,8-dimethylimidazo[1,2-b]pyridazin-6-yl)-8-fluoro-quinoxalin-2-yl]piperidine-1-carboxylate (44 mg, 52%). MS m/z 477.6 [M+H]$^+$.

Step E: tert-Butyl 4-[6-(2,8-dimethylimidazo[1,2-b]pyridazin-6-yl)-8-fluoro-quinoxalin-2-yl]piperidine-1-carboxylate (45 mg, 0.094 mmol) was dissolved in $CH_2Cl_2$ (2 mL) and TFA (2 mL). After 10 min, the volatile material was removed. The residue was dissolved in methanolic hydrogen chloride (1.25 M) and concentrated to yield 6-(2,8-dimethylimidazo[1,2-b]pyridazin-6-yl)-8-fluoro-2-(4-piperidyl)quinoxaline hydrochloride (47 mg, quant.).

MS m/z 377.3 [M+H]$^+$; $^1$H NMR (methanol-d$_4$) δ: 9.11 (s, 1H), 8.75 (s, 1H), 8.51 (d, J=0.9 Hz, 1H), 8.35-8.46 (m, 2H), 3.64 (dt, J=12.9, 3.2 Hz, 2H), 3.58 (tt, J=11.0, 3.8 Hz, 1H), 3.24-3.32 (m, 2H), 2.87 (s, 3H), 2.71 (s, 3H), 2.35-2.42 (m, 2H), 2.26-2.34 (m, 2H), NH and HCl protons not observed.

Example 39

Preparation of Compound 116

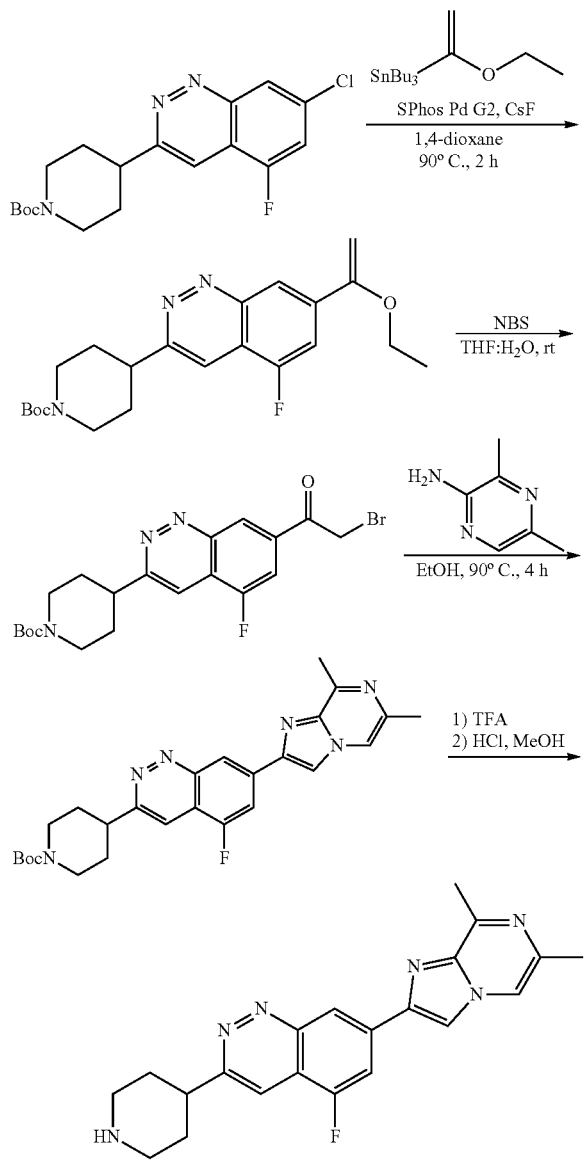

Step A: tert-Butyl 4-(7-chloro-5-fluorocinnolin-3-yl)piperidine-1-carboxylate (500 mg, 1.4 mmol) was combined with tri-butyl(1-ethoxyvinyl)tin (0.52 mL, 1.54 mmol) and CsF (470 mg, 3.08 mmol) in 1,4-dioxane (16 mL). The mixture was stirred at 90° C. for 2 h under $N_2$. The mixture was partitioned between EtOAc and $H_2O$. The organic layer was washed with brine, dried over $Na_2SO_4$, filtered and concentrated. The residue was chromatographed on silica gel, eluting with 10-20% EtOAc in petroleum ether to yield tert-butyl 4-(7-(1-ethoxyvinyl)-5-fluorocinnolin-3-yl)piperidine-1-carboxylate (500 mg, 90%). MS m/z 402.7 [M+H]⁺.

Step B: tert-Butyl 4-(7-(1-ethoxyvinyl)-5-fluorocinnolin-3-yl)piperidine-1-carboxylate (480 mg, 1.2 mmol) was combined with NBS (235 mg, 1.32 mmol) in THF (20 mL) and $H_2O$ (10 mL). The mixture was stirred at room temperature for 10 min. The THF was removed under reduce pressure. The solution was filtered. The solid was dried to yield tert-butyl 4-(7-(2-bromoacetyl)-5-fluorocinnolin-3-yl)piperidine-1-carboxylate (500 mg, 92%). MS m/z 474.0, 476.0 [M+Na]⁺.

Step C: tert-Butyl 4-(7-(2-bromoacetyl)-5-fluorocinnolin-3-yl)piperidine-1-carboxylate (477 mg, 1.06 mmol) was combined with 3,5-dimethylpyrazin-2-amine (234 mg, 1.9 mmol) in EtOH (20 mL). The mixture was stirred at 90° C. for 4 h. Then the mixture was cooled to room temperature, and the solvent was removed under reduced pressure. The residue was chromatographed on silica gel, eluting with 30-50% EtOAc in $CH_2Cl_2$ to yield tert-butyl 4-(7-(6,8-dimethylimidazo[1,2-a]pyrazin-2-yl)-5-fluorocinnolin-3-yl)piperidine-1-carboxylate (270 mg, 53%). MS m/z 477.2 [M+H]⁺.

Step D: tert-Butyl 4-(7-(6,8-dimethylimidazo[1,2-a]pyrazin-2-yl)-5-fluorocinnolin-3-yl)piperidine-1-carboxylate (230 mg, 0.48 mmol) was into TFA (2 mL). The mixture was stirred at room temperature for 1 h. The volatile material was removed under reduced pressure. The residue was purified by prep-HPLC to yield 7-(6,8-dimethylimidazo[1,2-a]pyrazin-2-yl)-5-fluoro-3-(piperidin-4-yl)cinnoline hydrochloride (86 mg, 45% Yield).

MS m/z 377.2 [M+H]⁺; ¹H NMR (DMSO-d₆) δ: 8.93 (s, 1H), 8.83 (s, 1H), 8.29-8.38 (m, 2H), 8.11 (s, 1H), 3.82 (s, 1H), 3.12 (dd, J=12.5, 9.5 Hz, 4H), 2.82 (d, J=13.2 Hz, 3H), 2.41 (s, 3H), 2.10-2.28 (m, 4H), NH proton not observed Example 40

Preparation of Compound 226

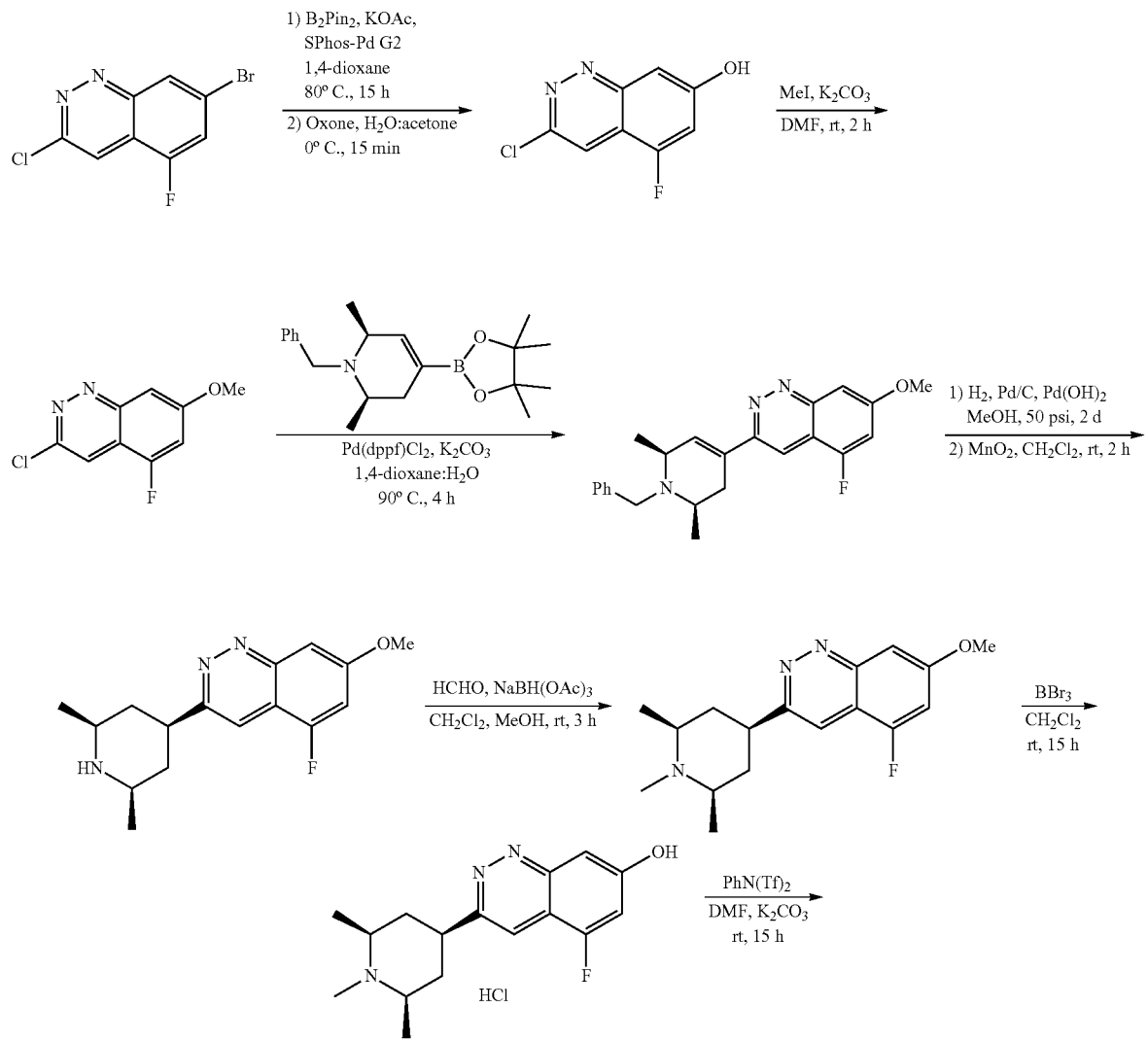

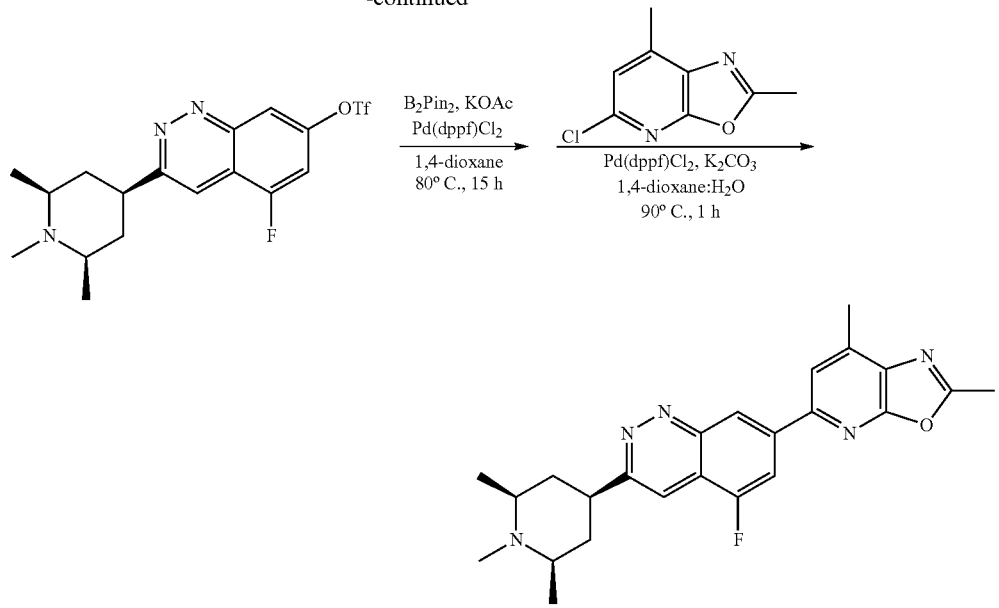

Step A: KOAc (6.6 g, 67 mmol) was dried under sweeping argon at 180° C. for 30 min. The mixture was cooled to room temperature. 7-Bromo-3-chloro-5-fluorocinnoline (90% purity, 3 g, 10.3 mmol) was added, along with bis(pinacolato)diboron (3 g, 11.8 mmol), SPhos Pd G2 (300 mg, 0.41 mmol) and 1,4-dioxane (40 mL). The mixture was heated at 80° C. for 15 h. The mixture was diluted in EtOAc and was filtered through Celite. The filtrate was concentrated under vacuum. The residue was chromatographed on silica gel, eluting with 20-50% EtOAc in $CH_2Cl_2$ to yield crude boronic acid. This material was suspended in 100 mL of 1:1 acetone:$H_2O$ at 0° C. Oxone (20 g, 32.3 mmol) was added. The mixture was stirred at 0° C. for 15 min. The reaction mixture was diluted in 600 mL $H_2O$ and then filtered. The collected material was dried to yield 3-chloro-5-fluorocinnolin-7-ol (1.92 g, 84%) as a dark yellow solid.

$^1$H NMR (DMSO-$d_6$) δ: 11.34 (s, 1H), 8.39 (s, 1H), 7.49 (s, 1H), 7.40 (dd, J=11, 2 Hz, 1H).

Step B: 3-Chloro-5-fluorocinnolin-7-ol (1.9 g, 8.6 mmol, 90% purity) was dissolved in DMF (37 mL). $K_2CO_3$ (3.8 g, 27 mmol) was added to the solution. The mixture was stirred at room temperature for 30 min. Iodomethane (1.9 mL, 31 mmol) was added to the mixture. The reaction mixture was stirred at room temperature for 2 h. The mixture was partitioned between $H_2O$ and EtOAc. The organic layer was washed with $H_2O$ and brine, dried over $MgSO_4$, filtered, and concentrated under vacuum. The residue was chromatographed on silica gel, eluting with 20% EtOAc in hexanes to yield 3-chloro-5-fluoro-7-methoxycinnoline (1.04 g, 57%) as a white solid.

$^1$H NMR (acetone-$d_4$) δ: 8.26 (s, 1H), 7.69 (s, 1H), 7.37 (dd, J=10.5, 2 Hz, 1H), 4.13 (s, 3H).

Step C: 3-Chloro-5-fluoro-7-methoxycinnoline (990 mg, 4.65 mmol), (2R,6S)-1-benzyl-2,6-dimethyl-4-(4,4,5,5-tetramethyl-1,3,2-dioxaborolan-2-yl)-1,2,3,6-tetrahydropyridine (80% purity, 2.14 g, 5.24 mmol), Pd(dppf)$Cl_2$—$CH_2Cl_2$ (190 mg, 0.23 mmol), 1,4-dioxane (26 mL), and aqueous $K_2CO_3$ (2.0 M, 13 mL, 26 mmol) were heated at 90° C. for 4 h. The mixture was partitioned between $CH_2Cl_2$ and $H_2O$. The organic layer was dried over $MgSO_4$, filtered, and concentrated under vacuum. The residue was chromatographed on silica gel, eluting with 10-20% acetone in $CH_2Cl_2$ to yield 3-((2R,6S)-1-benzyl-2,6-dimethyl-1,2,3,6-tetrahydropyridin-4-yl)-5-fluoro-7-methoxycinnoline (1.28 g, 73%) as an off-white solid.

$^1$H NMR (acetone-$d_4$) δ: 8.07 (s, 1H), 7.67 (s, 1H), 7.47-7.51 (m, 2H), 7.30-7.36 (m, 2H), 7.20-7.27 (m, 2H), 7.00 (s, 1H), 4.11 (s, 3H), 3.97 (d, J=16 Hz, 1H), 3.91 (d, J=16 Hz, 1H), 3.53-3.60 (m, 1H), 3.10-3.15 (m, 1H), 2.86-2.92 (m, 1H), 2.54-2.62 (m, 1H), 1.32 (d, J=6.5 Hz, 3H), 1.21 (d, J=6.5 Hz, 3H).

Step D: 3-((2R,6S)-1-Benzyl-2,6-dimethyl-1,2,3,6-tetrahydropyridin-4-yl)-5-fluoro-7-methoxycinnoline (1.28 g, 3.39 mmol) was dissolved in 140 mL of 1:1 $CH_2Cl_2$:MeOH. 10% Pd/C (300 mg) and 20% Pd(OH)$_2$/C (300 mg) were added. The mixture was stirred under $H_2$ (50 psi) for 2 d. The reaction mixture was filtered over Celite, washing with $CH_2Cl_2$:MeOH. The filtrate was concentrated under vacuum. The residue was partitioned between aqueous NaOH and $CH_2Cl_2$. The organic layer was dried over $MgSO_4$, filtered, and concentrated under vacuum. The residue was dissolved in $CH_2Cl_2$ (20 mL). To the solution was added $MnO_2$ (5 g, 57.5 mmol). The mixture was stirred at room temperature for 2 h. The reaction mixture was filtered over Celite, washing with $CH_2Cl_2$:MeOH. The filtrate was concentrated and the residue was chromatographed on silica gel, eluting with $CH_2Cl_2$:MeOH:$NH_4OH$ (9:1:0.1) to yield 3-((2S,4R,6R)-2,6-dimethylpiperidin-4-yl)-5-fluoro-7-methoxycinnoline (568 mg, 53%) as yellow solid. This compound is the higher Rf component of the product mixture.

$^1$H NMR (methanol-$d_4$) δ: 8.06 (s, 1H), 7.59 (s, 1H), 7.27 (dd, J=10.5, 1.5 Hz, 1H), 4.06 (s, 3H), 3.43 (tt, J=12.5, 3.5 Hz, 1H), 3.00-3.05 (m, 2H), 2.09 (d, J=12.5 Hz, 2H), 1.54 (q, J=12.5 Hz, 2H), 1.25 (d, J=6.5 Hz, 6H), NH proton not observed.

Step E: A solution of 3-((2S,4R,6R)-2,6-Dimethylpiperidin-4-yl)-5-fluoro-7-methoxycinnoline (565 mg, 1.95 mmol) in MeOH (2 mL) and $CH_2Cl_2$ (8 mL) was treated with 37% formaldehyde in water (4 mL, 54 mmol). Sodium triacetoxyborohydride (3.3 g, 16 mmol) was added in three portions over 3 h. The reaction mixture was partitioned between aqueous NaOH and $CH_2Cl_2$. The organic layer was dried over $MgSO_4$, filtered, and concentrated under vacuum to yield 5-fluoro-7-methoxy-3-((2S,4r,6R)-1,2,6-trimethylpiperidin-4-yl)cinnoline (566 mg, 95%) as a yellow solid.

$^1$H NMR (methanol-$d_4$) δ: 8.06 (s, 1H), 7.59 (s, 1H), 7.27 (dd, J=10.5, 1.5 Hz, 1H), 4.06 (s, 3H), 3.43 (m, 1H), 2.50 (m, 2H), 2.41 (s, 3H), 2.08 (d, J=11 Hz, 2H), 1.82 (q, J=12 Hz, 2H), 1.29 (d, J=6.5 Hz, 6H).

Step F: 5-Fluoro-7-methoxy-3-((2S,4R,6R)-1,2,6-trimethylpiperidin-4-yl)cinnoline (485 mg, 1.6 mmol) was dissolved in $CH_2Cl_2$ (4 mL) at 0° C. $BBr_3$ (2 mL, 21.2 mmol) was added dropwise. The mixture became difficult to stir after 10 min. The mixture was warmed to room temperature. The sticky clumps were broken up with a spatula until the mixture could be stirred. The mixture was stirred at room temperature for 16 h. The mixture was added slowly to ice. NaOH pellets were added until the solution was basic. The volatile material was removed under vacuum. The crude product was re-dissolved in 20 mL $H_2O$. Reverse-phase chromatography was used to desalt the product. Aqueous HCl was added to the purest fractions. The fractions were concentrated under reduced pressure to afford crude 5-fluoro-3-((2S,4R,6R)-1,2,6-trimethylpiperidin-4-yl)cinnolin-7-ol hydrochloride (70% purity, 687 mg, 92%). This material appears as a crude 2:1 tautomeric mixture by $^1$H NMR in $CD_3OD$. MS m/z 290.2 [M+H]$^+$.

Step G: Crude 5-fluoro-3-((2S,4R,6R)-1,2,6-trimethylpiperidin-4-yl)cinnolin-7-ol hydrochloride (70% purity, 685 mg, 1.47 mmol), N,N-bis(trifluoromethylsulfonyl)aniline (2.7 g, 7.6 mmol), $K_2CO_3$ (2.7 g, 20 mmol), and DMF (7 mL) were stirred at room temperature for 15 h. The volatile material was removed under vacuum. The crude product was dissolved in $CH_2Cl_2$ and was filtered to remove solid impurities. The filtrate was concentrated under vacuum. The residue was chromatographed on silica gel, eluting with 5-20% MeOH in $CH_2Cl_2$ to yield 5-fluoro-3-((2S,4R,6R)-1,2,6-trimethylpiperidin-4-yl)cinnolin-7-yl trifluoromethanesulfonate (535 mg, 79% over 2 steps) as a yellow solid.

$^1$H NMR (methanol-$d_4$) δ: 8.39 (s, 1H), 8.24 (s, 1H), 7.81 (dd, J=9.5, 2 Hz, 1H), 3.60 (m, 1H), 2.95 (br s, 2H), 2.63 (br s, 3H), 2.23 (d, J=12.5 Hz, 2H), 2.01 (q, J=12.5 Hz, 2H), 1.43 (d, J=6.5 Hz, 6H).

Step H: A mixture of 5-fluoro-3-((2S,4R,6R)-1,2,6-trimethylpiperidin-4-yl)cinnolin-7-yl trifluoromethanesulfonate (36 mg, 0.085 mmol), KOAc (30 mg, 0.30 mmol), bis(pinacolato)diboron (26 mg, 0.1 mmol), Pd(dppf)$Cl_2$ (7 mg, 0.0084 mmol), and 1,4-dioxane (0.35 mL) were heated at 90° C. for 15 h. The reaction mixture was diluted in EtOAc and was filtered over Celite. The filtrate was concentrated under vacuum. The crude boronic acid was dissolved in $Et_2O$ and filtered over Celite to remove black insoluble impurities. The filtrate was concentrated by nitrogen stream to afford 51 mg of crude boronic acid as a black oil. 5-Chloro-2,7-dimethyloxazolo[5,4-b]pyridine (11 mg, 0.06 mmol), Pd(dppf)$Cl_2$ (7 mg, 0.0084 mmol), 1,4-dioxane (0.3 mL), and aqueous $K_2CO_3$ (2.0 M, 0.15 mL, 0.3 mmol) were added to the crude boronic acid. The mixture was stirred at 90° C. for 1 h. The mixture was partitioned between $CH_2Cl_2$ and $H_2O$. The organic layer was dried over $MgSO_4$, filtered, and concentrated under vacuum. The residue chromatographed on silica gel, eluting with $CH_2Cl_2$:MeOH:$NH_4OH$ (95:5:0.5) to $CH_2Cl_2$:MeOH:$NH_4OH$ (90:10:1). Recrystallization from 1.5 mL methanol yielded 5-(5-fluoro-3-((2S,4R,6R)-1,2,6-trimethylpiperidin-4-yl)cinnolin-7-yl)-2,7-dimethyloxazolo[5,4-b]pyridine (17 mg, 47%) as a white solid.

MS m/z 420.3 [M+H]$^+$; $^1$H NMR (methanol-$d_4$) δ: 8.95 (s, 1H), 8.36 (d, J=11 Hz, 1H), 8.16 (s, 1H), 8.10 (s, 1H), 3.46-3.53 (m, 1H), 2.74 (s, 3H), 2.73 (s, 3H), 2.53 (m, 2H), 2.43 (s, 3H), 2.13 (d, J=12 Hz, 2H), 1.88 (q, J=12 Hz, 2H), 1.31 (d, J=6 Hz, 6H).

Using the procedure described for Example 40, above, additional compounds described herein were prepared by substituting the appropriate heteroaryl halide in Step H, suitable reagents and reaction conditions, obtaining compounds such as those selected from:

| Cpd | Data |
| --- | --- |
| 227 | MS m/z 419.3 [M + H]$^+$; $^1$H NMR (methanol-$d_4$) δ: 8.89 (s, 1H), 8.53 (s, 1H), 8.39 (dd, J = 11, 1.5 Hz, 1H), 8.16 (s, 1H), 7.95 (s, 1H), 4.33 (s, 3H), 3.45-3.51 (m, 1H), 2.76 (s, 3H), 2.50-2.55 (m, 2H), 2.43 (s, 3H), 2.13 (d, J = 13.5 Hz, 2H), 1.87 (q, J = 12.5 Hz, 2H), 1.31 (d, J = 6.5 Hz, 6H). |
| 228 | MS m/z 420.3 [M + H]$^+$; $^1$H NMR (methanol-$d_4$) δ: 9.08 (s, 1H), 8.32 (dd, J = 10, 1 Hz, 1H), 8.20 (s, 1H), 7.55 (s, 1H), 3.48-3.55 (m, 1H), 2.84 (s, 3H), 2.68 (s, 3H), 2.50-2.55 (m, 2H), 2.43 (s, 3H), 2.14 (d, J = 13.5 Hz, 2H), 1.89 (q, J = 13 Hz, 2H), 1.31 (d, J = 6.5 Hz, 6H). |

Biological Examples

The following in vitro biological examples demonstrate the usefulness of the compounds of the present description for treating Huntington's disease.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Compounds of Formula (I) were tested using the Meso Scale Discovery (MSD) Assay provided in International Application No. PCT/US2016/066042, filed on Dec. 11, 2016 and claiming priority to United States Provisional Application U.S. 62/265,652 filed on Dec. 10, 2015, the entire contents of which are incorporated herein by reference.

The Endogenous Huntingtin Protein assay used in Example 1 was developed using the ELISA-based MSD electrochemiluminescence assay platform.

Example 1

Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 μg/mL in PBS (30 μL per well). Plates were then washed three times with 300 μL wash buffer (0.05% Tween-20 in PBS) and blocked (100 μL blocking buffer; 5% BSA in PBS) for 4-5 hours at room temperature with rotational shaking and then washed three times with wash buffer.

Samples (25 μL) were transferred to the antibody-coated MSD plate and incubated overnight at 4° C. After removal of the lysates, the plate was washed three times with wash buffer, and 25 μL of #5656S (Cell signaling; rabbit monoclonal) secondary antibody (diluted to 0.25 μg/mL in 0.05% Tween-20 in blocking buffer) was added to each well and incubated with shaking for 1 Hour at room temperature. Following incubation with the secondary antibody, the wells were rinsed with wash buffer after which 25 μL of goat anti-rabbit SULFO TAG secondary detection antibody (required aspect of the MSD system) (diluted to 0.25 μg/mL in 0.05% Tween-20 in blocking buffer) was added to each well and incubated with shaking for 1 hour at room temperature. After rinsing three times with wash buffer, 150 μL of read buffer T with surfactant (MSD) were added to each empty well, and the plate was imaged on a SI 6000 imager (MSD) according to manufacturers' instructions provided for 96- or 384-well plates. The resulting $IC_{50}$ values (μM) for compounds tested are shown in Table 1.

As shown in Table 1, test compounds described herein had the following $IC_{50}$ values, an $IC_{50}$ value between >3 μM and <9 μM is indicated by a single star (*), an $IC_{50}$ value between >1 μM and ≤3 μM is indicated by two stars (), an $IC_{50}$ value between >0.5 μM and ≤1 μM is indicated by three stars (*), an $IC_{50}$ value between >0.1 μM and ≤0.5 μM is indicated by four stars (**) and an $IC_{50}$ value of ≤0.1 μM is indicated by five stars (***).

TABLE 1

| Cpd | $IC_{50}$ |
|---|---|
| 1 | ** |
| 2 | ** |
| 3 | **** |
| 4 | *** |
| 5 | ** |
| 6 | *** |
| 7 | ** |
| 9 | ** |
| 10 | **** |
| 11 | ** |
| 12 | *** |
| 13 | ** |
| 14 | **** |
| 15 | ***** |
| 16 | **** |
| 17 | ***** |
| 18 | **** |
| 19 | ***** |
| 20 | ***** |
| 23 | **** |
| 24 | **** |
| 25 | ***** |
| 26 | ***** |
| 27 | **** |
| 28 | ** |
| 29 | ** |
| 30 | **** |
| 31 | **** |
| 32 | ***** |
| 33 | ***** |
| 34 | ***** |
| 35 | ***** |
| 36 | ***** |
| 37 | ***** |
| 38 | ** |
| 39 | ** |
| 40 | **** |
| 41 | **** |
| 42 | **** |
| 43 | ***** |
| 44 | **** |
| 45 | ***** |
| 46 | ***** |
| 47 | ***** |
| 48 | ***** |
| 49 | ***** |
| 50 | ***** |
| 51 | ***** |
| 52 | ***** |
| 53 | **** |
| 54 | **** |
| 55 | ***** |
| 56 | ***** |
| 57 | ***** |
| 58 | ***** |
| 59 | ***** |
| 60 | **** |
| 61 | *** |
| 62 | ***** |
| 63 | ***** |
| 64 | ***** |
| 65 | **** |
| 66 | ***** |
| 67 | **** |
| 68 | ***** |
| 69 | ***** |
| 70 | ***** |
| 71 | ***** |
| 72 | ***** |
| 73 | ***** |
| 74 | ***** |
| 75 | ***** |
| 76 | ***** |
| 77 | ***** |
| 78 | ***** |
| 79 | ***** |
| 80 | ***** |
| 81 | ***** |

TABLE 1-continued

| Cpd | IC$_{50}$ |
|---|---|
| 82 | ***** |
| 83 | ***** |
| 84 | ***** |
| 85 | **** |
| 86 | ***** |
| 87 | ***** |
| 88 | ***** |
| 89 | ***** |
| 90 | ***** |
| 91 | ** |
| 92 | ***** |
| 93 | ***** |
| 94 | **** |
| 95 | ***** |
| 96 | ***** |
| 97 | *** |
| 98 | **** |
| 99 | ***** |
| 100 | ***** |
| 101 | ***** |
| 102 | ***** |
| 103 | ***** |
| 104 | ***** |
| 105 | ***** |
| 106 | ***** |
| 107 | ***** |
| 108 | ***** |
| 109 | *** |
| 110 | ***** |
| 111 | ***** |
| 112 | ***** |
| 113 | ***** |
| 114 | ***** |
| 115 | ***** |
| 116 | **** |
| 117 | ***** |
| 118 | **** |
| 119 | *** |
| 120 | ** |
| 121 | ***** |
| 122 | ***** |
| 123 | ***** |
| 124 | ***** |
| 125 | ***** |
| 126 | ***** |
| 127 | ***** |
| 128 | ***** |
| 129 | ***** |
| 130 | ***** |
| 131 | ***** |
| 132 | ***** |
| 133 | ***** |
| 134 | ***** |
| 135 | ***** |
| 136 | ***** |
| 137 | ***** |
| 138 | **** |
| 139 | ***** |
| 140 | ***** |
| 141 | ***** |
| 142 | **** |
| 143 | ***** |
| 144 | ***** |
| 145 | ***** |
| 146 | ***** |
| 147 | **** |
| 148 | ***** |
| 149 | ***** |
| 150 | ***** |
| 151 | ***** |
| 152 | ***** |
| 153 | ***** |
| 154 | ***** |
| 155 | ***** |
| 156 | ***** |
| 157 | ***** |
| 158 | ***** |
| 159 | ***** |
| 160 | ***** |
| 161 | ***** |
| 162 | ***** |
| 163 | ***** |
| 164 | ***** |
| 165 | ***** |
| 166 | ***** |
| 167 | ***** |
| 168 | **** |
| 169 | ***** |
| 170 | **** |
| 171 | ***** |
| 172 | ***** |
| 173 | ***** |
| 174 | ***** |
| 175 | ***** |
| 176 | ***** |
| 177 | ***** |
| 178 | ***** |
| 179 | ***** |
| 180 | ***** |
| 181 | ***** |
| 182 | ***** |
| 183 | ***** |
| 184 | ***** |
| 185 | ***** |
| 186 | ***** |
| 187 | ***** |
| 188 | ***** |
| 189 | ***** |
| 190 | ***** |
| 191 | **** |
| 192 | ***** |
| 193 | ***** |
| 194 | **** |
| 195 | ***** |
| 196 | ***** |
| 197 | ***** |
| 198 | **** |
| 199 | ***** |
| 200 | ***** |
| 201 | ***** |
| 202 | ***** |
| 203 | *** |
| 204 | ***** |
| 205 | **** |
| 206 | ***** |
| 207 | ***** |
| 208 | **** |
| 209 | **** |
| 210 | ***** |
| 211 | ***** |
| 212 | **** |
| 213 | **** |
| 214 | **** |
| 215 | ***** |
| 216 | ***** |
| 217 | ***** |
| 218 | ***** |
| 219 | ***** |
| 220 | **** |
| 221 | ***** |
| 222 | **** |
| 223 | ***** |
| 224 | ***** |
| 225 | ***** |
| 226 | ***** |
| 227 | ***** |
| 228 | **** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound of Formula (Ig1), Formula (Ii1), or Formula (Im1):

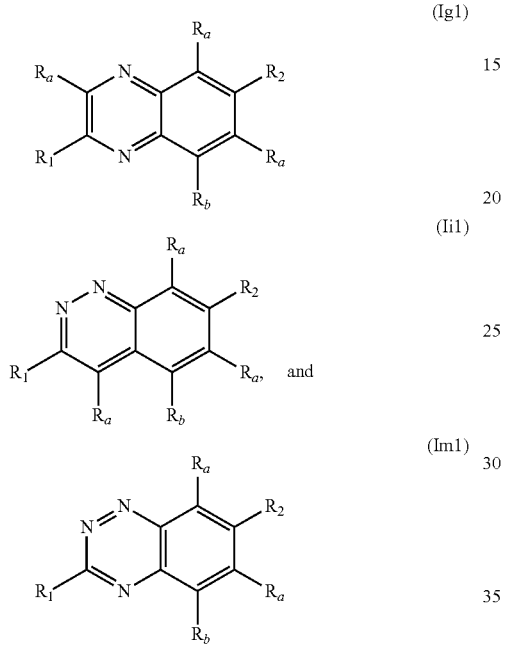

or a form thereof, wherein:

$R_1$ is heterocyclyl or heterocyclyl-amino, wherein heterocyclyl is selected from the group consisting of azetidinyl, tetrahydrofuranyl, pyrrolidinyl, piperidinyl, piperazinyl, azepanyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, hexahydro-1H-cyclobuta[1,2-c:1,4-c']dipyrrol-(3H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 1,4-diazabicyclo[3.1.1]heptyl, 3,6-diazabicyclo[3.2.0]heptyl, 2,5-diazabicyclo[2.2.2]octyl, 1,4-diazabicyclo[3.2.1]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 4,7-diazaspiro[2.5]octanyl, 2,6-diazaspiro[3.3]heptyl, 2,6-diazaspiro[3.4]octanyl, 1,7-diazaspiro[4.4]nonyl, 2,6-diazaspiro[3.5]nonyl, 2,7-diazaspiro[3.5]nonyl, 5,8-diazaspiro[3.5]non yl, 2,7-diazaspiro[4.4]nonyl, 2,7-diazaspiro[4.5]decanyl and 6,9-diazaspiro[4.5]decyl, wherein, each instance of heterocyclyl is optionally substituted with one, two or three $R_3$ substituents and optionally, with one additional $R_4$ substituent, or, wherein, alternatively, each instance of heterocyclyl is optionally substituted with one, two, three or four $R_3$ substituents;

$R_2$ is heteroaryl, selected from the group consisting of thienyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 2H-pyrazolo[3,4-c]pyridinyl, 2H-pyrazolo[4,3-b]pyridinyl, 2H-pyrazolo[4,3-c]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,3]oxazolo[4,5-c]pyridinyl, [1,3]thiazolo[4,5-c]pyridinyl, [1,3]thiazolo[5,4-b]pyridinyl, [1,2,4]triazolo[1,5-a]pyridinyl and quinoxalinyl, wherein, each instance of heteroaryl is optionally substituted with one, two or three $R_6$ substituents and optionally, with one additional $R_7$ substituent;

$R_a$ is, in each instance, independently selected from the group consisting of hydrogen and $C_{1-8}$alkyl;

$R_b$ is, in each instance, independently selected from the group consisting of hydrogen and halogen;

$R_3$ is, in each instance, independently selected from the group consisting of cyano, halogen, hydroxy, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl$)_2$-amino-$C_{1-8}$alkyl-amino, [$(C_{1-8}$alkyl$)_2$-amino-$C_{1-8}$alkyl$]_2$-amino, $(C_{1-8}$alkyl-amino-$C_{1-8}$alkyl$)(C_{1-8}$alkyl$)$amino, [$(C_{1-8}$alkyl$)_2$-amino-$C_{1-8}$alkyl$](C_{1-8}$alkyl$)$amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino and (hydroxy-$C_{1-8}$alkyl$)(C_{1-8}$alkyl$)$amino;

$R_4$ is $C_{3-14}$cycloalkyl, $C_{3-4}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl, heterocyclyl-$C_{1-8}$alkyl, heteroaryl or heteroaryl-$C_{1-8}$alkyl;
  wherein, each instance of $C_{3-14}$cycloalkyl, aryl, heterocyclyl and heteroaryl is optionally substituted with one, two or three $R_5$ substituents;

$R_5$ is, in each instance, independently selected from the group consisting of halogen, hydroxy, cyano, nitro, $C_{1-8}$alkyl, halo-$C_{1-8}$alkyl, $C_{1-8}$alkoxy, halo-$C_{1-8}$alkoxy, hydroxy-$C_{1-8}$alkyl, amino, $C_{1-8}$alkyl-amino, ($C_{1-8}$alkyl)$_2$-amino, ($C_{1-8}$alkyl)$_2$-amino-$C_{1-8}$alkyl, $C_{1-8}$alkyl-thio and heteroaryl-$C_{1-8}$alkyl;

$R_6$ is, in each instance, independently selected from the group consisting of halogen, hydroxy, cyano, nitro, $C_{1-8}$alkyl, $C_{2-8}$alkenyl, cyano-$C_{1-8}$alkyl, halo-$C_{1-8}$alkyl, hydroxy-$C_{1-8}$alkyl, $C_{1-8}$alkoxy, halo-$C_{1-8}$alkoxy, ($C_{1-8}$alkyl)$_2$-amino-$C_{1-8}$alkoxy, $C_{1-8}$alkoxy-$C_{1-8}$alkyl, $C_{1-8}$alkoxy-$C_{1-8}$alkoxy, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl, $C_{1-8}$alkyl)amino and $C_{1-8}$alkyl-thio; and, $R_7$ is $C_{3-14}$cycloalkyl, $C_{3-14}$cycloalkyl-oxy, aryl, heterocyclyl, heteroaryl or heteroaryl-$C_{1-8}$alkoxy, wherein the form of the compound is selected from the group consisting of a salt, hydrate, solvate, clathrate, isotopologue, racemate, enantiomer, diastereomer, stereoisomer, polymorph and tautomer form thereof.

2. A compound of claim 1, wherein the form of the compound is a compound salt selected from the group consisting of hydrochloride, hydrobromide, trifluoroacetate, formate, dihydrochloride, dihydrobromide, ditrifluoracetate, diformate, trihydrochloride, trihydrobromide, tritrifluororacetate and triformate.

* * * * *

UNITED STATES PATENT AND TRADEMARK OFFICE
CERTIFICATE OF CORRECTION

PATENT NO. : 12,384,789 B2  
APPLICATION NO. : 17/723163  
DATED : August 12, 2025  
INVENTOR(S) : Matthew G. Woll et al.

Page 1 of 1

It is certified that error appears in the above-identified patent and that said Letters Patent is hereby corrected as shown below:

In the Claims

At Column 276, Claim number 1, Line number 66, please replace "$C_{3-4}$cycloalkyl-$C_{1-8}$alkyl" with --$C_{3-14}$cycloalkyl-$C_{1-8}$alkyl--.

Signed and Sealed this  
Thirteenth Day of January, 2026

John A. Squires  
*Director of the United States Patent and Trademark Office*